(12) United States Patent
Heyduk et al.

(10) Patent No.: US 7,811,809 B2
(45) Date of Patent: Oct. 12, 2010

(54) MOLECULAR BIOSENSORS FOR USE IN COMPETITION ASSAYS

(75) Inventors: Tomasz Heyduk, Ballwin, MO (US); Ling Tian, St. Louis, MO (US)

(73) Assignee: Saint Louis University, St. Louis, MO (US)

( * ) Notice: Subject to any disclaimer, the term of this patent is extended or adjusted under 35 U.S.C. 154(b) by 274 days.

(21) Appl. No.: 11/836,339

(22) Filed: Aug. 9, 2007

(65) Prior Publication Data
US 2008/0171322 A1    Jul. 17, 2008

Related U.S. Application Data

(63) Continuation-in-part of application No. 10/539,107, filed on Jun. 15, 2005.

(60) Provisional application No. 60/821,876, filed on Aug. 9, 2006.

(51) Int. Cl.
*C12M 1/34* (2006.01)
*C12M 3/00* (2006.01)
*C12Q 1/68* (2006.01)

(52) U.S. Cl. ............... 435/287.2; 435/6; 435/7.2; 536/23.1; 536/24.3

(58) Field of Classification Search ............ 435/6, 435/7.2, 287.2; 536/23.1, 24.3
See application file for complete search history.

(56) References Cited

U.S. PATENT DOCUMENTS 5,270,163 A    12/1993    Gold et al.
(Continued)

FOREIGN PATENT DOCUMENTS

WO          9700446          1/1997
(Continued)

OTHER PUBLICATIONS

TriLink-PEG-282 brochure, Sep. 8, 2009.*
(Continued)

*Primary Examiner*—B J Forman
*Assistant Examiner*—Narayan K Bhat
(74) *Attorney, Agent, or Firm*—Polsinelli Shughart PC

(57) ABSTRACT

The invention generally provides molecular biosensors. The molecular biosensors are useful in competition assays to detect the presence of a target molecule.

18 Claims, 78 Drawing Sheets

U.S. PATENT DOCUMENTS

| | | | |
|---|---|---|---|
| 5,475,096 A | 12/1995 | Gold et al. | |
| 5,476,766 A | 12/1995 | Gold et al. | |
| 5,543,293 A | 8/1996 | Gold et al. | |
| 5,567,588 A | 10/1996 | Gold et al. | |
| 5,582,981 A | 12/1996 | Toole et al. | |
| 5,637,459 A | 6/1997 | Burke et al. | |
| 5,641,629 A | 6/1997 | Pitner et al. | |
| 5,650,275 A | 7/1997 | Pitner et al. | |
| 5,660,985 A | 8/1997 | Pieken et al. | |
| 5,670,637 A | 9/1997 | Gold et al. | |
| 5,683,867 A | 11/1997 | Biesecker et al. | |
| 5,688,935 A | 11/1997 | Stephens et al. | |
| 5,696,249 A | 12/1997 | Gold et al. | |
| 5,705,337 A | 1/1998 | Gold et al. | |
| 5,712,375 A | 1/1998 | Jensen et al. | |
| 5,723,289 A | 3/1998 | Eaton et al. | |
| 5,723,592 A | 3/1998 | Eaton et al. | |
| 5,750,342 A | 5/1998 | Stephens et al. | |
| 5,756,291 A | 5/1998 | Griffin et al. | |
| 5,763,566 A | 6/1998 | Jensen et al. | |
| 5,763,595 A | 6/1998 | Gold et al. | |
| 5,773,598 A | 6/1998 | Burke et al. | |
| 5,789,157 A | 8/1998 | Jensen et al. | |
| 5,789,160 A | 8/1998 | Eaton et al. | |
| 5,817,785 A | 10/1998 | Gold et al. | |
| 5,840,867 A | 11/1998 | Toole et al. | |
| 5,843,653 A | 12/1998 | Gold et al. | |
| 5,853,984 A | 12/1998 | Davis et al. | |
| 5,858,660 A | 1/1999 | Eaton et al. | |
| 5,861,254 A | 1/1999 | Schneider et al. | |
| 5,864,026 A | 1/1999 | Jensen et al. | |
| 5,874,218 A | 2/1999 | Drolet et al. | |
| 5,958,691 A | 9/1999 | Pieken et al. | |
| 5,962,219 A | 10/1999 | Gold et al. | |
| 5,989,823 A | 11/1999 | Jayasena et al. | |
| 5,998,142 A | 12/1999 | Gold et al. | |
| 6,001,570 A | 12/1999 | Grossman | |
| 6,001,577 A | 12/1999 | Gold et al. | |
| 6,011,020 A | 1/2000 | Gold et al. | |
| 6,013,443 A | 1/2000 | Heilig et al. | |
| 6,030,776 A | 2/2000 | Eaton et al. | |
| 6,048,698 A | 4/2000 | Eaton et al. | |
| 6,083,696 A | 7/2000 | Biesecker et al. | |
| 6,110,900 A | 8/2000 | Gold et al. | |
| 6,114,120 A | 9/2000 | Jensen et al. | |
| 6,127,119 A | 10/2000 | Stephens et al. | |
| 6,147,204 A | 11/2000 | Gold et al. | |
| 6,177,555 B1 | 1/2001 | Jayasena et al. | |
| 6,207,388 B1 | 3/2001 | Grossman | |
| 6,225,058 B1 | 5/2001 | Munishkin et al. | |
| 6,261,774 B1 | 7/2001 | Pagratis et al. | |
| 6,261,783 B1 * | 7/2001 | Jayasena et al. | 435/6 |
| 6,291,184 B1 | 9/2001 | Gold et al. | |
| 6,300,074 B1 | 10/2001 | Gold et al. | |
| 6,329,145 B1 | 12/2001 | Janjic et al. | |
| 6,331,398 B1 | 12/2001 | Gold et al. | |
| 6,344,318 B1 | 2/2002 | Gold et al. | |
| 6,376,190 B1 | 4/2002 | Gold et al. | |
| 6,391,593 B1 | 5/2002 | Weston | |
| 6,399,302 B1 | 6/2002 | Lannigan et al. | |
| 6,423,493 B1 | 7/2002 | Gorenstein et al. | |
| 6,451,588 B1 | 9/2002 | Egholm | |
| 6,465,188 B1 | 10/2002 | Gold et al. | |
| 6,506,887 B1 | 1/2003 | Smith et al. | |
| 6,511,809 B2 | 1/2003 | Baez | |
| 6,544,746 B2 | 4/2003 | Heyduk | |
| 6,593,091 B2 * | 7/2003 | Keys et al. | 435/6 |
| 6,613,526 B2 | 9/2003 | Heilig et al. | |
| 6,680,377 B1 | 1/2004 | Stanton et al. | |
| 6,716,583 B2 | 4/2004 | Gold et al. | |
| 6,730,482 B2 | 5/2004 | Gold et al. | |
| 6,878,515 B1 | 4/2005 | Landegren | |
| 6,916,613 B2 | 7/2005 | Munishkin et al. | |
| 2002/0022224 A1 | 2/2002 | Hornby et al. | |
| 2002/0037506 A1 | 3/2002 | Lin et al. | |
| 2002/0051986 A1 | 5/2002 | Baez | |
| 2003/0087239 A1 | 5/2003 | Stanton et al. | |
| 2003/0207271 A1 | 11/2003 | Holwitt et al. | |
| 2003/0224435 A1 | 12/2003 | Seiwert | |
| 2003/0232388 A1 | 12/2003 | Kreimer et al. | |
| 2004/0053310 A1 | 3/2004 | Shi et al. | |
| 2004/0058378 A1 | 3/2004 | Kong et al. | |
| 2004/0067501 A1 | 4/2004 | Kage | |
| 2004/0180360 A1 | 9/2004 | Wilson et al. | |
| 2004/0219523 A1 | 11/2004 | Stanton et al. | |
| 2005/0069910 A1 | 3/2005 | Turner et al. | |
| 2005/0095627 A1 * | 5/2005 | Kolman et al. | 435/6 |
| 2005/0106594 A1 | 5/2005 | Ellington et al. | |
| 2005/0112710 A1 | 5/2005 | Torres et al. | |
| 2006/0110739 A1 | 5/2006 | Heyduk et al. | |

FOREIGN PATENT DOCUMENTS

| | | |
|---|---|---|
| WO | WO 03/064657 A1 | 8/2003 |
| WO | WO 03/078449 A2 | 9/2003 |
| WO | WO2005/059509 A3 | 6/2005 |

OTHER PUBLICATIONS

SantaLucia, A ubified view of polymer, dumbell, and oligonucleotide DNA nearest neighbor themodynamics,1998, PNAS, 95, 1460-1465.*

Bock, L.C., et al., "Selection of single-stranged DNA molecules that bind and inhibit human thrombin", *Nature* (1992) pp. 564-566, vol. 355.

Burgstaller, P., et al., "Synthetic Ribozymes and the First Deoxyribozyme", *Angew. Chem. Int. Ed. Engl.* (1995) pp. 1189-1192, vol. 34, No. 11.

Ellington, A.D., et al., "In vitro selection of RNA molecules that bind specific ligands", *Nat.* (1990) pp. 818-822, vol. 346.

Famulok, M., et al., "In Vitro Selection of Specific Ligand-binding Nucleic Acids", *Angew. Chem. Int. Ed. Engl.* (1992) pp. 979-988, vol. 31.

Fang, et al., "Synthetic DNA Aptamers to Detect Protein Molecular Variants in a High-Throughput Fluorescence Quenching Assay", *ChemBioChem.* (2003) pp. 829-834, vol. 4.

Gold, L., et al., "Diversity of Oligonucleotide Functions", *Ann. Rev. Biochem.* (1995) pp. 763-797, vol. 64.

Hamaguchi, et al., "Aptamer Beacons for the Direct Detection of Proteins", *Analy. Biochem.* (2001) pp. 126-131, vol. 294.

Heyduk, E., et al., "Thiol-reactive, Luminescent Europium Chelates: Luminescence Probes for Resonance Energy Transfer Distance Measurements in Biomolecules", *Anal. Biochem.* (1997) pp. 216-227, vol. 248.

Heyduk, E., et al., "Conformational Changes of DNA Induced by Binding of *Chironomus* High Mobility Group Protein 1a (cHMG1a)", *J. Biol. Chem.* (1997) pp. 19763-19770, vol. 272, No. 32.

Heyduk, E., et al., "Homogeneous Fluorescence Assay for Cyclic AMP", *Comb. Chem. and High Throughput Screen.* (2003) pp. 347-354, vol. 6.

Heyduk, T., et al., "Luminscense Energy Transfer with Lanthanide Chelates: Interprepation of Sensitized Acceptor Decay Amplitudes", *Analy Biochem* (2001) pp. 60-67, vol. 289, No. 1.

Heyduk, T., et al., "Molecular beacons for detecting DNA binding proteins", *Nat. Biotech.* (2002) pp. 171-176, vol. 20.

Heyduk, E., et al., "Molecular beacons for detecting DNA binding proteins: mechanism of action", *Analyt. Biochem.* (2003) pp. 1-10, vol. 316.

Jayasena, S.D., "Aptamers: An Emerging Class of Molecules That Rival Antibodies in Diagnostics", *Clin. J. Chem.* (1999) pp. 1628-1650, vol. 45, No. 9.

Klug, S., et al., "All you wanted to know about SELEX (but were afraid to ask . . . )", *Mol. Biol. Rep* (1994) pp. 97-107, vol. 20.

Knoll, E., et al., "Unimolecular Beacons for the Detection of DNA-Binding Proteins", *Anal. Chem.* (2004) pp. 1156-1164, vol. 76, No. 4.
Li, J.J., et al., "Molecular Aptamer Beacons for Real-Time Protein Recognition", *Biochem. and Biophys. Res. Commun.* (2002) pp. 31-40, vol. 292, No. 1.
Mathis, G., "Probing Molecular Interactions with Homogeneous Techniques Based on Rare Earth Cryptrates and Fluorescence Energy Transfer", *Clinic. Chem.* (1995) pp. 1391-1317, vol. 41, No. 9.
Matlock, D.L., et al., "Sequence Determinants for the Recognition of the Fork Junction DNA Containing the—10 Region of Promoter DNA by *E. coli* RNA Polymerase", *Biochem.* (2000) pp. 12274-12283, vol. 39, No. 40.
Mills, J.B., et al., "Flexibility of Single-Stranged DNA: Use of Gapped Duplex Helices to Determine the Persistence Lengths of Poly(dT) and Poly(dA)", *J. Mol. Biol.* (1999) pp. 245-257, vol. 285.
Selvin, P.R., et al., "Luminescence Resonance Energy Transfer", *J. Am. Chem. Soc.* (1994) pp. 6029-6030, vol. 116.
Selvin, P.R., et al., "Luminescence energy transfer using a terbium chelate: Improvements on fluorescence energy transfer", *Proc. Natl. Acad. Sci USA* (1994) pp. 10024-10028, vol. 91.
Tasset, D.M., et al., "Oligonucleotide Inhibitors of Human Thrombin that Bind Distinct Epitopes", *J. Mol. Biol.* (1997) pp. 688-698, vol. 272.
Turek, C., et al., "Systematic Evolution of Ligands by Exponential Enrichment: RNA Ligands to Bacteriophage T4 DNA Polymerase", *Sci* (1990) pp. 505-510, vol. 249, No. 4968.
Wilson, D.S., et al., "In Vitro Selection of Functional Nucleic Acids", *Ann. Rev. Biochem.* (1999) pp. 611-647, vol. 68.
Xu, W., et al., "Anti-peptide aptamers recognize amino acid sequence and bind a protein epitope", *Proc. Natl. Acad. Sci. USA* (1996) pp. 7475-7480, vol. 93.
Yamamoto, R., et al., "Molecular beacon aptamer fluoresces in the presence of Tat protein of HIV-1", *Genes Cells* (2000) pp. 389-396, vol. 5.
International Search Report for PCT/US04/41315, dated Sep. 24, 2007; 4 pages.
Daniels et al., "Generation of RNA aptamers to the G-protein-coupled receptor for neurotensin, NTS-1", *Analytical Biochemistry*, 2002, pp. 214-226, vol. 305.
Sayer et al., "Structural characterization of 2F-RNA aptamer that binds a HIV-1 SU glycoprotein, gp 120" *Biochemical and Biophysical Research Communications*, 2002, pp. 924-931, vol. 293.
Heyduk et al., : Nucleic acid-based fluorescence sensors for detecting proteins, 2005 Anal Chem, vol. 77. pp. 1147-1156.
International Search Report regarding PCT/US07/75560 dated Aug. 25, 2008.
Abravaya, "Detection of point mutations with a modified ligase chain reaction (Gap-LCR)", Nucleic Acids Research, 1995, pp. 675-682, vol. 23, No. 4, Oxford University Press.
Fredricksson, "Protein detection using proximity-dependent DNA ligation assays", Nature Biotechnology, May 2002, pp. 473-477, vol. 20, Nature Publishing Group.
Sequence alignment brochure SEQ ID No. 1 and 3, http://blast.ncbi.nlm.nih.gov/Blast.cgi, printed Sep. 15, 2009, 1 pg.
Sequence alignment brochure SEQ ID No. 2 and 3, http:/lblast.ncbi.nlm.nih.gov/Blast.cgi, printed Sep. 13, 2009, 1 pg.
Sequence alignment brochure SEQ ID No. 5 and 12, http://blast.ncbi.nlm.nih.gov/Blast.cgi, printed Sep. 13, 2009, 1 pg.
Sequence alignment brochure SEQ ID No. 7 and 12, http://blast.ncbi.nlm.nih.gov/Blast.cgi, printed Sep. 15, 2009, 1 pg.
Sequence alignment brochure SEQ ID No. 1 and 2, http://blast.ncbi.nlm.nih.gov/Blast.cgi, printed Sep. 13, 2009, 1 pg.
Tanaka, "Specificity of Hybridization Between DNA Sequences Based on Free Energy", DNA Computing, 2006, pp. 371-379, Springer-Verlag, Berlin.
Uptima FT-UP17412 SMCC, sSMCC Heterobifunctional cross-linkers brochure, 3 pgs.
Uptima FT-UP79042 SPDP, lc-SPDP, Sulfo-lc-SPDP Heterobifunctional cross-linkers brochure, 3 pgs.
"Chemical bond", http://en.wikipedia.org/wiki/Chemical_bond, printed Jun. 24, 2008, 11 pgs.
Zalipski, "Chemistry of polyethylene glycol conjugates with biologically active molecules", Advanced Drug Delivery Reviews, 1995 pp. 157-182, vol. 16, Elsevier Science B.V.
Office Action dated Jul. 2, 2008 from related U.S. Appl. No. 10/539,107, 21 pgs.
Office Action dated Mar. 12, 2009 from related U.S. Appl. No. 10/539,107, 24 pgs.
Office Action dated Sep. 30, 2009 from related U.S. Appl. No. 11/836,333, 38 pgs.
"HyTher—Hybridization Thermodynamics—Module 1", http://ozone3.chem.wayne.edu/cgi-bin/login/execs/HytherMl.cgi, printed Mar. 5, 2009, 1 pg.
Office Action dated Dec. 18, 2009 from related U.S. Appl. No. 10/539,107, 21 pgs.

* cited by examiner

D

E

G ss DNA/RNA-ss DNA/RNA-ss DNA/RNA

H ds DNA-protein

I protein-protein

|  | SEQ. ID NO. |
|---|---|
| clone1   --GGCGGT-ATGGCATAGCGTAATGG-AGGTTGT-------------- | 45 |
| clone9   --GGCGGT-ATGGTATAGCGTAATGG-AGGTTGT-------------- | 53 |
| clone7   --GGCGGT-ATGGCATAGCGTAATGG-AGGTCTGC------------- | 51 |
| clone12  ---GCTGGATAGCGTCG-GTAGCTTAGGTAGGGTGG------------ | 56 |
| clone2   ------GGATGCGTAATGCTTAGGGTGGGTAGGGTATCC--------- | 46 |
| clone3   ------GGATGCGTAATGCTTAGGGTGGGTAGGGTATCC--------- | 47 |
| clone4   ------GGATGCGTAATGCTTAGGGTGGGTAGGGTATCC--------- | 48 |
| clone8   ------GGATGCGTAATGCTTAGGGTGGGTAGGGTATCC--------- | 52 |
| clone23  ------GCATACGTAATGCTCCGGTTGAGGCGGGTATGT--------- | 67 |
| clone22  ------GCAGACGTAATGCGTTGCTTGGAACTGGATCC---------- | 66 |
| clone11  CAGCAGGGAACGGAACGGTTAGCGTGGGTAGGG-------------- | 55 |
| clone32  ---------GCAGTAGGTACTATATTGGTAGGGTGGTCTGC-------- | 76 |
| clone33  ---------GCAGTAGGTACTATATTGGTAGGGTGGTCTGC-------- | 77 |
| clone29  ---------GCAGTAGGTACTATATTGGTAGGGTGGTCTGC-------- | 73 |
| clone31  ---------GCAGTAGGTACTATATTGGTAGGGTGGTCTGC-------- | 75 |
| clone5   ---------GCAGTAGGTACTATATTGGTAGGGTGGTCTGC-------- | 49 |
| clone6   ---------GCAGTAGGTACTATATTGGTAGGGTGGTCTGC-------- | 50 |
| clone35  ---------GCAGTAGGTACTATGTCGGTCGGTGGTCTGC-------- | 79 |
| clone10  ----GGGGGTACTAGGTATTAA--TGGTAGGGTGGTGT---------- | 54 |
| clone34  ----GGGGGTGCTAGGTATTAA--AGGTAGGGTGGTGT---------- | 78 |
| clone20  ----GGGGGTACTAGGTATCAA--TGGTAGGGTGGTGT---------- | 64 |
| clone21  ----GGGGGTACTAGGTATCAA--TGGTAGGGTGGTGT---------- | 65 |
| clone24  ----GGGGGTACTAGGTATCAA--TGGTAGGGTGGTGT---------- | 68 |
| clone26  ----GGGGGTACTAGGTATCAA--TGGTAGGGTGGTGT---------- | 70 |
| clone13  ---------------CAGGATGGGTAGGGTGGTCAGCGAAGCAGTAGG | 57 |
| clone15  ---------------CAGGATGGGTAGGGTGGTCAGCGAAGCAGTAGG | 59 |
| clone16  ---------------CAGGATGGGTAGGGTGGTCAGCGAAGCAGTAGG | 60 |
| clone19  ---------------CAGGATGGGTAGGGTGGTCAGCGAAGCAGTAGG | 63 |
| clone25  ----------GAGGGACTTAGGATGGGTAGGGTGGTAGGCCC------ | 69 |
| clone17  ---GGCGGAGCAGCGTAGTAGGGTGGGTAGGGTGG------------ | 61 |
| clone14  ---CAACGGCTTGGGTAACTGTAGTGGCTTGGGGTG----------- | 58 |
| clone27  ---GGTCGGGGCATAGT--AATGCTGGATTGGGCAGT---------- | 71 |
| clone28  ---GGGTAGGAGCAGTAC--A-CGCTGGAATGGGTCACT-------- | 72 |
| clone30  ---GGGTAGGGTGACAGG--GAGGACGGAATGGGC-ACT-------- | 74 |
| clone18  -------CAGGGTCAGGGCTAGAGAATGCGATTAACCAGG-------- | 62 |
| ruler    1........10........20........30........40........50.. | |

FIG. 28C clones 20,21,24,26

5'fluoresceinAGATGCGXXXX AG GTT GGG GGT ACT AGG TAT CAA TGG GTA GGG TGG TGT AACGC (SEQ ID NO:38) THR35

5'fluoresceinAGATGCGXXXXA GTG AAG GTT GGG GGT ACT AGG TAT CAA TGG GTA GGG TGG TGT AAC GCC ATA T (SEQ ID NO:39) THR36

```
clone1-1   --GGGTAGGGTGGTTGTAATAGGG--ATTGCGAT------
clone1-2   --GGGTAGGGTGGTTGTAATAGGG--ATTGCGAT------
clone1-4   --GGGTAGGGTGGTTGTAATAGGG--ATTGCGAT------
clone1-5   --GGGTAGGGTGGTTGTAATAGGG--ATTGCGAT------
clone1-9   --GGGTAGGGTGGTTGTAATAGGG--ATTGCGAT------
clone2-4   ---GGTAGGGTGGTTAAAATAGGGGAATGGCAG-------
clone2-7   ---GGTAGGGTGGTTAAAATAGGGGAATGGCAG-------
clone2-10  ---GGTAGGGTGGTTAAAATAGGGGAATGGCAG-------
clone2-8   -----TAGGATGGGTAGGGTGGTCCCAGGAATGGC-----
clone2-9   -----TAGGATGGGTAGGGTGGCCCCAGGAATGGC-----
clone2-12  -----TAGGATGGGTAGGGTGGTCCCAGGAATGGC-----
clone2-14  -----TAGGATGGGTAGGGTGGTCCCAGGAATGGC-----
clone1-8   ACGCGTAGGATGGGTAGGGTGGTCGCGTTA----------
clone2-2   -----TAGGGTGGGTAGGGTGGTCAACTATGGGGG-----
clone1-7   ---AATGGGGAGGTTGGGGTGCGGGAGAGTGGT-------
clone2-5   ---CACAAGAAGGGCGAGCGCTGAGCATAGTGC-------
clone2-13  ------GGAGATGCAGGTACTGAGTAGGGAGTGTGC----
clone2-3   ------GGGTGGCTGGTCAAGGAG-ATAGTACGATGC---
clone2-11  --------GATG--TGGCCCAGAAGCATAACACGACGTAC
clone2-1   --AAGGCCGCCATCTGGGTCCGACGAGTACCA--------
clone1-10  ------GGGCGAAGGTACCAAGACGGATGCACGTGC----
clone1-6   ------GGTGTGGGTGG-TTATTGGTGTAGAGCGGGT---
clone1-3   ------GGCACAACCCGATATGGCTATGAATCTGCC----
clone2-6   ---CCAACGACACATAGGGTACACGCCGCCTCC-------
ruler      1........10........20........30........40
```

| | SEQ. ID NO. |
|---|---|
| clone1-1 | 80 |
| clone1-2 | 81 |
| clone1-4 | 83 |
| clone1-5 | 84 |
| clone1-9 | 88 |
| clone2-4 | 93 |
| clone2-7 | 96 |
| clone2-10 | 99 |
| clone2-8 | 97 |
| clone2-9 | 98 |
| clone2-12 | 101 |
| clone2-14 | 103 |
| clone1-8 | 87 |
| clone2-2 | 91 |
| clone1-7 | 86 |
| clone2-5 | 94 |
| clone2-13 | 102 |
| clone2-3 | 92 |
| clone2-11 | 100 |
| clone2-1 | 90 |
| clone1-10 | 89 |
| clone1-6 | 85 |
| clone1-3 | 82 |
| clone2-6 | 95 |

FIG. 30C

```
                                                                    SEQ. ID NO.
 clone1  AATCAAGGCTGGTGTTAAAGGTGATCGACTAG---------------       104
clone23  ----------CAGGATAAAAGCCATCAACTAGAATGCGCATGG--------    126
 clone3  ------------------AAAGGCATCACCTAGAGTTGCCGCCGATACTTG-   106
clone17  -----------------ACAAGCCATCACGT-GAATGCCGACCGGTACTGT-   120
clone15  ------------------CAGGCATCCCAAGAAGTGTCAGCCGTTTCGTGG     118
 clone7  ---------------AGGGAAAGCCATCACCT--AGACACATACAGCATG---  110
clone20  -------------AACGGAAAGCCATCACC---ATATTTAT-CGTCCTG---   123
 clone5  ---------------CGAAAGCAGCCATCAACC-TTGAAACGCCCGTCC----  108
clone10  --------------ACAGACGCCCCTAGTAAACAATAAC-CGATGGCC---    113
clone13  ------------------GCAATATAGCACTAAGCCTTAAACTCCATGGTGG-- 116
 clone2  ---------------AAGGGGAGCCATCACACAGGAGGTCGCTTCGCT-----  105
 clone6  ------------CAGACGGGAGCCATCGACATAGAGGTGATTGCC--------  109
 clone9  ------------CCAACAGACGGTAGCACAACACTAGTACTCTGG--------  112
clone16  ------------CAACAGGAC--AGCCCGACAC-ACAGATCTGGCCCC---    119
clone21  -------------ACGGGCGCAAACAAGATGTACAAAAGCATGGTG----     124
 clone4  ---------------GGGGATGTGCGAAACTGGTGACTATGCGG-GTGC------ 107
clone22  ---------------AGCGGGATAGGGAACTATCGGACAATCGTCGTG-------- 125
 clone8  -----------------ATAAGAAGCCA-TCATAGGGACCTAGCTAGCCCC     111
clone14  ------------GCAAGGAAAAACAAGCAAGCCATCACGACCTAG--------  117
clone18  ------------------ACCGACAAACAAGTCAATACGGGACACGATCCT--  121
clone12  ------------------ATGGGCAACGCGGAGACCTGTCGGTACTGCCT--   115
clone19  ------------------CAGTGGGTCGGGTCACAGCCATGAGTGTTGCTG------ 122
clone11  ------------------ATAGCTACTCGCCAAGGGTGACTTCTGCTATTG-   114
   ruler 1.......10........20........30........40.........50..
```

| Concentration of THR or Beacon | Blood Clotting Time (sec) |
|---|---|
| 0 | 147 ± 15 |
| 7.5 nM of beacon (THR7; SEQ ID NO. 7) | 445 ± 24 |
| 15 nM of beacon (THR7; SEQ ID NO. 7) | Too long to measure |
| 168 nM of THR4 (SEQ ID NO. 4) | 192 ± 47 |
| 336 nM of THR4 (SEQ ID NO. 4) | 291 ± 18 |
| 600 nM of THR3 (SEQ ID NO. 3) | 191 ± 6 |
| 1200 nM of THR3 (SEQ ID NO. 3) | 267 ± 30 |
| 1800 nM of THR3 (SEQ ID NO. 3) | 339 ± 7 |

FIG. 44

MOLECULAR BIOSENSORS FOR USE IN COMPETITION ASSAYS

CROSS-REFERENCES TO RELATED APPLICATIONS

This application claims priority to U.S. Provisional Application Ser. No. 60/821,876 filed on Aug. 9, 2006, which is hereby incorporated by reference in its entirety. This application is also a continuation-in-part of U.S. application Ser. No. 10/539,107 that is presently pending, and was filed on Jun. 15, 2005, which is hereby incorporated by reference in its entirety.

GOVERNMENTAL RIGHTS

The present invention was supported by a Phased Innovation Grant (R21/R33CA 94356) and a STTR Grant (1 R41 GM079891-01) from the National Institutes of Health. The United States Government has certain rights in this invention.

FIELD OF THE INVENTION

The invention relates to molecular biosensors for use in competition assays. The molecular biosensors may be used to determine whether a target molecule is present in a sample.

BACKGROUND OF THE INVENTION

The detection, identification and quantification of specific molecules in our environment, food supply, water supply and biological samples (blood, cerebral spinal fluid, urine, et cetera) can be very complex, expensive and time consuming. Methods utilized for detection of these molecules include gas chromatography, mass spectroscopy, DNA sequencing, immunoassays, cell-based assays, biomolecular blots and gels, and myriad other multi-step chemical and physical assays.

There continues to be a high demand for convenient methodologies for detecting and measuring the levels of specific proteins in biological and environmental samples. Detecting and measuring levels of proteins is one of the most fundamental and most often performed methodologies in biomedical research. While antibody-based protein detection methodologies are enormously useful in research and medical diagnostics, they are not well adapted to rapid, high-throughput parallel protein detection.

Previously, the inventor had developed a fluorescent sensor methodology for detecting a specific subclass of proteins, i.e., sequence-specific DNA binding proteins (Heyduk, T.; Heyduk, E. Nature Biotechnology 2002, 20, 171-176; Heyduk, E.; Knoll, E.; Heyduk, T. Analyt. Biochem. 2003, 316, 1-10; U.S. Pat. No. 6,544,746 and copending patent applications No. 10/062,064, PCT/US02/24822 and PCT/US03/02157, which are incorporated herein by reference). This methodology is based on splitting the DNA binding site of proteins into two DNA "half-sites." Each of the resulting "half-sites" contains a short complementary single-stranded region of the length designed to introduce some propensity for the two DNA "half-sites" to associate recreating the duplex containing the fully functional protein binding site. This propensity is designed to be low such that in the absence of the protein only a small fraction of DNA half-sites will associate. When the protein is present in the reaction mixture, it will bind only to the duplex containing fully functional binding site. This selective binding will drive association of DNA half-sites and this protein-dependent association can be used to generate a spectroscopic signal reporting the presence of the target protein. The term "molecular beacons" is used in the art to describe the above assay to emphasize that selective recognition and generation of the signal reporting the recognition occur in this assay simultaneously. Molecular beacons for DNA binding proteins have been developed for several proteins illustrating their general applicability (Heyduk, T.; Heyduk, E. Nature Biotechnology 2002, 20, 171-176, which is herein incorporated by reference). Their physical mechanism of action has been established and they have also been used as a platform for the assay detecting the presence of ligands binding to DNA binding proteins (Heyduk, E.; Knoll, E.; Heyduk, T. Analyt. Biochem. 2003, 316, 1-10; Knoll, E.; Heyduk, T. Analyt. Chem. 2004, 76, 1156-1164; Heyduk, E.; Fei, Y.; Heyduk, T. Combinatorial Chemistry and High-throughput Screening 2003, 6, 183-194, which are incorporated herein by reference.) While already very useful, this assay is limited to proteins that exhibit natural DNA binding activity.

Aptamers in "Molecular Beacons"

Development of convenient, specific, sensitive high-throughput assays for detecting proteins remains an extremely important goal. Such assays find applications in research, drug discovery and medical diagnosis. Antibodies recognizing target proteins are the centerpieces of the great majority of protein detection assays so far. Development of in vitro methods for selecting aptamers recognizing target proteins from a population of random sequence nucleic acids provided the first real alternative to antibodies. One of the potentially important advantages of aptamers is that they are made of easy to propagate and synthesize oligonucleotides. Additionally, standard nucleic acid chemistry procedures can be used to engineer aptamers to contain reporter groups such as, for example, fluorescent probes. Thus, it is no wonder that there is significant interest in utilizing aptamers in various formats of protein detection assays. One of the most promising routes is the development of aptamer-based sensors combining recognition of the target protein with generation of an optical signal reporting the presence of the protein.

There are several published reports that document ingenious designs of aptamer-based "molecular beacons" which produced a fluorescent signal upon binding to a specific target protein. All of these designs rely on target protein-induced conformational transition in the aptamer to generate fluorescence signal change. Yamomoto and Kumar (Genes to Cells 2000, 5, 389-396) described a molecular beacon aptamer that produced an increase of fluorescence upon recognition of HIV Tat protein. Fluorescence signal was generated due to a change in proximity of a fluorophore-quencher pair resulting from Tat protein-induced transition between hairpin and duplex forms of the aptamer. Hamaguchi et al. (Analyt. Biochem. 2001, 294, 126-131) described a molecular beacon aptamer that produced an increase of fluorescence upon recognition of thrombin. In the absence of the target protein, the beacon was designed to form a stem-loop structure bringing the fluorophore and the quencher into close proximity. In the presence of the protein, the beacon was forced into a ligand-binding conformation resulting in increased separation between the fluorophore and the quencher and therefore, increased fluorescence signal. Li et al. (Biochem. Biophys. Res. Commun. 2002, 292, 31-40) described a molecular beacon aptamer that underwent a transition from loose random coil to a compact unimolecular quadruplex in the presence of a target protein. This protein-induced change in aptamer conformation resulted in a change of proximity between the fluorescence probes attached to the ends of the aptamer generating a fluorescence signal change. An analogous approach was used by Fang et al. (ChemBioChem. 2003, 4, 829-834) to design a molecular beacon aptamer recognizing PDGF. These examples illustrate the great potential of aptamers for designing sensors, which could transduce the presence of the protein into an optical signal.

SUMMARY OF THE INVENTION

One aspect of the invention encompasses a molecular biosensor. The molecular biosensor comprises two epitope binding agents, which together have formula (VI)

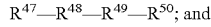

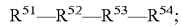 (VI)

wherein:
$R^{47}$ is an epitope-binding agent that binds to a first epitope on a target molecule;
$R^{48}$ is a flexible linker attaching $R^{47}$ to $R^{49}$;
$R^{49}$ and $R^{53}$ are a pair of complementary nucleotide sequences having a free energy for association from about 5.5 kcal/mole to about 8.0 kcal/mole at a temperature from about 21° C. to about 40° C. and at a salt concentration from about 1 mM to about 100 mM;
$R^{50}$ and $R^{54}$ together comprise a detection means such that when $R^{49}$ and $R^{53}$ associate a detectable signal is produced;
$R^{51}$ is an epitope binding agent that binds to $R^{47}$; and
$R^{52}$ is a flexible linker attaching $R^{51}$ to $R^{53}$.

Yet another aspect of the invention provides a molecular biosensor. The molecular biosensor comprises two epitope binding agents, which together have formula (VII)

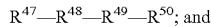

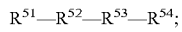 (VII)

wherein:
$R^{47}$ is a peptide, a small molecule, or protein epitope-binding agent that binds to a first epitope on a target molecule;
$R^{48}$ is a flexible linker attaching $R^{47}$ to $R^{49}$;
$R^{49}$ and $R^{53}$ are a pair of complementary nucleotide sequences having a free energy for association from about 5.5 kcal/mole to about 8.0 kcal/mole at a temperature from about 21° C. to about 40° C. and at a salt concentration from about 1 mM to about 100 mM;
$R^{50}$ and $R^{54}$ together comprise a detection means such that when $R^{49}$ and $R^{53}$ associate a detectable signal is produced;
$R^{51}$ is an antibody or antibody fragment epitope binding agent that binds to $R^{47}$; and
$R^{52}$ is a flexible linker attaching $R^{51}$ to $R^{53}$.

Another aspect of the invention provides a method for determining the presence of a target molecule in a sample. The method comprises measuring the signal of a molecular biosensor having either formula (VI) or (VII) without the target molecule being present. The molecular biosensor is then combined with the sample and the signal of the molecular biosensor is measured. A decrease in signal indicates the presence of a target molecule.

Other features and aspects of the invention are described in more detail herein.

(D) 532 nm laser—695 nm bandpass filter. Fluorescence is in arbitrary units (corrected for instrument response) and is plotted in a linear scale.

Figure 19:
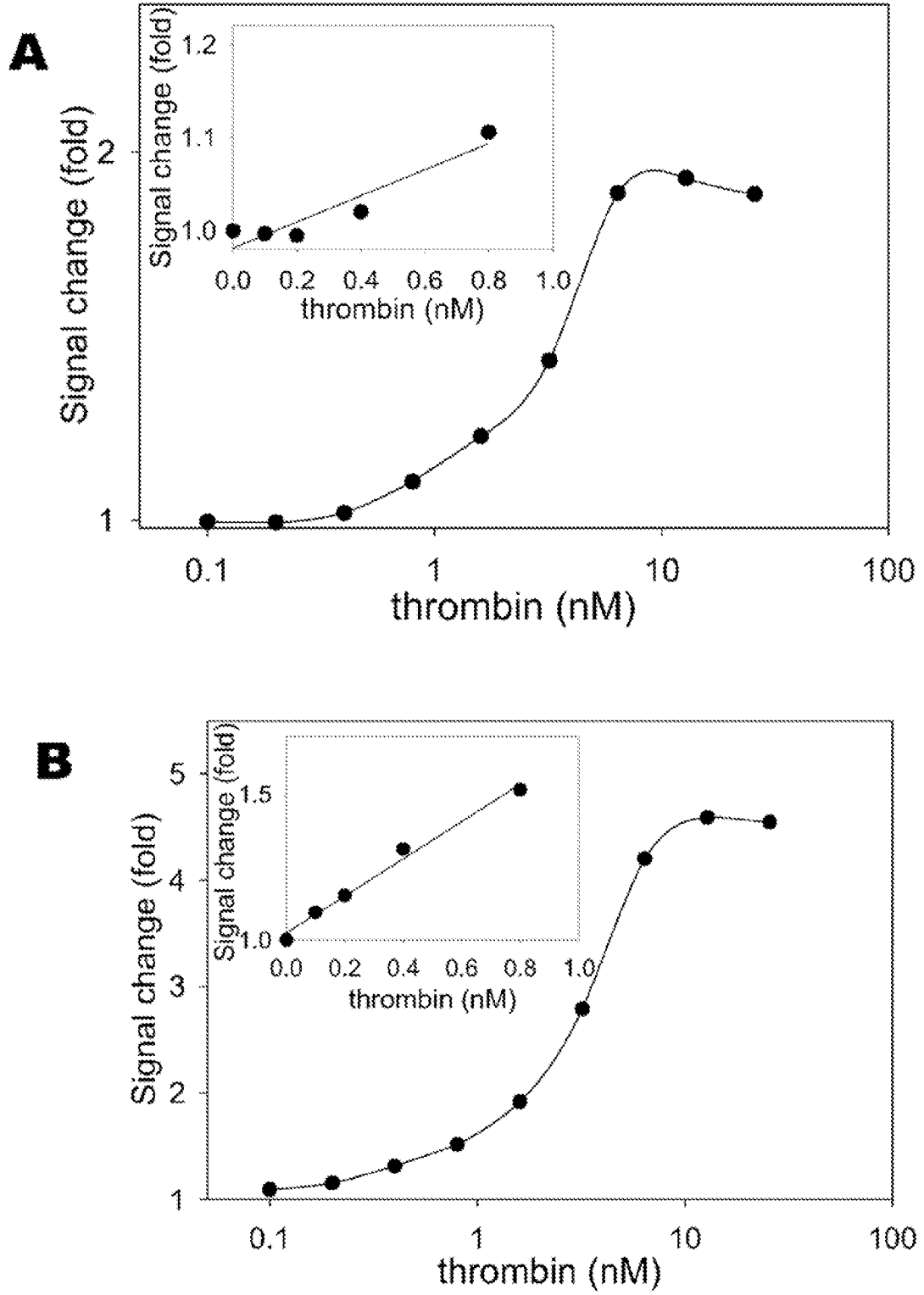
Figure 19:
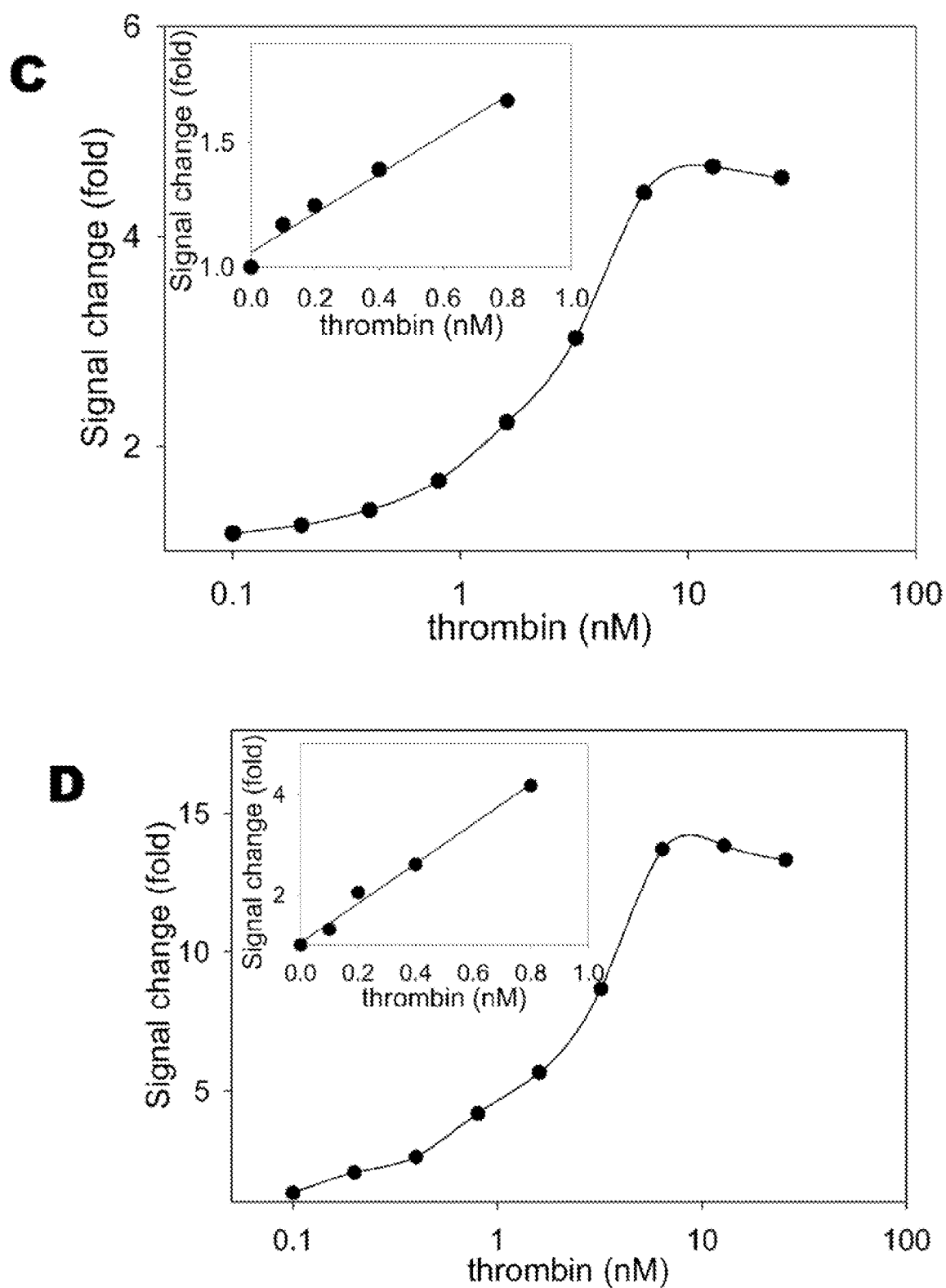
Figure 19:
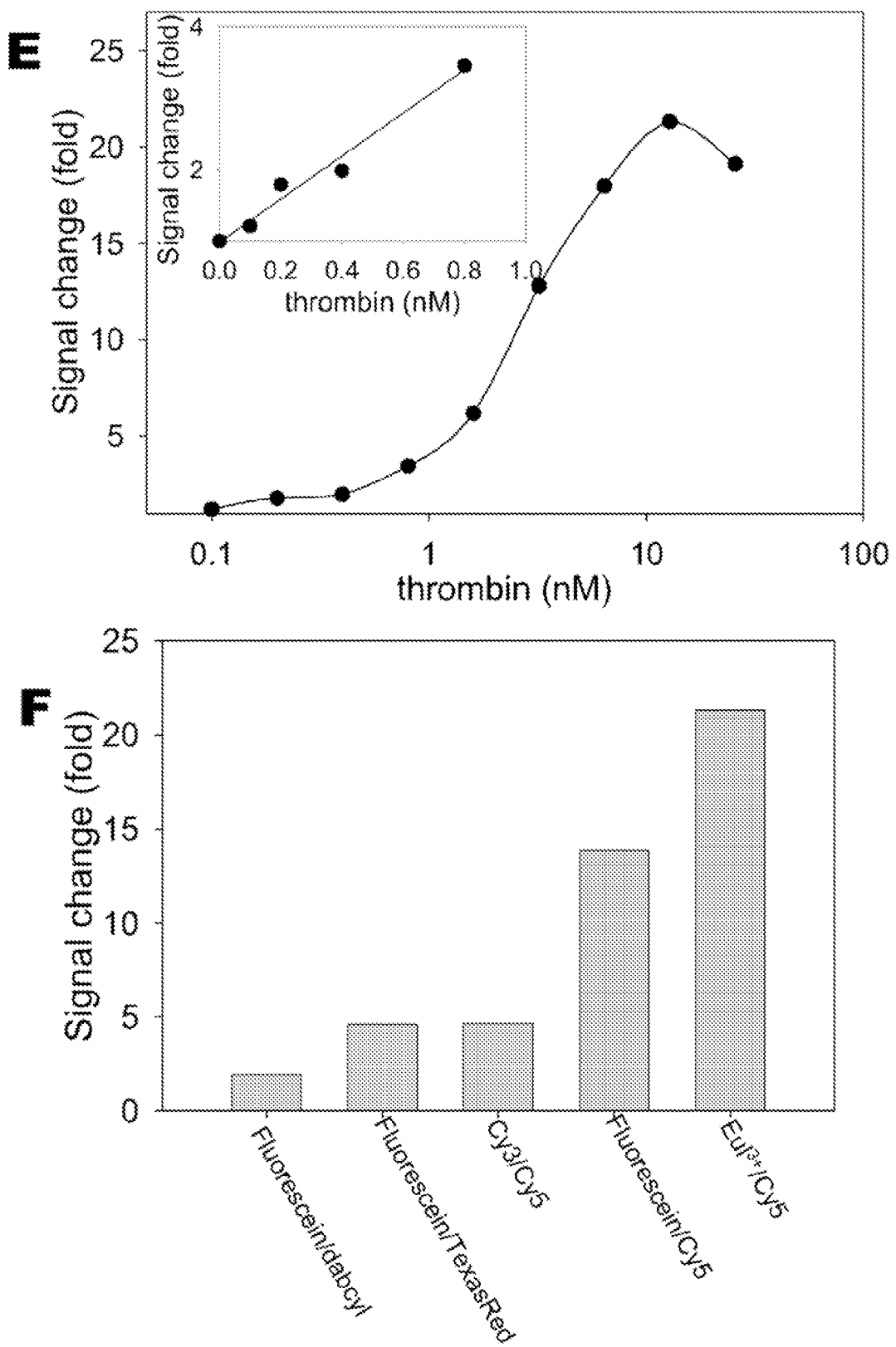

FIG. 19. Response curves for the beacon with various combinations of donor-acceptor pairs. (A) fluorescein-dabcyl, (B) fluorescein-Texas Red, (C) Cy3-Cy5, (D) fluorescein-Cy5, (E) europium chelate-Cy5, (F) Fold signal change observed for indicated donor-acceptor pair at saturating thrombin concentration. Insets show expanded view of data points at low thrombin concentrations. In all experiments 5 nM donor-labeled and 5.5 nM acceptor-labeled aptamer constructs were used. Signal change (fold) was calculated as I/Io where I and Io correspond to dilution-corrected acceptor fluorescence emission intensity (measured with donor excitation) observed in the presence and absence of a given thrombin concentration, respectively. Buffer background was subtracted from I and Io before calculating signal change.

Figure 20:
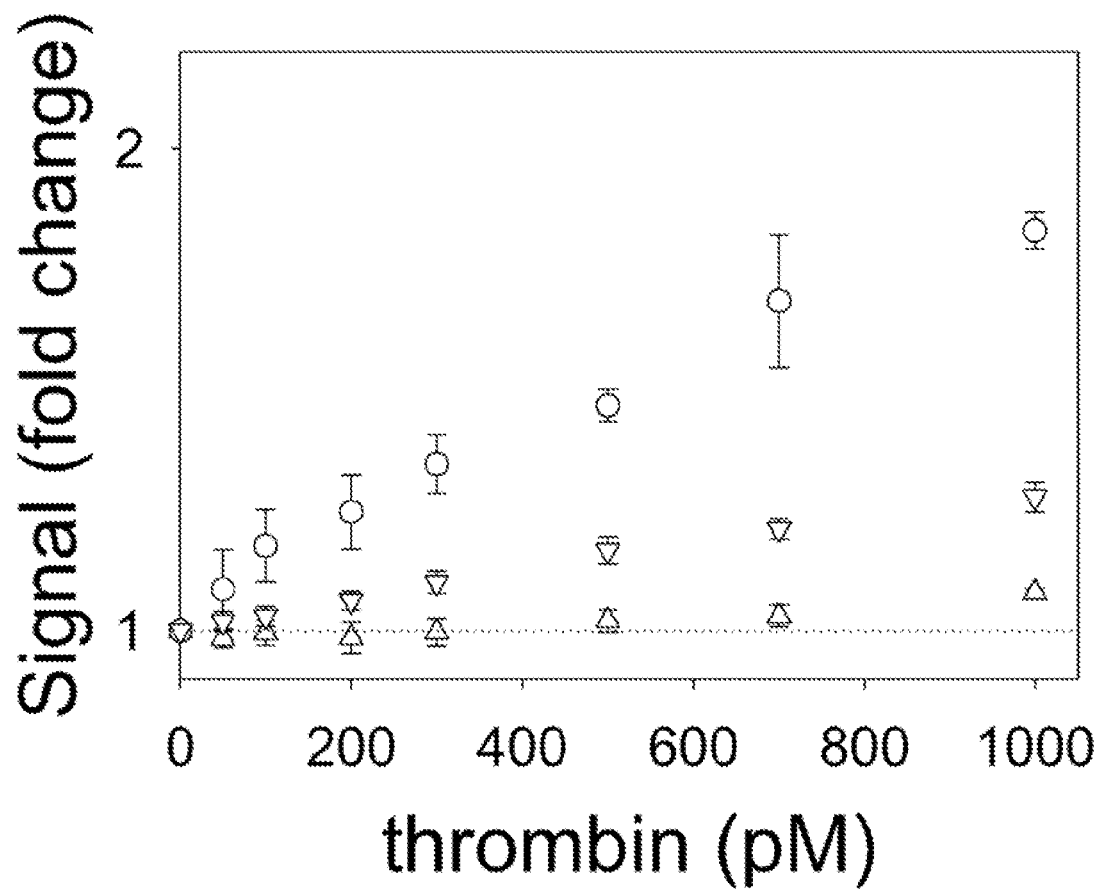

FIG. 20. The dependence of the sensitivity of the thrombin beacon on a donor-acceptor pair. Response of 10 nM donor-labeled and 11 nM acceptor-labeled beacon was determined at low thrombin concentrations using beacon labeled with fluorescein-dabcyl pair (triangles), fluorescein-Texas Red pair (inverted triangles), and fluorescein-Cy5 pair (circles). Averages and standard deviations of four independent experiments are shown.

Figure 21:
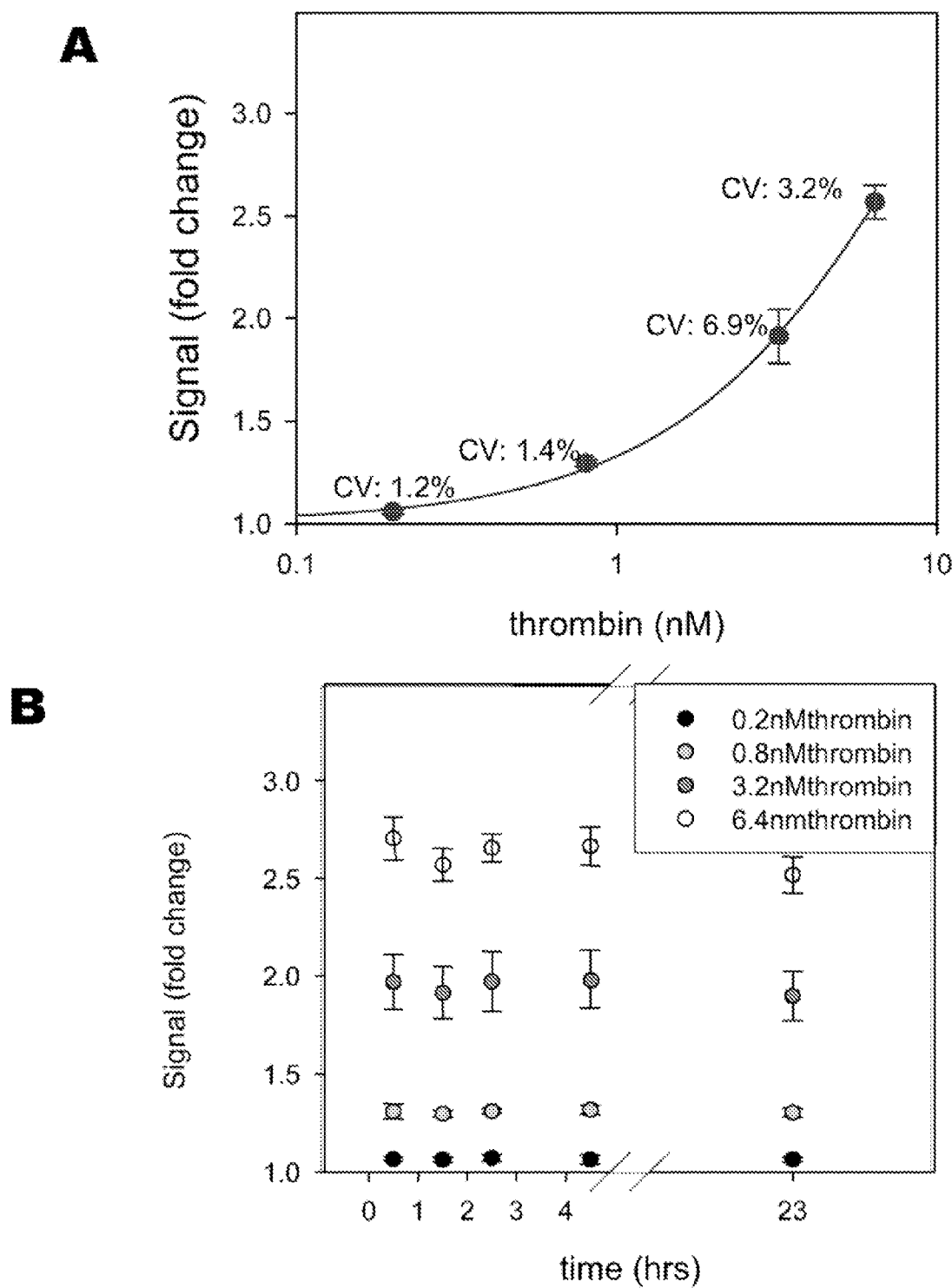

FIG. 21. The reproducibility and stability of thrombin beacon. (A) Five independent determinations of beacon signal at four different thrombin concentrations were performed. Data shown represent mean+/−standard deviation. (B) Thrombin beacon signal at four thrombin concentrations was monitored over time up to 24 hours. Data shown represent mean+/− standard deviation of 5 independent measurements. Beacon containing 5 nM fluorescein-labeled aptamer (THR21) and 5.5 nM Texas Red-labeled aptamer (THR27) was used in this experiment.

Figure 22:
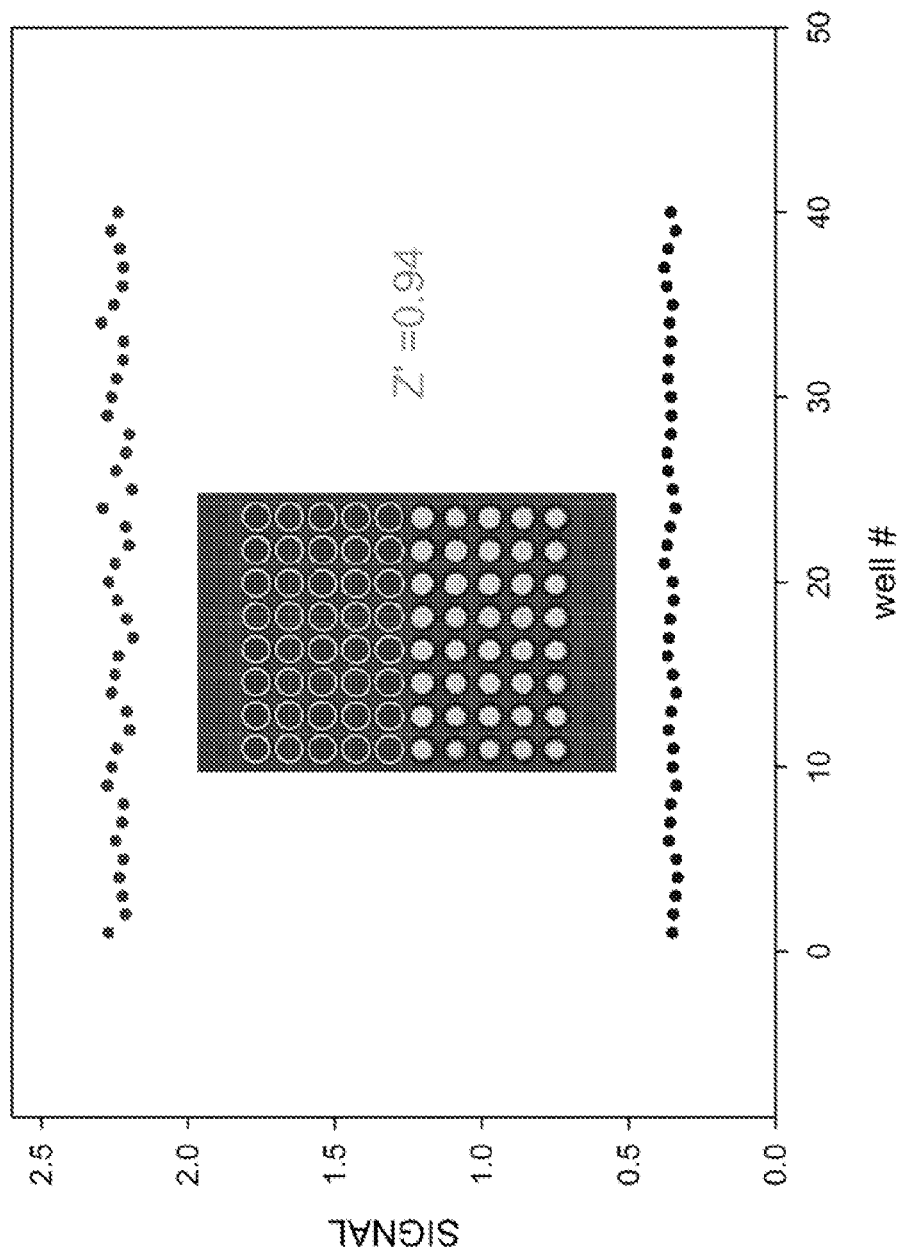

FIG. 22. shows the determination of Z'-factor for thrombin beacon. Panel in the middle of the plot shows an image of wells of the microplate corresponding to the experiment shown in a graph (the upper half of wells are +thrombin, the lower half of the wells is—thrombin. Beacon containing with 5 nM fluorescein-labeled aptamer (THR21) and 5.5 nM Texas Red-labeled aptamer (THR27) was used in this experiment. Signal corresponds to a ratio of acceptor to donor emission (in arbitrary units) measured with donor excitation.

Figure 23:
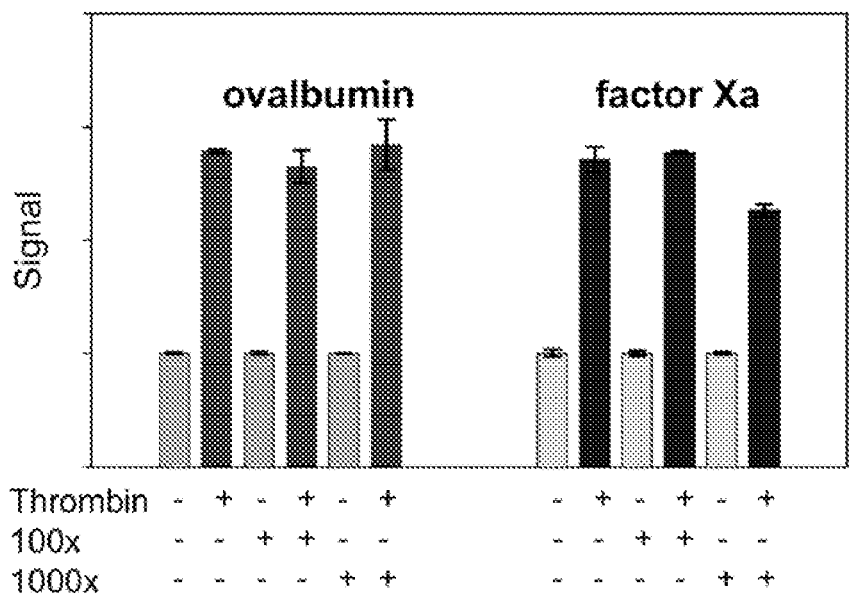
Figure 23:
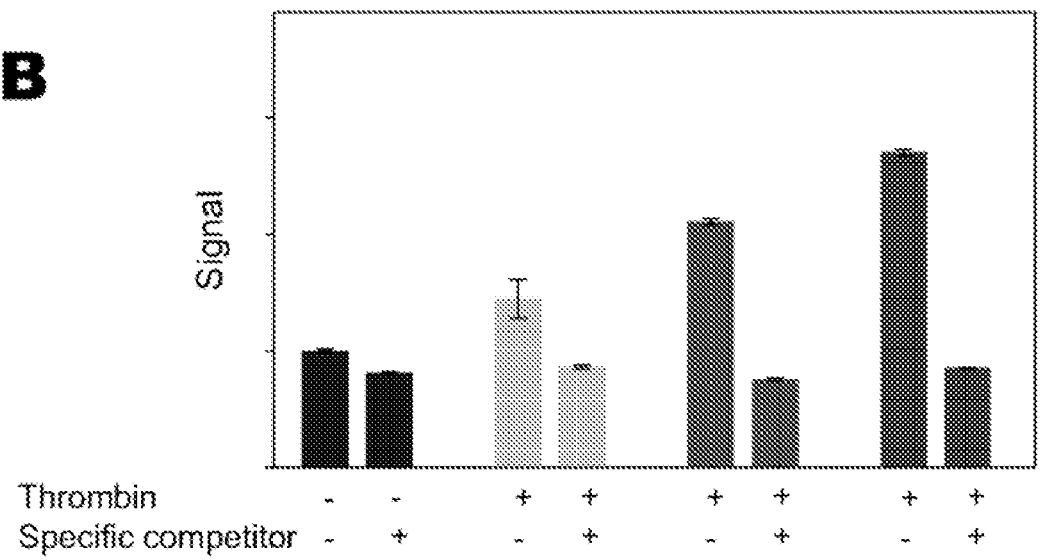
Figure 23:
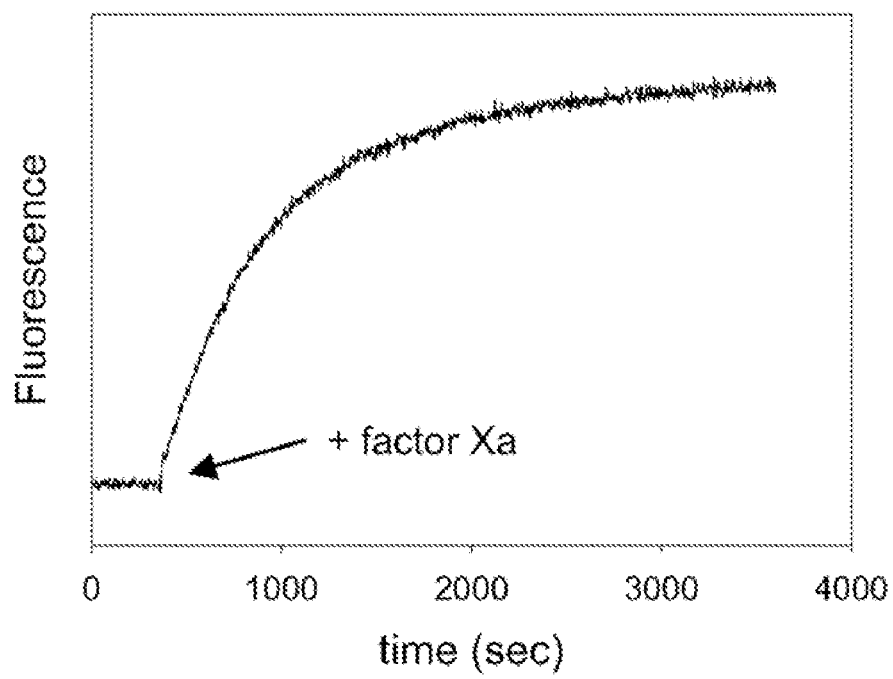
Figure 23:
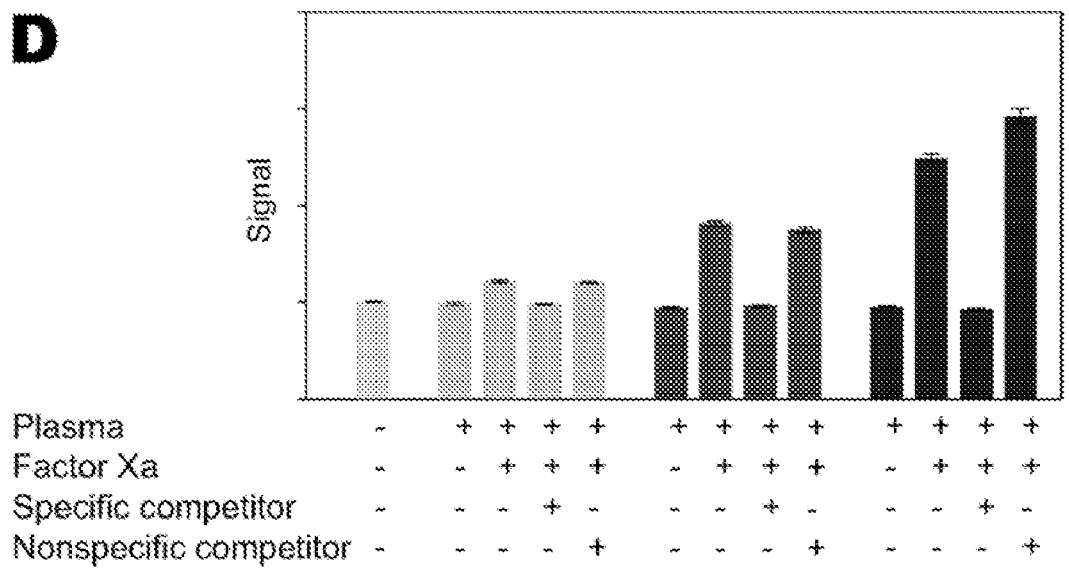

FIG. 23. The detection of thrombin in complex mixtures. (A) Response of thrombin beacon at 1 nM thrombin concentration in the absence and presence of the excess of unrelated proteins. The data shown are averages and standard deviation of 4 independent experiments. (B) Detection of thrombin in HeLa extract "spiked" with various amounts of thrombin. Data shown are averages and standard deviation from 3 independent measurements. Concentrations of thrombin in cell extract were (from left to right): 0, 1.88 nM, 3.75 nM, and 7.5 nM. Signal for beacon mixture alone was ~25% lower then when cell extract (no thrombin added) was present (not shown) which was essentially the same as the signal observed in the presence of cell extract and specific competitor. (C) Time course of prothrombin to thrombin conversion catalyzed by Factor Xa monitored by thrombin beacon. (D) Detection of thrombin in plasma. Data shown are averages and standard deviation from 4 independent measurements. The volumes of plasma used (per 20 ml assay mixture) were (from left to right): 0 ml, 0.005 ml, 0.015 ml, and 0.045 ml. "Specific" refers to unlabeled thrombin aptamer competitor (THR7) whereas "nonspecific" refers to random sequence 30 nt DNA. Signal in panels A, B and D corresponds to a ratio of acceptor to donor emission measured with donor excitation. Signals were normalized to value of 1 for beacon mixture alone (panels A and D) and beacon mixture in the presence of cell extract (panel B). Panel C shows raw acceptor fluorescence intensity (with donor excitation).

Figure 24:
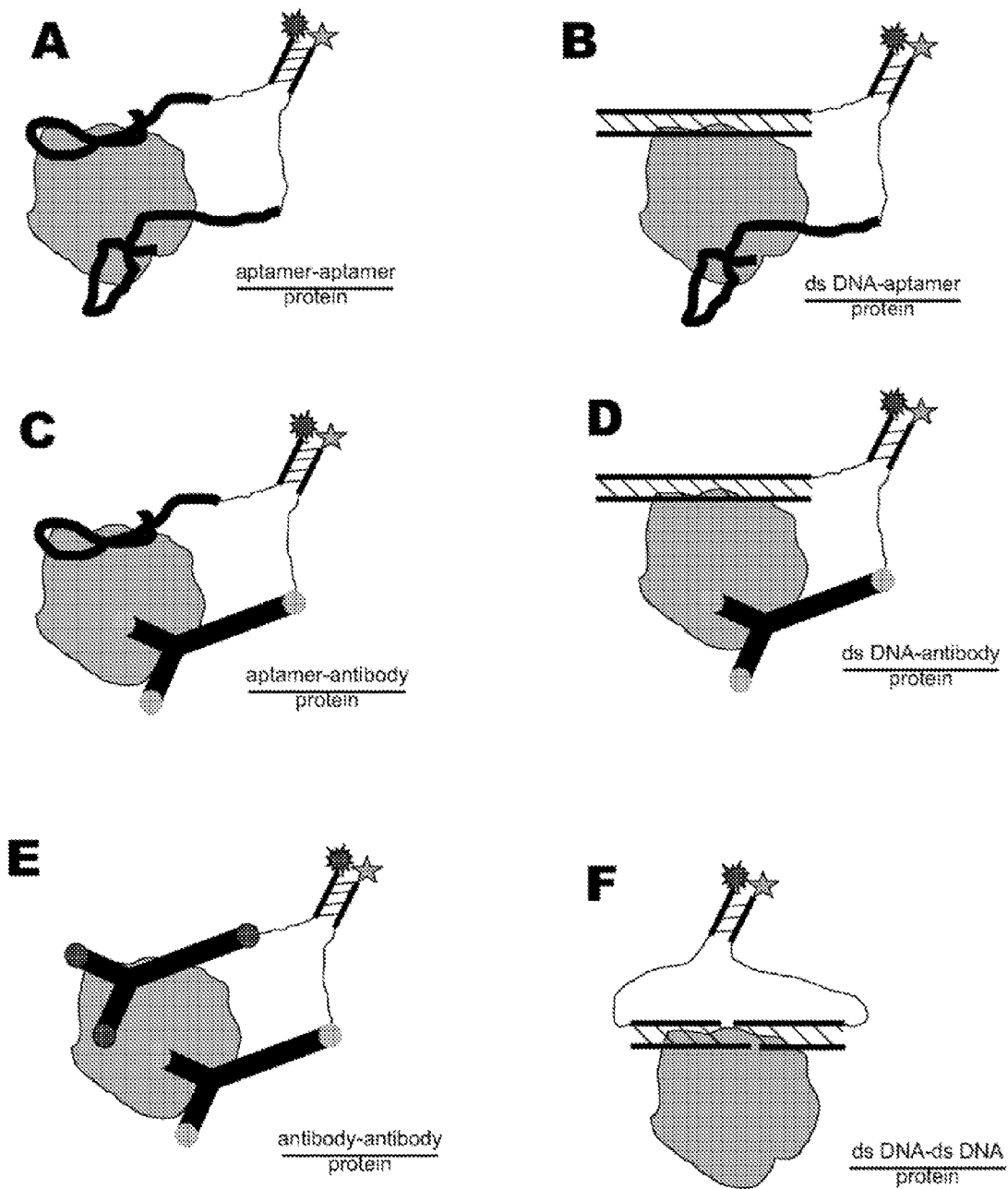
Figure 24:
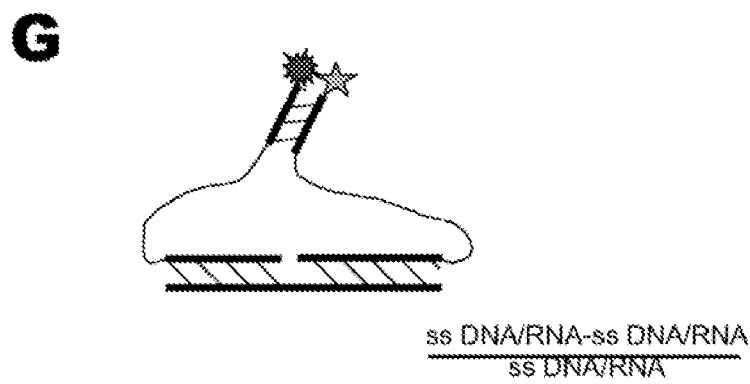
Figure 24:
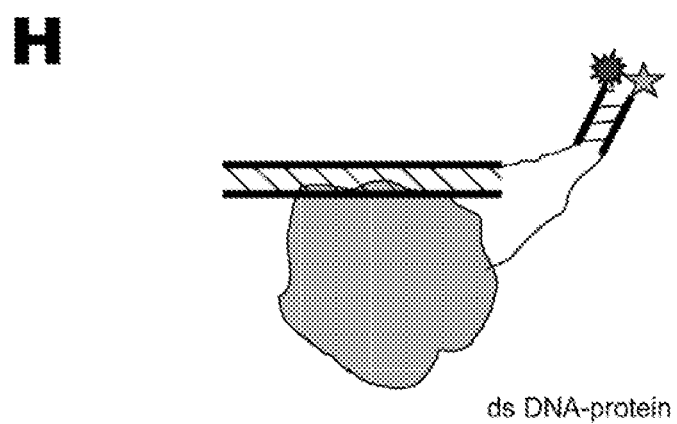
Figure 24:
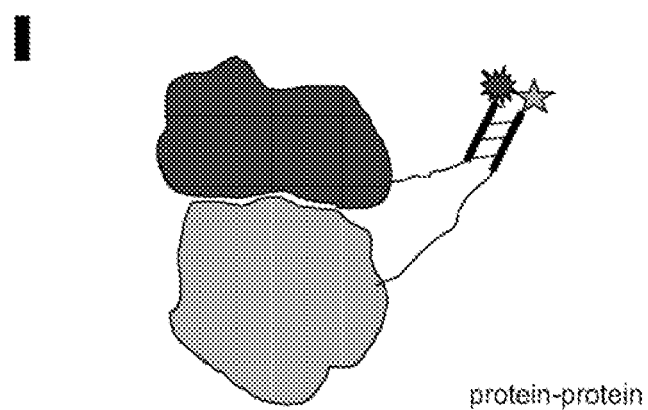

FIG. 24. Various formations of molecular biosensors.

Figure 25A:
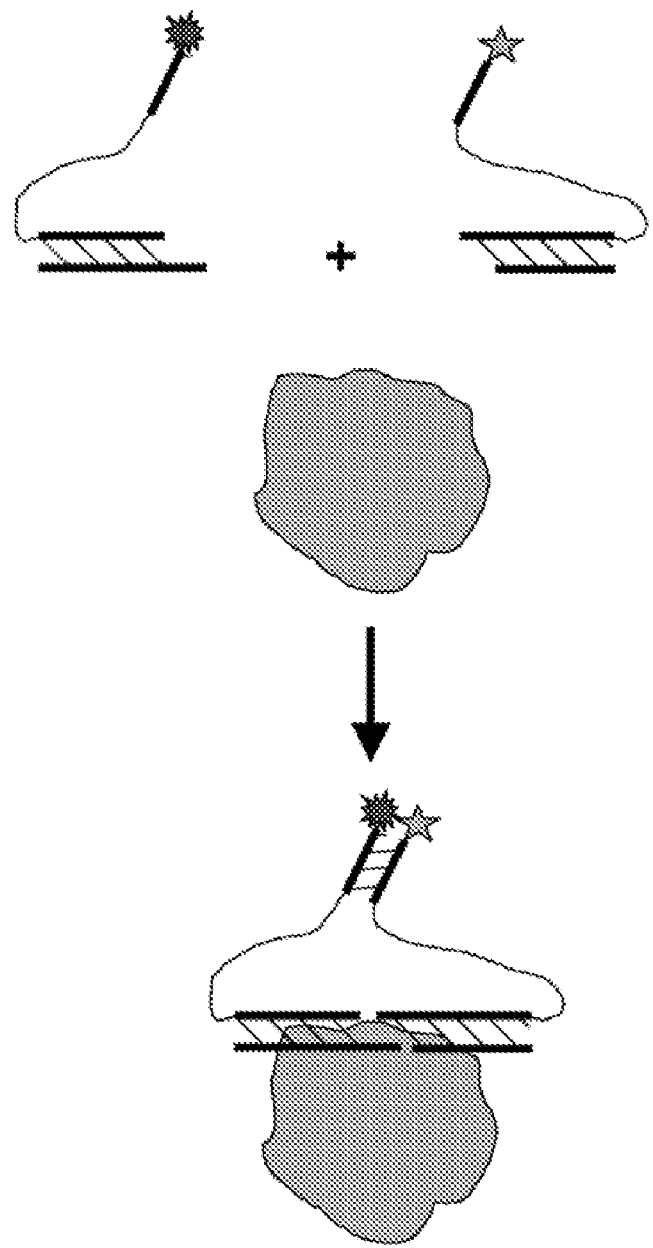

FIG. 25. The experimental demonstration of the sensor design shown in FIG. 24F. (A) Principle of sensor function. (B) Increase of sensitized acceptor fluorescence upon titration of increasing concentrations of DNA binding protein to the mixture of donor and acceptor labeled sensor components.

Figure 26:
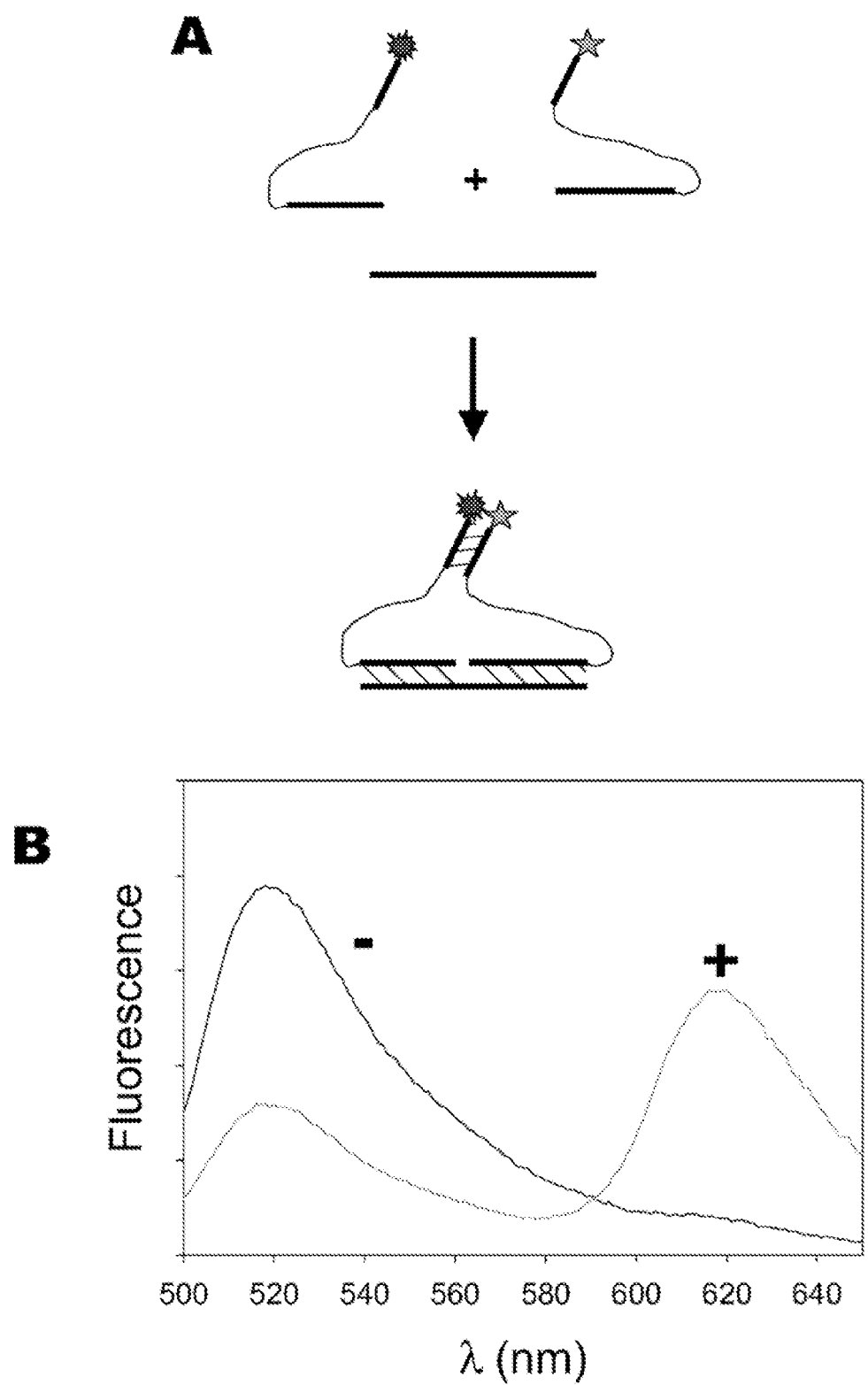

FIG. 26. The experimental demonstration of a functioning sensor design shown in FIG. 24G. (A) Principle of sensor function. (B) Increase of sensitized acceptor fluorescence (emission spectrum labeled with "+") upon addition of single-stranded DNA containing two distinct sequence elements complementary to sensor elements to the mixture of two donor and acceptor labeled sensor components (spectrum labeled with "−").

Figure 27:
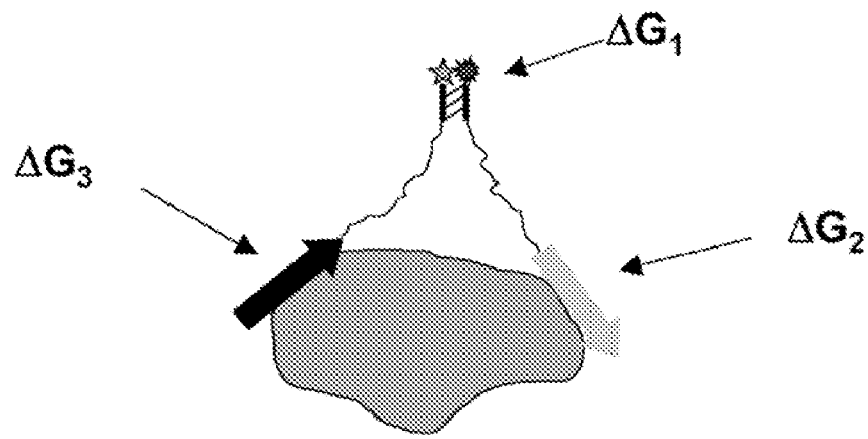
Figure 27:
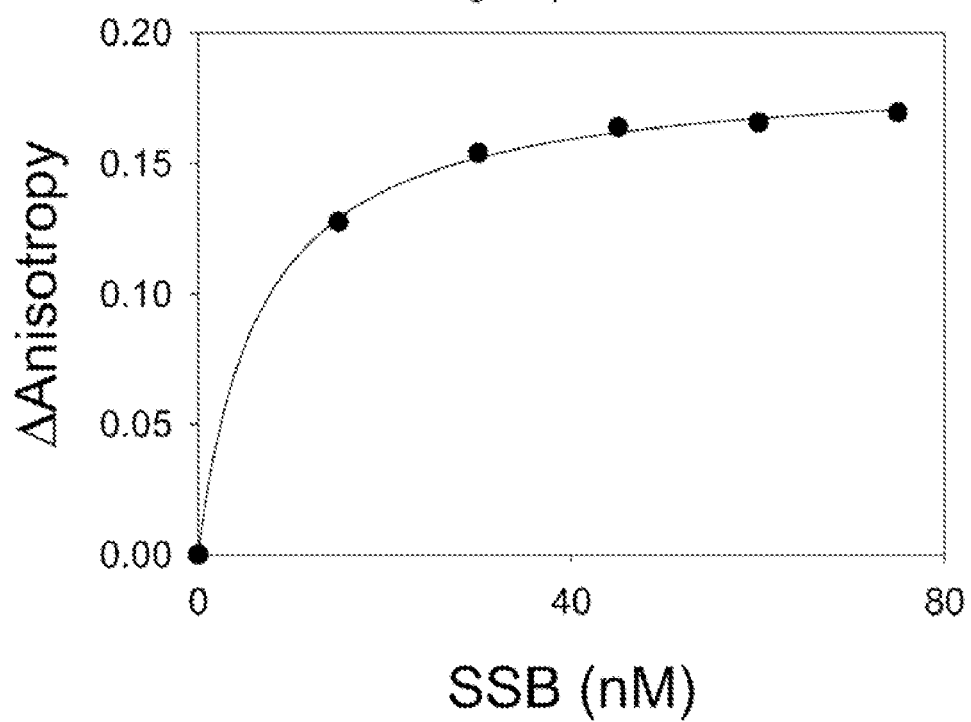
Figure 27C:
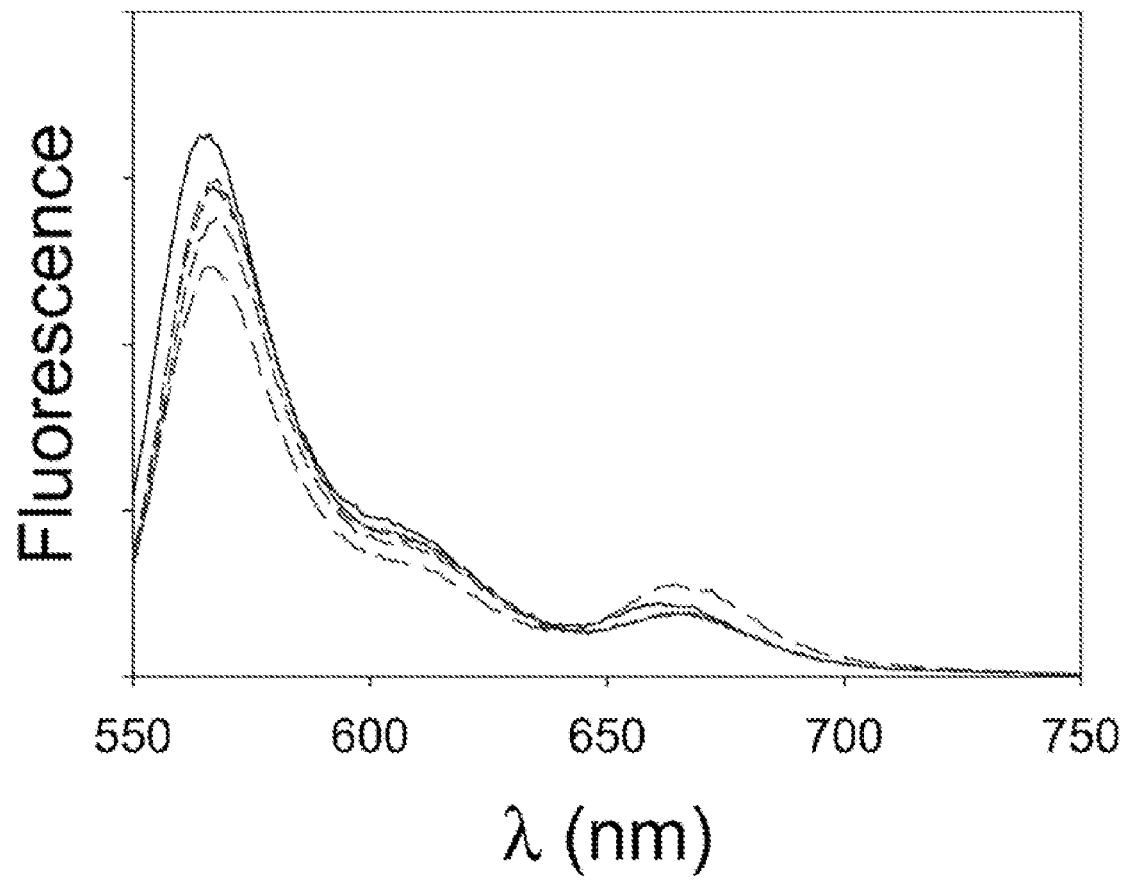

FIG. 27. The experimental demonstration of the increased specificity of the sensor design compared to assays based on a single, target macromolecule-recognizing element. (A) Three molecular contacts providing free energy ($\Delta G$). (B) Nonspecific binding. (C) No signal with the beacon.

Figure 28:
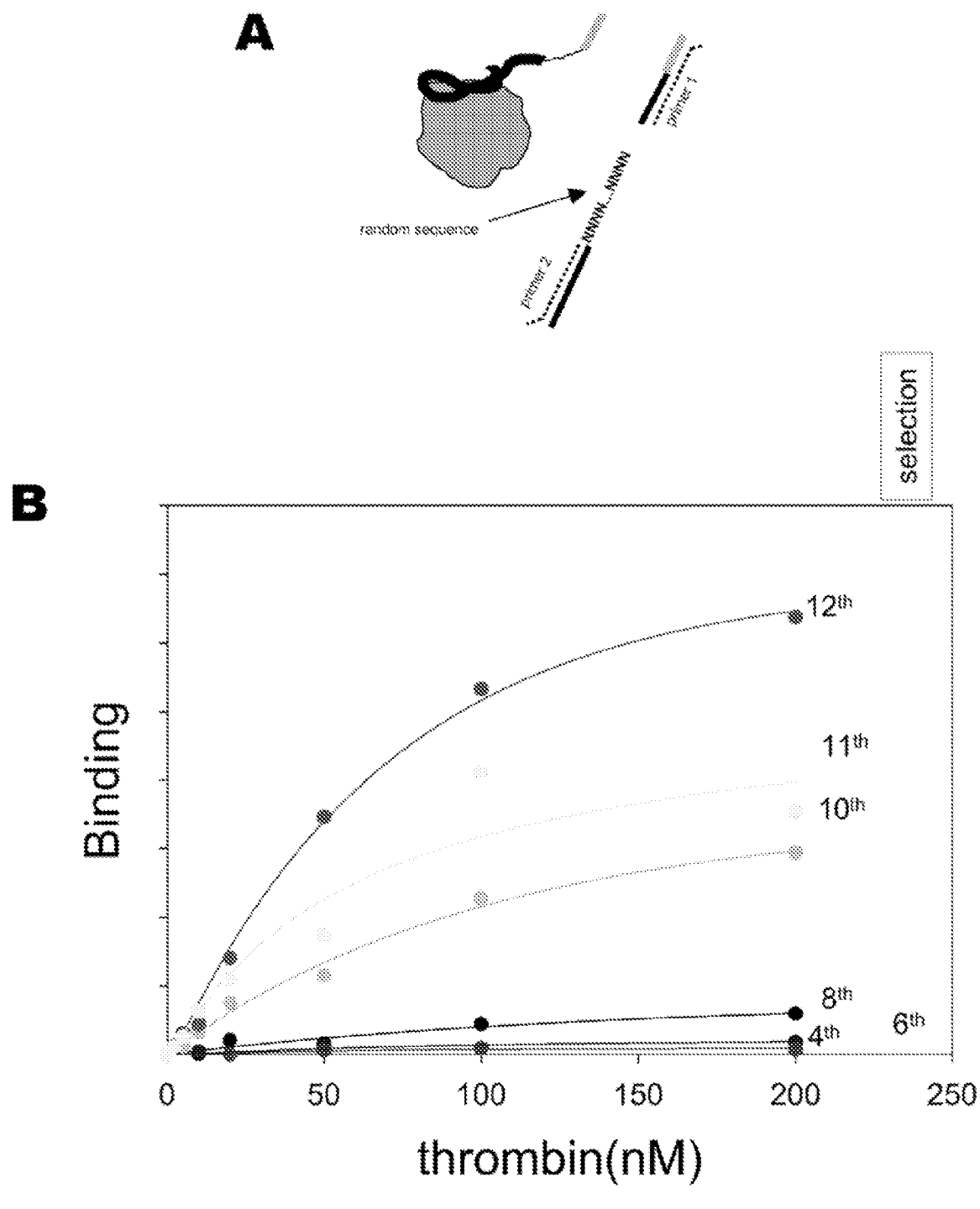

FIG. 28. Summarizes the selection of an aptamer that binds to thrombin at an epitope distinct from the binding site of the G15D aptamer. (A) An illustration of the reagents used to begin the process of selection. (B) The graph indicates the increase in thrombin binding with successive rounds of selection. (C) The sequences represent aptamers developed after 12 rounds of selection.

Figure 29:
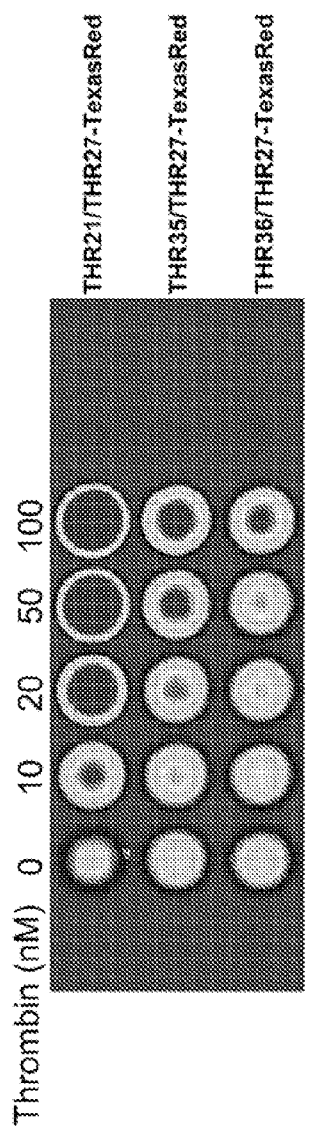
Figure 29:
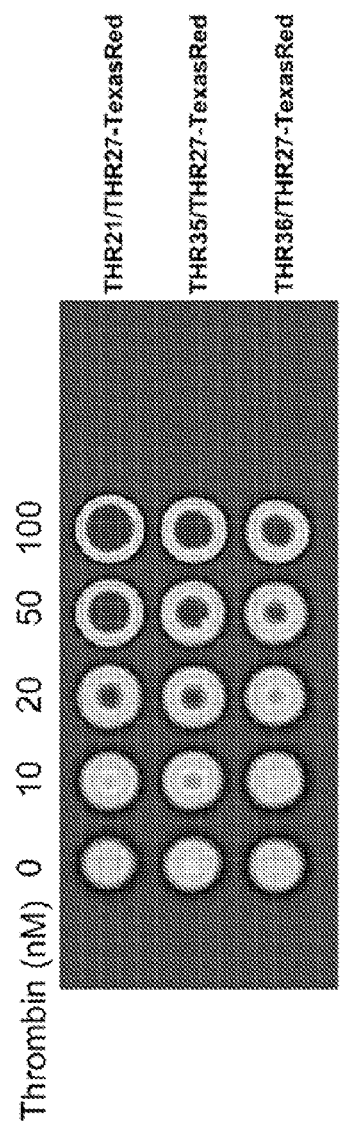

FIG. 29. The demonstration of the functional thrombin sensor comprising Texas Red-labeled THR27 and fluorescein-labeled THR35 or THR36 (both contain the sequence corresponding to that of clones 20, 21, 24, and 26 of FIG. 28C). The fluorescence image represents the specificity of either 20 nM (panel A) or 100 nM (panel B) of the indicated biosensor.

Figure 30:
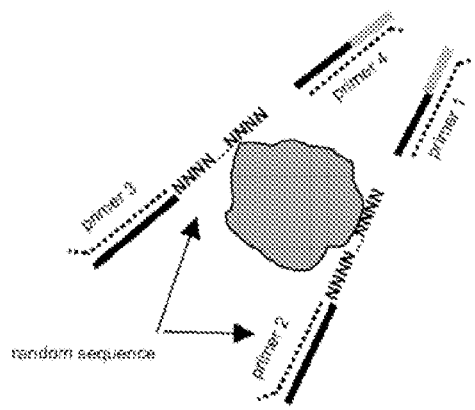
Figure 30:
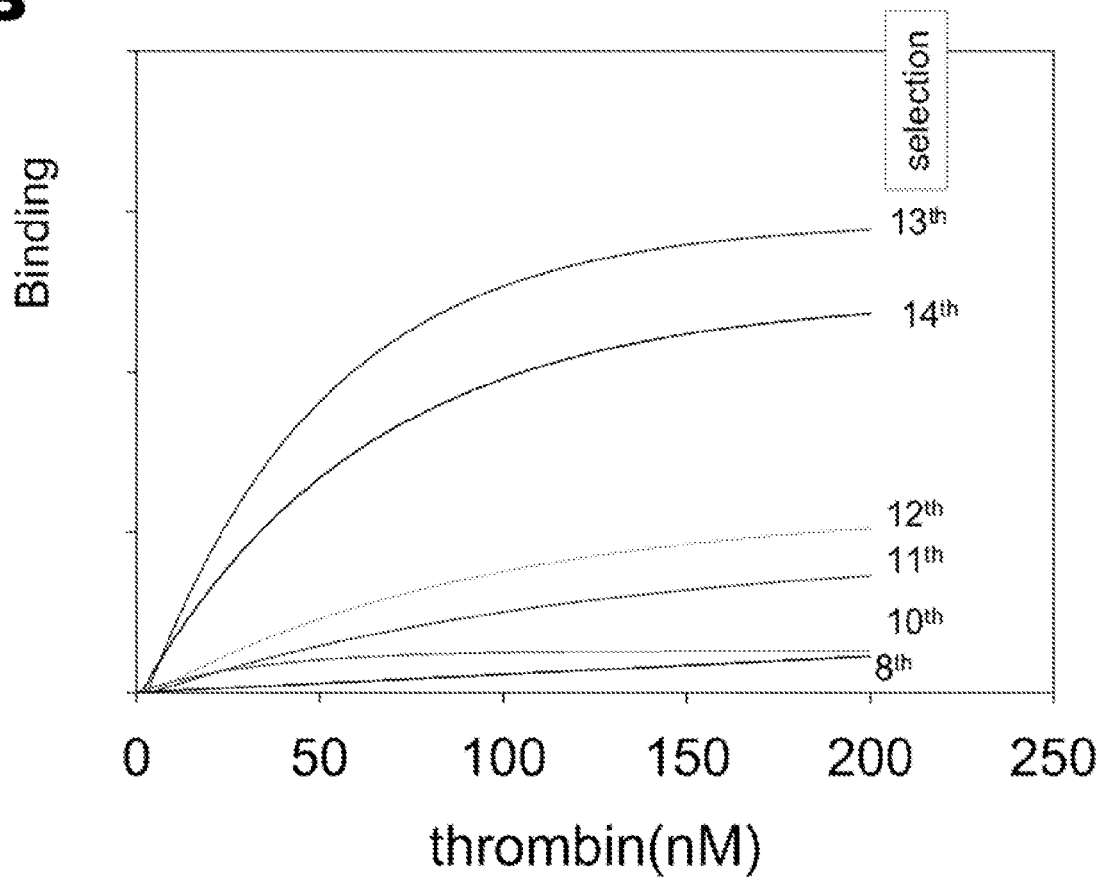

FIG. 30. Summarizes the simultaneous selection of two aptamers that bind to thrombin at distinct epitopes. (A) An illustration of the reagents used to begin the process of selection. (B) The graph indicates the increase in thrombin binding with successive rounds of selection. (C) The sequences represent aptamers developed after 13 rounds of selection.

Figure 31:
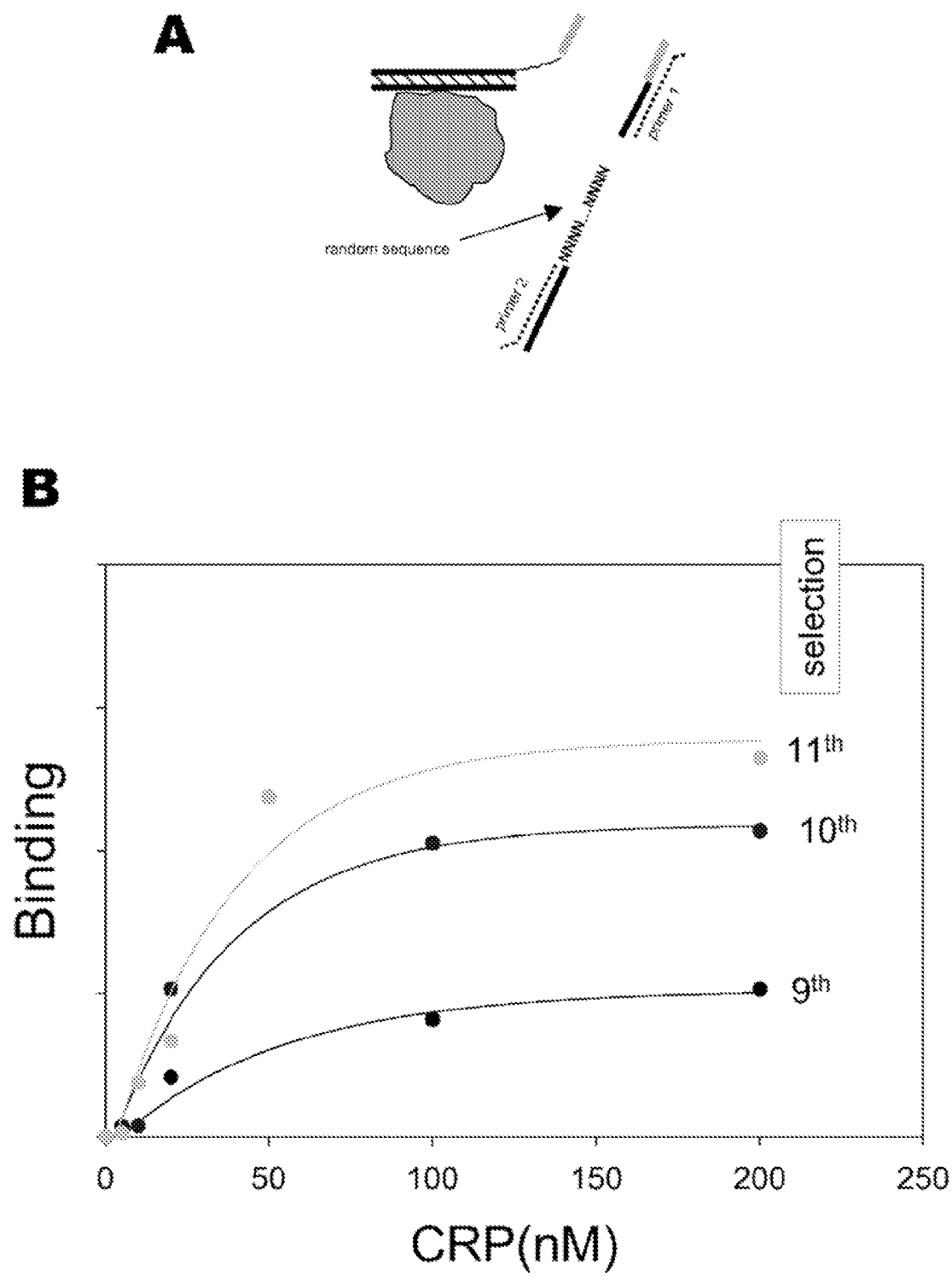

FIG. 31. Summarizes the selection of an aptamer that binds to CRP at an epitope distinct from the DNA-binding site. (A) An illustration of the reagents used to begin the process of selection. (B) The graph indicates the increase in thrombin binding with successive rounds of selection. (C) The sequences represent aptamers developed after 11 rounds of selection.

Figure 32:
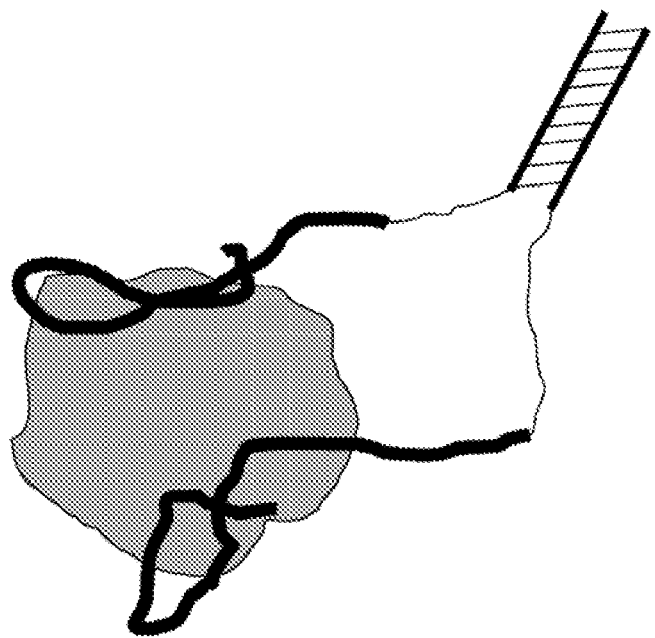
Figure 32:
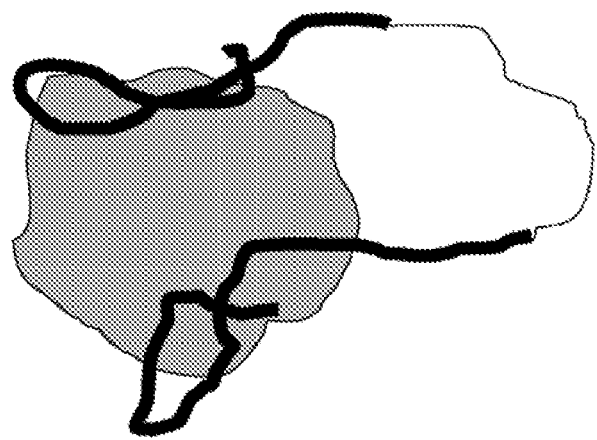

FIG. 32. A diagram of methods for permanently linking the two aptamers recognizing two distinct epitopes of the target. (A) Two complimentary oligonucleotides are attached using linkers to each of the aptamers. These oligonucleotides are long enough (typically >15 bps) to form a stable duplex permanently linking the two aptamers. (B) The two aptamers are connected directly via a linker.

Figure 33:
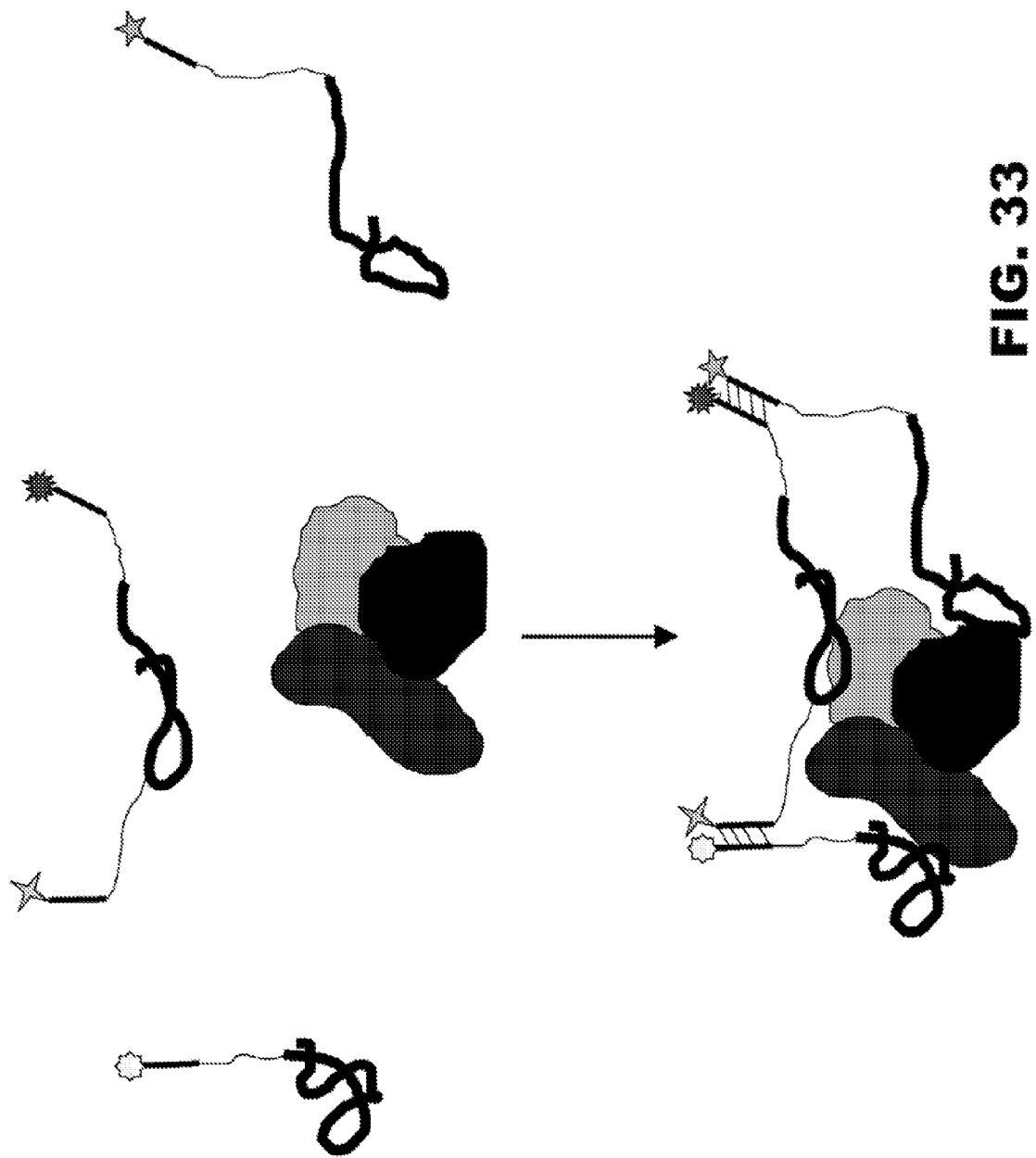

FIG. 33. Example of a potential sensor design utilizing three sensing components. In this design the target is a complex of three components (black, dark gray, and light gray ovals). Each of the aptamers recognizes one of the components of the complex. Signals of different color from each of the two signaling oligonucleotide pairs could be used to discriminate between the entire complex containing all three components with alternative sub-complexes containing only two of the components.

Figure 34:
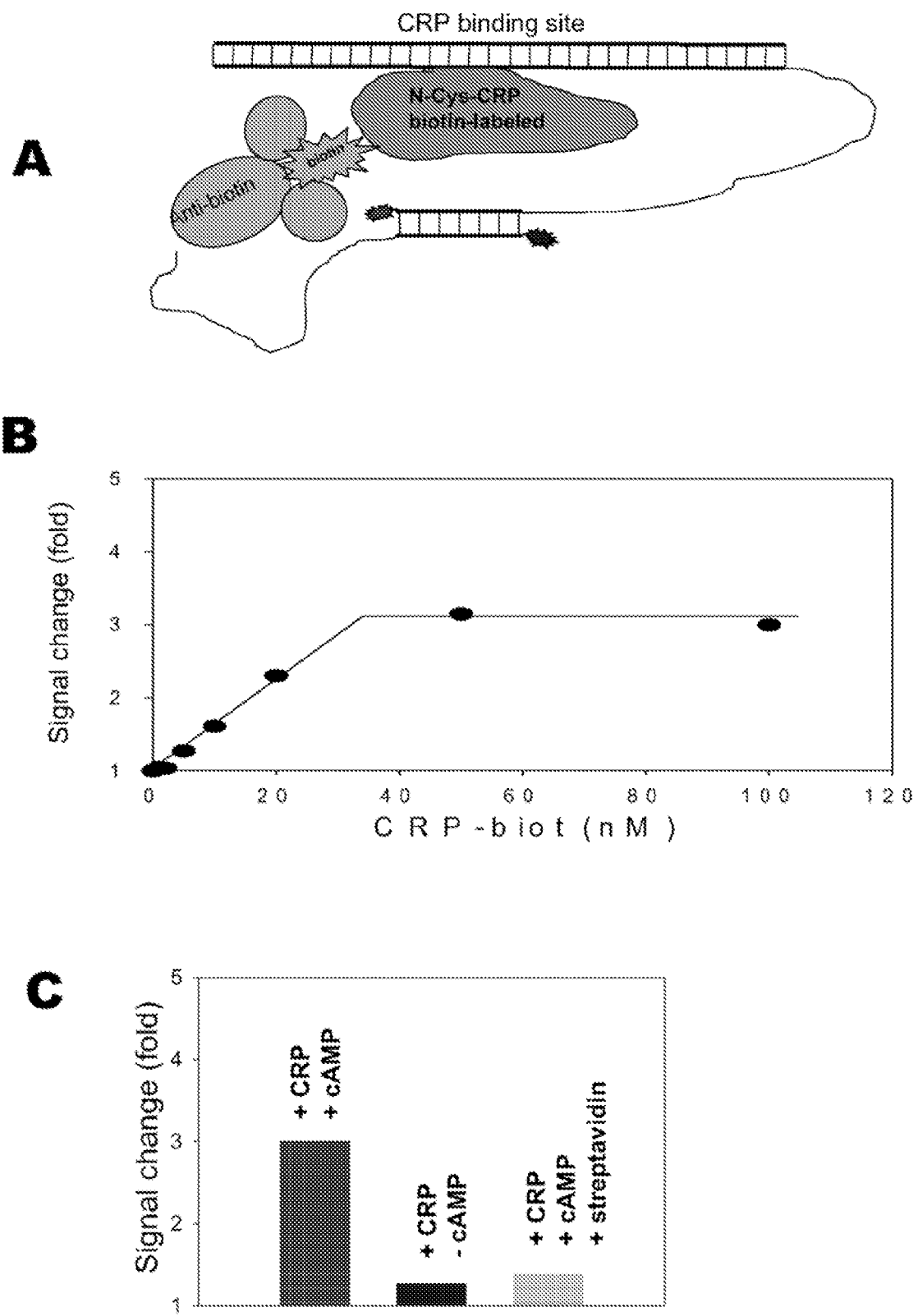

FIG. 34. Depicts an experiment demonstrating the feasibility of an antibody-based molecular biosensor as shown in FIG. 24D. (A) Design of the model system used; (B) Signal generated by the sensor at various concentrations of biotin labeled CRP. The signal corresponds to intensity of emission at 670 nm (Cy5) upon excitation at 520 nm (fluorescein) (C) Specificity of the sensor response. The FRET signal is responsive to both cAMP and streptavidin.

Figure 35:
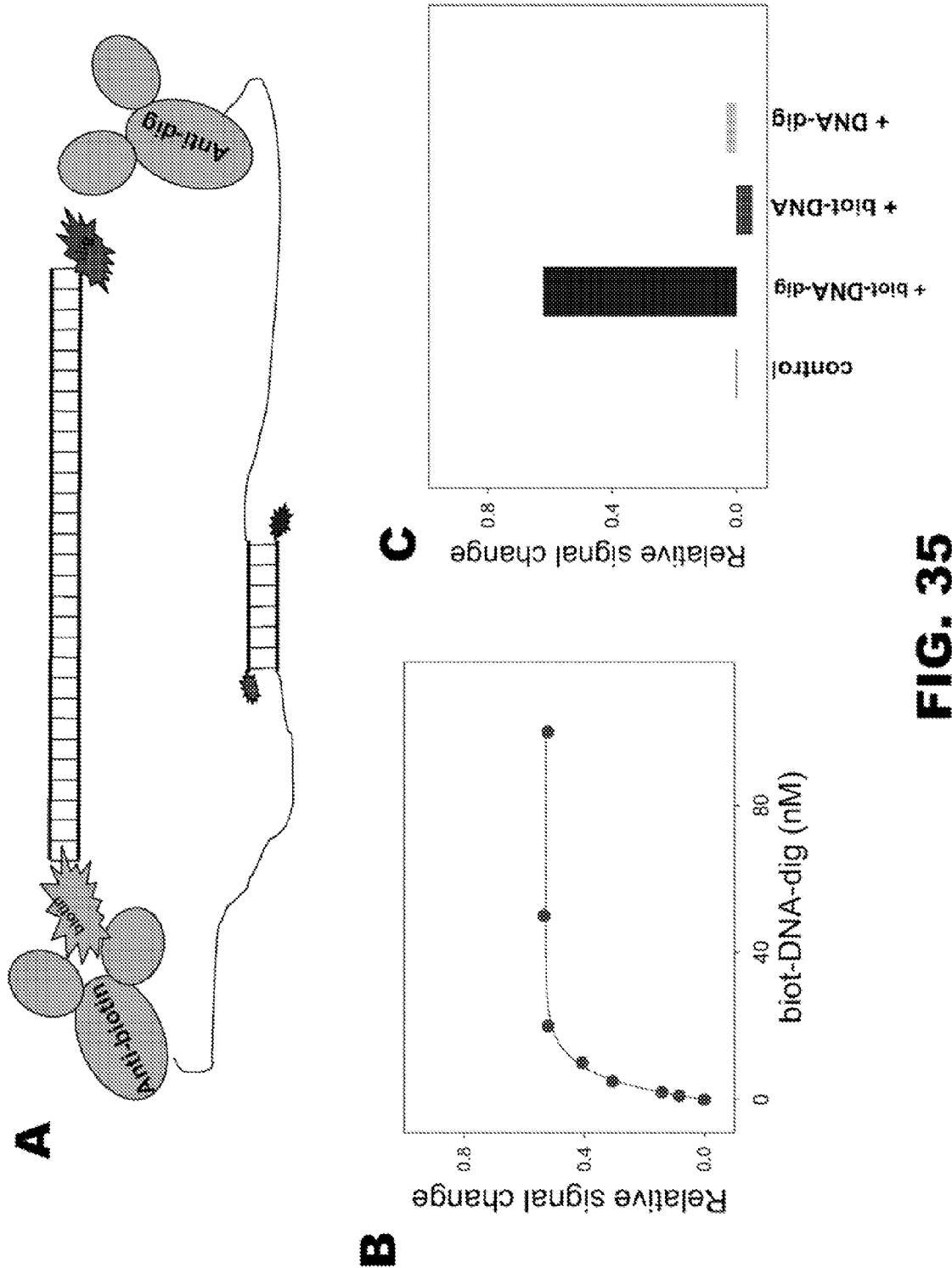

FIG. 35. Depicts an experiment demonstrating the feasibility of an antibody-based molecular biosensor composed of two antibodies recognizing distinct epitopes of the same target. (A) Design of the model system used; (B) Signal generated by the sensor at various concentrations of biotin-DNA-digoxin. Signal corresponds to intensity of emission at 670 nm (Cy5) upon excitation at 520 nm (fluorescein) (C) Specificity of pincer response.

Figure 36:
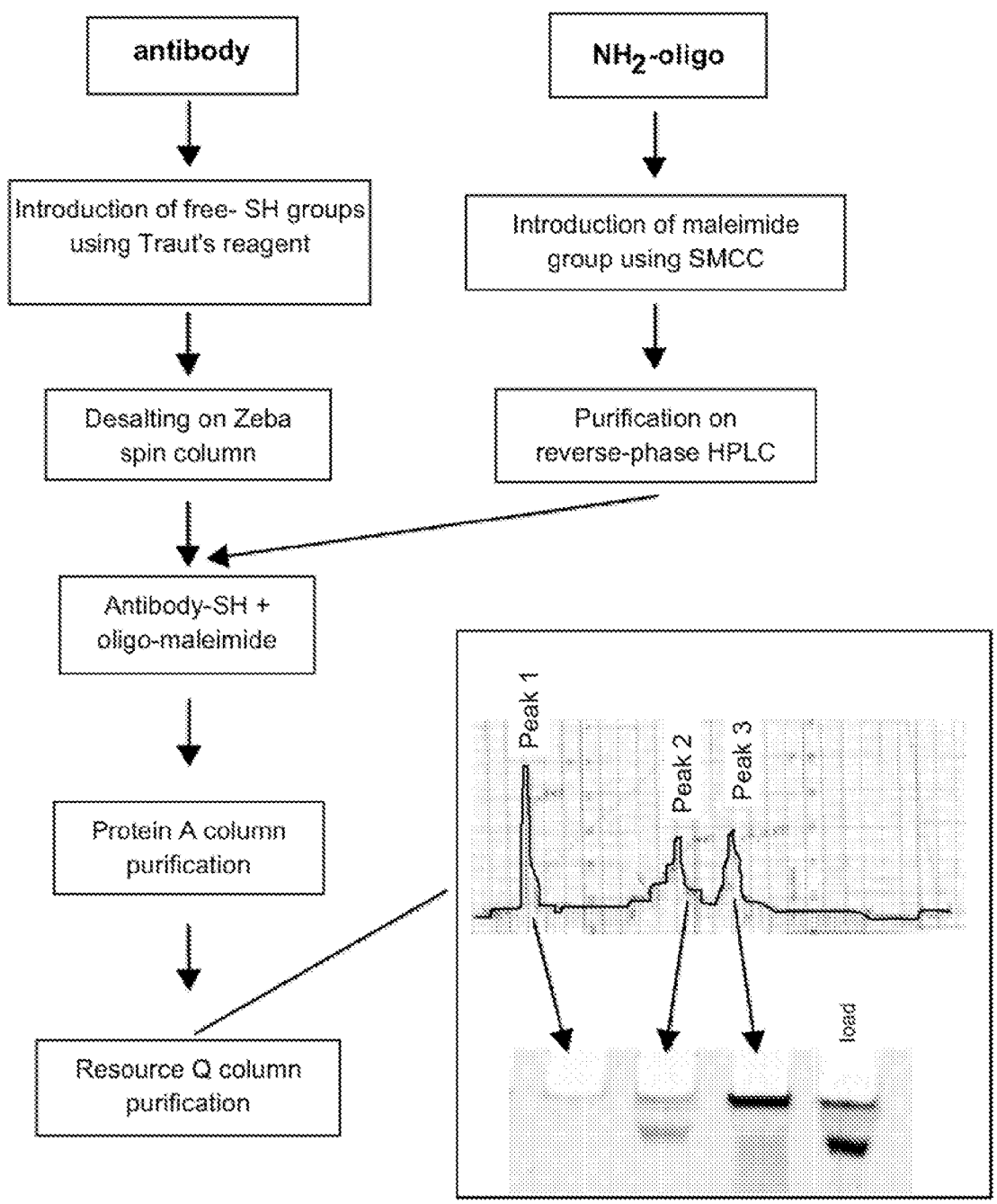

FIG. 36. Illustrates the procedure for attaching signaling oligonucleotides to antibodies. Peaks 1-3 denote three peaks eluting from a ResourceQ column. Samples from these peaks were run on a native polyacrylamide gel and visualized using a Molecular Imager FX with fluorescein emission settings (the signaling oligonucleotide used to label the antibody was labeled with fluorescein). No fluorescence was found in peak 1 (suggesting that it contained unlabeled antibody. Peaks 2 and 3 produced fluorescent bands of different mobility indicating that they contain antibody labeled with one (peak 2) or more (peak 3) signaling oligonucleotides.

Figure 37:
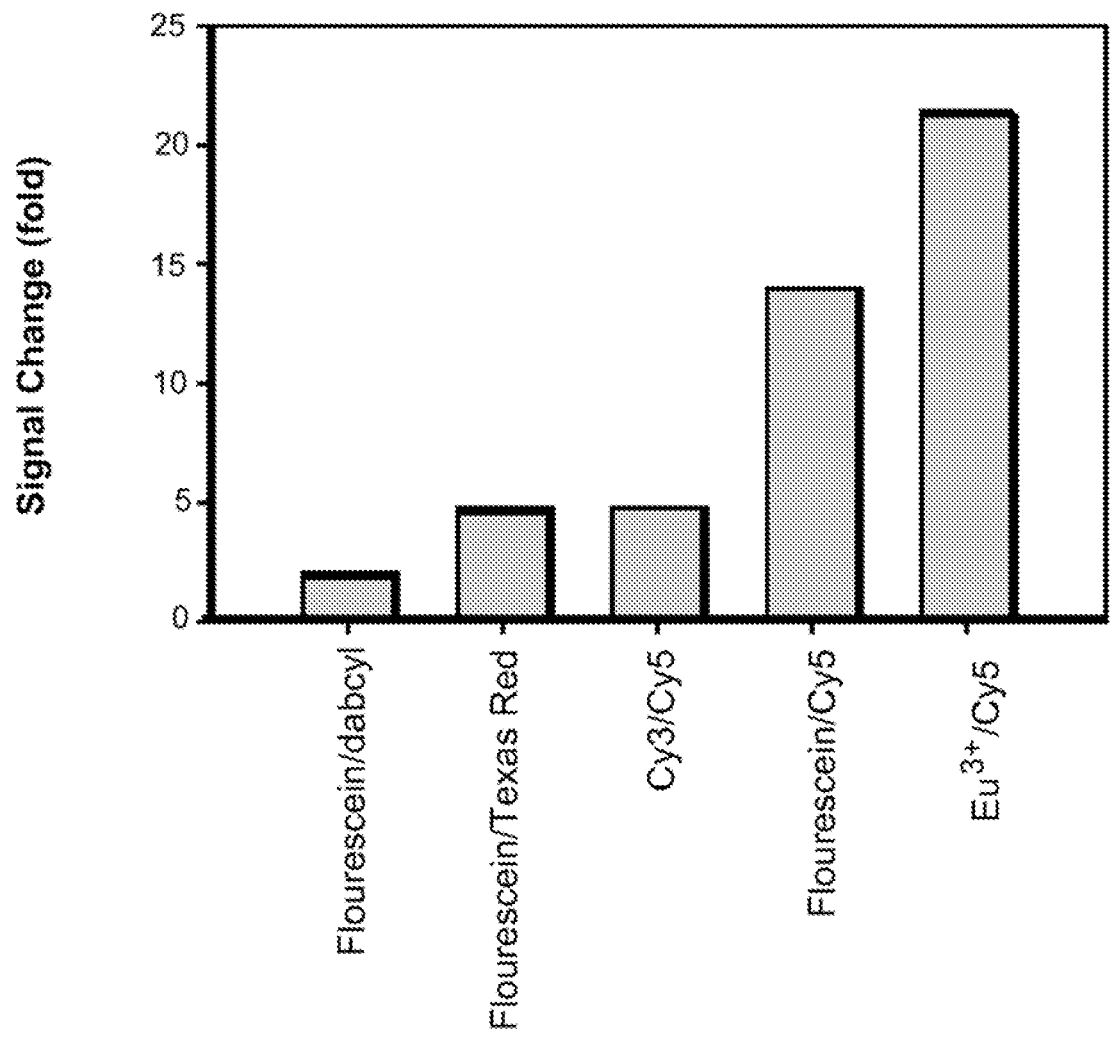

FIG. 37. Depicts the relative signal change for a thrombin sensor obtained with various combinations of donor-acceptor pairs (Heyduk and Heyduk, Anal Chem, 77:1147-56, 2005).

Figure 38:
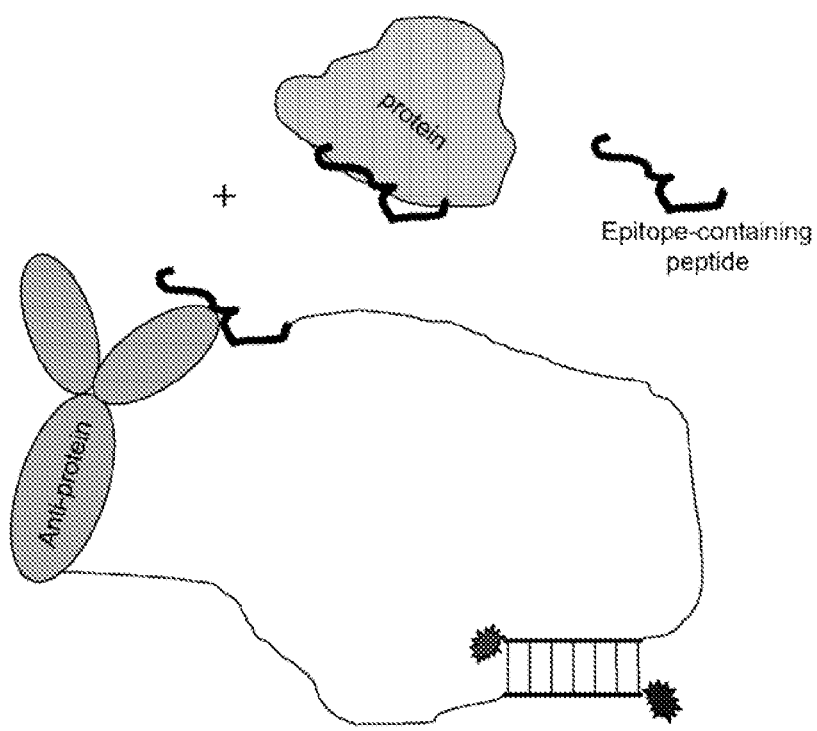
Figure 38:
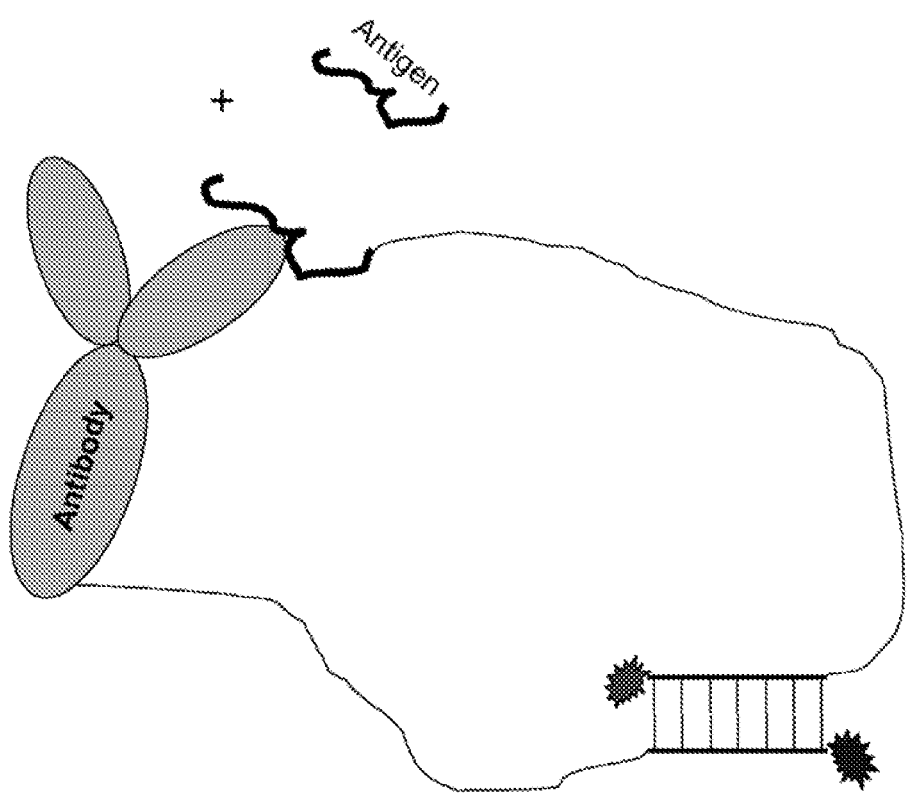

FIG. 38. (A) Design of the model for a competitive molecular sensor for detecting a protein. (B) Design of a competitive sensor for detecting an antigen.

Figure 39:
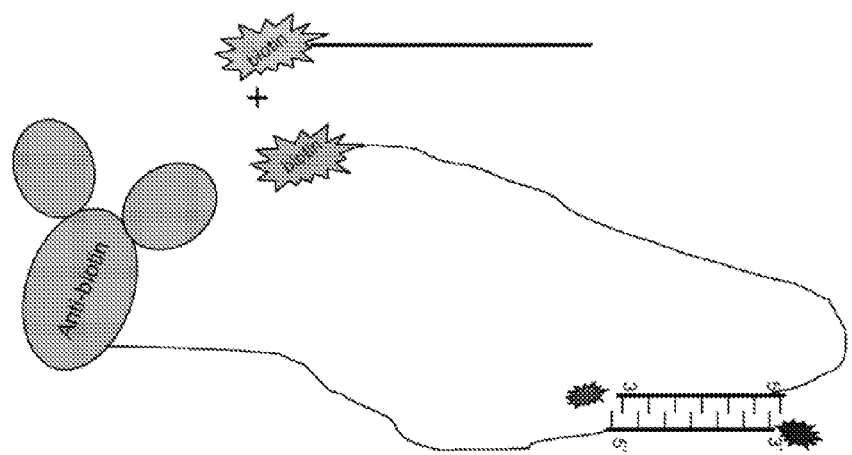
Figure 39:
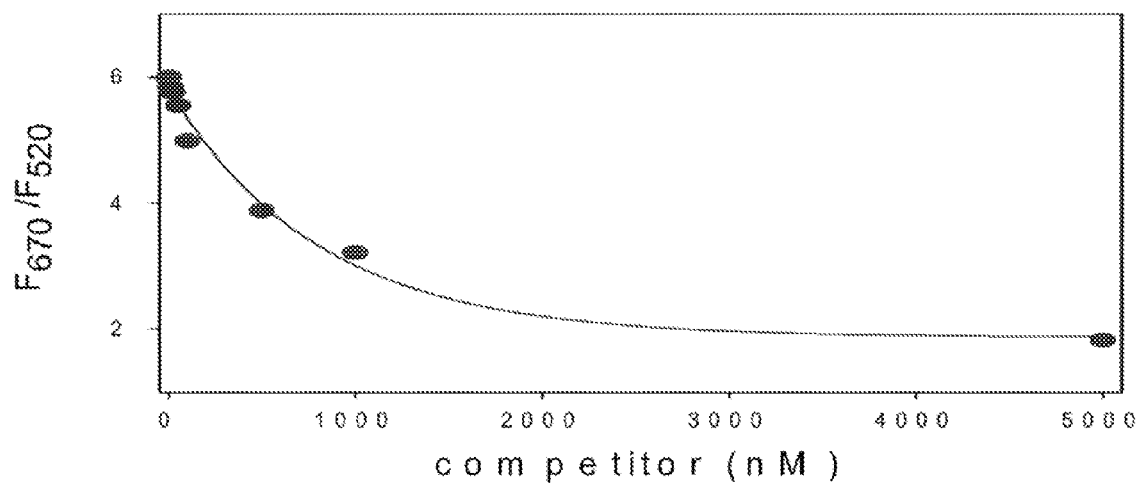

FIG. 39. Depicts an experiment demonstrating the feasibility of an antibody-based competitive molecular biosensor. (A) Design of the model for a competitive molecular sensor. (B) Titration of the beacon with unlabeled competitor (biotin-labeled oligonucleotide).

Figure 40:
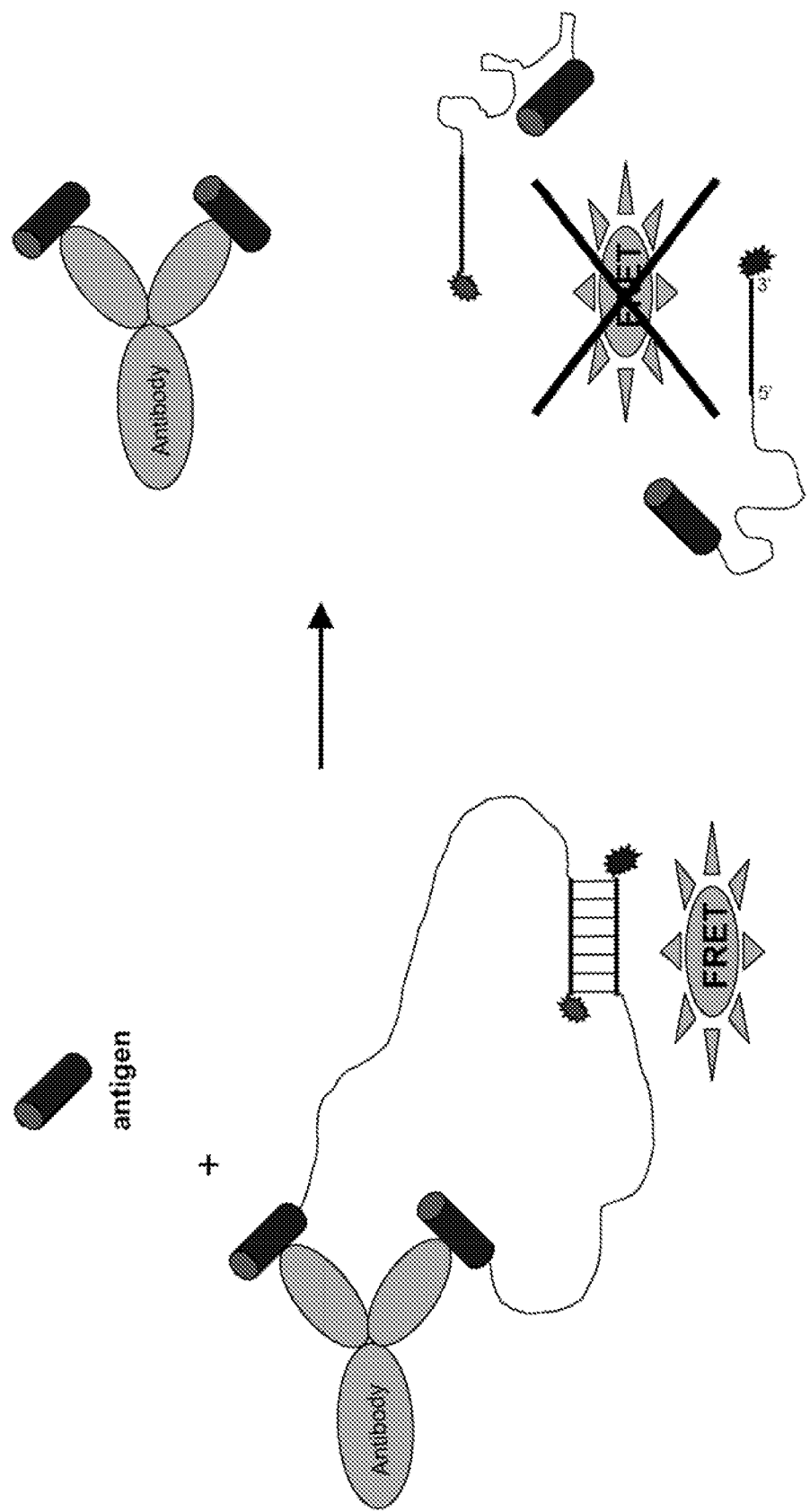

FIG. 40. Design of competitive antibody beacon utilizing the antigen attached to fluorochrome-labeled complementary signaling oligonucleotides. Binding of the antigens to the bivalent antibody results in proximity-driven hybridization of the signaling oligonucleotides generating a FRET signal. In the presence of the competitor antigen, fluorochrome-labeled antigen is displaced by the competitor resulting in a decrease in FRET signal. This decrease in FRET signal can be used to detect the presence of the antigen.

Figure 41:
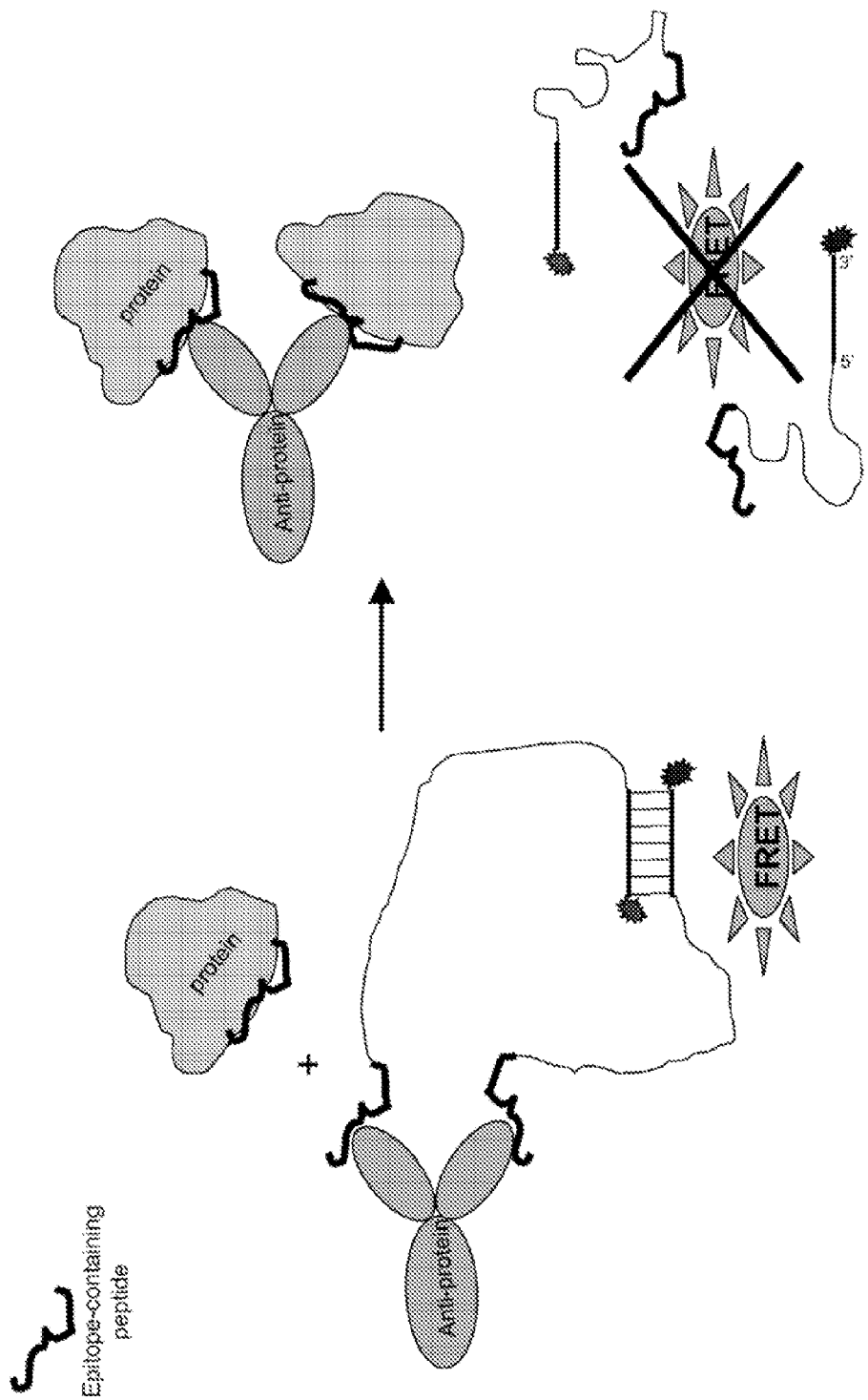

FIG. 41. Implementation of the design illustrated in FIG. 40 for detection of proteins. Synthetic peptide containing the epitope recognized by the antibody is attached to fluorochrome-labeled complementary signaling oligonucleotides. Binding of the peptide to the bivalent antibody results in proximity-driven hybridization of the signaling oligonucleotides generating a FRET signal. In the presence of the protein containing the same epitope, fluorochrome-labeled peptide is displaced by the competitor resulting in a decrease in FRET signal. This decrease in FRET signal can be used to detect the presence of the protein.

FIG. 42. (A) Design of a model system to test the design of competitive antibody beacon illustrated in FIG. 40. Fluorochrome-labeled complementary signaling oligonucleotides attached to long flexible linkers were labeled with biotin. In the presence of anti-biotin antibody the two constructs will bind to the antibody resulting in a FRET signal. (B) Experimental verification of the reaction shown in panel A. A mixture of biotinylated signaling oligonucleotides (50 nM biotinylated ANTB8 labeled with fluorescein and 50 nM biotinylated ANTB6 labeled with Cy5) was titrated with polyclonal anti-biotin antibody (upper curve). As a control, the same mixture of biotinylated oligonucleotides was also titrated with a monovalent Fab anti-biotin antibody fragment. No FRET signal was observed in this case (lower line) consistent with the need for a bivalent antibody to generate the FRET signal.

Figure 43A:
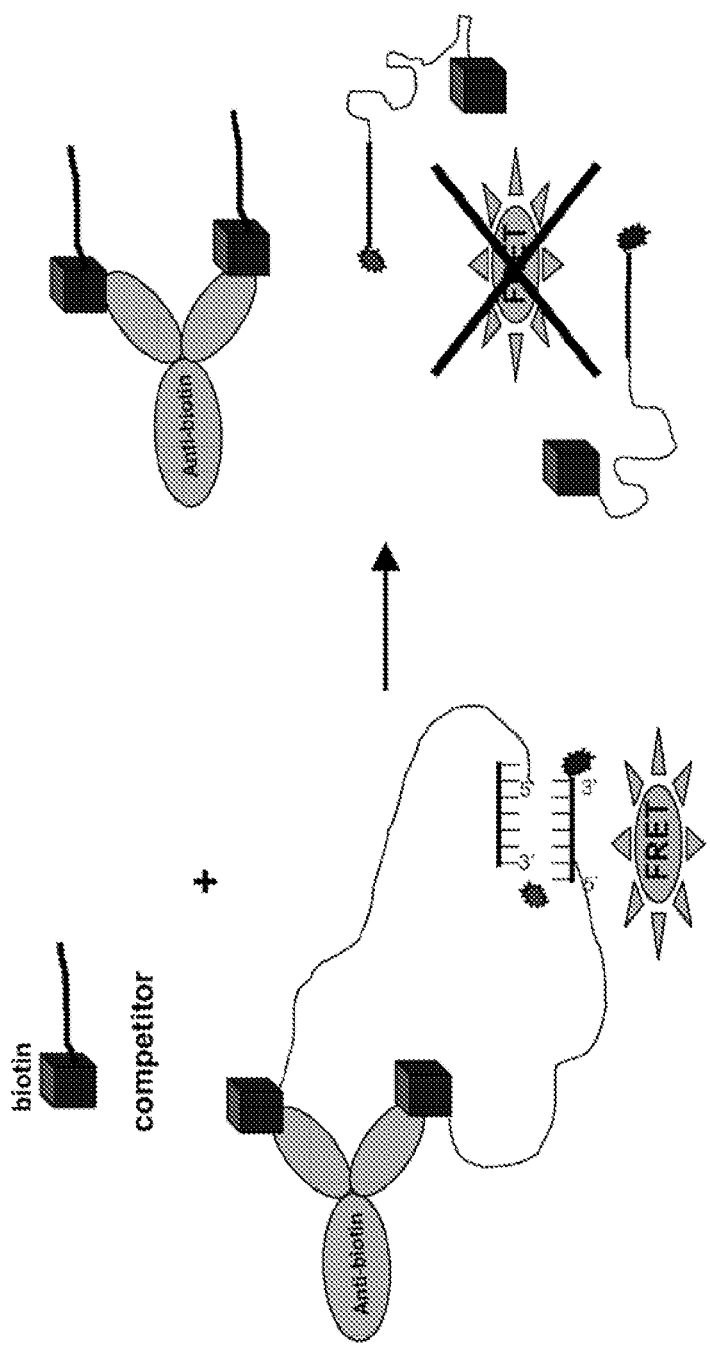
Figure 43B:
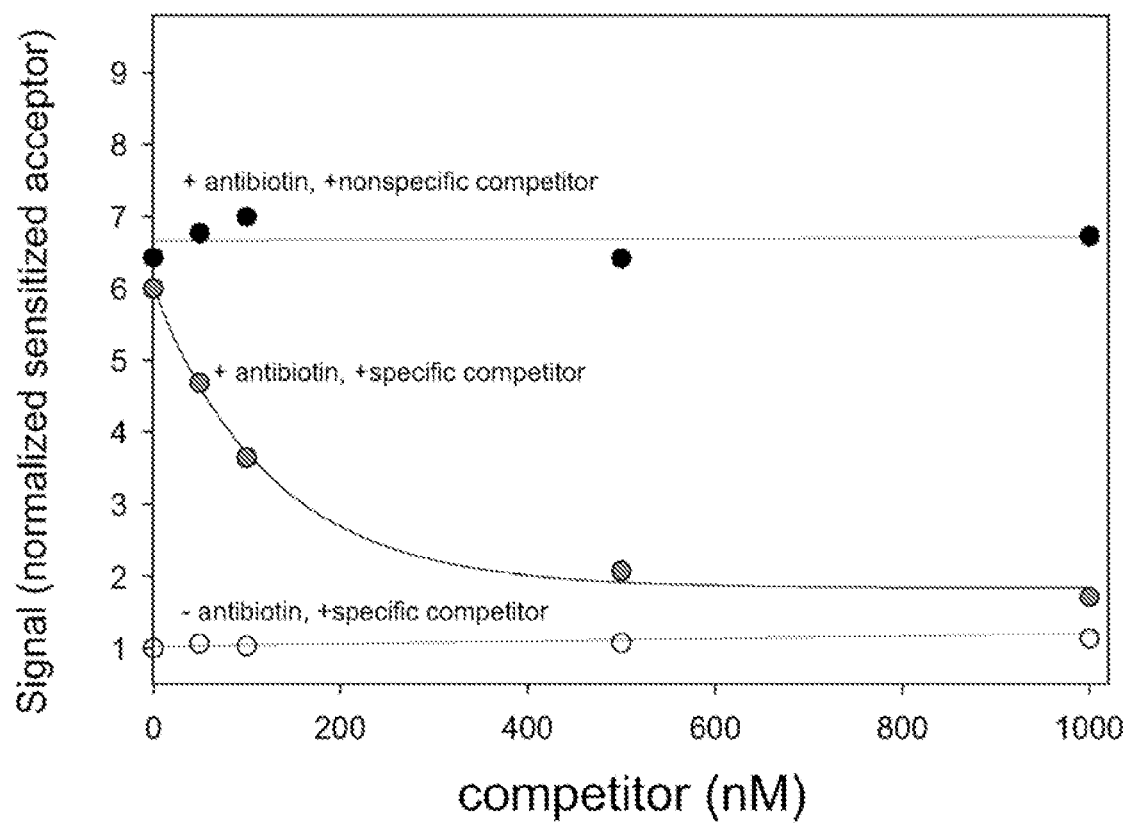

FIG. 43. Proof-of-principle evidence for the feasibility of the competitive antibody beacon illustrated in FIG. 40. (A) Design of the assay. (B) Mixture of 50 nM biotinylated ANTB8 labeled with fluorescein, 50 nM biotinylated ANTB6 labeled with Cy5 and 50 nM anti-biotin antibody was titrated with a specific competitor (unrelated biotinylated oligonucleotide) resulting in expected concentration-dependent decrease in FRET signal (gray circles). No decrease in FRET was observed upon titration with the same oligonucleotide lacking biotin (black circles). In the absence of anti-biotin antibody only background signal was observed which was unaffected by addition of the specific competitor (white circles).

FIG. 44. Table depicting blood clotting times for a thrombin beacon and its individual component aptamers.

Figure 45:
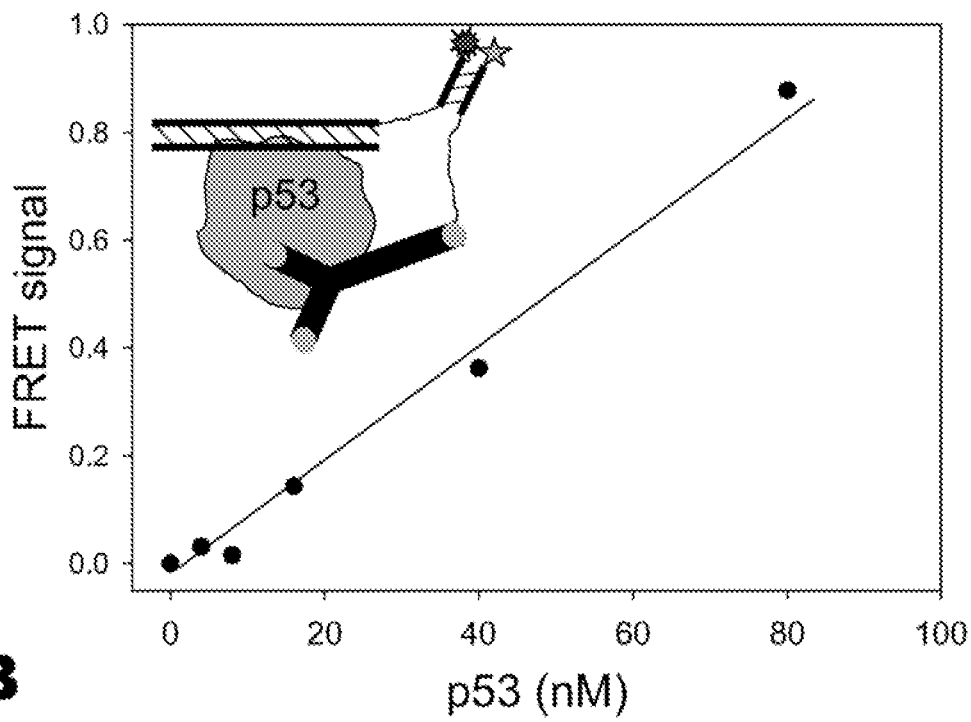
Figure 45:
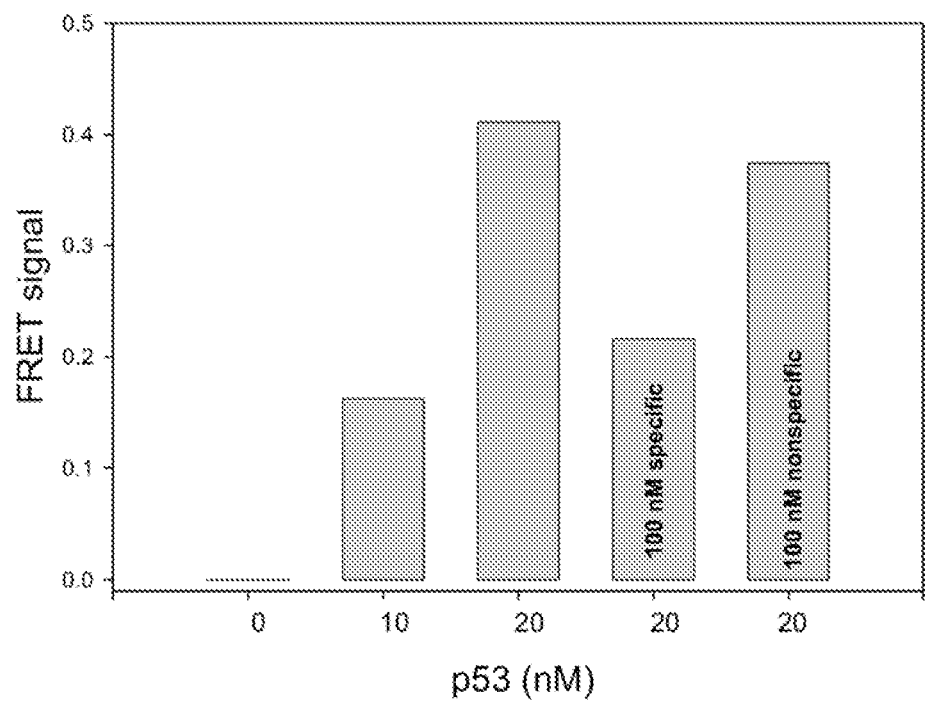

FIG. 45. Sensor for p53 protein comprising a DNA molecule containing a p53 binding site and an anti-p53 antibody. (A) FRET signal in the presence of varying concentrations of full-length recombinant p53. The sensor design is shown schematically in the inset. (B) Specificity of sensor signal in the presence of p53.

Figure 46:
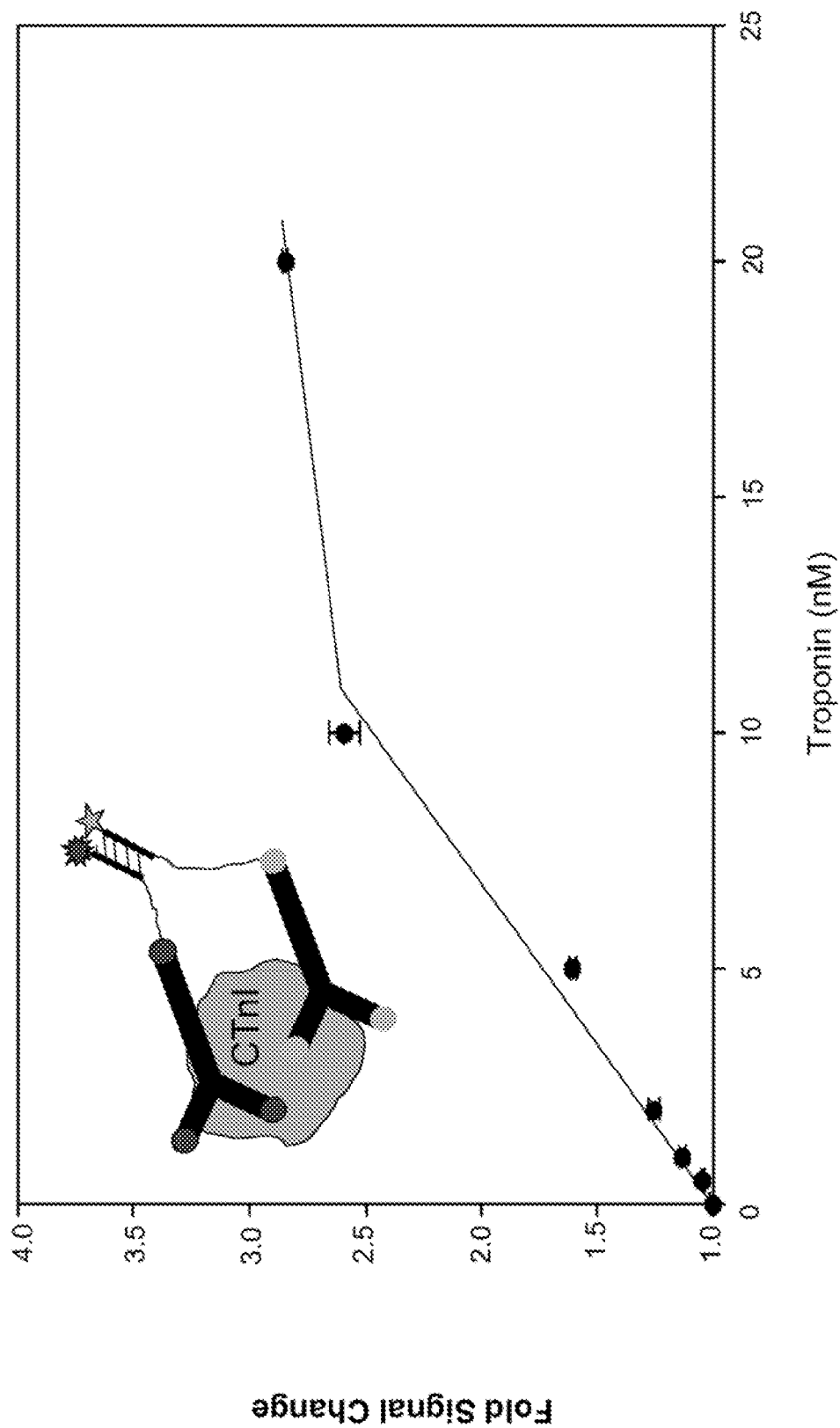

FIG. 46. Sensor for cardiac Troponin I (CTnI) based on two antibodies recognizing nonoverlapping epitopes of the protein. Plotted is the FRET signal with 50 nM of the sensor components in the presence of increasing concentrations of troponin I.

Figure 47:
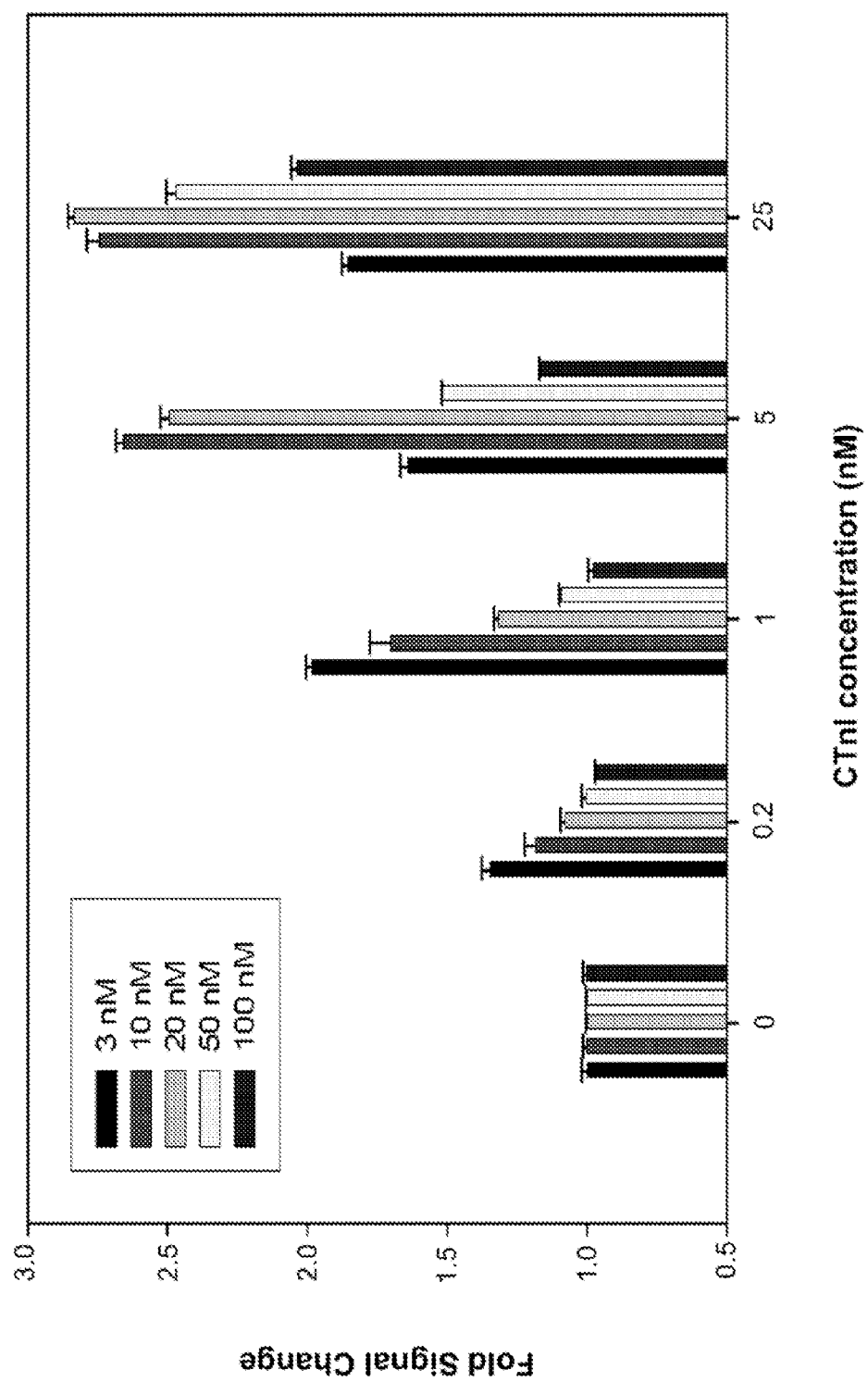

FIG. 47. Response of troponin sensor at various concentrations of sensor components to different concentration of troponin I (CtnI).

Figure 48:
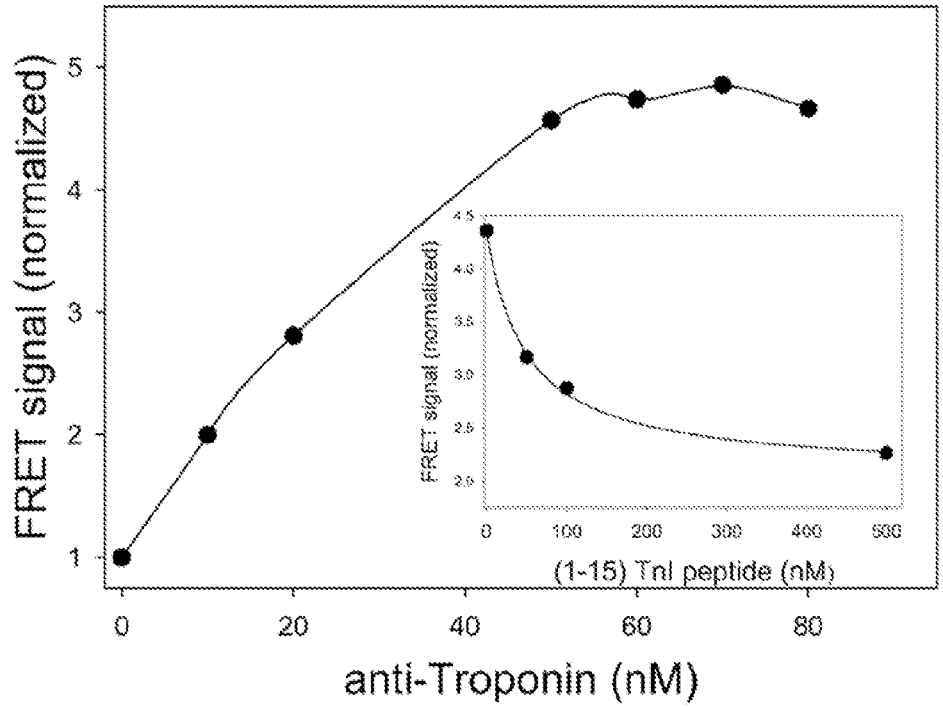
Figure 48:
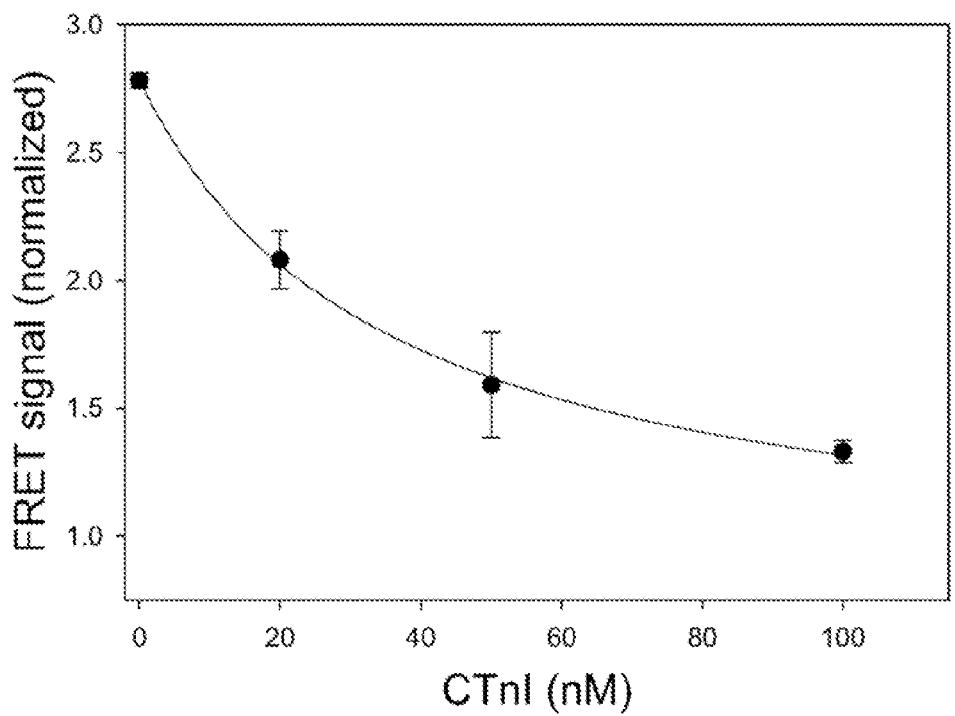
Figure 48C:
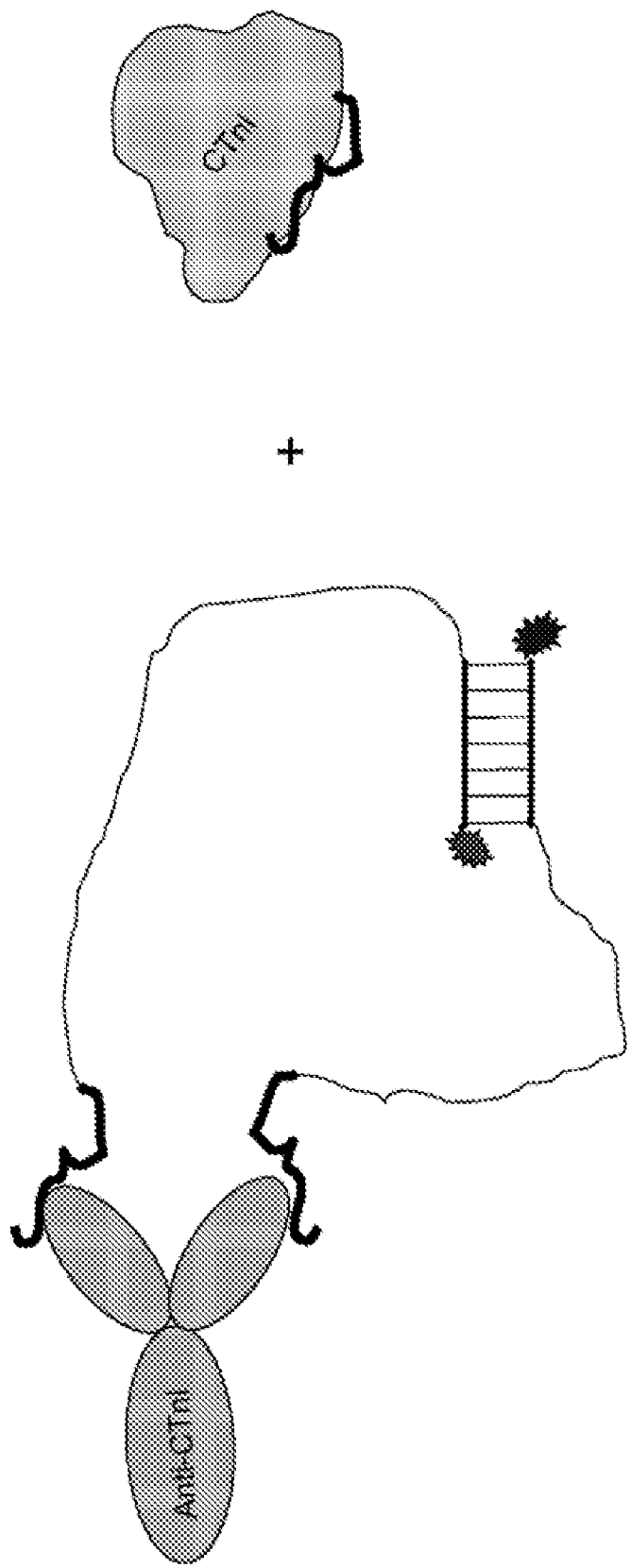

FIG. 48. Competitive sensor for cardiac Troponin I (CTnI). (A) FRET signal in the presence of increasing concentration of the anti-troponin antibody. The inset demonstrates competition by the unlabeled N-terminal CTnI peptide. (B) Competitions with intact CTnI protein. (C) Design of the sensor.

Figure 49:
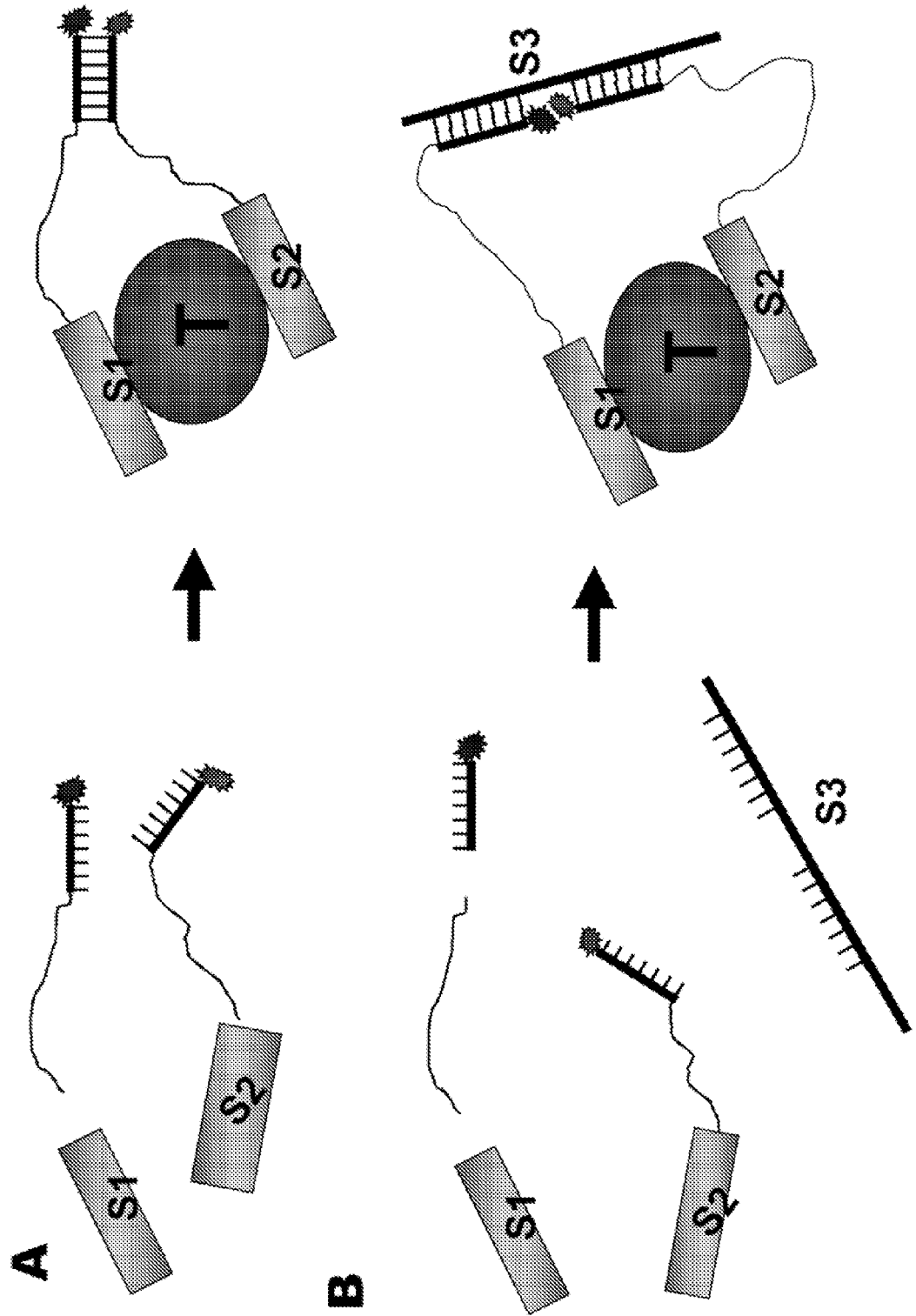

FIG. 49. Comparison of the two-component sensor design (A) and the three-component sensor design (B).

Figure 50:
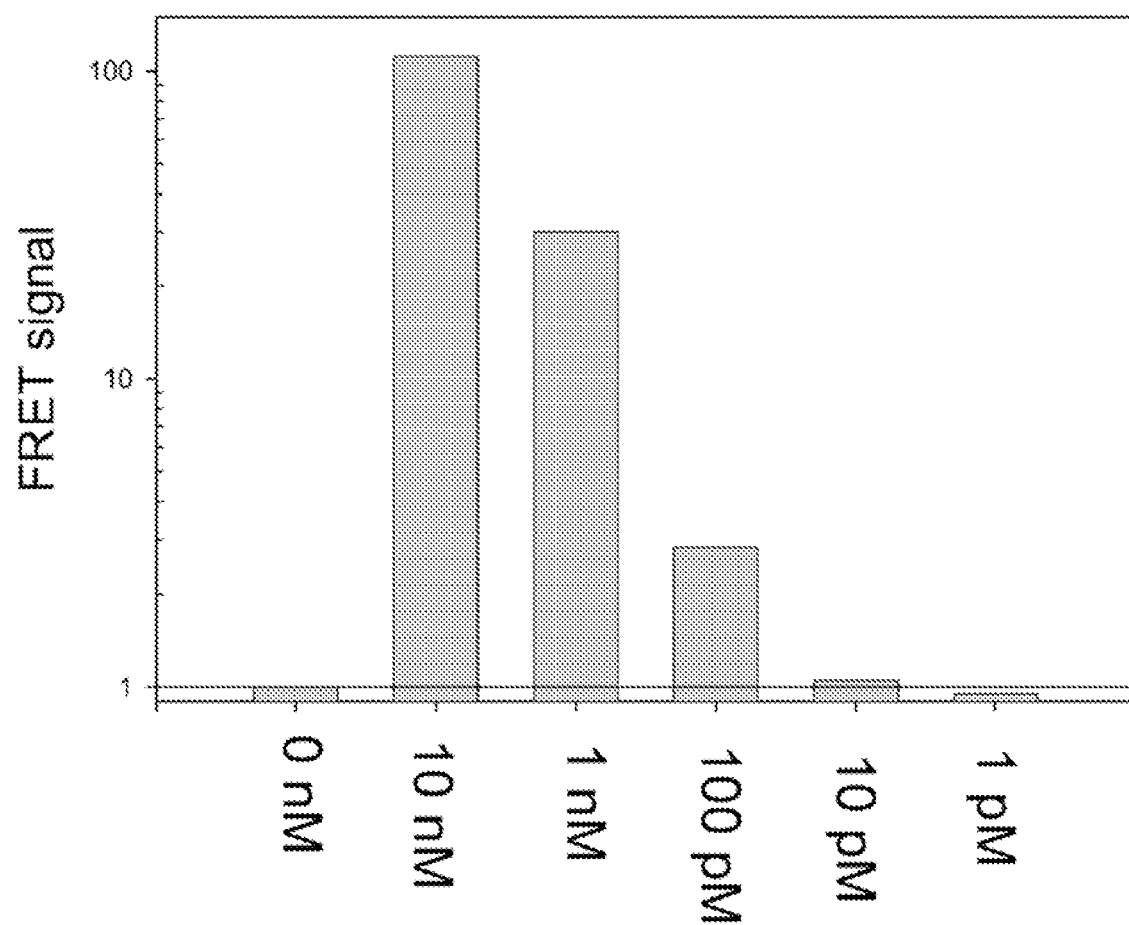

FIG. 50. Proof-of-principle for the three-component sensor design. The FRET signal is plotted as a function of various concentrations of the target.

Figure 51A:
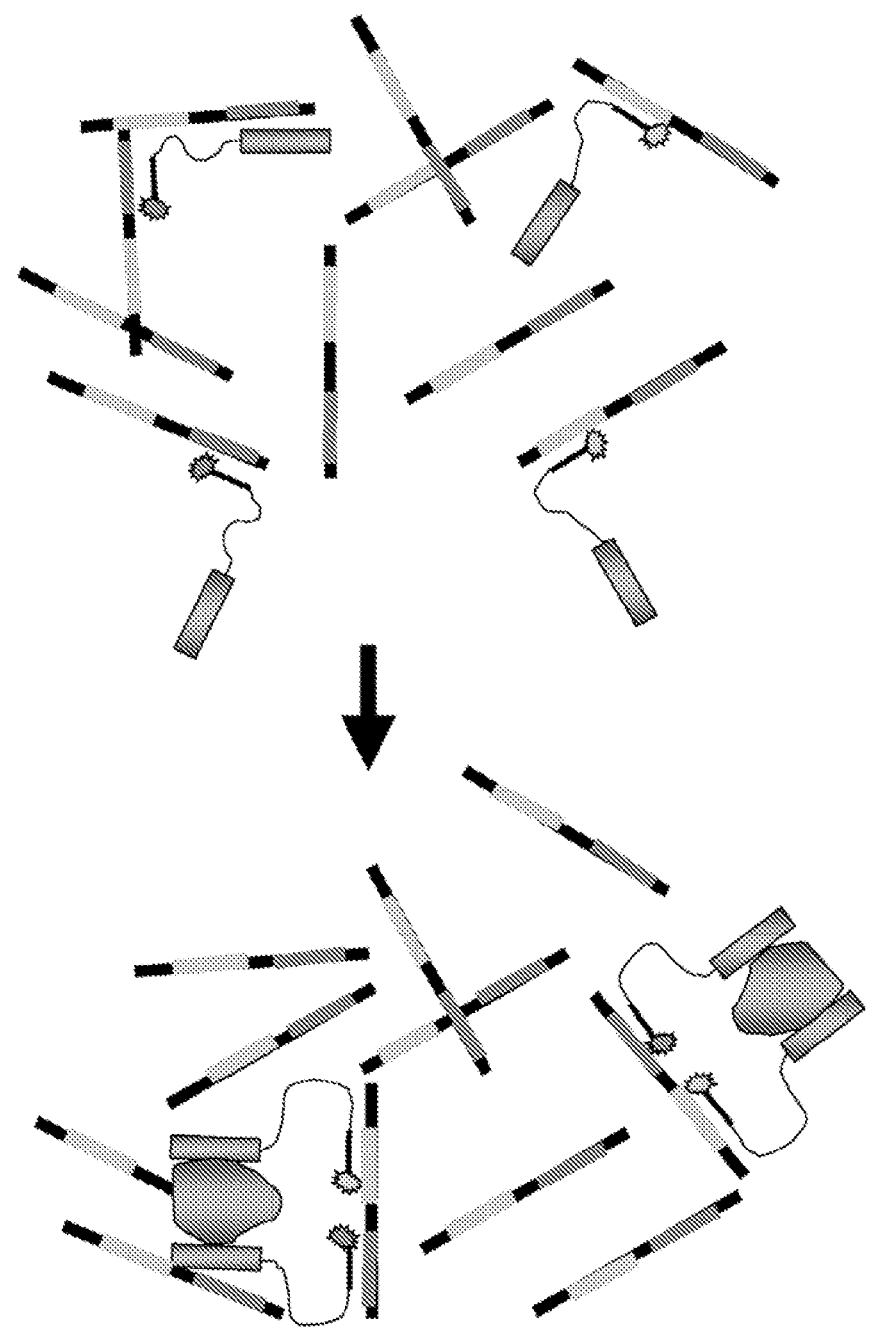

FIG. 51. Insensitivity of the three-component sensor design to the concentration of the S3 component. (A) Schematics illustrating the binding of S1 and S2 in the absence (top) and presence (bottom) of target. (B) Experimental confirmation of the principles described in (A). FRET signal of the sensor was measured in the presence and absence of target (T) at various concentrations of S3. Inset plots the background signal in the absence of T at various concentrations of S3.

Figure 52:
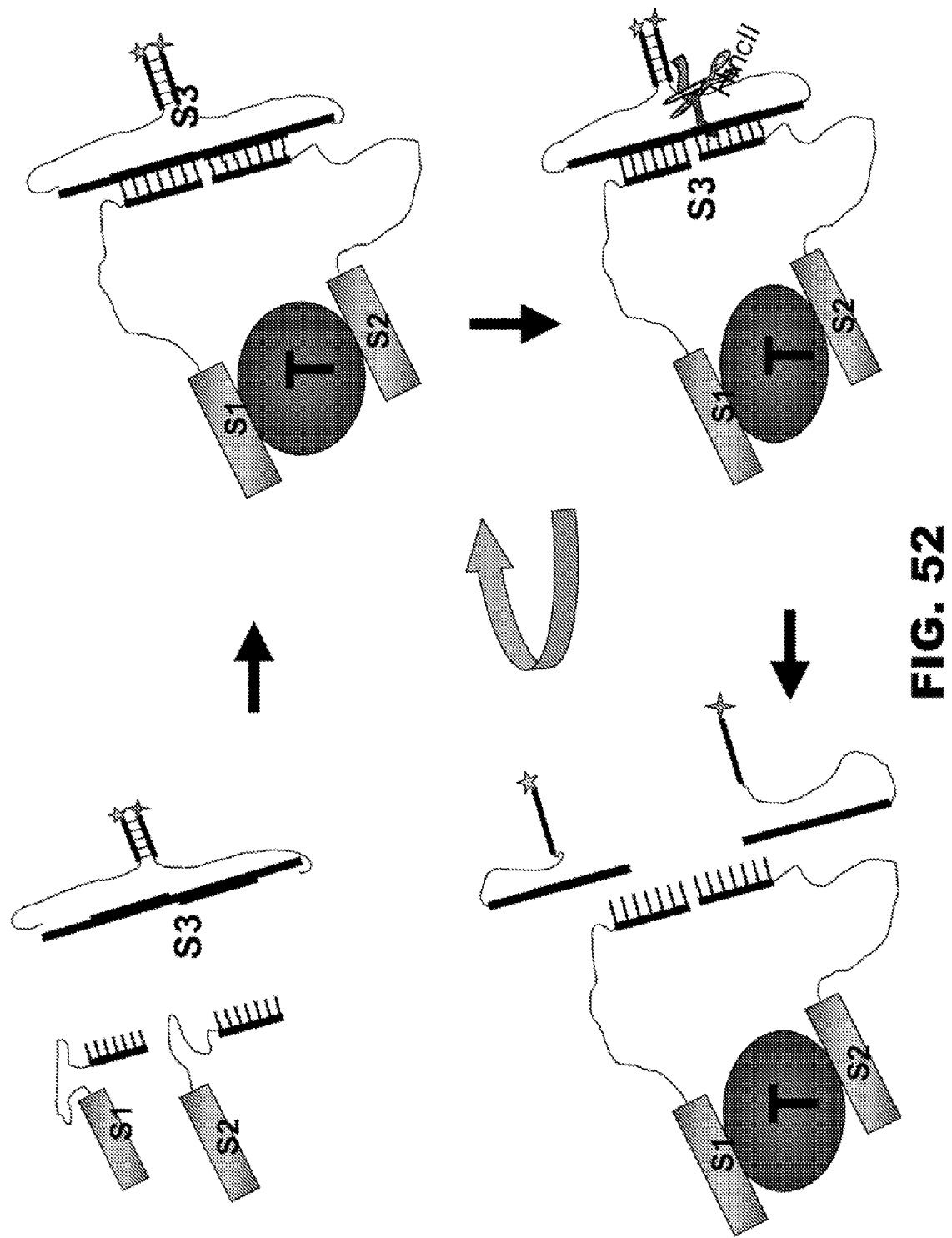

FIG. 52. Homogenous signal amplification utilizing the three-component sensor design. Hybridized S3 comprises a restriction endonuclease recognition site.

Figure 53:
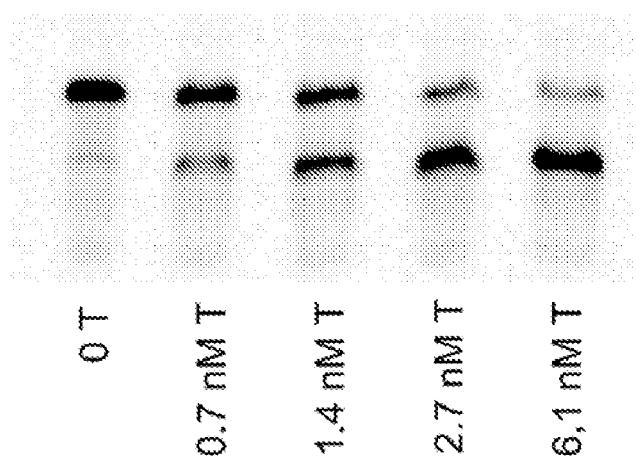
Figure 53:
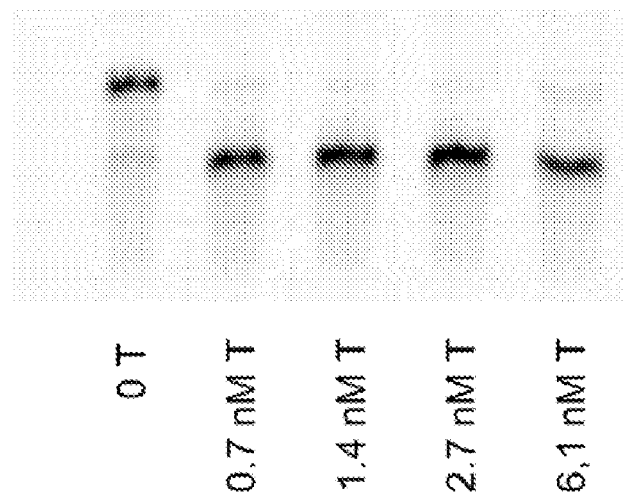

FIG. 53. Proof-of-principle for the signal amplification scheme depicted in FIG. 52. Cleavage of S3 by Hinc II was monitored by native gel electrophoresis at various concentrations of target (T) for 4 hours (A) or 24 hrs (B). (C) The proportion of cleaved S3 after 4 hrs is plotted as a function of T concentration.

Figure 54:
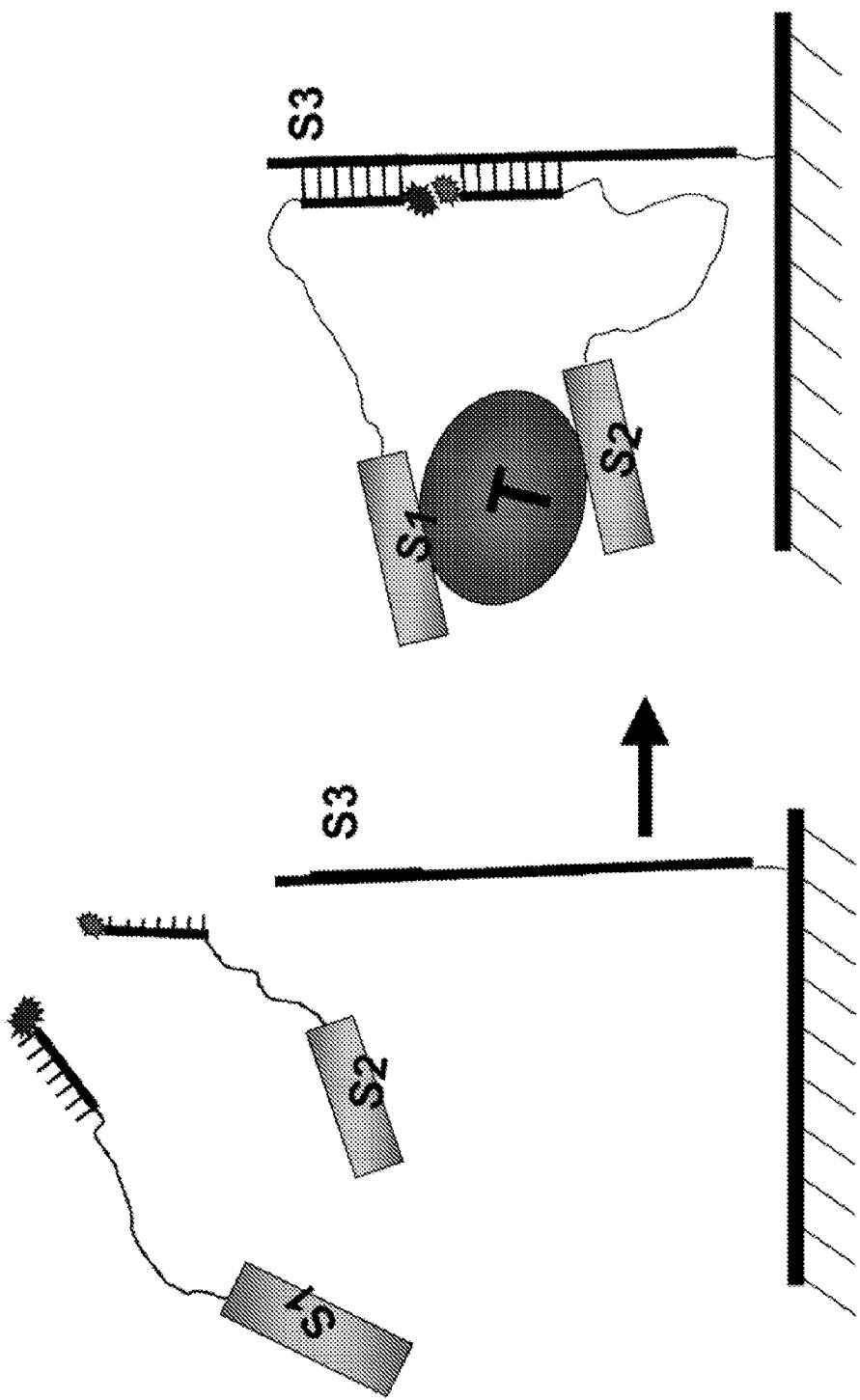

FIG. 54. Solid-surface implementation of the three-component biosensor design.

Figure 55:
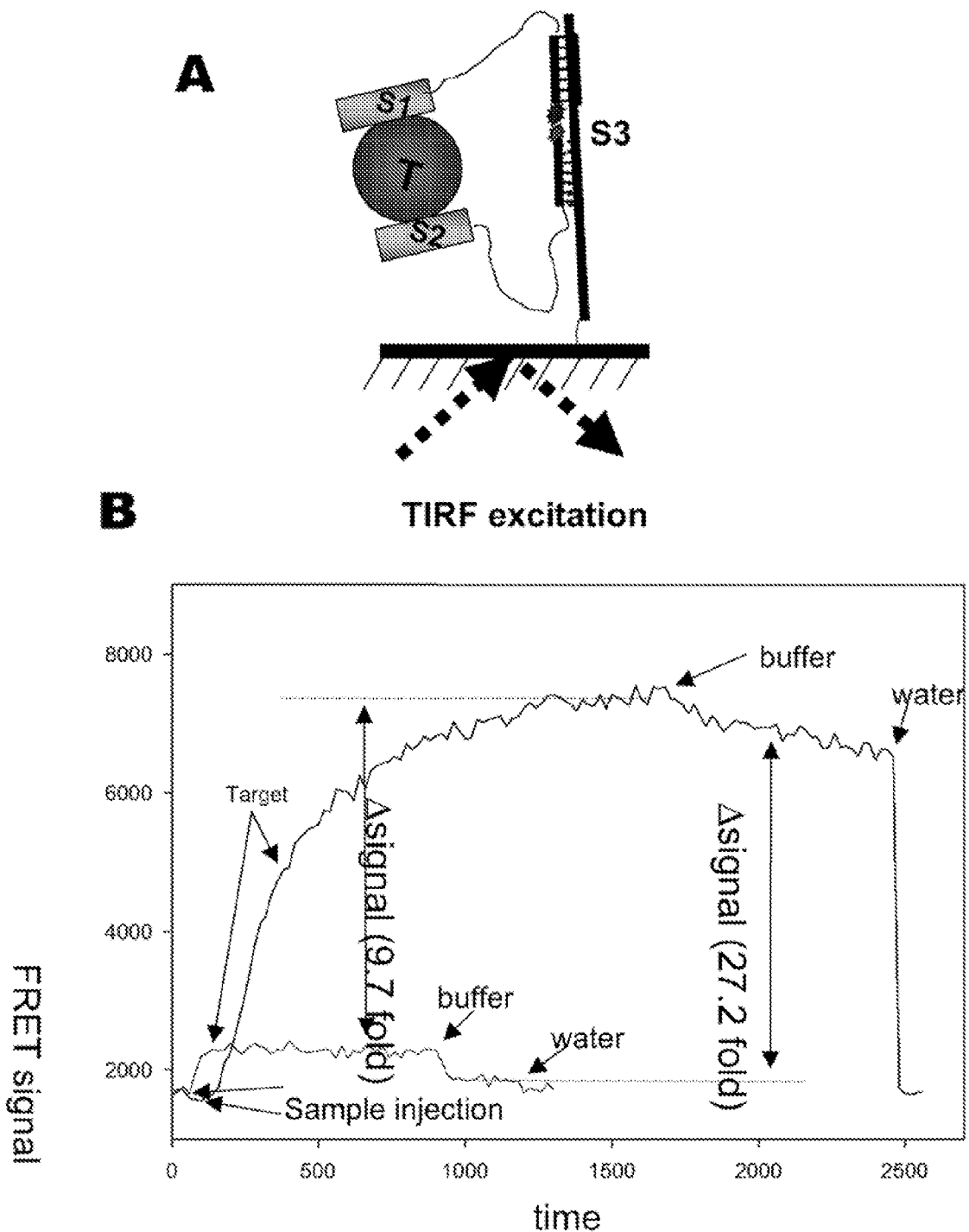

FIG. 55. Proof-of-principle for the solid-surface implementation of the three-component biosensor design. (A) Design of the sensor employing TIRF detection. (B) FRET signals in the presence and absence of target (T) over time.

Figure 56:
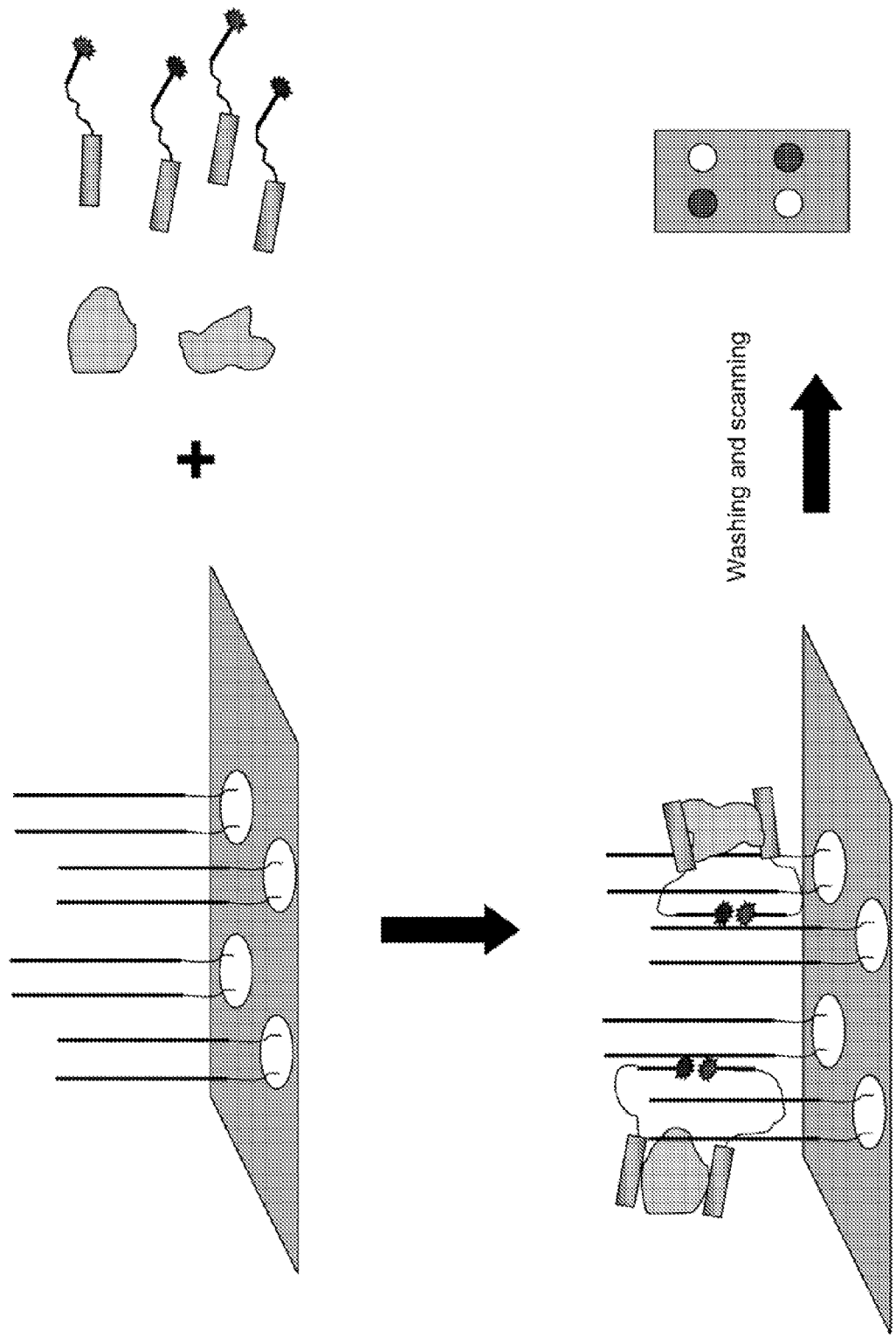

FIG. 56. Use of the three-component biosensor design for a microarray detection of a target.

DETAILED DESCRIPTION OF THE PREFERRED EMBODIMENTS

The present invention is directed to molecular biosensors that may be utilized in several different methods, such as the detection of a target molecule. In one design, the biosensor is comprised of two components, which comprise two epitope-binding agent constructs. In the two-component design, detection of a target molecule typically involves target-molecule induced co-association of two epitope-binding agent constructs that each recognize distinct epitopes on the target molecule. The epitope-binding agent constructs each comprise complementary signaling oligonucleotides that are labeled with detection means and are attached to the epitope-binding agents through a flexible linker. Co-association of the two epitope-binding agent constructs with the target molecule results in bringing the two signaling oligonucleotides into proximity such that a detectable signal is produced.

Alternatively, in another design the biosensor is comprised of three components, which comprise two epitope-binding agent constructs and an oligonucleotide construct. In the three-component design, analogous to the two-component design, detection of a target molecule typically involves target-molecule induced co-association of two epitope-binding agent constructs that each recognize distinct epitopes on the target molecule. Unlike the two-component design, however, the epitope-binding agent constructs each comprise non-complementary signaling oligonucleotides that are labeled with detection means and are attached to the epitope-binding agents through a flexible linker. Each signaling oligonucleotide is complementary to two distinct regions on the oligonucleotide construct. Co-association of the two epitope-binding agent constructs with the target molecule results in hybridization of each signaling oligonucleotide to the oligonucleotide construct. Binding of the two signaling oligonucleotides to the oligonucleotide construct brings them into proximity such that a detectable signal is produced.

Advantageously, the molecular biosensors, irrespective of the design, provide a rapid homogeneous means to detect a variety of target molecules, including but not limited to proteins, carbohydrates, macromolecules, and analytes. In particular, as illustrated in the Examples, the three-component biosensors are useful in several applications involving solid surfaces.

(I) Two-Component Molecular Biosensors

One aspect of the invention, accordingly, encompasses a two-component molecular biosensor. Several molecular configurations of biosensors are suitable for use in the invention as illustrated by way of non-limiting example in FIGS. 24, 33, and 38. In one embodiment, the molecular biosensor will be monovalent comprising a single epitope-binding agent that binds to an epitope on a target molecule. The molecular biosensor of the invention, however, is typically multivalent. It will be appreciated by a skilled artisan, depending upon the target molecule, that the molecular biosensor may comprise from about 2 to about 5 epitope binding agents. Typically, the molecular biosensor will comprise 2 or 3 epitope binding agents and more typically, will comprise 2 epitope binding agents. In one alternative of this embodiment, therefore, the molecular biosensor will be bivalent comprising a first epitope binding agent that binds to a first epitope on a target molecule and a second epitope binding agent that binds to a second epitope on the target molecule. In yet another alternative of this embodiment, the molecular biosensor will be trivalent comprising a first epitope binding agent that binds to a first epitope on a target molecule, a second epitope binding agent that binds to a second epitope on a target molecule and a third epitope binding agent that binds to a third epitope on a target molecule.

(a) Bivalent Molecular Sensors

In one alternative of the invention, the molecular biosensor will be bivalent. In a typical embodiment, the bivalent construct will comprise a first epitope binding agent that binds to a first epitope on a target molecule, a first linker, a first signaling oligo, a first detection means, a second epitope binding agent that binds to a second epitope on the target molecule, a second linker, a second signaling oligo, and a second detection means.

In one preferred embodiment, the molecular biosensor comprises two nucleic acid constructs, which together have formula (I):

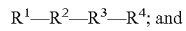

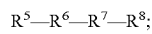

(I)

wherein:

$R^1$ is an epitope-binding agent that binds to a first epitope on a target molecule;

$R^2$ is a flexible linker attaching $R^1$ to $R^3$;

$R^3$ and $R^7$ are a pair of complementary nucleotide sequences having a free energy for association from about 5.5 kcal/mole to about 8.0 kcal/mole at a temperature from about 21° C. to about 40° C. and at a salt concentration from about 1 mM to about 100 mM;

$R^4$ and $R^8$ together comprise a detection means such that when $R^3$ and $R^7$ associate a detectable signal is produced;

$R^5$ is an epitope binding agent that binds to a second epitope on the target molecule; and $R^6$ is a flexible linker attaching $R^5$ to $R^7$.

As will be appreciated by those of skill in the art, the choice of epitope binding agents, $R^1$ and $R^5$, in molecular biosensors having formula (I) can and will vary depending upon the particular target molecule. By way of example, when the target molecule is a protein, $R^1$ and $R^5$ may be an aptamer, or antibody. By way of further example, when $R^1$ and $R^5$ are double stranded nucleic acid the target molecule is typically a macromolecule that binds to DNA or a DNA binding protein. In general, suitable choices for $R^1$ and $R^5$ will include two agents that each recognize distinct epitopes on the same target molecule. In certain embodiments, however, it is also envisioned that $R^1$ and $R^5$ may recognize distinct epitopes on different target molecules. Non-limiting examples of suitable epitope binding agents, depending upon the target molecule, include agents selected from the group consisting of an aptamer, an antibody, an antibody fragment, a double-stranded DNA sequence, modified nucleic acids, nucleic acid mimics, a ligand, a ligand fragment, a receptor, a receptor fragment, a polypeptide, a peptide, a coenzyme, a coregulator, an allosteric molecule, and an ion. In an exemplary embodiment, $R^1$ and $R^5$ are each aptamers having a sequence ranging in length from about 20 to about 110 bases. In another embodiment, $R^1$ and $R^5$ are each antibodies selected from the group consisting of polyclonal antibodies, ascites, Fab fragments, Fab' fragments, monoclonal antibodies, and humanized antibodies. In an alternative embodiment, $R^1$ and $R^5$ are peptides. In a preferred embodiment, $R^1$ and $R^5$ are each monoclonal antibodies. In an additional embodiment, $R^1$ and $R^5$ are each double stranded DNA. In a further embodiment, $R^1$ is a double stranded nucleic acid and $R^5$ is an aptamer. In an additional embodiment, $R^1$ is an antibody and $R^5$ is an aptamer. In another additional embodiment, $R^1$ is an antibody and $R^5$ is a double stranded DNA.

In an additional embodiment for molecular biosensors having formula (I), exemplary linkers, $R^2$ and $R^6$, will functionally keep $R^3$ and $R^7$ in close proximity such that when $R^1$ and $R^5$ each bind to the target molecule, $R^3$ and $R^7$ associate in a manner such that a detectable signal is produced by the detection means, $R^4$ and $R^8$. $R^2$ and $R^6$ may each be a nucleotide sequence from about 10 to about 100 nucleotides in length. In one embodiment, $R^2$ and $R^6$ are from 10 to about 25 nucleotides in length. In another embodiment, $R^2$ and $R^6$ are from about 25 to about 50 nucleotides in length. In a further embodiment, $R^2$ and $R^6$ are from about 50 to about 75 nucleotides in length. In yet another embodiment, $R^2$ and $R^6$ are from about 75 to about 100 nucleotides in length. In each embodiment, the nucleotides comprising the linkers may be any of the nucleotide bases in DNA or RNA (A, C, T, G in the case of DNA, or A, C, U, G in the case of RNA). In one embodiment $R^2$ and $R^6$ are comprised of DNA bases. In another embodiment, $R^2$ and $R^6$ are comprised of RNA bases. In yet another embodiment, $R^2$ and $R^6$ are comprised of modified nucleic acid bases, such as modified DNA bases or modified RNA bases. Modifications may occur at, but are not restricted to, the sugar 2' position, the C-5 position of pyrimidines, and the 8-position of purines. Examples of suitable modified DNA or RNA bases include 2'-fluoro nucleotides, 2'-amino nucleotides, 5'-aminoallyl-2'-fluoro nucleotides and phosphorothioate nucleotides (monothiophosphate and dithiophosphate). In a further embodiment, $R^2$ and $R^6$ may be nucleotide mimics. Examples of nucleotide mimics include locked nucleic acids (LNA), peptide nucleic acids (PNA), and phosphorodiamidate morpholino oligomers (PMO). Alternatively, $R^2$ and $R^6$ may be a polymer of bifunctional chemical linkers. In one embodiment the bifunctional chemical linker is heterobifunctional. Suitable heterobifunctional chemical linkers include sulfoSMCC (Sulfosuccinimidyl-4-(N-maleimidomethyl)cyclohexane-1-carboxylate), and Ic-SPDP (N-Succinimidyl-6-(3'-(2-PyridylDithio)-Propionamido)-hexanoate). In another embodiment the bifunctional chemical linker is homobifunctional. Suitable homobifunctional linkers include disuccinimidyl suberate, disuccinimidyl glutarate, and disuccinimidyl tartrate. Additional suitable linkers are illustrated in the Examples, such as the phosphoramidate form of Spacer 18 comprised of polyethylene glycol. In one embodiment, $R^2$ and $R^6$ are from 0 to about 500 angstroms in length. In another embodiment, $R^2$ and $R^6$ are from about 20 to about 400 angstroms in length. In yet another embodiment, $R^2$ and $R^6$ are from about 50 to about 250 angstroms in length.

In a further embodiment for molecular biosensors having formula (I), $R^3$ and $R^7$ are complementary nucleotide sequences having a length such that they preferably do not associate unless $R^1$ and $R^5$ bind to separate epitopes on the target molecule. When $R^1$ and $R^5$ bind to separate epitopes of the target molecule, $R^3$ and $R^7$ are brought to relative proximity resulting in an increase in their local concentration, which drives the association of $R^3$ and $R^7$. $R^3$ and $R^7$ may be from about 2 to about 20 nucleotides in length. In another embodiment, $R^3$ and $R^7$ are from about 4 to about 15 nucleotides in length. In an exemplary embodiment, $R^3$ and $R^7$ are from about 5 to about 7 nucleotides in length. In one embodiment, $R^3$ and $R^7$ have a free energy for association from about 5.5 kcal/mole to about 8.0 kcal/mole as measured in the selection buffer conditions, defined below. In another embodiment, $R^3$ and $R^7$ have a free energy for association from about 6.0 kcal/mole to about 8.0 kcal/mole as measured in the selection buffer conditions defined below. In yet another embodiment, $R^3$ and $R^7$ have a free energy for association from about 7.0 kcal/mole to 8.0 kcal/mole in the selection buffer conditions. In a preferred embodiment, $R^3$ and $R^7$ have a free energy for association of 7.5 kcal/mole in the selection buffer conditions described below. Preferably, in each embodiment $R^3$ and $R^7$ are not complementary to $R^1$ and $R^5$.

In a typical embodiment for molecular biosensors having formula (I), $R^4$ and $R^8$ may together comprise several suitable detection means such that when $R^3$ and $R^7$ associate, a detectable signal is produced. Exemplary detections means suitable for use in the molecular biosensors include fluorescent resonance energy transfer (FRET), lanthamide resonance energy transfer (LRET), fluorescence cross-correlation spectroscopy, fluorescence quenching, fluorescence polarization, flow cytometry, scintillation proximity, luminescence resonance energy transfer, direct quenching, ground-state complex formation, chemiluminescence energy transfer, bioluminescence resonance energy transfer, excimer formation, colorimetric substrates detection, phosphorescence, electrochemical changes, and redox potential changes.

In a further embodiment, the molecular biosensor will have formula (I) wherein:

$R^1$ is an epitope-binding agent that binds to a first epitope on a target molecule and is selected from the group consisting of an aptamer, an antibody, a peptide, and a double stranded nucleic acid;

$R^2$ is a flexible linker attaching $R^1$ to $R^3$ by formation of a covalent bond with each of $R^1$ and $R^3$, wherein $R^2$ comprises a bifunctional chemical cross linker and is from 0 to 500 angstroms in length;

$R^3$ and $R^7$ are a pair of complementary nucleotide sequences from about 4 to about 15 nucleotides in length and having a free energy for association from about 5.5 kcal/mole to about 8.0 kcal/mole at a temperature from about 21° C. to about 40° C. and at a salt concentration from about 1 mM to about 100 mM;

$R^4$ and $R^8$ together comprise a detection means selected from the group consisting of fluorescent resonance energy transfer (FRET), lanthamide resonance energy transfer (LRET), fluorescence cross-correlation spectroscopy, fluorescence quenching, fluorescence polarization, flow cytometry, scintillation proximity, luminescence resonance energy transfer, direct quenching, ground-state complex formation, chemiluminescence energy transfer, bioluminescence resonance energy transfer, excimer formation, colorimetric substrates detection, phosphorescence, electro-chemical changes, and redox potential changes;

$R^5$ is an epitope binding agent that binds to a second epitope on the target molecule and is selected from the group consisting of an aptamer, an antibody, a peptide, and a double stranded nucleic acid; and $R^6$ is a flexible linker attaching $R^5$ to $R^7$ by formation of a covalent bond with each of $R^5$ and $R^7$, wherein $R^6$ comprises a bifunctional chemical cross linker and is from 0 to 500 angstroms in length.

Yet another embodiment of the invention encompasses a molecular biosensor having formula (I)
wherein:

$R^1$ is an aptamer that binds to a first epitope on a target molecule;

$R^2$ is a flexible linker attaching $R^1$ to $R^3$;

$R^3$ and $R^7$ are a pair of complementary nucleotide sequences having a free energy for association from about 5.5 kcal/mole to about 8.0 kcal/mole at a temperature from about 21° C. to about 40° C. and at a salt concentration from about 1 mM to about 100 mM;

$R^4$ and $R^8$ together comprise a detection means such that when $R^3$ and $R^7$ associate a detectable signal is produced;

$R^5$ is an aptamer that binds to a second epitope on the target molecule; and $R^6$ is a flexible linker attaching $R^5$ to $R^7$.

A further embodiment of the invention encompasses a molecular biosensor having formula (I)
wherein:

$R^1$ is an aptamer that binds to a first epitope on a target molecule;

$R^2$ is a flexible linker attaching $R^1$ to $R^3$ by formation of a covalent bond with each of $R^1$ and $R^3$, wherein $R^2$ comprises a bifunctional chemical cross linker and is from 0 to 500 angstroms in length;

$R^3$ and $R^7$ are a pair of complementary nucleotide sequence from about 4 to about 15 nucleotides in length and having a free energy for association from about 5.5 kcal/mole to about 8.0 kcal/mole at a temperature from about 21° C. to about 40° C. and at a salt concentration from about 1 mM to about 100 mM;

$R^4$ and $R^8$ together comprise a detection means selected from the group consisting of fluorescence resonance energy transfer (FRET), lanthamide resonance energy transfer (LRET), fluorescence cross-correlation spectroscopy, fluorescence quenching, fluorescence polarization, flow cytometry, scintillation proximity, luminescence resonance energy transfer, direct quenching, ground-state complex formation, chemiluminescence energy transfer, bioluminescence resonance energy transfer, excimer formation, colorimetric substrates detection, phosphorescence, electro-chemical changes, and redox potential changes;

$R^5$ is an aptamer that binds to a second epitope on the target molecule; and $R^6$ is a flexible linker attaching $R^5$ to $R^7$ by formation of a covalent bond with each of $R^5$ and $R^7$, wherein $R^6$ comprises a bifunctional chemical cross linker and is from 0 to 500 angstroms in length.

Yet another embodiment of the invention encompasses a molecular biosensor having formula (I)
wherein:

$R^1$ is an peptide that binds to a first epitope on a target molecule;

$R^2$ is a flexible linker attaching $R^1$ to $R^3$;

$R^3$ and $R^7$ are a pair of complementary nucleotide sequences having a free energy for association from about 5.5 kcal/mole to about 8.0 kcal/mole at a temperature from about 21° C. to about 40° C. and at a salt concentration from about 1 mM to about 100 mM;

$R^4$ and $R^8$ together comprise a detection means such that when $R^3$ and $R^7$ associate a detectable signal is produced;

$R^5$ is an peptide that binds to a second epitope on the target molecule; and $R^6$ is a flexible linker attaching $R^5$ to $R^7$.

Yet another embodiment of the invention encompasses a molecular biosensor having formula (I)
wherein:

$R^1$ is an antibody that binds to a first epitope on a target molecule;

$R^2$ is a flexible linker attaching $R^1$ to $R^3$;

$R^3$ and $R^7$ are a pair of complementary nucleotide sequences having a free energy for association from about 5.5 kcal/mole to about 8.0 kcal/mole at a temperature from about 21° C. to about 40° C. and at a salt concentration from about 1 mM to about 100 mM;

$R^4$ and $R^8$ together comprise a detection means such that when $R^3$ and $R^7$ associate a detectable signal is produced;

$R^5$ is an antibody that binds to a second epitope on the target molecule; and $R^6$ is a flexible linker attaching $R^5$ to $R^7$.

In each of the foregoing embodiments for molecular biosensors having formula (I), the first nucleic acid construct, $R^1$-$R^2$-$R^3$-$R^4$, and the second nucleic acid construct, $R^5$-$R^6$-$R^7$-$R^8$, may optionally be attached to each other by a linker $R^{LA}$ to create tight binding bivalent ligands. Typically, the attachment is by covalent bond formation. Alternatively, the attachment may be by non covalent bond formation. In one embodiment, $R^{LA}$ attaches $R^1$ of the first nucleic acid construct to $R^5$ of the second nucleic acid construct to form a molecule comprising:

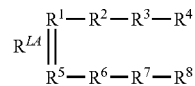

In a further embodiment, $R^{LA}$ attaches $R^2$ of the first nucleic acid construct to $R^6$ of the second nucleic acid construct to form a molecule comprising:

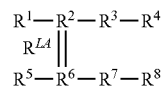

In yet another embodiment, $R^{LA}$ attaches $R^3$ of the first nucleic acid construct to $R^7$ of the second nucleic acid construct to form a molecule comprising:

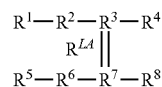

Generally speaking, $R^{LA}$ may be a nucleotide sequence from about 10 to about 100 nucleotides in length. The nucleotides comprising $R^{LA}$ may be any of the nucleotide bases in DNA or RNA (A, C, T, G in the case of DNA, or A, C, U, G in the case of RNA). In one embodiment, $R^{LA}$ is comprised of DNA bases. In another embodiment, $R^{LA}$ is comprised of RNA bases. In yet another embodiment, $R^{LA}$ is comprised of modified nucleic acid bases, such as modified DNA bases or modified RNA bases. Modifications may occur at, but are not restricted to, the sugar 2' position, the C-5 position of pyrimidines, and the 8-position of purines. Examples of suitable modified DNA or RNA bases include 2'-fluoro nucleotides, 2'-amino nucleotides, 5'-aminoallyl-2'-fluoro nucleotides and phosphorothioate nucleotides (monothiophosphate and dithiophosphate). In a further embodiment, $R^2$ and $R^6$ may be nucleotide mimics. Examples of nucleotide mimics include locked nucleic acids (LNA), peptide nucleic acids (PNA), and phosphorodiamidate morpholino oligomers (PMO). Alternatively, $R^{LA}$ may be a polymer of bifunctional chemical linkers.

In one embodiment the bifunctional chemical linker is heterobifunctional. Suitable heterobifunctional chemical linkers include sulfo SMCC (Sulfosuccinimidyl-4-(N-maleimidomethyl)cyclohexane-1-carboxylate), and Ic-SPDP (N-Succinimidyl-6-(3'-(2-PyridylDithio)-Propionamido)-hexanoate). In another embodiment the bifunctional chemical linker is homobifunctional. Suitable homobifunctional linkers include disuccinimidyl suberate, disuccinimidyl glutarate, and disuccinimidyl tartrate. An exemplary $R^{LA}$ is the phosphoramidate form of Spacer 18 comprised of polyethylene glycol. In one embodiment, $R^{LA}$ is from about 1 to about 500 angstroms in length. In another embodiment, $R^{LA}$ is from about 20 to about 400 angstroms in length. In yet another embodiment, $R^{LA}$ is from about 50 to about 250 angstroms in length.

(b) Trivalent Molecular Sensors

In an additional alternative embodiment, the molecular biosensor will be trivalent. In a typical embodiment, the trivalent sensor will comprise a first epitope binding agent that binds to a first epitope on a target molecule, a first linker, a first signaling oligo, a first detection means, a second epitope binding agent that binds to a second epitope on the target molecule, a second linker, a second signaling oligo, a second detection means, a third epitope binding agent that binds to a third epitope on a target molecule, a third linker, a third signaling oligo, and a third detection means.

In one preferred embodiment, the molecular biosensor comprises three nucleic acid constructs, which together have formula (II):

$$R^{15}-R^{14}-R^{13}-R^{9}-R^{10}-R^{11}-R^{12};$$

$$R^{16}-R^{17}-R^{18}-R^{19}; \text{ and}$$

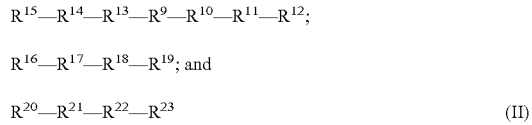

wherein:

$R^9$ is an epitope-binding agent that binds to a first epitope on a target molecule;

$R^{10}$ is a flexible linker attaching $R^9$ to $R^{11}$;

$R^{11}$ and $R^{22}$ are a first pair of complementary nucleotide sequences having a free energy for association from about 5.5 kcal/mole to about 8.0 kcal/mole at a temperature from about 21° C. to about 40° C. and at a salt concentration from about 1 mM to about 100 mM;

$R^{12}$ and $R^{23}$ together comprise a detection means such that when $R^{11}$ and $R^{22}$ associate a detectable signal is produced;

$R^{13}$ is a flexible linker attaching $R^9$ to $R^{14}$;

$R^{14}$ and $R^{18}$ are a second pair of complementary nucleotide sequences having a free energy for association from about 5.5 kcal/mole to about 8.0 kcal/mole at a temperature from about 21° C. to about 40° C. and at a salt concentration from about 1 mM to about 100 mM;

$R^{15}$ and $R^{19}$ together comprise a detection means such that when $R^{14}$ and $R^{18}$ associate a detectable signal is produced;

$R^{16}$ is an epitope-binding agent that binds to a second epitope on a target molecule;

$R^{17}$ is a flexible linker attaching $R^{16}$ to $R^{18}$;

$R^{20}$ is an epitope binding agent that binds to a third epitope on a target molecule; and $R^{21}$ is a flexible linker attaching $R^{20}$ to $R^{22}$.

The choice of epitope binding agents, $R^9$, $R^{16}$ and $R^{20}$, in molecular biosensors having formula (II) can and will vary depending upon the particular target molecule. Generally speaking, suitable choices for $R^9$, $R^{16}$ and $R^{20}$ will include three agents that each recognize distinct epitopes on the same target molecule or on different target molecules. Non-limiting examples of suitable epitope binding agents, depending upon the target molecule(s), include agents selected from the group consisting of an aptamer, an antibody, an antibody fragment, a double-stranded DNA sequence, modified nucleic acids, nucleic acid mimics, a ligand, a ligand fragment, a receptor, a receptor fragment, a polypeptide, a peptide, a coenzyme, a coregulator, an allosteric molecule, and an ion. In one embodiment, $R^9$, $R^{16}$ and $R^{20}$ are each aptamers having a sequence ranging in length from about 20 to about 110 nucleotide bases. In another embodiment, $R^9$, $R^{16}$, and $R^{20}$ are peptides. In yet another embodiment, $R^9$, $R^{16}$, and $R^{20}$ are antibodies or antibody fragments.

In an additional embodiment for molecular biosensors having formula (II), exemplary linkers, $R^{10}$ and $R^{21}$, will functionally keep $R^{11}$ and $R^{22}$ in close proximity such that when $R^9$ and $R^{20}$ each bind to the target molecule(s), $R^{11}$ and $R^{22}$ associate in a manner such that a detectable signal is produced by the detection means, $R^{12}$ and $R^{23}$. In addition, exemplary linkers, $R^{13}$ and $R^{17}$, will functionally keep $R^{14}$ and $R^{18}$ in close proximity such that when $R^9$ and $R^{16}$ each bind to the target molecule(s), $R^{14}$ and $R^{18}$ associate in a manner such that a detectable signal is produced by the detection means, $R^{15}$ and $R^{19}$. In one embodiment, the linkers utilized in molecular biosensors having formula (II) may each be a nucleotide sequence from about 10 to about 100 nucleotides in length. In one embodiment, the linkers are from 10 to about 25 nucleotides in length. In another embodiment, the linkers are from about 25 to about 50 nucleotides in length. In a further embodiment, the linkers are from about 50 to about 75 nucleotides in length. In yet another embodiment, the linkers are from about 75 to about 100 nucleotides in length. In each embodiment, the nucleotides comprising the linkers may be any of the nucleotide bases in DNA or RNA (A, C, T, G in the case of DNA, or A, C, U, G in the case of RNA). In one embodiment, the linkers are comprised of DNA bases. In another embodiment, the linkers are comprised of RNA bases. In yet another embodiment, the linkers are comprised of modified nucleic acid bases, such as modified DNA bases or modified RNA bases. Modifications may occur at, but are not restricted to, the sugar 2' position, the C-5 position of pyrimidines, and the 8-position of purines. Examples of suitable modified DNA or RNA bases include 2'-fluoro nucleotides, 2'-amino nucleotides, 5'-aminoallyl-2'-fluoro nucleotides and phosphorothioate nucleotides (monothiophosphate and dithiophosphate). In a further embodiment, $R^2$ and $R^6$ may be nucleotide mimics. Examples of nucleotide mimics include locked nucleic acids (LNA), peptide nucleic acids (PNA), and phosphorodiamidate morpholino oligomers (PMO). Alternatively, the linkers may be a polymer of bifunctional chemical linkers. In one embodiment the bifunctional chemical linker is heterobifunctional. Suitable heterobifunctional chemical linkers include sulfo SMCC (Sulfosuccinimidyl-4-(N-maleimidomethyl)cyclohexane-1-carboxylate), and Ic-SPDP (N-Succinimidyl-6-(3'-(2-PyridylDithio)-Propionamido)-hexanoate). In another embodiment the bifunctional chemical linker is homobifunctional. Suitable homobifunctional linkers include disuccinimidyl suberate, disuccinimidyl glutarate, and disuccinimidyl tartrate. Additional suitable linkers are illustrated in the Examples, such as the phosphoramidate form of Spacer 18 comprised of polyethylene glycol. In one embodiment, the linkers are from 0 to about 500 angstroms in length. In another embodiment, the linkers are from about 20 to about 400 angstroms in length. In yet another embodiment, the linkers are from about 50 to about 250 angstroms in length.

In a further embodiment for molecular biosensors having formula (II), $R^{11}$ and $R^{22}$ are complementary nucleotide sequences having a length such that they preferably do not associate unless $R^9$ and $R^{20}$ bind to separate epitopes on the target molecule(s). In addition, $R^{14}$ and $R^{18}$ are complementary nucleotide sequences having a length such that they preferably do not associate unless $R^9$ and $R^{16}$ bind to separate epitopes on the target molecule(s). $R^{11}$ and $R^{22}$ and $R^{14}$ and $R^{18}$ may be from about 2 to about 20 nucleotides in length. In another embodiment, $R^{11}$ and $R^{22}$ and $R^{14}$ and $R^{18}$ are from about 4 to about 15 nucleotides in length. In an exemplary embodiment, $R^{11}$ and $R^{22}$ and $R^{14}$ and $R^{18}$ are from about 5 to about 7 nucleotides in length. In one embodiment, $R^{11}$ and $R^{22}$ and $R^{14}$ and $R^{18}$ have a free energy for association from about 5.5 kcal/mole to about 8.0 kcal/mole as measured in the selection buffer conditions, defined below. In another embodiment, $R^{11}$ and $R^{22}$ and $R^{14}$ and $R^{18}$ have a free energy for association from about 6.0 kcal/mole to about 8.0 kcal/mole as measured in the selection buffer conditions defined below. In yet another embodiment, $R^{11}$ and $R^{22}$ and $R^{14}$ and $R^{18}$ have a free energy for association from about 7.0 kcal/mole to 8.0 kcal/mole in the selection buffer conditions. In a preferred embodiment, $R^{11}$ and $R^{22}$ and $R^{14}$ and $R^{18}$ have a free energy for association of 7.5 kcal/mole in the selection buffer conditions described below. Preferably, in each embodiment $R^{11}$ and $R^{22}$ and $R^{14}$ and $R^{18}$ are not complementary to any of $R^9$, $R^{16}$ or $R^{20}$.

In a typical embodiment for molecular biosensors having formula (II), $R^{12}$ and $R^{23}$ may together comprise several suitable detection means such that when $R^{11}$ and $R^{22}$ associate, a detectable signal is produced. In addition, $R^{15}$ and $R^{19}$ may together comprise several suitable detection means such that when $R^{14}$ and $R^{18}$ associate, a detectable signal is produced. Exemplary detections means suitable for use in the molecular biosensors include fluorescent resonance energy transfer (FRET), lanthamide resonance energy transfer (LRET), fluorescence cross-correlation spectroscopy, fluorescence quenching, fluorescence polarization, flow cytometry, scintillation proximity, luminescence resonance energy transfer, direct quenching, ground-state complex formation, chemiluminescence energy transfer, bioluminescence resonance energy transfer, excimer formation, colorimetric substrates detection, phosphorescence, electro-chemical changes, and redox potential changes.

(II) Three-Component Molecular Biosensors

Another aspect of the invention comprises three-component molecular biosensors. In certain embodiments, the three-component molecular biosensor will comprise an endonuclease restriction site. In alternative embodiments, the three-component molecular biosensor will not have an endonuclease restriction site.

(a) Biosensors with No Endonuclease Restriction Site

In one embodiment, the three-component biosensor will comprise: (1) a first epitope binding agent construct that binds to a first epitope on a target molecule, a first linker, a first signaling oligo, and a first detection means; (2) a second epitope binding agent construct that binds to a second epitope on the target molecule, a second linker, a second signaling oligo, and a second detection means; and (3) an oligonucleotide construct that comprises a first region that is complementary to the first oligo and a second region that is complementary to the second oligo. The first signaling oligo and second signaling oligo, as such, are not complementary to each other, but are complementary to two distinct regions on the oligonucleotide construct. Co-association of the two epitope-binding agent constructs with the target molecule results in hybridization of each signaling oligos to the oligonucleotide construct. Binding of the two signaling oligo to the oligonucleotide construct brings them into proximity such that a detectable signal is produced.

In an exemplary embodiment, the three-component molecular biosensor comprises three nucleic acid constructs, which together have formula (III):

$R^{24}$—$R^{25}$—$R^{26}$—$R^{27}$;

$R^{28}$—$R^{29}$—$R^{30}$—$R^{31}$;

O (III)

wherein:

$R^{24}$ is an epitope-binding agent that binds to a first epitope on a target molecule;

$R^{25}$ is a flexible linker attaching $R^{24}$ to $R^{26}$;

$R^{26}$ and $R^{30}$ are a pair of nucleotide sequences that are not complementary to each other, but are complementary to two distinct regions on O;

$R^{27}$ and $R^{31}$ together comprise a detection means such that when $R^{26}$ and $R^{30}$ associate a detectable signal is produced;

$R^{28}$ is an epitope-binding agent that binds to a second epitope on the target molecule;

$R^{29}$ is a flexible linker attaching $R^{28}$ to $R^{30}$; and

O is a nucleotide sequence comprising a first region that is complementary to $R^{26}$, and a second region that is complementary to $R^{30}$.

The choice of epitope binding agents, $R^{24}$ and $R^{28}$, in molecular biosensors having formula (III) can and will vary depending upon the particular target molecule. By way of example, when the target molecule is a protein, $R^{24}$ and $R^{28}$ may be an aptamer, or antibody. By way of further example, when $R^{24}$ and $R^{28}$ are double stranded nucleic acid the target molecule is typically a macromolecule that binds to DNA or a DNA binding protein. In general, suitable choices for $R^{24}$ and $R^{28}$ will include two agents that each recognize distinct epitopes on the same target molecule. In certain embodiments, however, it is also envisioned that $R^{24}$ and $R^{28}$ may recognize distinct epitopes on different target molecules. Non-limiting examples of suitable epitope binding agents, depending upon the target molecule, include agents selected from the group consisting of an aptamer, an antibody, an antibody fragment, a double-stranded DNA sequence, modified nucleic acids, nucleic acid mimics, a ligand, a ligand fragment, a receptor, a receptor fragment, a polypeptide, a peptide, a coenzyme, a coregulator, an allosteric molecule, and an ion. In an exemplary embodiment, $R^{24}$ and $R^{28}$ are each aptamers having a sequence ranging in length from about 20 to about 110 bases. In another embodiment, $R^{24}$ and $R^{28}$ are each antibodies selected from the group consisting of polyclonal antibodies, ascites, Fab fragments, Fab' fragments, monoclonal antibodies, and humanized antibodies. In an alternative embodiment, $R^{24}$ and $R^{28}$ are peptides. In a preferred alternative of this embodiment, $R^{24}$ and $R^{28}$ are each monoclonal antibodies. In an additional embodiment, $R^{24}$ and $R^{28}$ are each double stranded DNA. In a further embodiment, $R^{24}$ is a double stranded nucleic acid and $R^{28}$ is an aptamer. In an additional embodiment, $R^{24}$ is an antibody and $R^{28}$ is an aptamer. In another additional embodiment, $R^{24}$ is an antibody and $R^{28}$ is a double stranded DNA.

In an additional embodiment for molecular biosensors having formula (III), exemplary linkers, $R^{25}$ and $R^{29}$ may each be a nucleotide sequence from about 10 to about 100 nucleotides in length. In one embodiment, $R^{25}$ and $R^{29}$ are from 10 to about 25 nucleotides in length. In another embodiment, $R^2$ and $R^6$ are from about 25 to about 50 nucleotides in length. In a further embodiment, $R^{25}$ and $R^{29}$ are from about 50 to about 75 nucleotides in length. In yet another embodiment, $R^{25}$ and $R^{29}$ are from about 75 to about 100 nucleotides in length. In each embodiment, the nucleotides comprising the linkers may be any of the nucleotide bases in DNA or RNA (A, C, T, G in the case of DNA, or A, C, U, G in the case of RNA). In one embodiment $R^{25}$ and $R^{29}$ are comprised of DNA bases. In another embodiment, $R^{25}$ and $R^{29}$ are comprised of RNA bases. In yet another embodiment, $R^{25}$ and $R^{29}$ are comprised of modified nucleic acid bases, such as modified DNA bases or modified RNA bases. Modifications may occur at, but are not restricted to, the sugar 2' position, the C-5 position of pyrimidines, and the 8-position of purines. Examples of suitable modified DNA or RNA bases include 2'-fluoro nucleotides, 2'-amino nucleotides, 5'-aminoallyl-2'-fluoro nucleotides and phosphorothioate nucleotides (monothiophosphate and dithiophosphate). In a further embodiment, $R^{25}$ and $R^{29}$ may be nucleotide mimics. Examples of nucleotide mimics include locked nucleic acids (LNA), peptide nucleic acids (PNA), and phosphorodiamidate morpholino oligomers (PMO).

Alternatively, $R^{25}$ and $R^{29}$ may be a polymer of bifunctional chemical linkers. In one embodiment the bifunctional chemical linker is heterobifunctional. Suitable heterobifunctional chemical linkers include sulfoSMCC (Sulfosuccinimidyl-4-(N-maleimidomethyl)cyclohexane-1-carboxylate), and Ic-SPDP (N-Succinimidyl-6-(3'-(2-Pyridyl Dithio)-Propionamido)-hexanoate). In another embodiment the bifunctional chemical linker is homobifunctional. Suitable homobifunctional linkers include disuccinimidyl suberate, disuccinimidyl glutarate, and disuccinimidyl tartrate. Additional suitable linkers are illustrated in the Examples, such as the phosphoramidate form of Spacer 18 comprised of polyethylene glycol. In one embodiment, $R^{25}$ and $R^{29}$ are from 0 to about 500 angstroms in length. In another embodiment, $R^{25}$ and $R^{29}$ are from about 20 to about 400 angstroms in length. In yet another embodiment, $R^{25}$ and $R^{29}$ are from about 50 to about 250 angstroms in length.

In a further embodiment for molecular biosensors having formula (III), $R^{26}$ and $R^{30}$ are nucleotide sequences that are not complementary to each other, but that are complementary to two distinct regions of O. $R^{26}$ and $R^{30}$ may be from about 2 to about 20 nucleotides in length. In another embodiment, $R^{26}$ and $R^{30}$ are from about 4 to about 15 nucleotides in length. In an exemplary embodiment, $R^{26}$ and $R^{30}$ are from about 5 to about 7 nucleotides in length. Preferably, in each embodiment $R^{26}$ and $R^{30}$ are not complementary to $R^{24}$ and $R^{28}$.

In a typical embodiment for molecular biosensors having formula (III), $R^{27}$ and $R^{31}$ may together comprise several suitable detection means such that when $R^{26}$ and $R^{30}$ each bind to complementary, distinct regions on O, a detectable signal is produced. Exemplary detections means suitable for use in the molecular biosensors include fluorescent resonance energy transfer (FRET), lanthamide resonance energy transfer (LRET), fluorescence cross-correlation spectroscopy, fluorescence quenching, fluorescence polarization, flow cytometry, scintillation proximity, luminescence resonance energy transfer, direct quenching, ground-state complex formation, chemiluminescence energy transfer, bioluminescence resonance energy transfer, excimer formation, colorimetric substrates detection, phosphorescence, electrochemical changes, and redox potential changes.

For molecular biosensors having formula (III), O comprises a first region that is complementary to $R^{26}$, and a second region that is complementary to $R^{30}$. O may be from about 8 to about 100 nucleotides in length. In other embodiments, O is from about 10 to about 15 nucleotides in length, or from about 15 to about 20 nucleotides in length, or from about 20 to about 25 nucleotides in length, or from about 25 to about 30 nucleotides in length, or from about 30 to about 35 nucleotides in length, or from about 35 to about 40 nucleotides in length, or from about 40 to about 45 nucleotides in length, or from about 45 to about 50 nucleotides in length, or from about 50 to about 55 nucleotides in length, or from about 55 to about 60 nucleotides in length, or from about 60 to about 65 nucleotides in length, or from about 65 to about 70 nucleotides in length, or from about 70 to about 75 nucleotides in length, or from about 75 to about 80 nucleotides in length, or from about 80 to about 85 nucleotides in length, or from about 85 to about 90 nucleotides in length, or from about 90 to about 95 nucleotides in length, or greater than about 95 nucleotides in length.

In an exemplary embodiment, O will comprise formula (IV):

$$R^{32}\text{—}R^{33}\text{—}R^{34}\text{—}R^{35}\text{—}R^{36} \qquad (IV)$$

wherein:

$R^{32}$, $R^{34}$, and $R^{36}$ are nucleotide sequences not complementary to any of $R^{26}$, $R^{30}$, $R^{33}$, or $R^{35}$. $R^{32}$, $R^{34}$, and $R^{36}$ may independently be from about 2 to about 20 nucleotides in length. In other embodiments, $R^{32}$, $R^{34}$, and $R^{36}$ may independently be from about 2 to about 4 nucleotides in length, or from about 4 to about 6 nucleotides in length, or from about 6 to about 8 nucleotides in length, or from about 8 to about 10 nucleotides in length, or from about 10 to about 12 nucleotides in length, or from about 12 to about 14 nucleotides in length, or from about 14 to about 16 nucleotides in length, or from about 16 to about 18 nucleotides in length, or from about 18 to about 20 nucleotides in length, or greater than about 20 nucleotides in length;

$R^{33}$ is a nucleotide sequence complementary to $R^{26}$, and $R^{35}$ is a nucleotide sequence that is complementary to $R^{30}$.

$R^{33}$ and $R^{35}$ generally have a length such that the free energy of association between $R^{33}$ and $R^{26}$ and $R^{35}$ and $R^{30}$ is from about −5 to about −12 kcal/mole at a temperature from about 21° C. to about 40° C. and at a salt concentration from about 1 mM to about 100 mM. In other embodiments, the free energy of association between $R^{33}$ and $R^{26}$ and $R^{35}$ and $R^{30}$ is about −5 kcal/mole, about −6 kcal/mole, about −7 kcal/mole, about −8 kcal/mole, about −9 kcal/mole, about −10 kcal/mole, about −11 kcal/mole, or greater than about −12 kcal/mole at a temperature from about 21° C. to about 40° C. and at a salt concentration from about 1 mM to about 100 mM. In additional embodiments, $R^{33}$ and $R^{35}$ may range from about 4 to about 20 nucleotides in length. In other embodiments, $R^{33}$ and $R^{35}$ may about 4, about 5, about 6, about 7, about 8, about 9, about 10, about 11, about 12, about 13, about 14, about 15, about 16, about 17, about 18, about 19, or greater than about 10 nucleotides in length.

(b) Biosensors with an Endonuclease Restriction Site

In an alternative embodiment, the three-component biosensor will comprise: (1) a first epitope binding agent construct that binds to a first epitope on a target molecule, a first linker, and a first signaling oligo; (2) a second epitope binding agent construct that binds to a second epitope on the target molecule, a second linker, a second signaling oligo and (3) an oligonucleotide construct that comprises a first region that is complementary to the first oligo, a second region that is complementary to the second oligo, two flexible linkers, an endonuclease restriction site overlapping the first and the second regions complementary to the first and the second oligos, and a pair of complementary nucleotides with detection means. The first signaling oligo and second signaling oligo are not complementary to each other, but are complementary to two distinct regions on the oligonucleotide construct. Referring to FIG. 52, when the oligonucleotide construct is intact, the complementary nucleotides are annealed and produce a detectable signal. Co-association of the two epitope-binding agent constructs with the target molecule results in hybridization of each signaling oligo to the oligonucleotide construct. The signaling oligos hybridize to two distinct locations on the oligonucleotide construct such that a double-stranded DNA molecule containing the restriction site is produced, with a gap between the signaling oligos located exactly at the site of endonuclease cleavage in one strand of the double-stranded DNA substrate. When a restriction endonuclease is present, accordingly, it will cleave the oligonucleotide construct only when the target is present (i.e., when the signaling oligos are bound to the oligonucleotide construct). Upon this cleavage, the detection means present on the oligonucleotide are separated-resulting in no detectable signal. Upon dissociation of the cleaved oligonucleotide construct, another oligonucleotide construct may hybridize with the signaling oligos of the two epitope-binding agents co-associated with the target and the cleavage reaction may be repeated. This cycle of hybridization and cleavage may be repeated many times resulting in cleavage of multiple oligonucleotide constructs per one complex of the two epitope-binding agents with the target.

In exemplary alternative of this embodiment, the three-component molecular biosensor comprises three nucleic acid constructs, which together have formula (V):

$$R^{36}-R^{37}-R^{38};$$

$$R^{39}-R^{40}-R^{41}$$

O  (V)

wherein:
- $R^{36}$ is an epitope-binding agent that binds to a first epitope on a target molecule;
- $R^{37}$ is a flexible linker attaching $R^{36}$ to $R^{38}$;
- $R^{38}$ and $R^{41}$ are a pair of nucleotide sequences that are not complementary to each other, but are complementary to two distinct regions on O;
- $R^{39}$ is an epitope-binding agent that binds to a second epitope on the target molecule;
- $R^{40}$ is a flexible linker attaching $R^{39}$ to $R^{41}$; and
- O comprises:
  - $R^{42}$ is a nucleotide construct comprising an endonuclease restriction site, a first region that is complementary to $R^{38}$, and a second region that is complementary to $R^{41}$.
  - $R^{43}$ is a first flexible linker;
  - $R^{44}$ is a first nucleotide sequence that is complementary to $R^{46}$ attached to a detection means;
  - $R^{45}$ is a second flexible linker;
  - $R^{46}$ is a second nucleotide sequence that is complementary to $R^{44}$ attached to a second detection means; and
  - $R^{43}$ attaches $R^{42}$ to $R^{44}$ and $R^{45}$ attaches $R^{42}$ to $R^{46}$.

Suitable linkers, epitope binding agents, and detection means for three-component molecular biosensors having formula (V) are the same as three component molecular biosensors having formula (III). Suitable, endonuclease restriction sites comprising $R^{42}$ include sites that are recognized by restriction enzymes that cleave double stranded nucleic acid, but not single stranded nucleic acid. By way of non-limiting example, these sites include AccI, AgeI, BamHI, BgI, BglII, BsiWI, BstBI, ClaI, CviQI, DdeI, DpnI, DraI, EagI, EcoRI, EcoRV, FseI, FspI, HaeII, HaeIII, HhaI, Hinc II, HinDIII, HpaI, HpaII, KpnI, KspI, MboI, MfeI, NaeI, NarI, NcoI, NdeI, NheI, NotI, PhoI, PstI, PvuI, PvuII, SacI, SacI, SalI, SbfI, SmaI, SpeI, SphI, StuI, TaqI, TfiI, TliI, XbaI, XhoI, XmaI, XmnI, and ZraI. Optionally, $R^{42}$ may comprise nucleotide spacers that precede or follow one or more of the endonuclease restriction site, the first region that is complementary to $R^{38}$, and/or the second region that is complementary to $R^{41}$. Suitable nucleotide spacers, for example, are detailed in formula (IV).

(III) Methods for Selecting Epitope Binding Agents

A further aspect of the invention provides methods for selecting epitope-binding agents, and in particular aptamers for use in making any of the molecular biosensors of the present invention. Generally speaking, epitope binding agents comprising aptamers, antibodies, peptides, modified nucleic acids, nucleic acid mimics, or double stranded DNA may be purchased if commercially available or may be made in accordance with methods generally known in the art.

For example, in vitro methods of selecting peptide epitope binding agents include phage display (Ozawa et al., J. Vet. Med. Sci. 67(12):1237-41, 2005), yeast display (Boder et al., Nat. Biotech. 15:553-57, 1997), ribosome display (Hanes et al., PNAS 94:4937-42, 1997; Lipovsek et al., J. Imm. Methods, 290:51-67, 2004), bacterial display (Francisco et al., PNAS 90:10444-48, 1993; Georgiou et al., Nat. Biotech. 15:29-34, 1997), mRNA display (Roberts et al., PNAS 94:12297-302, 1997; Keefe et al., Nature 410:715-18, 2001), and protein scaffold libraries (Hosse et al., Protein Science 15:14-27, 2006). In one embodiment, the peptide epitope binding agents are selected by phage display. In another embodiment, the peptide epitope binding agents are selected by yeast display. In yet another embodiment, the peptide epitope binding agents are selected via ribosome display. In still yet another embodiment, the peptide epitope binding agents are selected via bacterial display. In an alternative embodiment, the peptide epitope binding agents are selected by mRNA display. In another alternative embodiment, the peptide epitope binding agents are selected using protein scaffold libraries.

The invention, however, provides methods for simultaneously selecting two or more aptamers that each recognize distinct epitopes on a target molecule or on separate target molecules. Alternatively, the invention also provides novel methods directed to selecting at least one aptamer in the presence of an epitope binding agent construct. The aptamer and epitope binding agent construct also each recognize distinct epitopes on a target molecule.

(a) Method for Selection of an Aptamer in the Presence of an Epitope Binding Agent Construct One aspect of the invention encompasses a method for selecting an aptamer in the presence of an epitope binding agent construct. The aptamer and epitope binding agent construct are selected so that they each bind to the same target at two distinct epitopes. Typically, the method comprises contacting a plurality of nucleic acid constructs and epitope-binding agent constructs with a target molecule to form a mixture. The mixture will generally comprise complexes having target molecule bound with nucleic acid constructs and epitope binding agent constructs. According to the method, the complex is isolated from the mixture and the nucleic acid construct is purified from the complex. The aptamer selected by the method of the invention will comprise the purified nucleic acid construct.

In this method of selection, a plurality of nucleic acid constructs is utilized in the presence of the epitope binding agent construct to facilitate aptamer selection. The nucleic acid constructs comprise:

A-B-C-D

The epitope binding agent construct comprises:

P-Q-R wherein:
  A and C are each different DNA sequences from about 10 to about 30 nucleotides in length, A and C together comprising a sequence to prime a polymerase chain reaction for amplifying the aptamer sequence;
  B is a single-stranded nucleotide of random sequence from about 20 to about 110 nucleotides in length that contains specific sequences binding to a first epitope of the target molecule;
  D and R are a pair of complementary nucleotide sequences from about 2 to about 20 nucleotides in length, wherein D and R have a free energy for association from about 5.5 kcal/mole to about 8.0 kcal/mole at a temperature from approximately 21° C. to about 40° C. and at a salt concentration of approximately 1 mM to about 100 mM;
  P is an epitope-binding agent that binds to a second epitope on the target molecule. The epitope binding agent will vary depending upon the embodiment, but is selected from the group comprising an aptamer, an antibody, an antibody fragment, a double-stranded DNA sequence, modified nucleic acids, nucleic acid mimics, a ligand, a ligand fragment, a receptor, a receptor fragment, a polypeptide, a peptide, a coenzyme, a coregulator, an allosteric molecule, and an ion; and
  Q is a flexible linker.

Generally speaking, A and C are each different DNA sequences ranging from about 7 to about 35 nucleotides in length and function as polymerase chain reaction primers to amplify the nucleic acid construct. In another embodiment, A and C range from about 15 to about 25 nucleotides in length. In yet another embodiment, A and C range from about 15 to about 20 nucleotides in length. In still another embodiment, A and C range from about 16 to about 18 nucleotides in length. In an exemplary embodiment, A and C are 18 nucleotides in length. Typically, A and C have an average GC content from about 53% to 63%. In another embodiment, A and C have an average GC content from about 55% to about 60%. In a preferred embodiment, A and C will have an average GC content of about 60%.

B is typically a single-stranded oligonucleotide synthesized by randomly selecting and inserting a nucleotide base (A, C, T, G in the case of DNA, or A, C, U, G in the case of RNA) at every position of the oligonucleotide. In one embodiment, B encodes an aptamer sequence that binds to the first epitope on the target. In another embodiment B is comprised of DNA bases. In yet another embodiment, B is comprised of RNA bases. In another embodiment, B is comprised of modified nucleic acid bases, such as modified DNA bases or modified RNA bases. Modifications may occur at, but are not restricted to, the sugar 2' position, the C-5 position of pyrimidines, and the 8-position of purines. Examples of suitable modified DNA or RNA bases include 2'-fluoro nucleotides, 2'-amino nucleotides, 5'-aminoallyl-2'-fluoro nucleotides and phosphorothioate nucleotides (monothiophosphate and dithiophosphate). In a further embodiment, B is about 20 to 110 nucleotides in length. In another embodiment, B is from about 25 to about 75 nucleotides in length. In yet another embodiment, B is from about 30 to about 60 nucleotides in length.

In one embodiment, D and R are complementary nucleotide sequences from about 2 to about 20 nucleotides in length. In another embodiment, D and R are from about 4 to about 15 nucleotides in length. In a preferred embodiment, D and R are from about 5 to about 7 nucleotides in length. In one embodiment, D and R have a free energy for association from about 5.2 kcal/mole to about 8.2 kcal/mole as measured in the selection buffer conditions, defined below. In another embodiment, D and R have a free energy for association from about 6.0 kcal/mole to about 8.0 kcal/mole as measured in the selection buffer conditions defined below. In yet another embodiment, D and R have a free energy for association from about 7.0 kcal/mole to 8.0 kcal/mole in the selection buffer conditions. In a preferred embodiment, D and R have a free energy for association of 7.5 kcal/mole in the selection buffer conditions described below.

Q may be a nucleotide sequence from about 10 to about 100 nucleotides in length. In one embodiment, Q is from 10 to about 25 nucleotides in length. In another embodiment, Q is from about 25 to about 50 nucleotides in length. In a further embodiment, Q is from about 50 to about 75 nucleotides in length. In yet another embodiment, Q is from about 75 to about 100 nucleotides in length. In each embodiment, the nucleotides may be any of the nucleotide bases in DNA or RNA (A, C, T, G in the case of DNA, or A, C, U, G in the case of RNA). In one embodiment Q is comprised of DNA bases. In another embodiment, Q is comprised of RNA bases. In yet another embodiment, Q is comprised of modified nucleic acid bases, such as modified DNA bases or modified RNA bases. Modifications may occur at, but are not restricted to, the sugar 2' position, the C-5 position of pyrimidines, and the 8-position of purines. Examples of suitable modified DNA or RNA bases include 2'-fluoro nucleotides, 2'-amino nucleotides, 5'-aminoallyl-2'-fluoro nucleotides and phosphorothioate nucleotides (monothiophosphate and dithiophosphate). In a further embodiment, $R^2$ and $R^6$ may be nucleotide mimics. Examples of nucleotide mimics include locked nucleic acids (LNA), peptide nucleic acids (PNA), and phosphorodiamidate morpholino oligomers (PMO). Alternatively, Q may be a polymer of bifunctional chemical linkers. In one embodiment the bifunctional chemical linker is heterobifunctional. Suitable heterobifunctional chemical linkers include sulfoSMCC (Sulfosuccinimidyl-4-(N-maleimidomethyl)cyclohexane-1-carboxylate), and Ic-SPDP (N-Succinimidyl-6-(3'-(2-PyridylDithio)-Propionamido)-hexanoate). In another embodiment the bifunctional chemical linker is homobifunctional. Suitable homobifunctional linkers include disuccinimidyl suberate, disuccinimidyl glutarate, and disuccinimidyl tartrate. Additional suitable linkers are illustrated in the Examples, such as the phosphoramidate form of Spacer 18 comprised of polyethylene glycol. In one embodiment, Q is from 0 to about 500 angstroms in length. In another embodiment, Q is from about 20 to about 400 angstroms in length. In yet another embodiment, Q is from about 50 to about 250 angstroms in length.

In a preferred embodiment, A and C are approximately 18 nucleotides in length and have an average GC content of about 60%; B is about 30 to about 60 nucleotides in length; Q is a linker comprising a nucleotide sequence that is from about 10 to 100 nucleotides in length or a bifunctional chemical linker; and D and R range from about 5 to about 7 nucleotides in length and have a free energy of association of about 7.5 kcal/mole.

As will be appreciated by those of skill in the art, the choice of epitope binding agent, P, can and will vary depending upon the particular target molecule. By way of example, when the target molecule is a protein P may be an aptamer, or antibody. By way of further example, when P is double stranded nucleic acid the target molecule is typically a macromolecule that binds to DNA or a DNA binding protein. Suitable epitope binding agents, depending upon the target molecule, include agents selected from the group consisting of an aptamer, an antibody, an antibody fragment, a double-stranded DNA sequence, modified nucleic acids, nucleic acid mimics, a ligand, a ligand fragment, a receptor, a receptor fragment, a polypeptide, a peptide, a coenzyme, a coregulator, an allosteric molecule, and an ion. In an exemplary embodiment, P is an aptamer sequence ranging in length from about 20 to about 110 bases. In another embodiment, P is an antibody selected from the group consisting of polyclonal antibodies, ascites, Fab fragments, Fab' fragments, monoclonal antibodies, and humanized antibodies. In a preferred embodiment, P is a monoclonal antibody. In an additional embodiment, P is a double stranded DNA. In yet another embodiment, P is a peptide.

Typically in the method, a plurality of nucleic acid constructs, A-B-C-D, are contacted with the epitope bind agent construct, P-Q-R, and the target molecular in the presence of a selection buffer to form a mixture. Several selection buffers are suitable for use in the invention. A suitable selection buffer is typically one that facilitates non-covalent binding of the nucleic acid construct to the target molecule in the presence of the epitope binding agent construct. In one embodiment, the selection buffer is a salt buffer with salt concentrations from about 1 mM to 100 mM. In another embodiment, the selection buffer is comprised of Tris-HCl, NaCl, KCl, and $MgCl_2$. In a preferred embodiment, the selection buffer is comprised of 50 mM Tris-HCl, 100 mM NaCl, 5 mM KCl, and 1 mM $MgCl_2$. In one embodiment, the selection buffer has a pH range from about 6.5 to about 8.5. In another embodiment, the selection buffer has a pH range from about 7.0 to 8.0. In a preferred embodiment, the pH is 7.5. Alternatively, the selection buffer may additionally contain analytes that assist binding of the constructs to the target molecule. Suitable examples of such analytes can include, but are not limited to, protein co-factors, DNA-binding proteins, scaffolding proteins, or divalent ions.

The mixture of the plurality of nucleic acid constructs, epitope-binding agent constructs and target molecules are incubated in selection buffer from about 10 to about 45 min. In yet another embodiment, the incubation is performed for about 15 to about 30 min. Typically, the incubation is performed at a temperature range from about 21° C. to about 40° C. In another embodiment, the incubation is performed at a temperature range from about 20° C. to about 30° C. In yet another embodiment, the incubation is performed at 35° C. In a preferred embodiment, the incubation is performed at 25° C. for about 15 to about 30 min. Generally speaking after incubation, the mixture will typically comprise complexes of the target molecule having nucleic acid construct bound to a first epitope and epitope binding agent construct bound to a second epitope of the target molecule. The mixture will also comprise unbound nucleic acid constructs and epitope binding agent constructs.

The complex comprising the target molecule having bound nucleic acid construct and bound epitope binding agent construct is preferably isolated from the mixture. In one embodiment, nitrocellulose filters are used to separate the complex from the mixture. In an alternative embodiment magnetic beads are used to separate the complex from the mixture. In yet another embodiment sepharose beads can be used to separate the complex from the mixture. In an exemplary embodiment, streptavidin-linked magnetic beads are used to separate the complex from the mixture.

Optionally, the target molecules are subjected to denaturation and then the nucleic acid constructs purified from the complex. In one embodiment, urea is used to denature the target molecule. In a preferred embodiment, 7 M urea in 1M NaCl is used to denature the target molecule. The nucleic acid constructs may be purified from the target molecule by precipitation. In another embodiment, the nucleic acid constructs are precipitated with ethanol. In yet another embodiment, the nucleic acid constructs are precipitated with isopropanol. In one embodiment, the precipitated DNA is resuspended in water. Alternatively, the precipitated DNA is resuspended in TE buffer.

Generally speaking, the purified, resuspended nucleic acid constructs are then amplified using the polymerase chain reaction (PCR). If the nucleic acid construct contains a B comprised of RNA bases, reverse transcriptase is preferably used to convert the RNA bases to DNA bases before initiation of the PCR. The PCR is performed with primers that recognize both the 3' and the 5' end of the nucleic acid constructs in accordance with methods generally known in the art. In one embodiment, either the 3' or 5' primer is attached to a fluorescent probe. In an alternative embodiment, either the 3' or the 5' primer is attached to fluorescein. In another embodiment, either the 3' or 5' primer is biotinylated. In a preferred embodiment, one primer is labeled with fluorescein, and the other primer is biotinylated.

In addition to primers, the PCR reaction contains buffer, deoxynucleotide triphosphates, polymerase, and template nucleic acid. In one embodiment, the PCR can be performed with a heat-stable polymerase. In a preferred embodiment, the concentrations of PCR reactants are outlined in the examples section as follows: 80 µL of dd $H_2O$, 10 µL of 10×PCR buffer, 6 µL of $MgCl_2$, 0.8 µL 25 mM dNTPs, 1 µL 50 µM primer 1 (modified with fluorescein), 1 µL 50 µM primer 2 (biotinylated), 0.5 µL Taq polymerase, and 1 µL of template.

In another embodiment, the PCR consists of a warm-up period, where the temperature is held in a range between about 70° C. and about 74° C. Subsequently, the PCR consists of several cycles (about 8 to about 25) of a) incubating the reaction at a temperature between about 92° C. and about 97° C. for about 20 sec to about 1 min; b) incubating the reaction at a temperature between about 48° C. and about 56° C. for about 20 sec to about 1 min; and c) incubating the reaction at a temperature between about 70° C. and about 74° C. for about 45 sec to about 2 min. After the final cycle, the PCR is concluded with incubation between about 70° C. and about 74° C. for about 3 min to about 10 min. In an alternative embodiment, the reaction consists of 12-18 cycles. A preferred embodiment of the PCR, as outlined in the examples section, is as follows: 5 min at 95° C., sixteen cycles of 30 s at 95° C., 30 s at 50° C., and 1 min at 72° C., and then an extension period of 5 min at 72° C.

Typically after PCR amplification, the double-stranded DNA PCR product is separated from the remaining PCR reactants. One exemplary embodiment for such separation is subjecting the PCR product to agarose gel electrophoresis. In another embodiment, the PCR product is separated in a low melting point agarose gel. In a preferred embodiment, the gel is a native 10% acrylamide gel made in TBE buffer. In one embodiment, the band(s) having the double-stranded DNA PCR product are visualized in the gel by ethidium bromide staining. In another embodiment, the band(s) are visualized by fluorescein fluorescence. Irrespective of the embodiment, the bands are typically excised from the gel by methods generally known in the art.

Generally speaking, the double-stranded gel-purified PCR product is separated into single-stranded DNA in accordance with methods generally known in the art. One such embodiment involves using a basic pH to denature the double helix. In another embodiment, 0.15N NaOH is used to denature the helix. In still another embodiment, streptavidin linked beads are used to separate the denatured DNA strands. In a preferred embodiment, magnetic streptavidin beads are used to separate the denatured DNA strands.

The method of the invention typically involves several rounds of selection, separation, amplification and purification in accordance with the procedures described above until nucleic acid constructs having the desired binding affinity for the target molecule are selected. In accordance with the method, the single-stranded DNA of estimated concentration is used for the next round of selection. In one embodiment, the cycle of selection, separation, amplification, purification, and strand separation is performed from about 4 to about 20 times. In another embodiment, the said cycle is performed from about 12 to about 18 times. In yet another embodiment, the said cycle is performed until the measured binding-activity of the selected nucleic acid constructs reaches the desired strength.

Alternatively, the single DNA strand attached to the streptavidin-linked beads is used as a template for RNA polymerase. In this embodiment, after the RNA polymerase is finished, the supernatant contains the RNA nucleic acid construct that can be used in another round of RNA aptamer selection.

In an alternative method, if a RNA aptamer is being selected, the double-stranded, gel-purified PCR DNA product is transcribed with RNA polymerase to produce a single-stranded RNA construct. In such a case, A will typically contain a sequence encoding a promoter recognized by RNA polymerase. In one embodiment, double-stranded, gel-purified PCR DNA product attached to streptavidin-linked beads is used as a template for RNA polymerase. In this embodiment, after the RNA polymerase reaction, the supernatant containing the RNA nucleic acid construct can used in another round of RNA aptamer selection.

Generally speaking, after the nucleic acid constructs have reached the desired binding specificity, the nucleic acid constructs are cloned, and the cloned DNA is sequenced. In one embodiment, the sequences are used in aptamer constructs either alone or as part of a molecular biosensor.

(b) Method for Simultaneous Selection of Two or More Aptamers

Another aspect of the invention is a method for simultaneously selecting two or more aptamers for use in making molecular biosensors having two or more aptamers. The aptamers selected by the method each bind to the same target molecule at distinct epitopes. Typically, the method comprises contacting a plurality of pairs of nucleic acid constructs with a target molecule to form a mixture. The mixture will generally comprise complexes having target molecule bound with a pair of nucleic acid constructs at distinct epitope sites. According to the method, the complex is isolated from the mixture and the nucleic acid constructs are purified from the complex. The aptamers selected by the method of the invention will comprise the pair of purified nucleic acid constructs.

In the method of the invention, the first nucleic acid constructs comprises:

A-B-C-D

The second nucleic acid construct comprises:

E-F-G-H.

wherein:

A, C, E, and G are each different DNA sequences from about 10 to about 30 nucleotides in length, A and C together comprising a sequence to prime a polymerase chain reaction for amplifying a first aptamer sequence, and E and G together comprising a sequence to prime a polymerase chain reaction for amplifying a second aptamer sequence;

B is a single-stranded nucleotide random sequence from about 20 to about 110 nucleotides in length that contains specific sequences binding to a first epitope of the target molecule;

D and H are a pair of complementary nucleotide sequences from about 2 to about 20 nucleotides in length, wherein D and H have a free energy for association from about 5.5 kcal/mole to about 8.0 kcal/mole at a temperature from approximately 21° C. to about 40° C. and at a salt concentration of approximately 1 mM to about 100 mM; and F is a single-stranded nucleotide random sequence from about 20 to about 110 nucleotides in length that contains specific sequences binding to the second epitope of the target molecule.

In another embodiment, A, C, E and G are each different DNA sequences ranging from about 7 to about 35 nucleotides in length. In another embodiment, A, C, E, and G range from about 15 to about 25 nucleotides in length. In yet another embodiment, A, C, E, and G range from about 15 to about 20 nucleotides in length. In still another embodiment, A, C, E and G range from about 16 to about 18 nucleotides in length. In an exemplary embodiment, A, C, E and G are 18 nucleotides in length. Generally speaking, A, C, E and G have an average GC content from about 53% to 63%. In another embodiment, A, C, E and G have an average GC content from about 55% to about 60%. In a preferred embodiment, A, C, E and G will have an average GC content of about 60%.

In one embodiment, B and F are single-stranded oligonucleotides synthesized by randomly selecting and inserting a nucleotide base (A, C, T, G in the case of DNA, or A, C, U, G in the case of RNA) at every position of the oligonucleotide. In a preferred embodiment, B and F encode an aptamer sequence, such that B binds to the first epitope on the target molecule and F binds to the second epitope on the target molecule. In one embodiment B and F are comprised of DNA bases. In another embodiment, B and F are comprised of RNA bases. In yet another embodiment, B and F are comprised of modified nucleic acid bases, such as modified DNA bases. Modifications may occur at, but are not restricted to, the sugar 2' position, the C-5 position of pyrimidines, and the 9-position of purines. Examples of suitable modified DNA or RNA bases include 2'-fluoro nucleotides, 2'-amino nucleotides, 5'-aminoallyl-2'-fluoro nucleotides and phosphorothioate nucleotides (monothiophosphate and dithiophosphate). In typical embodiments, B and F are about 20 to 110 nucleotides in length. In another embodiment, B and F are from about 25 to about 75 nucleotides in length. In yet another embodiment, B and F are from about 30 to about 60 nucleotides in length.

D and H are complementary nucleotide sequences from about 2 to about 20 nucleotides in length. In another embodiment, D and H are from about 4 to about 15 nucleotides in length. In a preferred embodiment, D and H are from about 5 to about 7 nucleotides in length. In one embodiment, D and H have a free energy for association from about 5.2 kcal/mole to about 8.2 kcal/mole as measured in the selection buffer conditions, defined below. In another embodiment, D and H have a free energy for association from about 6.0 kcal/mole to about 8.0 kcal/mole as measured in the selection buffer conditions. In yet another embodiment, D and H have a free energy for association from about 7.0 kcal/mole to 8.0 kcal/mole in the selection buffer conditions. In a preferred embodiment, D and H have a free energy for association of 7.5 kcal/mole in the selection buffer conditions.

In a preferred embodiment, A, C, E and G are approximately 18 nucleotides in length and have an average GC content of about 60%, B and F are about 30 to about 60 nucleotides in length, and D and H range from about 5 to about 7 nucleotides in length and have a free energy of association of about 7.5 kcal/mole.

The method for simultaneous selection is initiated by contacting a plurality of pairs of the nucleic acid constructs A-B-C-D and E-F-G-H with the target molecule in the presence of a selection buffer to form a complex. Generally speaking, suitable selection buffers allow non-covalent simultaneous binding of the nucleic acid constructs to the target molecule. The method for simultaneous selection then involves the same steps of selection, separation, amplification and purification as described in section (a) above involving methods for the selection of an aptamer in the presence of an epitope binding agent construct, with the exception that the PCR is designed to amplify both nucleic acid constructs (A-B-C-D and E-F-G-H), using primers to A, C, E, and F. Typically several rounds of selection are performed until pairs of nucleic acid constructs having the desired affinity for the target molecule are selected. In one embodiment, the cycle of selection, separation, amplification, purification, and strand separation is performed from about 4 to about 20 times. In another embodiment, the cycle is performed from about 12 to about 18 times. After the pair of nucleic acid constructs has reached the desired binding specificity, the nucleic acid constructs are cloned, and the cloned DNA is sequenced. The resulting nucleic acid constructs comprise a first aptamer that binds to a first epitope on the target molecule and a second aptamer that binds to a second epitope on the target molecule.

In another aspect of the invention, two aptamers can be simultaneously selected in the presence of a bridging construct comprised of S-T-U. In one embodiment, S and U are complementary nucleotide sequences from about 2 to about 20 nucleotides in length. In another embodiment, S and U are from about 4 to about 15 nucleotides in length. In a preferred embodiment, S and U are from about 5 to about 7 nucleotides in length. In one embodiment, S and U have a free energy for association from about 5.2 kcal/mole to about 8.2 kcal/mole as measured in the selection buffer conditions, defined below. In another embodiment, S and U have a free energy for association from about 6.0 kcal/mole to about 8.0 kcal/mole as measured in the selection buffer conditions. In yet another embodiment, S and U have a free energy for association from about 7.0 kcal/mole to 8.0 kcal/mole in the selection buffer conditions. In a preferred embodiment, S and U have a free energy for association of 7.5 kcal/mole in the selection buffer conditions.

T may be a nucleotide sequence from about 10 to about 100 nucleotides in length. In one embodiment, T is from 10 to about 25 nucleotides in length. In another embodiment, T is from about 25 to about 50 nucleotides in length. In a further embodiment, T is from about 50 to about 75 nucleotides in length. In yet another embodiment, T is from about 75 to about 100 nucleotides in length. In each embodiment, the nucleotides may be any of the nucleotide bases in DNA or RNA (A, C, T, G in the case of DNA, or A, C, U, G in the case of RNA). In one embodiment T is comprised of DNA bases. In another embodiment, T is comprised of RNA bases. In yet another embodiment, T is comprised of modified nucleic acid bases, such as modified DNA bases or modified RNA bases. Modifications may occur at, but are not restricted to, the sugar 2' position, the C-5 position of pyrimidines, and the 8-position of purines. Examples of suitable modified DNA or RNA bases include 2'-fluoro nucleotides, 2'-amino nucleotides, 5'-aminoallyl-2'-fluoro nucleotides and phosphorothioate nucleotides (monothiophosphate and dithiophosphate). In a further embodiment, $R^2$ and $R^6$ may be nucleotide mimics. Examples of nucleotide mimics include locked nucleic acids (LNA), peptide nucleic acids (PNA), and phosphorodiamidate morpholino oligomers (PMO). Alternatively, T may be a polymer of bifunctional chemical linkers. In one embodiment the bifunctional chemical linker is heterobifunctional. Suitable heterobifunctional chemical linkers include sulfoSMCC (Sulfosuccinimidyl-4-(N-maleimidomethyl)cyclohexane-1-carboxylate), and Ic-SPDP (N-Succinimidyl-6-(3'-(2-PyridylDithio)-Propionamido)-hexanoate). In another embodiment the bifunctional chemical linker is homobifunctional. Suitable homobifunctional linkers include disuccinimidyl suberate, disuccinimidyl glutarate, and disuccinimidyl tartrate. Additional suitable linkers are illustrated in the Examples, such as the phosphoramidate form of Spacer 18 comprised of polyethylene glycol. In one embodiment, Q is from 0 to about 500 angstroms in length. In another embodiment, Q is from about 20 to about 400 angstroms in length. In yet another embodiment, Q is from about 50 to about 250 angstroms in length.

In one embodiment, S is complementary to D and U is complementary to H. In another embodiment, S and U will not bind to D and H unless S, U, D, and H are brought in close proximity by the A-B-C-D construct and the E-F-G-H construct binding to the target.

In this embodiment of the invention utilizing the bridging construct, the method is initiated in the presence of nucleic acid constructs A-B-C-D and E-F-G-H, and the bridging construct S-T-U. Generally speaking, the method is performed as described with the same steps detailed above. In one embodiment, after the final round of selection, but before cloning, the bridging construct is ligated to the A-B-C-D construct and the E-F-G-H construct. This embodiment allows the analysis of pairs of selected nucleic acid sequences that are best suited for use in a molecular biosensor.

(c) Selection of Aptamers by In Vitro Evolution

A further aspect of the invention encompasses selection of aptamers by in vitro evolution in accordance with methods generally known in the art.

In another embodiment, the invention is directed to a method of making a set of aptamer constructs, comprising a first and second aptamer construct, comprising the steps of (a) selecting a first aptamer against a first substrate, which comprises a first epitope, and selecting a second aptamer against a second substrate, which comprises a second epitope, wherein the first aptamer is capable of binding to the first epitope and the second aptamer is capable of binding to the second epitope, (b) attaching a first label to the first aptamer and attaching a second label to the second aptamer, (c) attaching a first signaling oligo to the first aptamer and attaching a second signaling oligo to the second aptamer, wherein the second signaling oligo is complementary to the first signaling oligo, and (d) such that (i) the first aptamer construct comprises the first aptamer, the first label and the first signaling oligo, and (ii) the second aptamer construct comprises the second aptamer, the second label and the second signaling oligo. Preferably, the aptamers are selected using in vitro evolution methods, however, natural DNA binding elements may be used in the practice of this invention.

In a preferred embodiment, the first substrate is a polypeptide and the second substrate is the polypeptide bound to the first aptamer, wherein the first aptamer masks the first epitope, such that the first epitope is not available for the second aptamer to bind. Alternatively, the first aptamer may be replaced by a first aptamer construct that contains (i) the first aptamer and signaling oligo, or (ii) the first aptamer, signaling oligo and label, thereby producing a second substrate that allows for the selection of the optimum second aptamer or aptamer construct for signal detection. As a further step, the first and second aptamer constructs may then be joined together by a flexible linker, as described above.

In an alternate preferred embodiment, the first substrate is a peptide consisting essentially of the first epitope and the second substrate is a peptide consisting essentially of the second epitope. Thus, in this alternate embodiment, there is no need to mask an epitope in the production or selection of aptamers. Again, the first and second aptamer constructs created by this method may be linked together by a flexible linker, as described above.

(IV) Methods Utilizing the Molecular Biosensors

A further aspect of the invention encompasses the use of the molecular biosensors of the invention in several applications. In certain embodiments, the molecular biosensors are utilized in methods for detecting one or more target molecules. In other embodiments, the molecular biosensors may be utilized in kits and for therapeutic and diagnostic applications.

(a) Detection Methods

In one embodiment, the molecular biosensors may be utilized for detection of a target molecule. The method generally involves contacting a molecular biosensor of the invention with the target molecule. To detect a target molecule utilizing two-component biosensors, the method typically involves target-molecule induced co-association of two epitope-binding agents (present in the molecular biosensor of the invention) that each recognize distinct epitopes on the target molecule. The epitope-binding agents each comprise complementary signaling oligonucleotides that are labeled with detection means and are attached to the epitope-binding agents through a flexible linker. Co-association of the two epitope-binding agents with the target molecule results in bringing the two signaling oligonucleotides into proximity such that a detectable signal is produced. Typically, the detectable signal is produced by any of the detection means known in the art or as described herein. Alternatively, for three-component biosensors, co-association of the two epitope-binding agent constructs with the target molecule results in hybridization of each signaling oligos to the oligonucleotide construct. Binding of the two signaling oligo to the oligonucleotide construct brings them into proximity such that a detectable signal is produced.

In one particular embodiment, a method for the detection of a target molecule that is a protein or polypeptide is provided. The method generally involves detecting a polypeptide in a sample comprising the steps of contacting a sample with a molecular biosensor of the invention. By way of non-limiting example, several useful molecular biosensors are illustrated in FIGS. 24, 33 and 38. Panel 24A depicts a molecular biosensor comprising two aptamers recognizing two distinct epitopes of a protein. Panel 24B depicts a molecular biosensor comprising a double stranded polynucleotide containing binding site for DNA binding protein and an aptamer recognizing a distinct epitope of the protein. Panel 24C depicts a molecular biosensor comprising an antibody and an aptamer recognizing distinct epitopes of the protein. Panel 24D depicts a molecular biosensor comprising a double stranded polynucleotide containing a binding site for a DNA binding protein and an antibody recognizing a distinct epitope of the protein. Panel 24E depicts a molecular biosensor comprising two antibodies recognizing two distinct epitopes of the protein. Panel 24F depicts a molecular biosensor comprising two double stranded polynucleotide fragments recognizing two distinct sites of the protein. Panel 24G depicts a molecular biosensor comprising two single stranded polynucleotide elements recognizing two distinct sequence elements of another single stranded polynucleotide. Panel 24H depicts a molecular biosensor that allows for the direct detection of formation of a protein-polynucleotide complex using a double stranded polynucleotide fragment (containing the binding site of the protein) labeled with a first signaling oligonucleotide and the protein labeled with a second signaling oligonucleotide. Panel 24I depicts a molecular biosensor that allows for the direct detection of the formation of a protein-protein complex using two corresponding proteins labeled with signaling oligonucleotides. FIG. 33 depicts a tri-valent biosensor that allows for detection of a target molecule or complex with three different epitope binding agents. FIG. 38 depicts a competitive biosensor that allows detection of a target competitor in a solution.

In another embodiment, the molecular biosensors may be used to detect a target molecule that is a macromolecular complex in a sample. In this embodiment, the first epitope is preferably on one polypeptide and the second epitope is on another polypeptide, such that when a macromolecular complex is formed, the one and another polypeptides are bought into proximity, resulting in the stable interaction of the first aptamer construct and the second aptamer construct to produce a detectable signal, as described above. Also, the first and second aptamer constructs may be fixed to a surface or to each other via a flexible linker, as described above.

In another embodiment, the molecular biosensors may be used to detect a target molecule that is an analyte in a sample. In this embodiment, when the analyte is bound to a polypeptide or macromolecular complex, a first or second epitope is created or made available to bind to a first or second aptamer construct. Thus, when an analyte is present in a sample that contains its cognate polypeptide or macromolecular binding partner, the first aptamer construct and the second aptamer construct are brought into stable proximity to produce a detectable signal, as described above. Also, the first and second aptamer constructs may be fixed to a surface or to each other via a flexible linker, as described above.

(b) Solid Surfaces

Optionally, the invention also encompasses a solid surface having the molecular constructs of the invention attached thereto. For example, in an embodiment for two-component biosensors, the first epitope binding agent construct may be fixed to a surface, the second epitope binding agent construct may be fixed to a surface, or both may be fixed to a surface. Non-limiting examples of suitable surfaces include microtitre plates, test tubes, beads, resins and other polymers, as well as other surfaces either known in the art or described herein. In a preferred embodiment, the first aptamer construct and the second aptamer construct may be joined with each other by a flexible linker to form a bivalent aptamer. Preferred flexible linkers include Spacer 18 polymers and deoxythymidine ("dT") polymers.

Referring to FIGS. 54 and 56, in an exemplary embodiment the solid surface utilizes a three-component biosensor. In this embodiment, the oligonucleotide construct (e.g., O as described in (II), and S3 as described in the examples and figures) may be immobilized on a solid surface. The first epitope binding agent and second epitope binding agent (e.g., S1 and S2 in the figure) are contacted with the surface comprising immobilized O and a sample that may comprise a target (e.g., T in figure). In the presence of target, the first epitope binding agent, second epitope binding agent, and target bind to immobilized O to form a complex. Several methods may be utilized to detect the presence of the complex comprising target. The method may include detecting a probe attached to the epitope-binding agents after washing out the unbound components. Alternatively, several surface specific real-time detection methods may be employed, including but not limited to surface plasmon resonance (SPR) or total internal reflection fluorescence (TIRF).

The oligonucleotide construct, O, may be immobilized to several types of suitable surfaces. The surface may be a material that may be modified to contain discrete individual sites appropriate for the attachment or association of the three-component biosensor and is amenable to at least one detection method. Non-limiting examples of surface materials include glass, modified or functionalized glass, plastics (including acrylics, polystyrene and copolymers of styrene and other materials, polypropylene, polyethylene, polybutylene, polyurethanes, TeflonJ, etc.), nylon or nitrocellulose, polysaccharides, nylon, resins, silica or silica-based materials including silicon and modified silicon, carbon, metals, inorganic glasses and plastics. The size and shape of the surface may also vary without departing from the scope of the invention. A surface may be planar, a surface may be a well, i.e. a 364 well plate, or alternatively, a surface may be a bead or a slide.

The oligonucleotide construct, O, may be attached to the surface in a wide variety of ways, as will be appreciated by those in the art. O, for example, may either be synthesized first, with subsequent attachment to the surface, or may be directly synthesized on the surface. The surface and O may be derivatized with chemical functional groups for subsequent attachment of the two. For example, the surface may be derivatized with a chemical functional group including, but not limited to, amino groups, carboxyl groups, oxo groups or thiol groups. Using these functional groups, the O may be attached using functional groups either directly or indirectly using linkers. Alternatively, O may also be attached to the surface non-covalently. For example, a biotinylated O can be prepared, which may bind to surfaces covalently coated with streptavidin, resulting in attachment. Alternatively, O may be synthesized on the surface using techniques such as photopolymerization and photolithography. Additional methods of attaching O to a surface and methods of synthesizing O on surfaces are well known in the art, i.e. VLSIPS technology from Affymetrix (e.g., see U.S. Pat. No. 6,566,495, and Rockett and Dix, "DNA arrays: technology, options and toxicological applications," Xenobiotica 30(2):155-177, all of which are hereby incorporated by reference in their entirety).

(c) Competition Assays

In a further embodiment, a competitive molecular biosensor can be used to detect a competitor in a sample. Typically, the molecular biosensor used for competition assays will be a two-component molecular biosensor, as detailed in section (I) above. In an exemplary embodiment, the competitive molecular biosensor will comprise two epitope binding agents, which together have formula (VI)

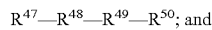

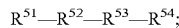 (VI)

wherein:
$R^{47}$ is an epitope-binding agent that binds to a first epitope on a target molecule;
$R^{48}$ is a flexible linker attaching $R^{47}$ to $R^{49}$;
$R^{49}$ and $R^{53}$ are a pair of complementary nucleotide sequences having a free energy for association from about 5.5 kcal/mole to about 8.0 kcal/mole at a temperature from about 21° C. to about 40° C. and at a salt concentration from about 1 mM to about 100 mM;
$R^{50}$ and $R^{54}$ together comprise a detection means such that when $R^{49}$ and $R^{53}$ associate a detectable signal is produced;
$R^{51}$ is an epitope binding agent that binds to $R^{47}$; and
$R^{52}$ is a flexible linker attaching $R^{51}$ to $R^{53}$.

In another alternative, the competitive molecular biosensor will comprise formula (VII) wherein:
$R^{47}$ is a peptide, a small molecule, or protein epitope-binding agent that binds to a first epitope on a target molecule;
$R^{48}$ is a flexible linker attaching $R^{47}$ to $R^{49}$;
$R^{49}$ and $R^{53}$ are a pair of complementary nucleotide sequences having a free energy for association from about 5.5 kcal/mole to about 8.0 kcal/mole at a temperature from about 21° C. to about 40° C. and at a salt concentration from about 1 mM to about 100 mM;
$R^{50}$ and $R^{54}$ together comprise a detection means such that when $R^{49}$ and $R^{53}$ associate a detectable signal is produced;
$R^{51}$ is an antibody or antibody fragment epitope binding agent that binds to $R^{47}$; and
$R^{52}$ is a flexible linker attaching $R^{51}$ to $R^{53}$.

For each embodiment for competitive molecular biosensors having formula (VI), suitable flexible linkers, complementary nucleotide sequences, detection means, and epitope binding agents are described in section (I) for two-component molecular biosensors having formula (I).

To detect the presence of a target, referring to FIGS. 38 and 39, the molecular biosensor is comprised of two epitope binding agents—the first epitope binding agent is a peptide that is a solvent exposed epitope of a target protein, and the second epitope binding agent is an antibody which binds to the first epitope binding agent. When the biosensor is in solution without the target, a signal is created because the first epitope binding agent and the second epitope binding agent bind, thereby bringing the first signaling oligo and the second signaling oligo into close proximity, producing a detectable signal from the first and second label. When the target competitive protein (comprising the solvent exposed epitope used for the first epitope binding agent) is added to the biosensor, the target protein competes with the first epitope binding agent for binding to the second epitope binding agent. This competition displaces the first epitope-binding agent from the second epitope binding agent, which destabilizes the first signaling oligo from the second signaling oligo, resulting in a decrease in signal. The decrease in signal can be used as a measurement of the concentration of the competitive target, as illustrated in example 5.

(d) Use of Biosensors with No Detection Means

Alternatively, in certain embodiments it is contemplated that the molecular biosensor may not include a detections means. By way of example, when the molecular biosensor is a bivalent aptamer construct, the bivalent aptamer construct may not have labels for detection. It is envisioned that these alternative bivalent aptamer constructs may be used much like antibodies to detect molecules, bind molecules, purify molecules (as in a column or pull-down type of procedure), block molecular interactions, facilitate or stabilize molecular interactions, or confer passive immunity to an organism. It is further envisioned that the bivalent aptamer construct can be used for therapeutic purposes. This invention enables the skilled artisan to build several combinations of aptamers that recognize any two or more disparate epitopes form any number of molecules into a bivalent, trivalent, or other multivalent aptamer construct to pull together those disparate molecules to test the effect or to produce a desired therapeutic outcome. For example, a bivalent aptamer construct may be constructed to facilitate the binding of a ligand to its receptor in a situation wherein the natural binding kinetics of that ligand to the receptor is not favorable (e.g., insulin to insulin receptor in patients suffering diabetes.)

(e) Kits

In another embodiment, the invention is directed to a kit comprising a first epitope binding agent, to which is attached a first label, and a second epitope binding agent, to which is attached a second label, wherein (a) when the first epitope binding agent and the second epitope binding agent bind to a first epitope of a polypeptide and a second epitope of the polypeptide, respectively, (b) the first label and the second label interact to produce a detectable signal. In a preferred embodiment the epitope-binding agent is an aptamer construct, which comprises an aptamer, a label and a signaling oligo. However, the epitope-binding agent may be an antibody, antibody fragment, or peptide. The kit is useful in the detection of polypeptides, analytes or macromolecular complexes, and as such, may be used in research or medical/veterinary diagnostics applications.

(f) Diagnostics

In yet another embodiment, the invention is directed to a method of diagnosing a disease comprising the steps of (a) obtaining a sample from a patient, (b) contacting the sample with a first epitope binding agent construct and a second epitope binding agent construct, and (c) detecting the presence of a polypeptide, analyte or macromolecular complex in the sample using a detection method, wherein the presence of the polypeptide, analyte or macromolecular complex in the sample indicates whether a disease is present in the patient. In a one embodiment, (a) the first epitope binding agent construct is a first aptamer to which a first label and a first signaling oligo are attached, (b) the second epitope binding agent construct is a second aptamer to which a second label and a second signaling oligo, which is complementary to the first signaling oligo, are attached, and (c) the detection method is a fluorescence detection method, wherein, (d) when the first aptamer binds to the polypeptide and the second aptamer binds to the polypeptide, (e) the first signaling oligo and the second signaling oligo associate with each other, and (f) the first label is brought into proximity to the second label such that a change in fluorescence occurs. In another embodiment, (a) the first epitope binding agent construct is a first peptide to which a first label and a first signaling oligo are attached, (b) the second epitope binding agent construct is a second peptide to which a second label and a second signaling oligo, which is complementary to the first signaling oligo, are attached, and (c) the detection method is a fluorescence detection method, wherein, (d) when the first aptamer binds to the polypeptide and the second aptamer binds to the polypeptide, (e) the first signaling oligo and the second signaling oligo associate with each other, and (f) the first label is brought into proximity to the second label such that a change in fluorescence occurs. In yet another embodiment, (a) the first epitope binding agent construct is a first antibody to which a first label and a first signaling oligo are attached, (b) the second epitope binding agent construct is a second antibody to which a second label and a second signaling oligo, which is complementary to the first signaling oligo, are attached, and (c) the detection method is a fluorescence detection method, wherein, (d) when the first aptamer binds to the polypeptide and the second aptamer binds to the polypeptide, (e) the first signaling oligo and the second signaling oligo associate with each other, and (f) the first label is brought into proximity to the second label such that a change in fluorescence occurs. In other embodiments, the first epitope binding agent and the second epitope-binding agents are different types of epitope binding agents (i.e. an antibody and a peptide, an aptamer and an antibody, etc.). Preferred samples include blood, urine, ascites, cells and tissue samples/biopsies. Preferred patients include humans, farm animals and companion animals.

In yet another embodiment, the invention is directed to a method of screening a sample for useful reagents comprising the steps of (a) contacting a sample with a first epitope binding agent construct and a second epitope binding agent construct, and (b) detecting the presence of a useful reagent in the sample using a detection method. Preferred reagents include a polypeptide, which comprises a first epitope and a second epitope, an analyte that binds to a polypeptide (in which case the method further comprises the step of adding the polypeptide to the screening mixture) and a potential therapeutic composition. In one embodiment, (a) the first epitope binding agent is a first aptamer to which a first label and a first signaling oligo are attached, (b) the second epitope binding agent is a second aptamer to which a second label and a second signaling oligo, which is complementary to the first signaling oligo, are attached, and (c) the detection method is a fluorescence detection method, wherein, (d) when the first aptamer binds to the polypeptide and the second aptamer binds to the polypeptide, (e) the first signaling oligo and the second signaling oligo associate with each other, and (f) the first label is brought into proximity to the second label such that a change in fluorescence occurs. In another embodiment, (a) the first epitope binding agent is a first peptide to which a first label and a first signaling oligo are attached, (b) the second epitope binding agent is a second peptide to which a second label and a second signaling oligo, which is complementary to the first signaling oligo, are attached, and (c) the detection method is a fluorescence detection method, wherein, (d) when the first aptamer binds to the polypeptide and the second aptamer binds to the polypeptide, (e) the first signaling oligo and the second signaling oligo associate with each other, and (f) the first label is brought into proximity to the second label such that a change in fluorescence occurs. In yet another embodiment, (a) the first epitope binding agent is a first antibody to which a first label and a first signaling oligo are attached, (b) the second epitope binding agent is a second antibody to which a second label and a second signaling oligo, which is complementary to the first signaling oligo, are attached, and (c) the detection method is a fluorescence detection method, wherein, (d) when the first aptamer binds to the polypeptide and the second aptamer binds to the polypeptide, (e) the first signaling oligo and the second signaling oligo associate with each other, and (f) the first label is brought into proximity to the second label such that a change in fluorescence occurs. In other embodiments, the first epitope binding agent and the second epitope-binding agents are different types of epitope binding agents (i.e. an antibody and a peptide, an aptamer and an antibody, etc.).

DEFINITIONS

As used herein, the term "analyte" refers generally to a ligand, chemical moiety, compound, ion, salt, metal, enzyme, secondary messenger of a cellular signal transduction pathway, drug, nanoparticle, environmental contaminant, toxin, fatty acid, steroid, hormone, carbohydrate, amino acid, peptide, polypeptide, protein or other amino acid polymer, microbe, virus or any other agent which is capable of binding to a polypeptide, protein or macromolecular complex in such a way as to create an epitope or alter the availability of an epitope for binding to an aptamer.

The term "antibody" generally means a polypeptide or protein that recognizes and can bind to an epitope of an antigen. An antibody, as used herein, may be a complete antibody as understood in the art, i.e., consisting of two heavy chains and two light chains, or be selected from a group comprising polyclonal antibodies, ascites, Fab fragments, Fab' fragments, monoclonal antibodies, chimeric antibodies, humanized antibodies, and a peptide comprising a hypervariable region of an antibody.

The term "aptamer" refers to a polynucleotide, generally a RNA or a DNA that has a useful biological activity in terms of biochemical activity, molecular recognition or binding attributes. Usually, an aptamer has a molecular activity such as binding to a target molecule at a specific epitope (region). It is generally accepted that an aptamer, which is specific in its binding to any polypeptide, may be synthesized and/or identified by in vitro evolution methods.

As used herein, "detection method" means any of several methods known in the art to detect a molecular interaction event. The phrase "detectable signal", as used herein, is essentially equivalent to "detection method." Detection methods include detecting changes in mass (e.g., plasmin resonance), changes in fluorescence (e.g., fluorescent resonance energy transfer (FRET), lanthamide resonance energy transfer (LRET), FCCS, fluorescence quenching or increasing fluorescence, fluorescence polarization, flow cytometry), enzymatic activity (e.g., depletion of substrate or formation of a product, such as a detectable dye—NBT-BCIP system of alkaline phosphatase is an example), changes in chemiluminescence or scintillation (e.g., scintillation proximity assay, luminescence resonance energy transfer, bioluminescence resonance energy transfer and the like), and ground-state complex formation, excimer formation, colorimetric substance detection, phosphorescence, electro-chemical changes, and redox potential changes.

The term "epitope" refers generally to a particular region of a target molecule. Examples include an antigen, a hapten, a molecule, a polymer, a prion, a microbe, a cell, a peptide, polypeptide, protein, or macromolecular complex. An epitope may consist of a small peptide derived from a larger polypeptide. An epitope may be a two or three-dimensional surface or surface feature of a polypeptide, protein or macromolecular complex that comprises several non-contiguous peptide stretches or amino acid groups.

The term "epitope binding agent" refers to a substance that is capable of binding to a specific epitope of an antigen, a polypeptide, a protein or a macromolecular complex. Non-limiting examples of epitope binding agents include aptamers, thioaptamers, double-stranded DNA sequence, peptides and polypeptides, ligands and fragments of ligands, receptors and fragments of receptors, antibodies and fragments of antibodies, polynucleotides, coenzymes, coregulators, allosteric molecules, peptide nucleic acids, locked nucleic acids, phosphorodiamidate morpholino oligomers (PMO) and ions. Peptide epitope binding agents include ligand regulated peptide epitope binding agents.

The term "epitope binding agent construct" refers to a construct that contains an epitope-binding agent and can serve in a "molecular biosensor" with another molecular biosensor. Preferably, an epitope binding agent construct also contains a "linker," and a "signaling oligo". Epitope binding agent constructs can be used to initiate the aptamer selection methods of the invention. A first epitope binding agent construct and a second epitope binding agent construct may be joined together by a "linker" to form a "bivalent epitope binding agent construct." An epitope binding agent construct can also be referred to as a molecular recognition construct. An aptamer construct is a special kind of epitope binding agent construct wherein the epitope binding agent is an aptamer.

The phrase "in vitro evolution" generally means any method of selecting for an aptamer that binds to a biomolecule, particularly a peptide or polypeptide. In vitro evolution is also known as "in vitro selection", "SELEX" or "systematic evolution of ligands by exponential enrichment." Briefly, in vitro evolution involves screening a pool of random polynucleotides for a particular polynucleotide that binds to a biomolecule or has a particular activity that is selectable. Generally, the particular polynucleotide (i.e., aptamer) represents a very small fraction of the pool, therefore, a round of aptamer amplification, usually via polymerase chain reaction, is employed to increase the representation of potentially useful aptamers. Successive rounds of selection and amplification are employed to exponentially increase the abundance of the particular and useful aptamer. In vitro evolution is described in Famulok, M.; Szostak, J. W., In Vitro Selection of Specific Ligand Binding Nucleic Acids, Angew. Chem. 1992, 104, 1001. (Angew. Chem. Int. Ed. Engl. 1992, 31, 979-988.); Famulok, M.; Szostak, J. W., Selection of Functional RNA and DNA Molecules from Randomized Sequences, Nucleic Acids and Molecular Biology, Vol 7, F. Eckstein, D. M. J. Lilley, Eds., Springer Verlag, Berlin, 1993, pp. 271; Klug, S.; Famulok, M., All you wanted to know about SELEX; Mol. Biol. Reports 1994, 20, 97-107; and Burgstaller, P.; Famulok, M. Synthetic ribozymes and the first deoxyribozyme; Angew. Chem. 1995, 107, 1303-1306 (Angew. Chem. Int. Ed. Engl. 1995, 34, 1189-1192), which are incorporated herein by reference.

In the practice of certain embodiments of the invention, in vitro evolution is used to generate aptamers that bind to distinct epitopes of any given polypeptide or macromolecular complex. Aptamers are selected against "substrates", which contain the epitope of interest. As used herein, a "substrate" is any molecular entity that contains an epitope to which an aptamer can bind and that is useful in the selection of an aptamer.

The term "label", as used herein, refers to any substance attachable to a polynucleotide, polypeptide, aptamer, nucleic acid component, or other substrate material, in which the substance is detectable by a detection method. Non-limiting examples of labels applicable to this invention include but are not limited to luminescent molecules, chemiluminescent molecules, fluorochromes, fluorescent quenching agents, colored molecules, radioisotopes, scintillants, massive labels (for detection via mass changes), biotin, avidin, streptavidin, protein A, protein G, antibodies or fragments thereof, Grb2, polyhistidine, Ni2+, Flag tags, myc tags, heavy metals, enzymes, alkaline phosphatase, peroxidase, luciferase, electron donors/acceptors, acridinium esters, and colorimetric substrates. The skilled artisan would readily recognize other useful labels that are not mentioned above, which may be employed in the operation of the present invention.

As used herein, the term "macromolecular complex" refers to a composition of matter comprising a macromolecule. Preferably, these are complexes of one or more macromolecules, such as polypeptides, lipids, carbohydrates, nucleic acids, natural or artificial polymers and the like, in association with each other. The association may involve covalent or non-covalent interactions between components of the macromolecular complex. Macromolecular complexes may be relatively simple, such as a ligand bound polypeptide, relatively complex, such as a lipid raft, or very complex, such as a cell surface, virus, bacteria, spore and the like. Macromolecular complexes may be biological or non-biological in nature.

The term "molecular biosensor" and "molecular beacon" are used interchangeably herein to refer to a construct comprised of at least two epitope binding agent constructs. The molecular biosensor can be used for detecting or quantifying the presence of a target molecule using a chemical-based system for detecting or quantifying the presence of an analyte, a prion, a protein, a nucleic acid, a lipid, a carbohydrate, a biomolecule, a macromolecular complex, a fungus, a microbial organism, or a macromolecular complex comprised of biomolecules using a measurable read-out system as the detection method.

The phrase "natural cognate binding element sequence" refers to a nucleotide sequence that serves as a binding site for a nucleic acid binding factor. Preferably the natural cognate binding element sequence is a naturally occurring sequence that is recognized by a naturally occurring nucleotide binding factor.

The term "nucleic acid construct" refers to a molecule comprising a random nucleic acid sequence flanked by two primers. Preferably, a nucleic acid construct also contains a signaling oligo. Nucleic acid constructs are used to initiate the aptamer selection methods of the invention.

The term "signaling oligo" means a short (generally 2 to 15 nucleotides, preferably 5 to 7 nucleotides in length) single-stranded polynucleotide. Signaling oligos are typically used in pairs comprising a first signaling oligo and a second signaling oligo. Preferably, the first signaling oligo sequence is complementary to the second signaling oligo. Preferably, the first signaling oligo and the second signaling oligo can not form a stable association with each other through hydrogen bonding unless the first and second signaling oligos are brought into close proximity to each other through the mediation of a third party agent.

EXAMPLES

The following examples illustrate various iterations of the invention.

Example 1

General Method for Preparing Specific Aptamer Constructs Introduction

Figure 1A:
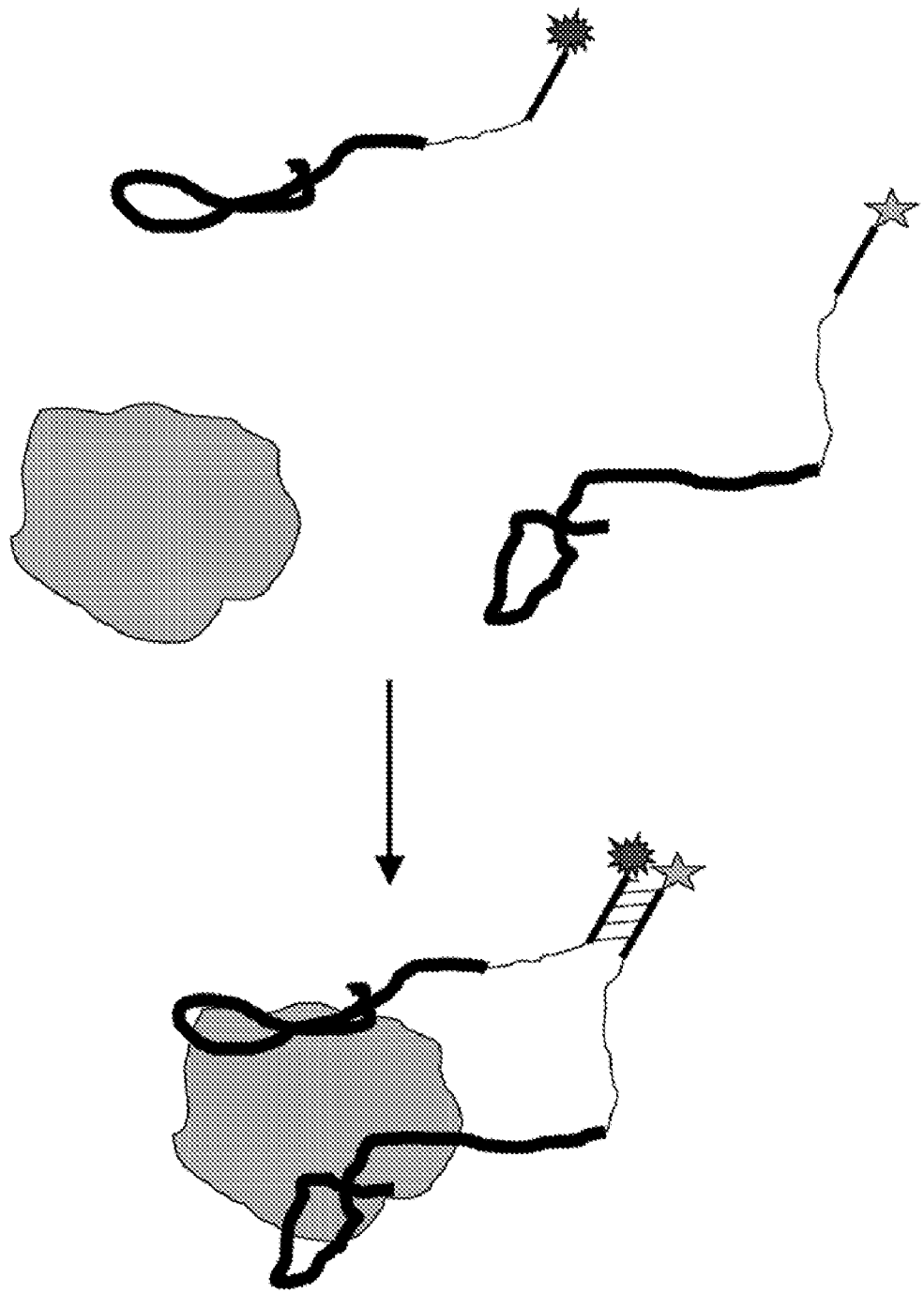
FIG. 1. Overall design of molecular beacons for detecting proteins. (A) Variant of the design for targets lacking natural DNA binding activity. The beacon in this case will be composed of two aptamers developed to recognize two different epitopes of the protein. (B) Variant of the design for a target exhibiting natural DNA binding activity. The beacon in this case will be composed of a short double-stranded DNA fragment containing the DNA sequence corresponding to the DNA-binding site and an aptamer developed to recognize a different epitope of the protein.
Figure 1B:
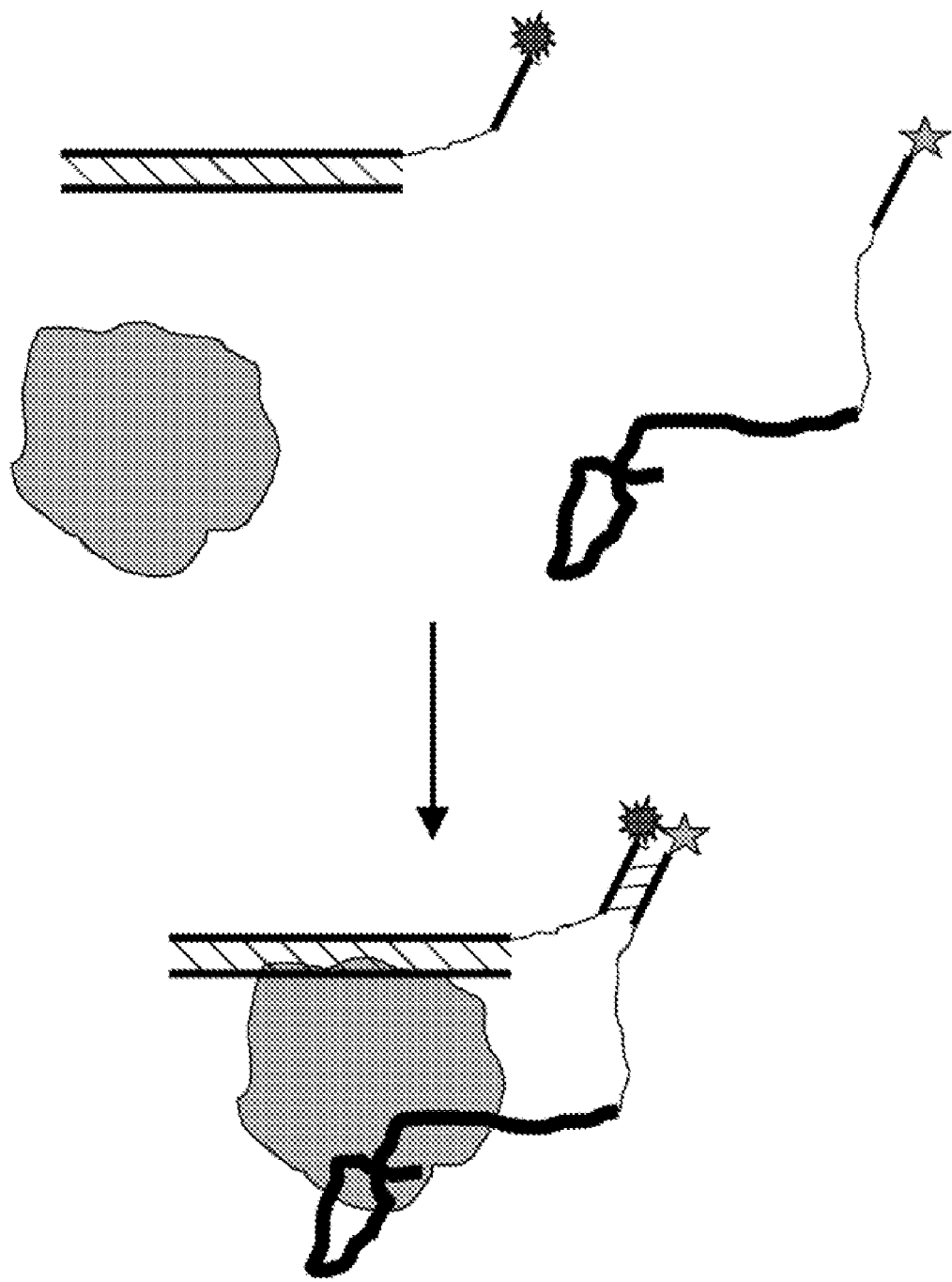

Disclosed is a method for the rapid and sensitive detection of proteins, protein complexes, or analytes that bind to proteins. This method is based on the protein-driven association of two constructs containing aptamers that recognize two distinct epitopes of a protein (a.k.a. "aptamer constructs") (FIG. 1A). These two aptamer constructs contain short complementary signaling oligonucleotides attached to the aptamers through a flexible linker. Upon the simultaneous binding of the two aptamers to the target protein, the complementary oligonucleotides (a.k.a. "signaling oligos") are brought into relative proximity that promotes their association to form a stable duplex. Attaching fluorescence probes to the ends of the signaling oligos provides a means of detecting the protein-induced association of the two aptamers constructs (FIG. 1A). In the case of proteins that possess natural nucleic acid binding activity, one of the aptamers can be substituted with a nucleic acid sequence containing the DNA-binding sequence that the protein naturally binds to protein (FIG. 1B).

Development or selection of aptamers directed to two distinct epitopes of a given protein is an essential step in developing the aptamer constructs depicted in FIG. 1. Review of the available literature on aptamers reveals at least two possible approaches to achieve this goal. The first approach is to perform in vitro selection (a.k.a. in vitro evolution) of nucleic acid aptamers using different methods for the separation of protein-bound and protein-unbound nucleic acid aptamers. The rationale here is that in these different partitioning methods different regions of the protein are preferentially displayed resulting in aptamers directed to different regions of the protein surface. Aptamers selected to thrombin (infra) are an example of such an approach.

The in vitro selection of a first aptamer using as a substrate thrombin immobilized on agarose beads resulted in an aptamer binding the thrombin at the heparin exosite. Additional in vitro selection using as a substrate the thrombin-first aptamer complex, which was bound to nitrocellulose as the partitioning method, resulted in a second aptamer binding the thrombin at the fibrinogen exosite.

While useful, this partitioning approach relies on the chance selection of distinct epitopes rather than on intelligent design. The second approach is to raise or select the aptamers using as substrates peptides that correspond to selected regions of the target protein molecule. There is evidence in the art, which demonstrates that such strategy can be used to develop aptamers capable of recognizing the intact protein from which the peptide used as a substrate for aptamer development was derived. Furthermore, this approach has been widely used to generate antibodies, which recognize an intact protein.

The general approach for preparing a set of aptamers directed to an epitope of the protein distinct from the binding site of the first aptamer can be also used for proteins that possess natural DNA binding activity. That is, co-aptamers, which bind the substrate protein at a site distinct from the natural DNA binding site, can be produced. Co-aptamers produced by this method are optimized for functioning in the molecular detection method depicted in FIG. 1.

Results and Discussion

Figure 2:
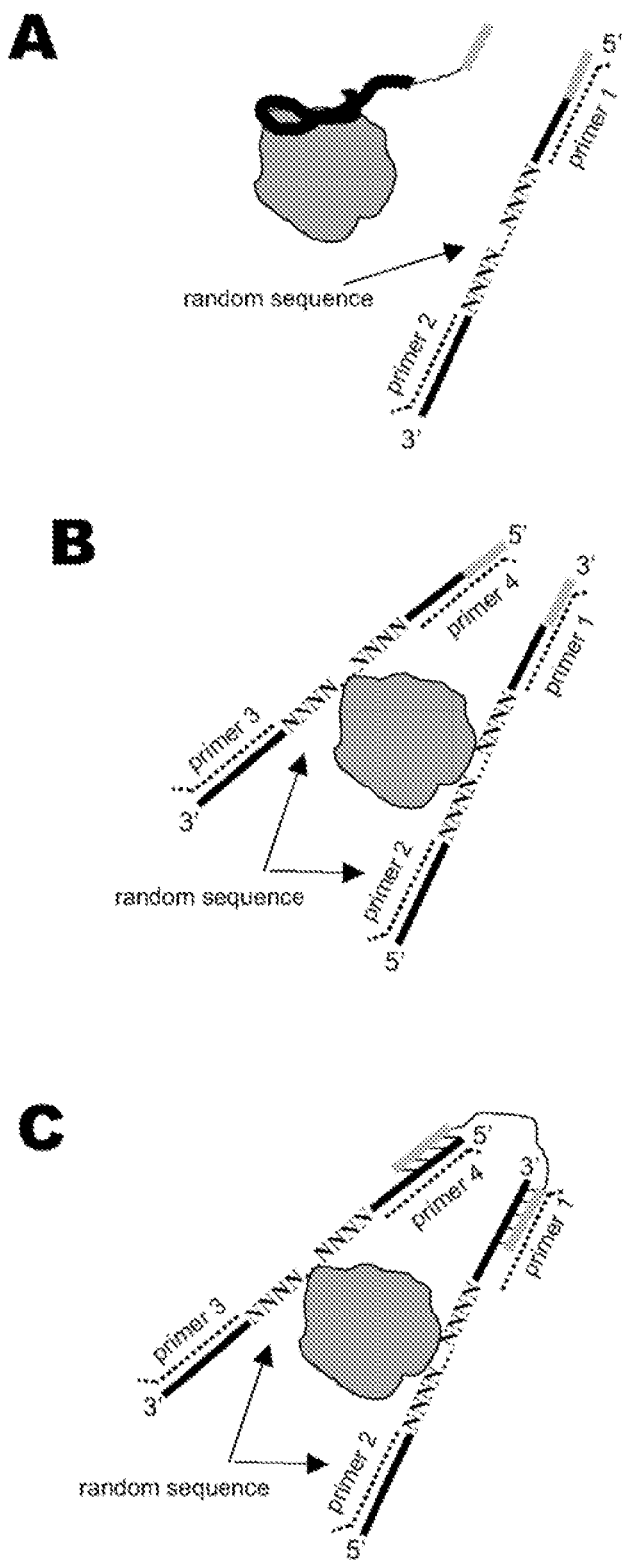
FIG. 2. Methods for preparing aptamers to be used in molecular biosensors. (A) Selection of an aptamer in the presence of a known aptamer construct. The in vitro evolution process is initiated with a nucleic acid construct, an aptamer construct (composed of a known aptamer (thick black line), a linker (thin black line), and a short oligonucleotide sequence (light gray bar)), and the target (gray). The light gray bars depict complementary short oligonucleotide sequences. (B) Simultaneous selection of two aptamers that bind distinct epitopes of the same target (gray). The in vitro evolution process is initiated with two types of nucleic acid constructs (the primer1-2 construct and the primer3-4 construct) and the target. The light gray bars depict short complementary sequences at the end of the two types of nucleic acid constructs. (C) Alternative design for simultaneous selection of two aptamers that bind distinct epitopes of the same target (gray). An additional pair of short oligonucleotides (light gray bars) connected by a flexible linker is present during the selection process. These oligonucleotides will be complementary to short oligonucleotide sequences at the end of the nucleic acid constructs (in primer 1 and primer 4). Their presence during selection will provide a bias towards selecting pairs of aptamers capable of simultaneously binding to the target. Before cloning of the selected nucleic acid constructs the pairs of selected sequences will be ligated to preserve the information regarding the preferred pairs between various selected constructs. (D) Selection of an aptamer in the presence of a known antibody construct. The in vitro evolution process is initiated with a nucleic acid construct, an antibody construct (composed of a known antibody (black), a linker, and a short oligonucleotide sequence (light gray)), and the target (gray). The light gray colored bars depict complementary short oligonucleotide sequences. (E) Selection of an aptamer in the presence of a known double-stranded DNA construct. The in vitro evolution process is initiated with a nucleic acid construct, an aptamer construct (composed of a known double-stranded DNA sequence (black), a linker, and a short oligonucleotide sequence (light gray)), and the target (gray). The light gray bars depict complementary short oligonucleotide sequences.
Figure 2:
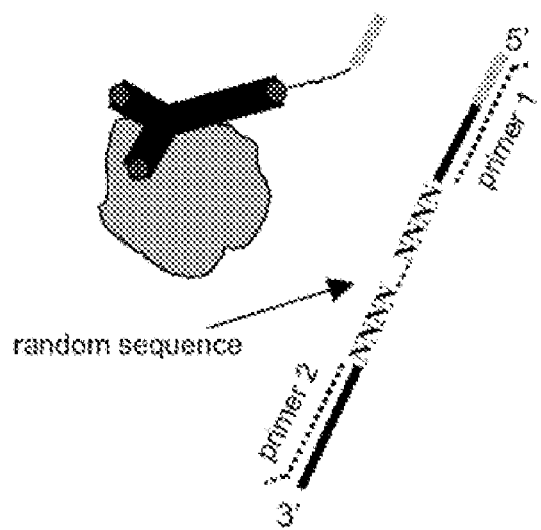
Figure 2:
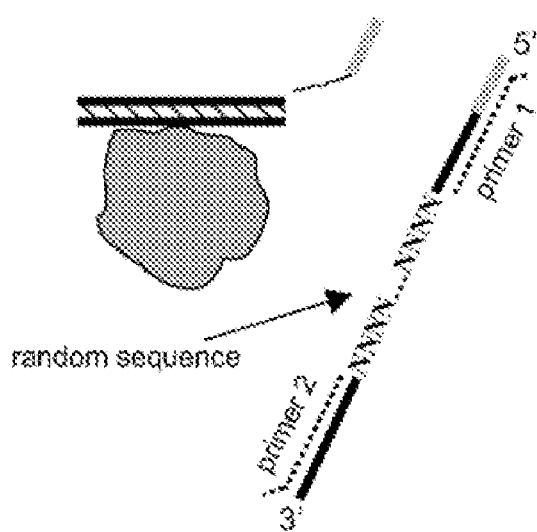

FIG. 2 summarizes five possible methods for selecting aptamers useful in the practice of the invention. Panel A depicts the selection of an additional aptamer in the presence of a target bound to a known aptamer. The nucleic acid construct is comprised of a signaling oligo, represented by the light gray bar, and two primers flanking a random DNA sequence. In practice, the signaling oligo is treated as a specific subpart of the primer in the nucleic acid construct. A complimentary signaling oligo is attached to the pre-selected aptamer via a long flexible linker. Here, the process begins by combining the nucleic acid construct, the target, and the known aptamer construct. Selection of aptamers using such a random DNA (or RNA) construct will be biased towards aptamers capable of binding to the target at an epitope distinct from the epitope of the known aptamer construct, and that will function in molecular biosensors depicted in FIG. 3B.

An alternative scenario is depicted in panel B of FIG. 2, which describes the simultaneous selection of two aptamers binding two distinct epitopes of the target. The nucleic acid constructs are comprised of signaling oligos (represented by the light gray bars at the end of primer 1 and primer 4) and two primers flanking either side of a random-sequence. There are at least two different types of nucleic acid constructs, each type containing unique primer sequences. In panel B, one type contains primers 1 and 2, and the second contains primers 3 and 4. In this example, the process begins with combining both types of nucleic acid constructs, and the target. Selection of aptamers using such random DNA (or RNA) constructs will be biased towards aptamers capable of binding to the target simultaneously at two distinct epitopes of the protein, and that will function in sensors depicted in FIG. 3B.

Panel C of FIG. 2 depicts an alternative design for simultaneous selection of two aptamers binding two distinct epitopes of the target. In addition to the two different types of nucleic acid constructs, a third bridging construct is used. The bridging construct comprises an additional pair of short oligonucleotides (light gray bars) connected by a flexible linker. These oligonucleotides will be complementary to the short oligonucleotides at the end of the nucleic acid constructs. The presence of the bridging construct during selection will provide a bias towards selecting pairs of aptamers capable of simultaneously binding the target. Before cloning of the selected aptamers (after the last selection) the pairs of selected sequences will be enzymatically ligated using T4 ligase to preserve the information regarding the preferred pairs between various selected aptamers.

In a fourth alternate embodiment, a second aptamer can be selected in the presence of a target bound by an antibody (FIG. 2D). The signaling oligo in the nucleic acid construct, depicted by the light gray bar, is complementary to the signaling oligo attached to the antibody via a long flexible linker. The process begins by combining the nucleic acid construct, the target, and the antibody construct. Selection of an aptamer using such a random DNA (or RNA) construct will be biased towards aptamers able to bind to the protein at an epitope distinct from the antibody epitope and will function in sensors depicted in FIG. 24C.

In a fifth alternate embodiment, a second aptamer can be selected in the presence of the target bound to a double-stranded DNA fragment (FIG. 2E). The signaling oligo in the nucleic acid construct, depicted by the light gray bar, is complementary to the signaling oligo attached to the double-stranded DNA construct via a long flexible linker. The process begins by combining the nucleic acid construct, the target, and the double-stranded DNA construct. Selection of an aptamer using such a random DNA (or RNA) construct will be biased towards aptamers able to bind to the target at a site distinct from the double-stranded DNA binding site and will function in sensors depicted in FIG. 1B or 24B.

Example 2

Methods and Aptamers for Detecting Thrombin

Introduction

Figure 3A:
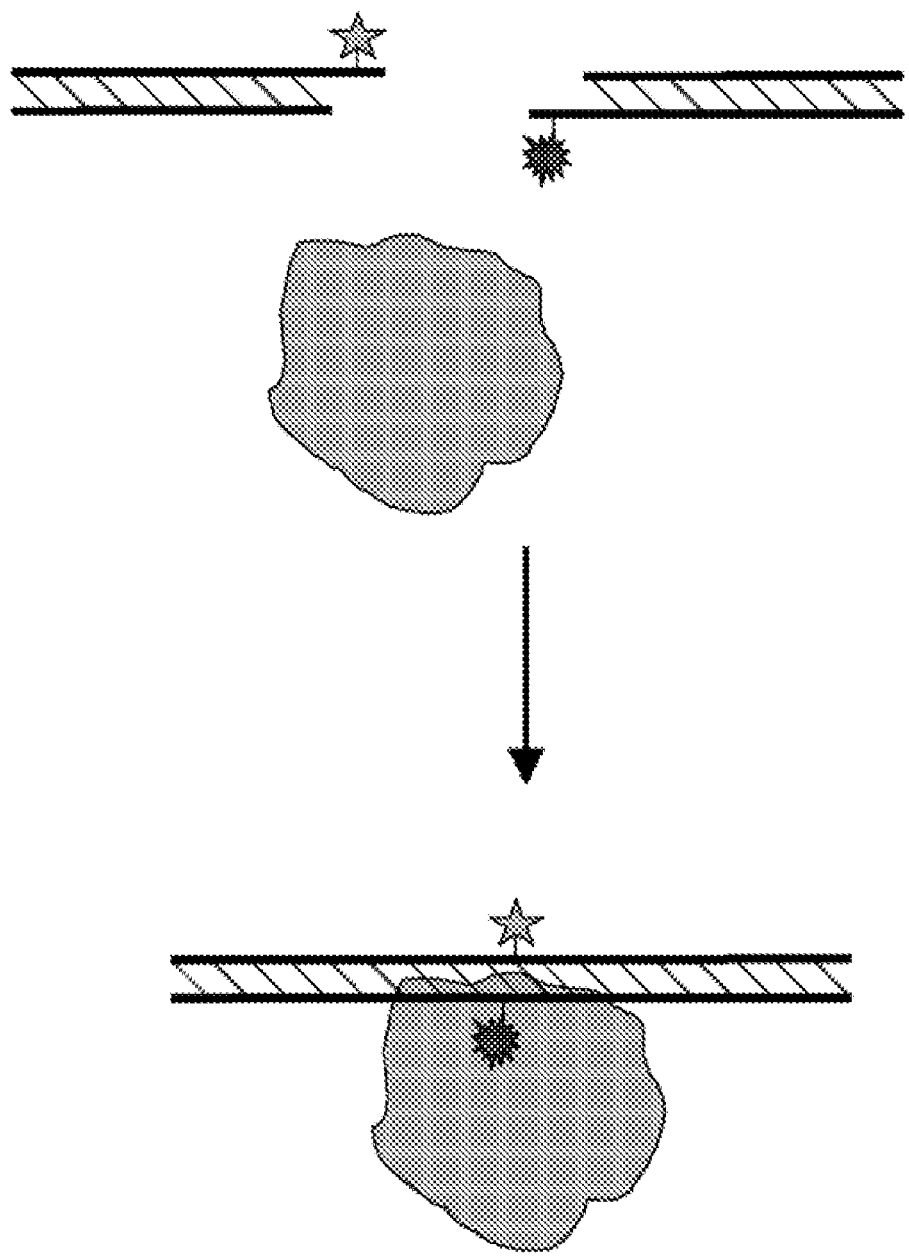
FIG. 3. Comparison of the design of molecular beacons for DNA binding proteins (A) and molecular beacons for detecting proteins based on aptamers directed to two different epitopes of the protein (B).

The inventors of the instant invention have developed a methodology for detecting DNA binding proteins, as described in Heyduk, T. and Heyduk, E. "Molecular beacons for detecting DNA binding proteins," Nature Biotechnology, 20, 171-176, 2002, Heyduk, E., Knoll, E., and Heyduk, T. "Molecular beacons for detecting DNA binding proteins: mechanism of action," Analyt. Biochem. 316, 1-10, 2003, and copending patent applications Ser. No. 09/928,385, which issued as U.S. Pat. No. 6,544,746, Ser. No. 10/062,064, PCT/US02/24822 and PCT/US03/02157, all of which are incorporated herein by reference. This methodology is based on splitting the DNA binding site for a protein into two DNA "half-sites" (FIG. 3A). Each of the resulting "half-sites" contains a short complementary single-stranded region of the length designed to introduce some propensity for the two DNA "half-sites" to associate recreating the duplex containing the fully functional cognate protein binding site. This propensity is designed to be low such that in the absence of the protein only a small fraction of DNA half-sites will associate. When the protein is present in the reaction mixture, it will bind only to the duplex containing a full and functional binding site. This selective binding drives the association of DNA half-sites and this protein-dependent association can be used to generate a spectroscopic or other signal reporting the presence of the target protein.

The term "molecular beacons" is used in the scientific literature to describe this assay in order to emphasize the fact that the selective recognition and generation of the reporting signal occur simultaneously. Molecular beacons for DNA binding proteins have been developed for several proteins (Heyduk and Heyduk, 2002) illustrating their general applicability. Their physical mechanism of action has been established (Heyduk, Knoll and Heyduk, 2003) and they have also been used as a platform for the assay detecting the presence of ligands binding to DNA binding proteins (Heyduk, E., Fei, Y., and Heyduk, T. Homogenous fluorescence assay for cAMP. Combinatorial Chemistry and High-throughput Screening 6, 183-194, 2003). While already very useful, this assay is limited to proteins, which exhibit natural DNA binding activity.

It has been well established that nucleic acid (DNA or RNA) aptamers capable of specific binding to proteins lacking natural DNA binding activity can be produced by in vitro selection methods (Ellington, A. D., and Szostak, J. W. In vitro selection of RNA molecules that bind specific ligands. Nature 346, 818-822, 1990; Tuerk, C., and Gold, L. Systematic evolution of ligands by exponential enrichment: RNA ligands to bacteriophage T4 DNA polymerase. Science 249, 505-510, 1990; Gold, L., Polisky, B., Uhlenbeck, O. & Yarus, M. Diversity of Oligonucleotide Function. Ann. Rev. Biochem. 64, 763-797, 1995; and Wilson, D. S. & Szostak, J. W. In vitro selection of functional nucleic acids. Ann. Rev. Biochem. 68, 611-647, 1999; all of which are incorporated herein by reference). In vitro selection involves selection of nucleic acid sequences, which bind to a specific substrate target, from a pool of random DNA sequences by cycles of binding, washing out unbound sequences and PCR amplification of target-bound sequences. Numerous examples of the successful selection of aptamers that specifically bind to a variety of proteins as well as other target molecules (Ellington and Szostak, 1990; Tuerk and Gold, 1990; Gold et alia, 1995; Wilson and Szostak, 1999) provide a strong indication that producing aptamers to any and all proteins is possible.

Described in this example is the novel concept of nucleic acid-based molecular beacons for protein detection, which is not limited to proteins with natural DNA binding activity. The example of thrombin (infra) provides experimental validation for this invention.

Results and Discussion

Figure 3B:
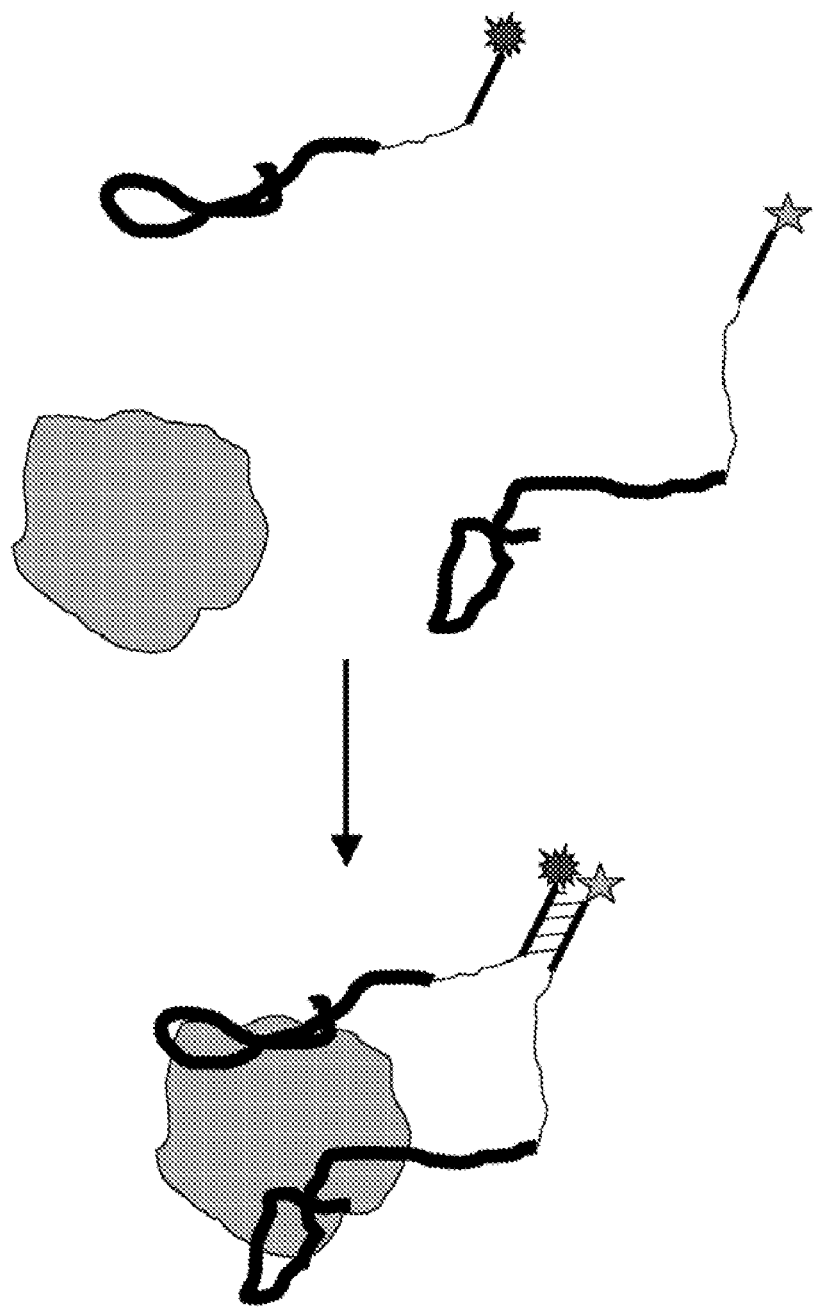

FIG. 3 illustrates the overall concept of molecular beacons recognizing any target protein. This design shares some general similarities with molecular beacons for DNA binding proteins described previously and supra (FIG. 3A). Instead of splitting the DNA duplex containing the natural binding site for a protein into the two "half-sites", two aptamers recognizing two different epitopes of the protein are used as functional equivalents of the "half-sites." Short complementary oligonucleotides (signaling oligos) containing the fluorophore (first label) and the quencher (second label) are attached to the two aptamers via a flexible linker (FIG. 3B). In the absence of the target protein, the two aptamer constructs do not associate since the complementary signal oligos are too short to promote association. In the presence of the target protein, the preferential binding of the protein to the two aptamers should drive the association of the two aptamers constructs resulting in a fluorescence signal change due to bringing the first and second labels into close proximity.

Figure 4:
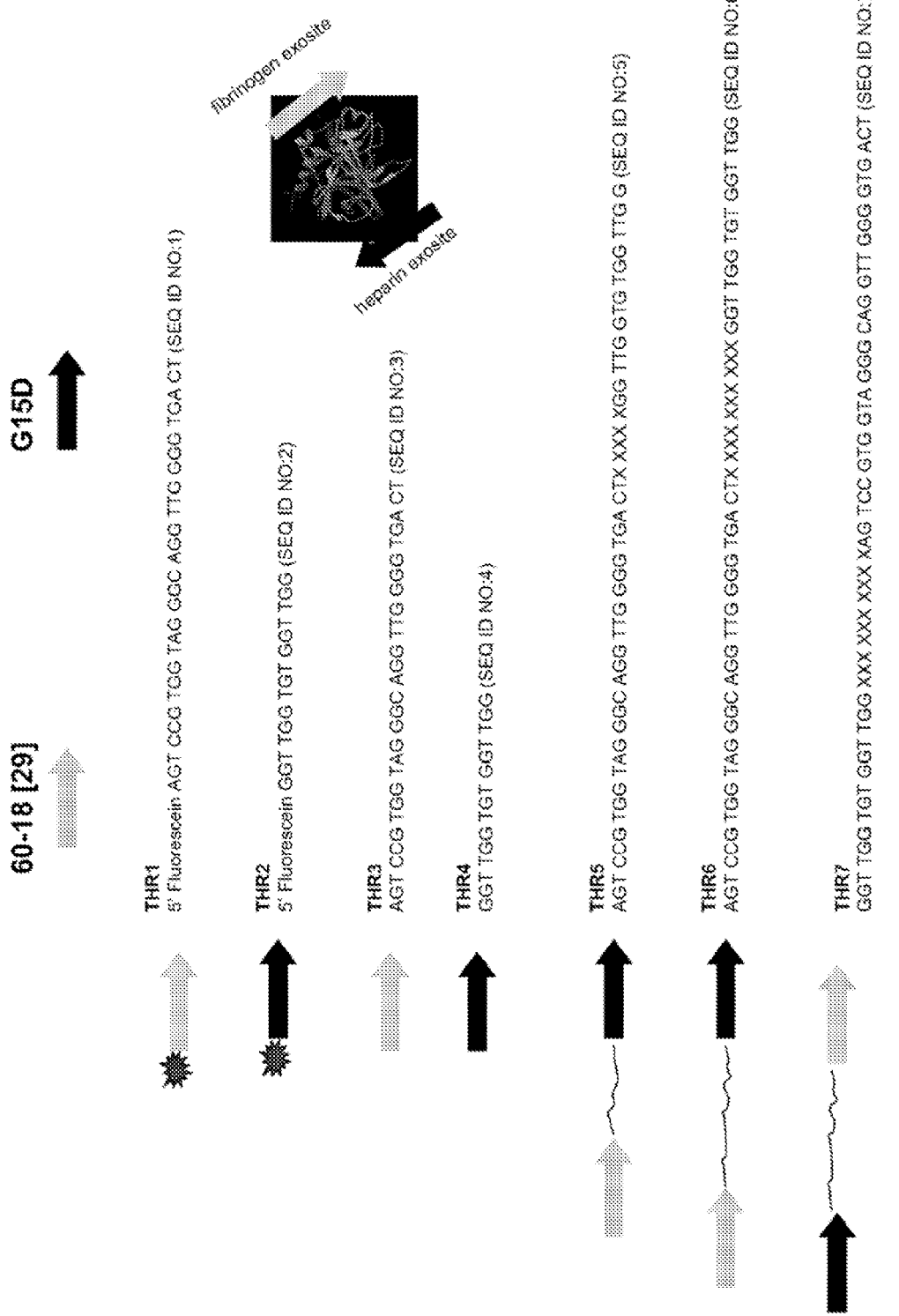
FIG. 4. Aptamer constructs containing aptamers binding thrombin at fibrinogen exosite (60-18 [29]) (gray arrow) and at heparin exosite (G15D) (black arrow).

Thrombin was selected as a model non-DNA-binding-protein system to provide experimental verification of the concept illustrated in FIG. 3B. Two laboratories have previously identified DNA aptamers that selectively recognized two distinct epitopes of the protein (Bock, L. C., Griffin, L. C., Latham, J. A., Vermass, E. H., and Toole, J. J. Selection of single-stranded DNA molecules that bind and inhibit human thrombin, Nature 355, 564-566, 1992; and Tasset, D. M., Kubik, M. F., and Steiner, W. Oligonucleotide inhibitors of human thrombin that bind distinct epitopes, J. Mol. Biol. 272, 688 98, 1997, which are incorporated herein by reference). Oligonucleotide constructs used herein are listed in Table 1. One aptamer (G15D; THR4 in FIG. 4) was shown to bind to the heparin exosite whereas the other aptamer (60-18 [29]; THR3 in FIG. 4) was shown to bind to the fibrinogen exosite. As a first step towards developing a set of aptamer constructs useful for recognizing thrombin, we prepared various aptamer constructs in which the above aptamers were covalently linked by flexible linkers (FIG. 4). The primary purpose of these experiments was to determine if indeed linking the two aptamer constructs with a flexible linker would produce a bivalent aptamer construct capable of binding thrombin with higher affinity compared to a set of individual aptamer constructs. A second purpose of these experiments was to establish a suitable length of the linker and the appropriate orientation of 5' and 3' ends of the two aptamers with respect to the linker.

Figure 5:
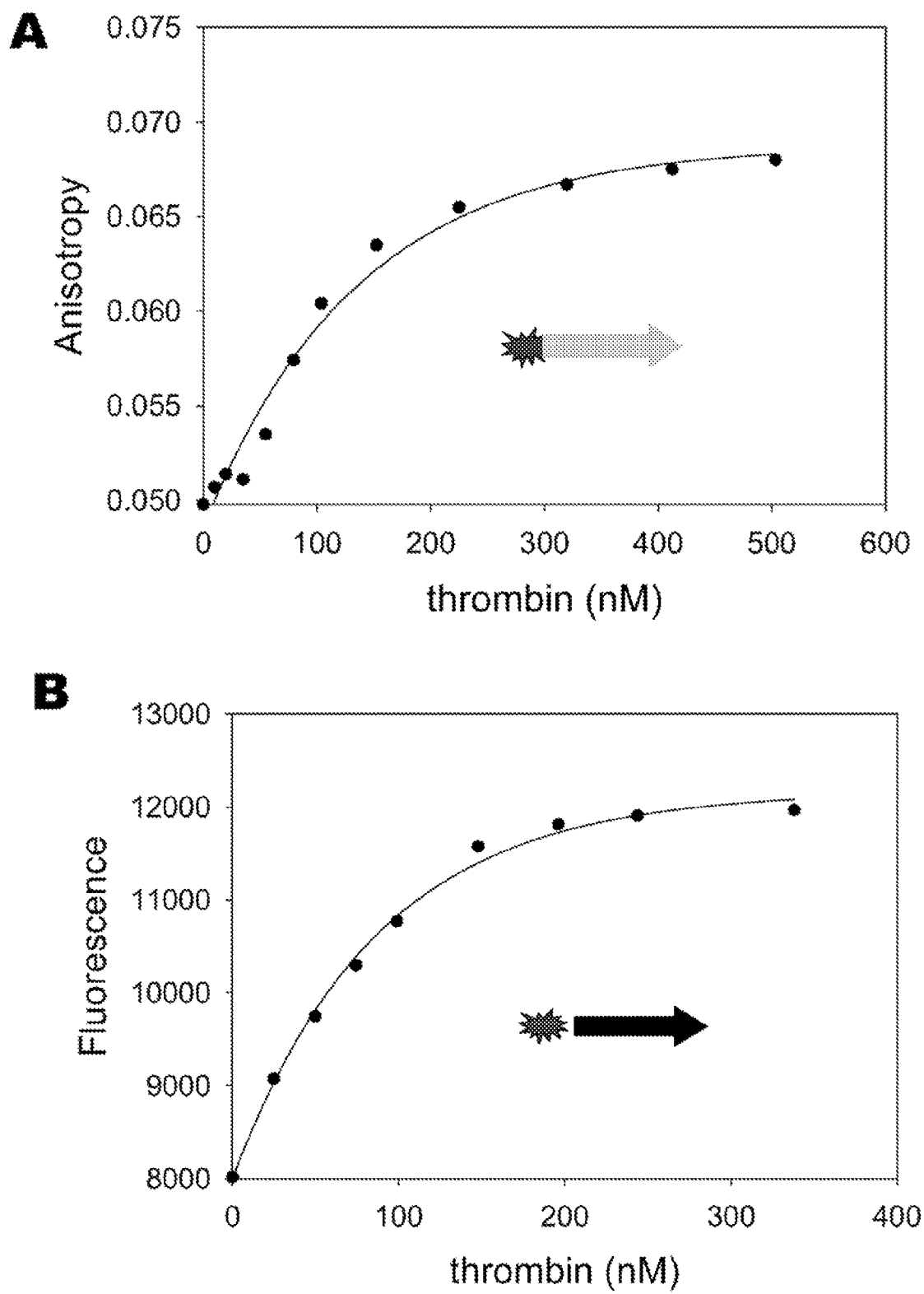
FIG. 5. Binding of fluorescein-labeled aptamers to thrombin. (A) Binding of 60-18 [29] aptamer (THR1) (50 nM) detected by fluorescence polarization; (B) Binding of G15D aptamer (THR2) (50 nM) detected by change in fluorescence intensity; (C) Quantitative equilibrium titration of fluorescein-labeled G15D aptamer (THR2) (20 nM) with thrombin. Solid line represents nonlinear fit of experimental data to an equation describing formation of 1:1 complex between the aptamer and thrombin; (D) Quantitative equilibrium titration of fluorescein-labeled G15D aptamer (THR2) (20 nM) with thrombin in the presence of ten fold excess of unlabeled 60-18 [29] aptamer (THR3). Solid line represents nonlinear fit of experimental data to an equation describing formation of 1:1 complex between the aptamer and thrombin.
Figure 5:
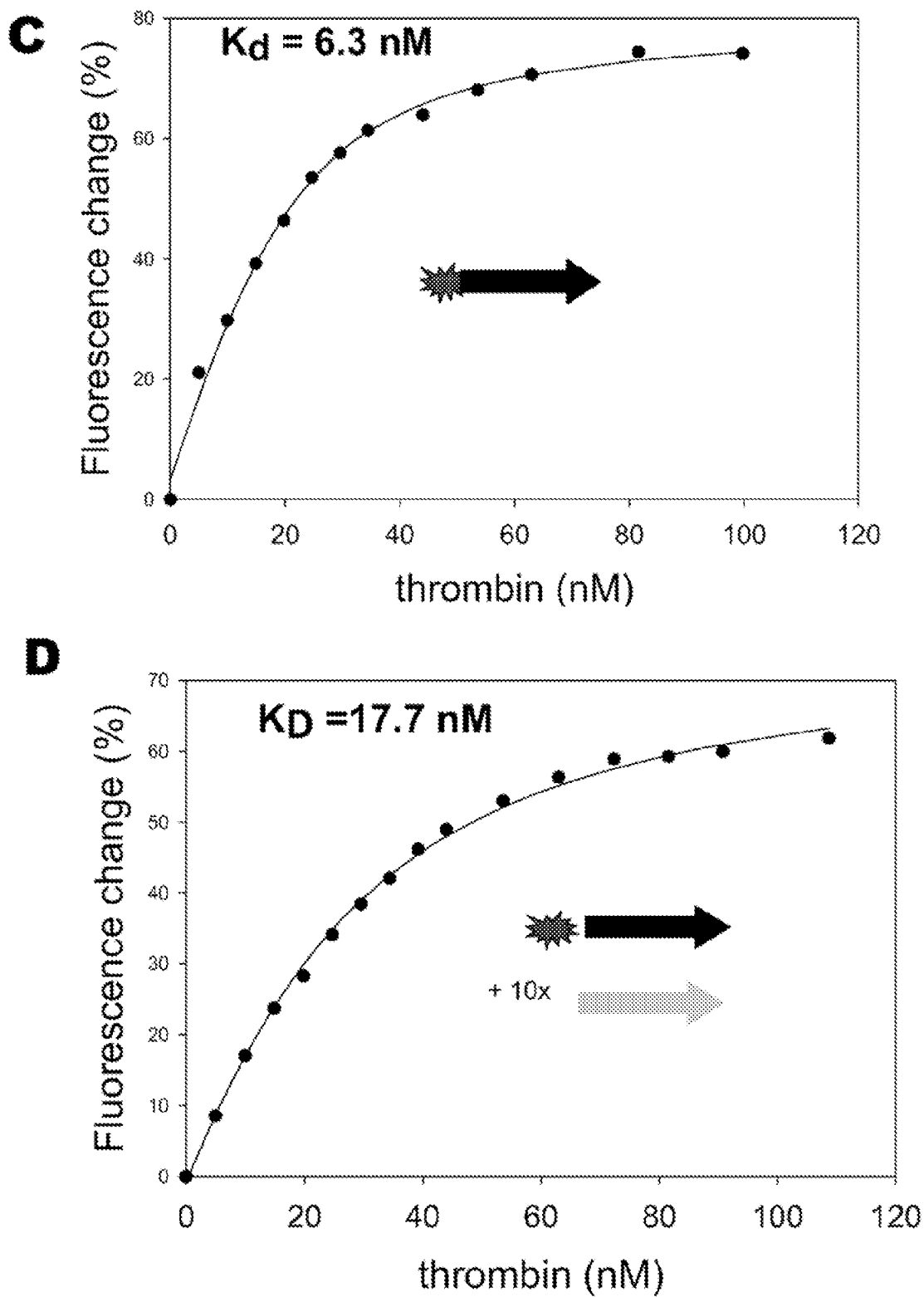

Individual aptamers were labeled with fluorescein (THR1 and THR2 in FIG. 4) to facilitate determination of the affinity of various constructs for thrombin. Formation of a complex between thrombin and fluorescein-labeled 60-18 [29] aptamer (THR1) could be conveniently followed by fluorescence polarization (FIG. 5A) whereas binding of the fluorescein-labeled G15D aptamer (THR2) could be followed by changes in fluorescence intensity (FIG. 5B). Both aptamers bound thrombin in the nanomolar concentration range (FIGS. 5A and 5B). Quantitative analysis of the binding in the case of THR2 (FIG. 5C) returned the value of Kd of 6.3 nM. This is somewhat of a higher affinity than that previously suggested (Bock et alia, 1992), which could be explained by the true equilibrium-binding assay used herein vs. the non-equilibrium methodology used previously. When the binding of THR2 was performed in the presence of 10-fold excess of unlabeled 60-18 [29] aptamer (THR3) (FIG. 5D) only a small and insignificant decrease in affinity was observed. This shows that indeed G15D and 60-18 [29] aptamers bind independently to two distinct epitopes of thrombin.

Figure 6:
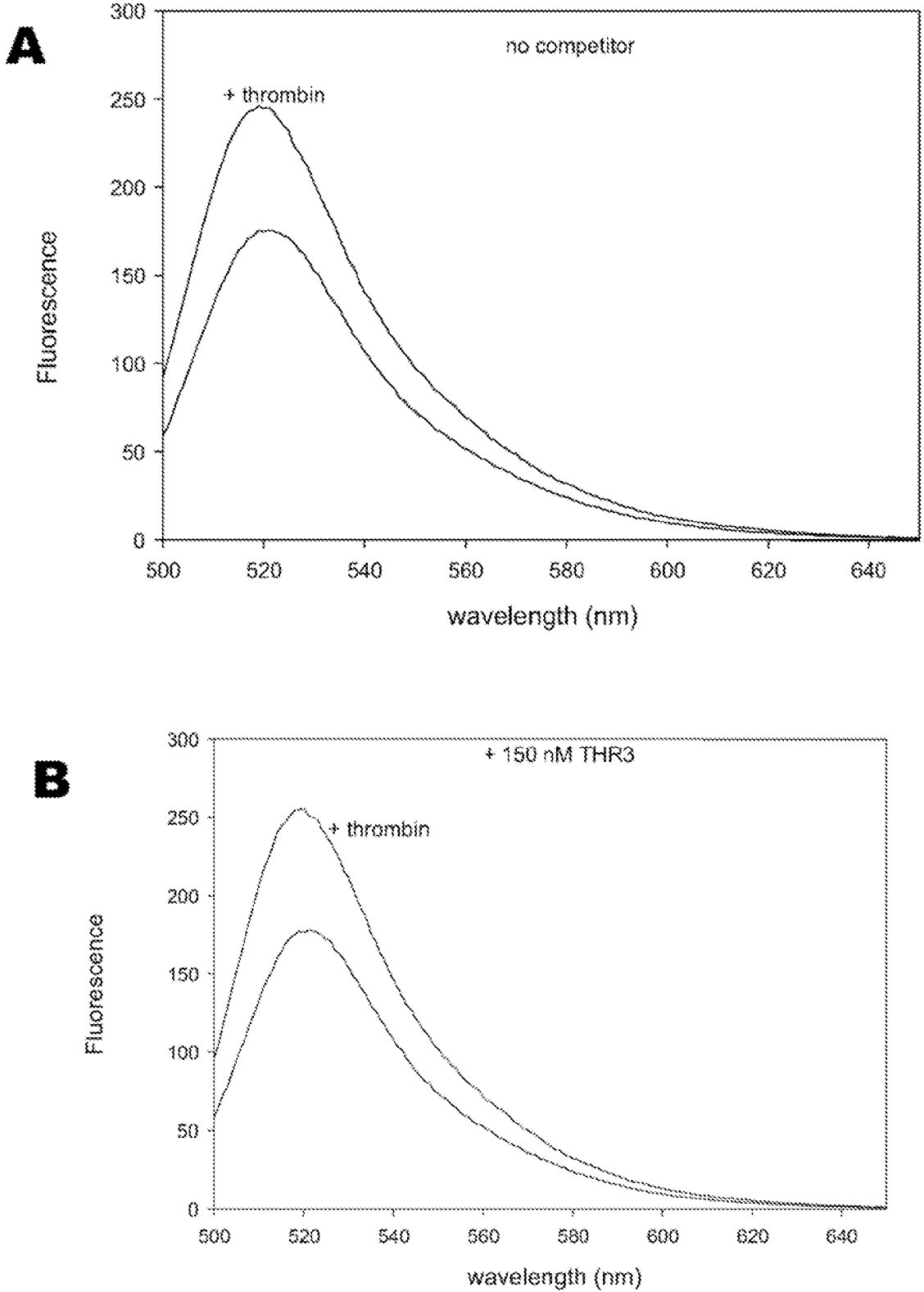
FIG. 6. Illustration of the competition between thrombin aptamer constructs and fluorescein-labeled G15D aptamer (THR2) for binding to thrombin. Fluorescence spectra of 50 nM fluorescein-labeled G15D (THR2) with and without thrombin in the absence of competitor (A), in the presence of 150 nM THR3 (B), in the presence of 150 nM THR4 (C), and in the presence of 150 nM THR7 (D).
Figure 6:
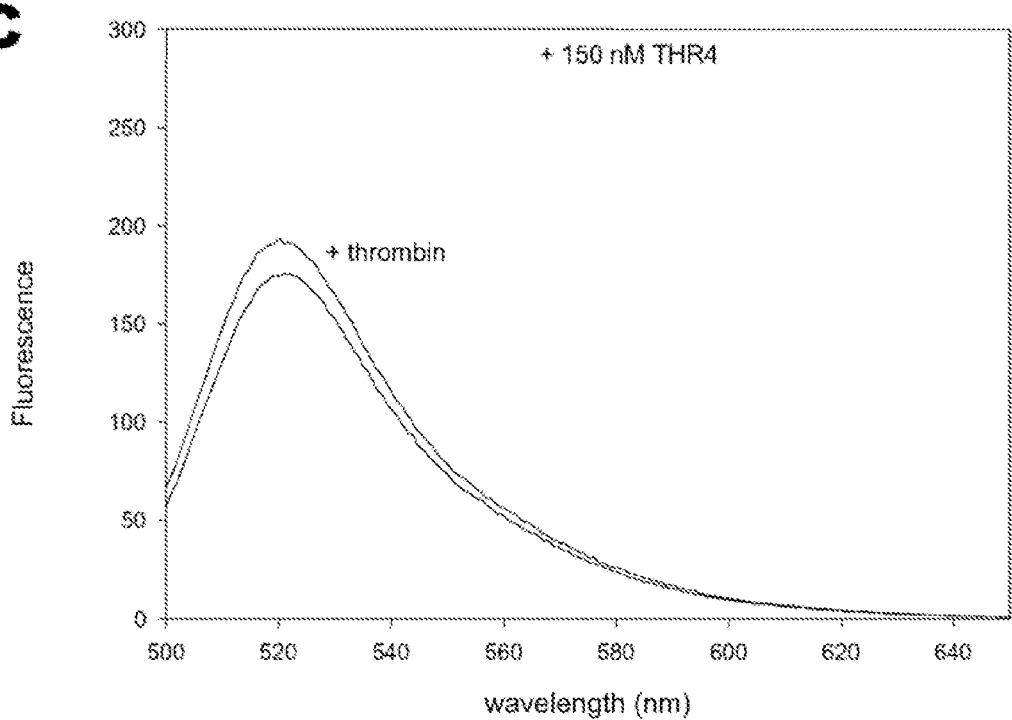
Figure 6:
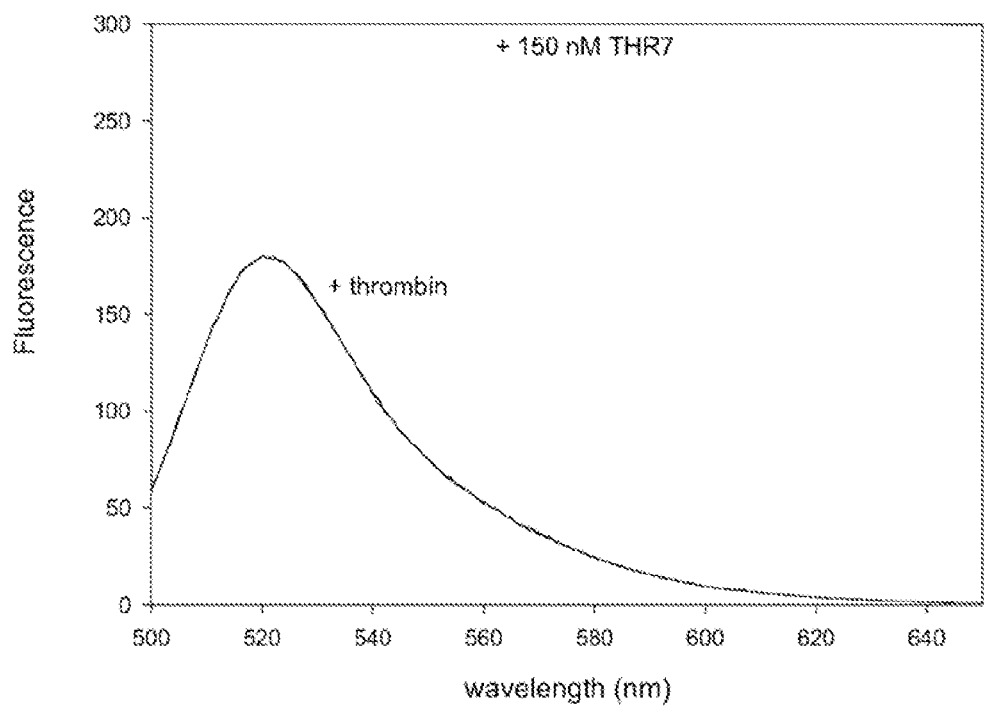
Figure 7:
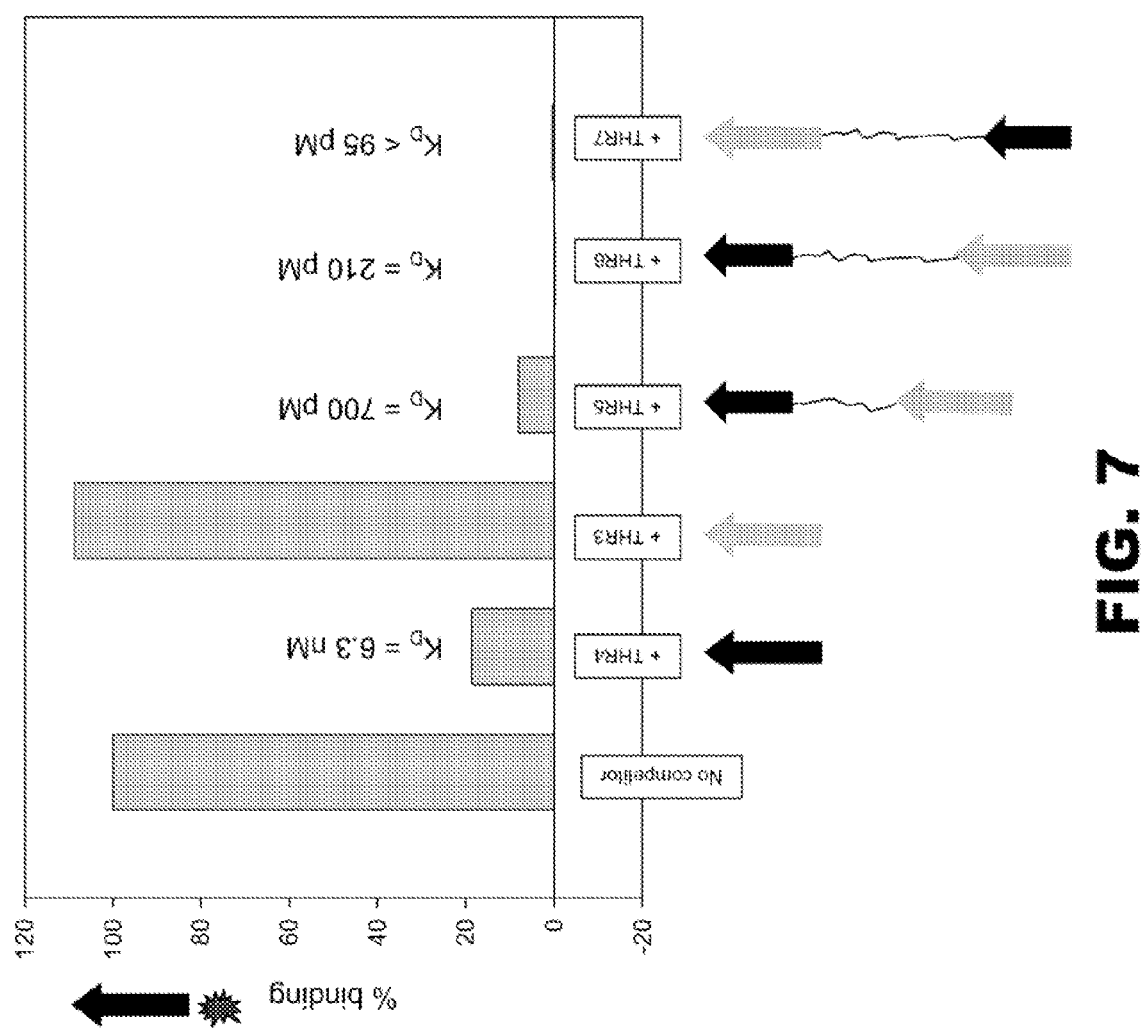
FIG. 7. Summary of experiments probing competition between thrombin aptamer constructs and fluorescein-labeled G15D aptamer (THR2) for binding to thrombin. Fluorescence intensity of fluorescein-labeled G15D aptamer (THR2) (50 nM) in the absence and the presence of the competitor (250 nM) was used to determine % of THR2 bound in the presence of the competitor. Thrombin concentration was 75 nM. The values of dissociation constants shown in the figure were calculated from a separate experiment in which 200 nM fluorescein-labeled G15D aptamer (THR2), 200 nM competitor and 150 nM thrombin were used.

In the next step the ability of various aptamer constructs illustrated in FIG. 4 to compete with THR2 for binding to thrombin was evaluated. FIG. 6 illustrates the manner in which these experiments were performed. Fluorescence spectra of HR2 were recorded in the presence and absence of thrombin (FIG. 6A). Thrombin produced ~50% increase in fluorescence of THR2. Unlabeled competitor aptamer constructs were then added (FIGS. 6B-D). A small effect of thrombin on the fluorescence of THR2 in the presence of a competitor would be a hallmark of an efficient competitor. THR3 was not a competitor (FIG. 6B) in agreement with the data shown in FIGS. 5 C and D. THR4 (an unlabeled variant of THR2) was able to compete as expected (FIG. 6C). However, THR7 (one of the bivalent aptamer constructs) was a much better competitor than THR4 (FIG. 6D). No fluorescence change of THR2 in the presence of thrombin was detected when THR7 was present in solution. FIG. 7 shows a summary of the competition experiments with all of the constructs shown in FIG. 4.

All bivalent aptamer constructs were shown to bind to thrombin much tighter (Kd's in pM range) than individual aptamers, thus providing validation of the expectation that linking two aptamers, which recognize two different epitopes of the protein, with flexible linkers should produce high-affinity thrombin ligands. Additionally, these data showed that linking two aptamers by a longer linker containing 10 Spacer 18 units produced slightly better affinity for thrombin (compare binding of THR5 vs. THR6). Also, these data showed that orientation of the aptamers with respect to the linker as in THR7 produced better affinity (compare affinity of THR6 vs. THR7). Thus, in all subsequent experiments constructs having an aptamer orientation as in THR7 were used.

Figure 8:
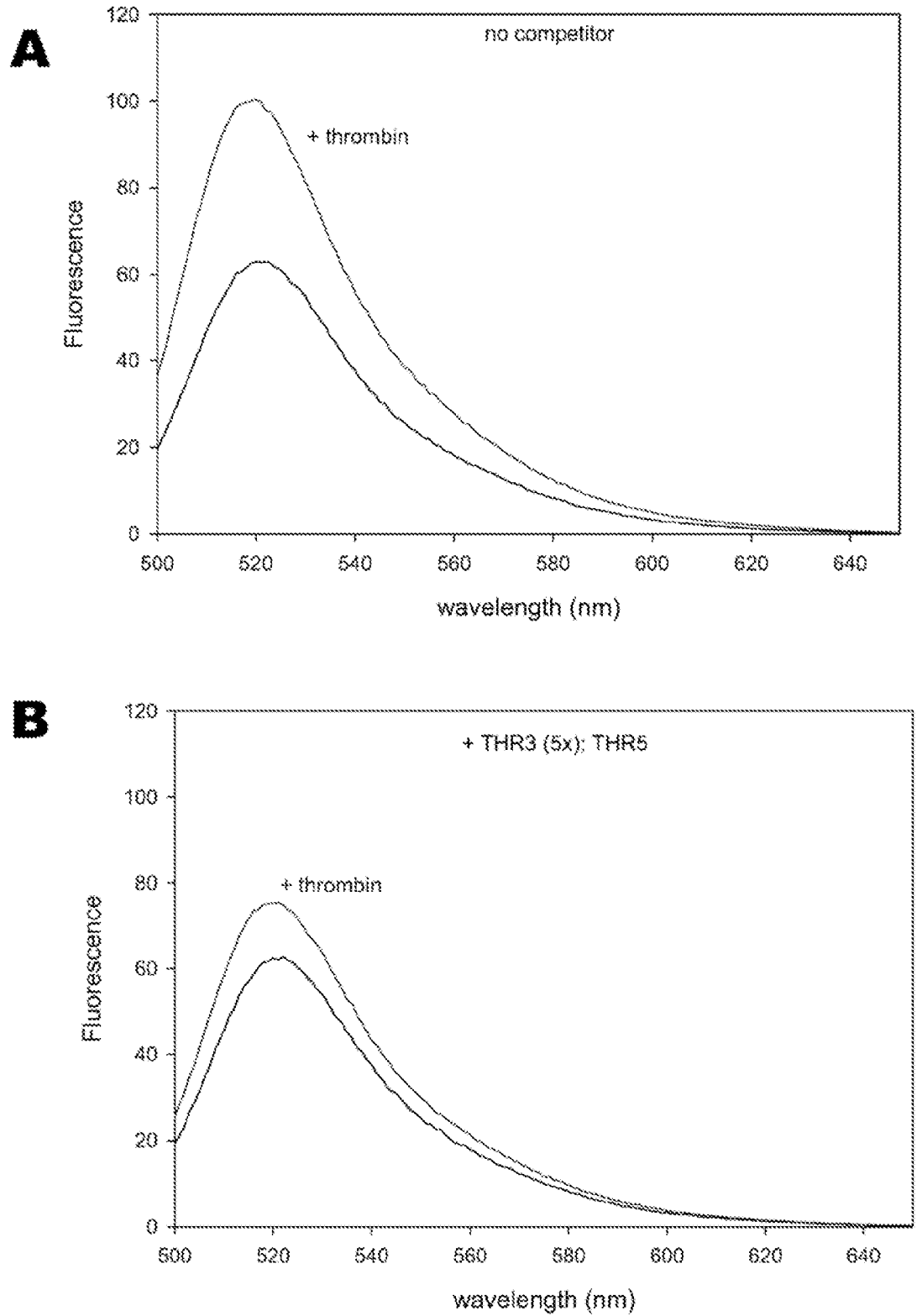
FIG. 8. The effect of 60-18 [29] aptamer (THR3) on the competition between fluorescein-labeled G15D aptamer (THR2) and THR5 construct for binding to thrombin. Fluorescence spectra of 200 nM fluorescein-labeled G15D (THR2) with and without thrombin (150 nM) in the absence of the competitor (A), in the presence of 1000 nM THR3 and 200 nM THR5 (B), in the presence of 1000 nM THR3 (C), and in the presence of 200 nM THR5 (D).
Figure 8:
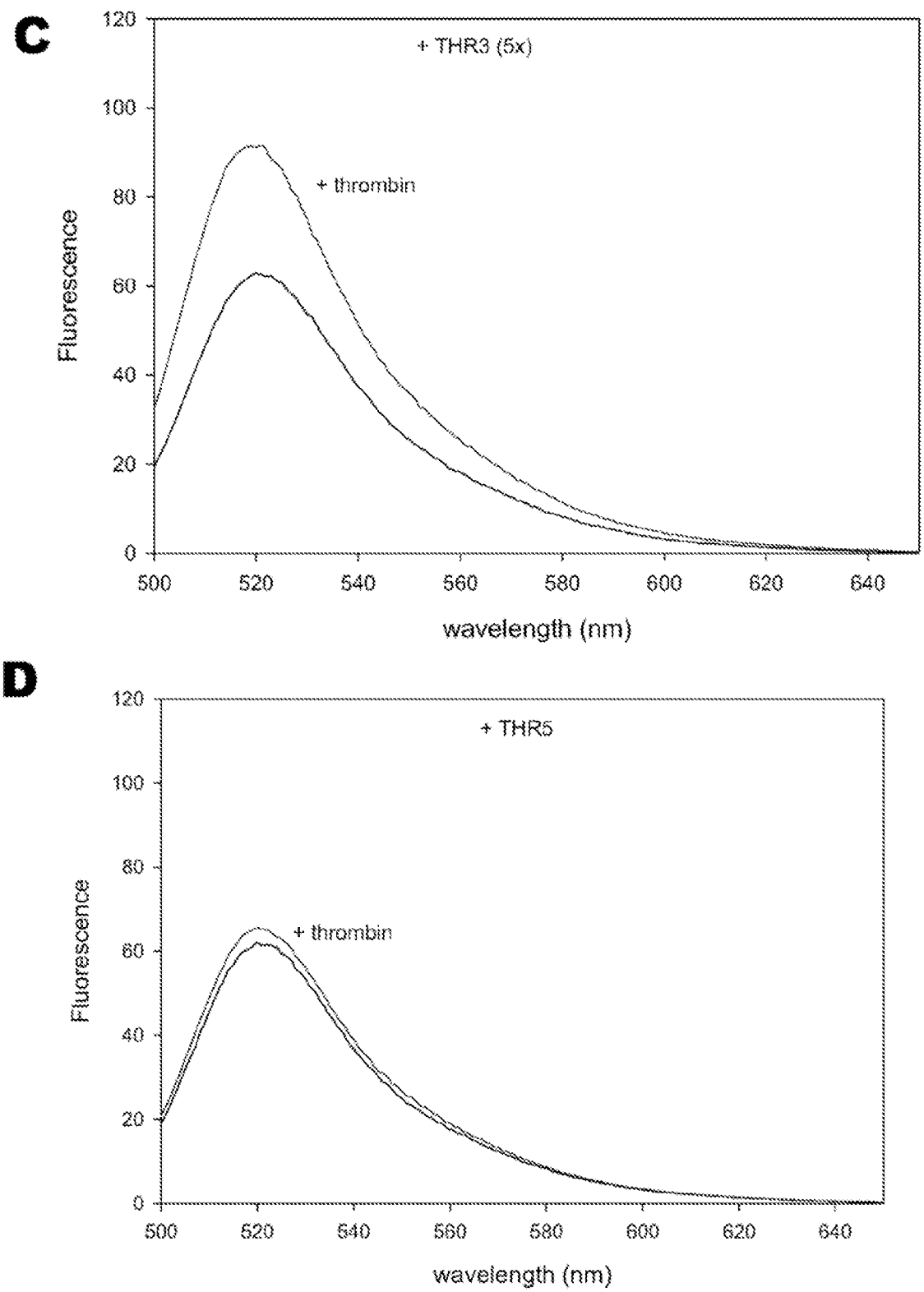

The purpose of the experiments shown in FIG. 8 was to demonstrate that both epitopes of thrombin are important for high affinity binding of bivalent aptamer constructs. Direct competition between binding of THR2 and the bivalent aptamer construct provided evidence that the epitope recognized by THR2 (heparin exosite) was necessary for bivalent aptamer binding. To demonstrate that the second epitope was also important, we compared the ability of a bivalent aptamer construct (THR5, see FIG. 4) to compete with THR2 for binding to thrombin in the absence and presence of excess of unlabeled THR3. We expected that if THR5 needs both thrombin epitopes for high-affinity binding, in the presence of THR3 one should observe diminished ability of THR5 to compete with THR2. This is exactly what has been observed in experiments illustrated in FIG. 8. THR5 alone was a very effective competitor for THR2 (compare FIG. 8D with 8A). THR3 alone was not a competitor for THR2 (compare FIGS. 8A and C). THR5 in the presence of THR3 was a worse competitor than THR5 alone (compare FIG. 8B with 8C). We therefore concluded that high-affinity binding of the bivalent aptamer constructs to thrombin involves both first and second aptamer epitopes.

Figure 9:
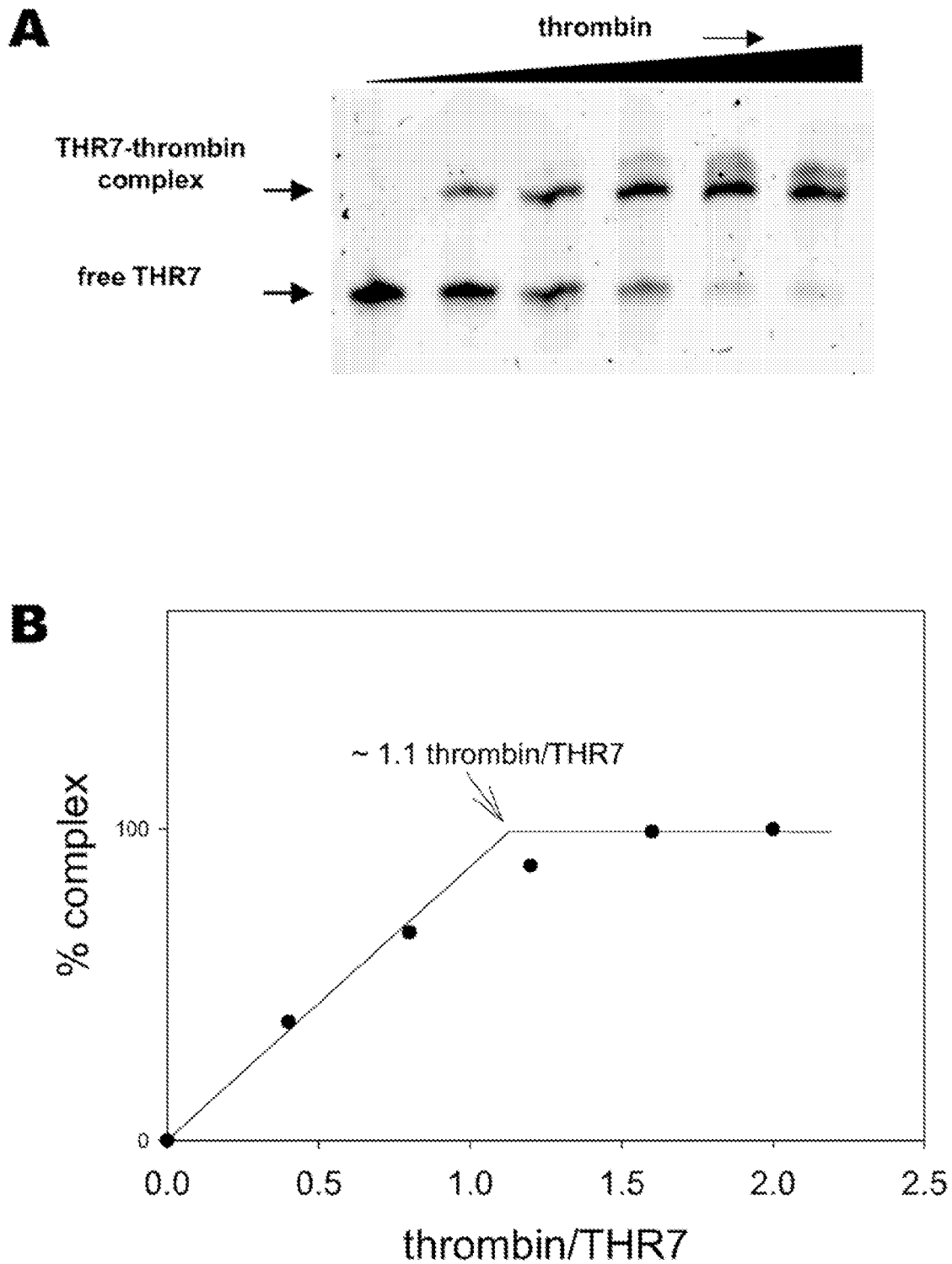
FIG. 9. Binding of THR7 aptamer construct to thrombin detected by gel electrophoresis mobility shift assay. Samples of 417 nM THR7 were incubated with various amounts of thrombin (0 to 833 nM) and after 15 min incubation were loaded on a native 10% polyacrylamide gel. (A) Image of the gel stained with Sybr Green. (B) Intensity of the band corresponding to THR7-thrombin complex as a function of thrombin concentration.

The bivalent aptamer construct-thrombin complex was stable enough to survive electrophoresis in native polyacrylamide gel (FIG. 9A). We took advantage of this attribute to determine the In an alternative embodiment, the three-component biosensor will comprise: (1) a first epitope binding agent construct that binds to a first epitope on a target molecule, a first linker, and a first signaling oligo; (2) a second epitope binding agent construct that binds to a second epitope on the target molecule, a second linker, a second signaling oligo and (3) an oligonucleotide construct that comprises a first region that is complementary to the first oligo, a second region that is complementary to the second oligo, two flexible linkers, an endonuclease restriction site overlapping the first and the second regions complementary to the first and the second oligos, and a pair of complementary nucleotides with detection means. The first signaling oligo and second signaling oligo are not complementary to each other, but are complementary to two distinct regions on the oligonucleotide construct. Referring to FIG. 52, when the oligonucleotide construct is intact, the complementary nucleotides are annealed and produce a detectable signal. Co-association of the two epitope-binding agent constructs with the target molecule results in hybridization of each signaling oligo to the oligonucleotide construct. The signaling oligos hybridize to two distinct locations on the oligonucleotide construct such that a double-stranded DNA molecule containing the restriction site is produced, with a gap between the signaling oligos located exactly at the site of endonuclease cleavage in one strand of the double-stranded DNA substrate. When a restriction endonuclease is present, accordingly, it will cleave the oligonucleotide construct only when the target is present (i.e., when the signaling oligos are bound to the oligonucleotide construct). Upon this cleavage, the detection means present on the oligonucleotide are separated-resulting in no detectable signal. Upon dissociation of the cleaved oligonucleotide construct, another oligonucleotide construct may hybridize with the signaling oligos of the two epitope-binding agents co-associated with the target and the cleavage reaction may be repeated. This cycle of hybridization and cleavage may be repeated many times resulting in cleavage of multiple oligonucleotide constructs per one complex of the two epitope-binding agents with the target. of the complex using EMSA to follow THR7-thrombin complex formation. We performed a titration of THR7 with thrombin at high concentrations of both molecules. Under these conditions, the binding should be stoichiometric. The plot of the complex formed vs. the ratio of thrombin to THR7 did in fact show a 1:1 stoichiometry of the complex (FIG. 9B).

Figure 10:
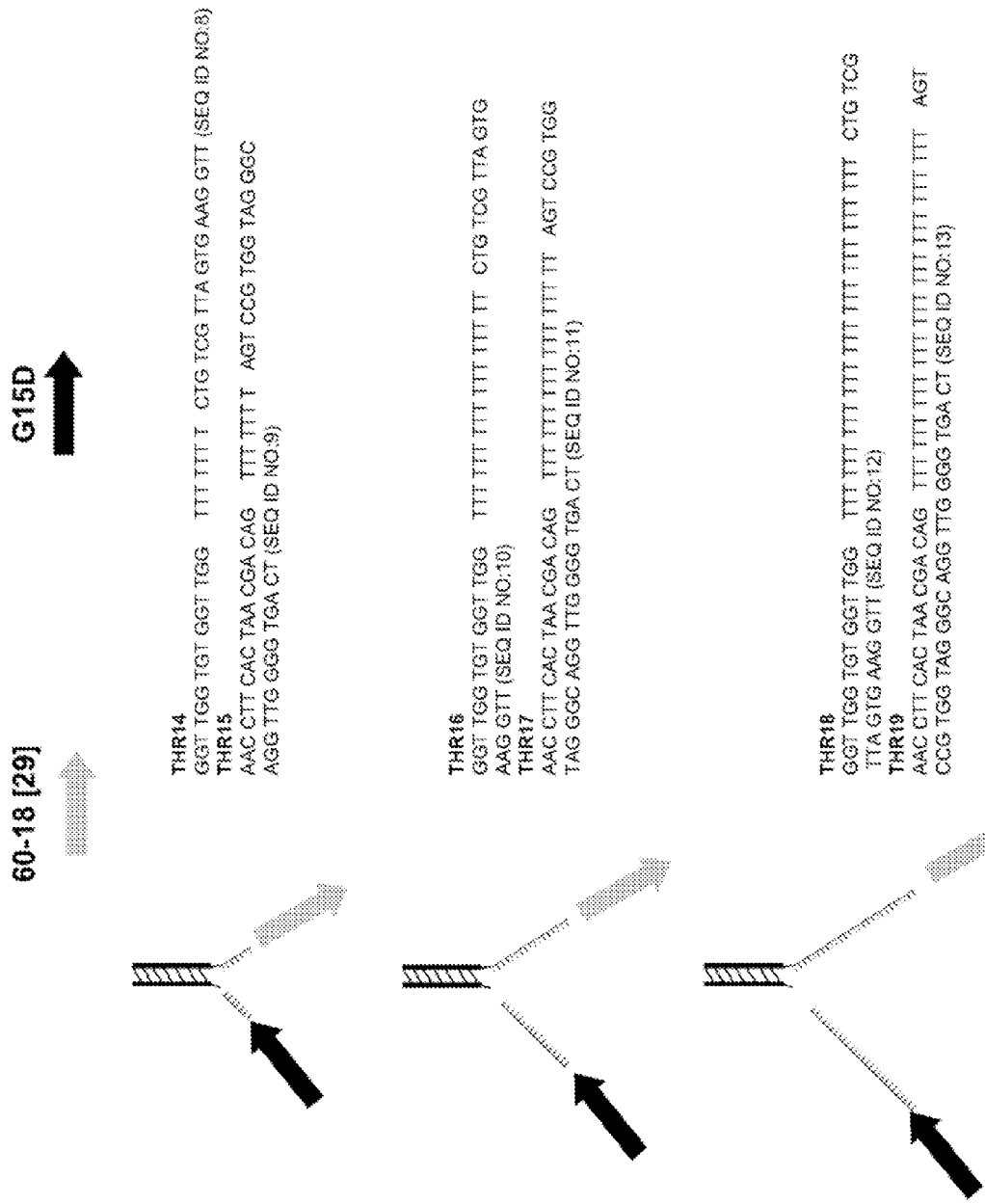
FIG. 10. Family of bivalent thrombin aptamer constructs in which G15D (black arrows) and 60-18 [29] (gray arrows) aptamers were connected to a 20 bp DNA duplex by a 9-27 nt long poly T linker.
Figure 11:
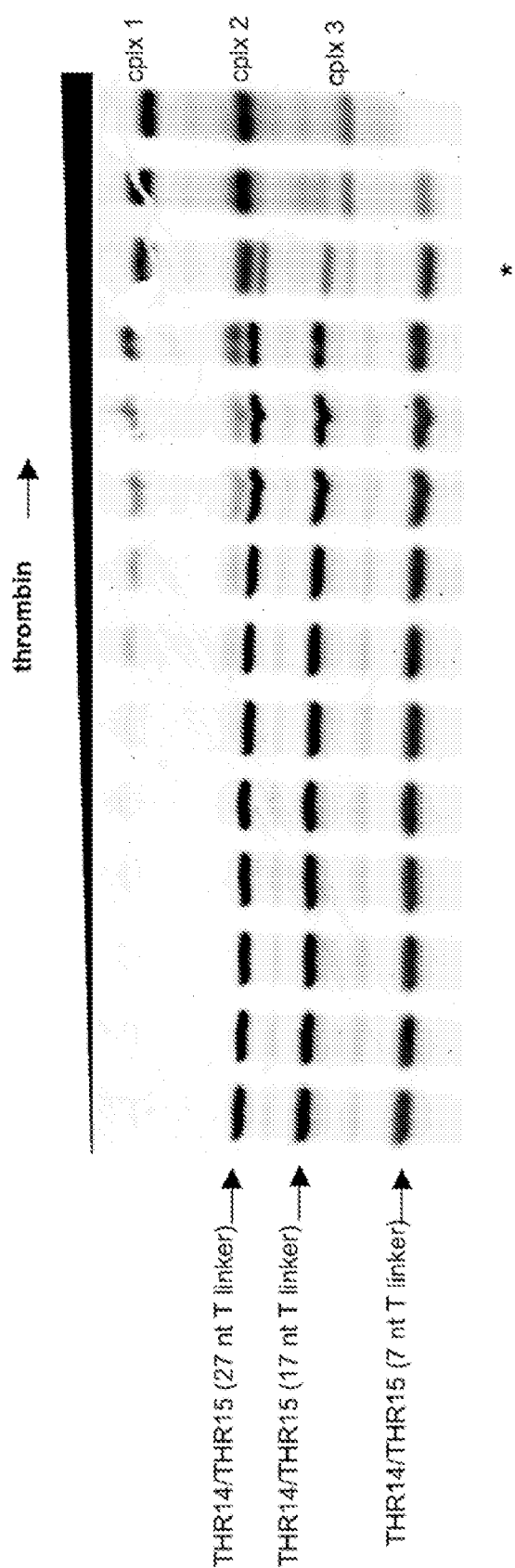
FIG. 11. Binding of thrombin to bivalent aptamer constructs (33 nM each) illustrated in FIG. 10 detected by electrophoretic mobility shift assay (EMSA). Asterisk marks the lane best illustrating preferential binding of thrombin to constructs with 27 and 17 nt poly T linker over the constructs with 9 nt poly T linker. Thrombin concentration was varied from 0 to 400 nM.

The experiments illustrated in FIGS. 10 and 11 were performed to test if an alternative design of bivalent aptamer constructs could be used to prepare these constructs. We designed bivalent aptamer constructs shown in FIG. 10 such that they were made entirely of DNA, avoiding the use of a non-DNA linker (poly dT was used as the linker in this case) (FIG. 10). This could potentially offer more flexibility in designing such constructs and could also lower the cost of making the aptamer constructs. Two aptamers were joined together by a DNA duplex at the end of flexible linkers (FIG. 10). This aspect of the invention was intended to mimic the design of signaling "beacons" (FIG. 3B) in which the signaling function involves formation of a DNA duplex at the end of the linkers connecting the aptamers to the duplex. Three different lengths of the poly dT linker were tested (7, 17 and 27 nt) to determine the minimal linker length requirement for high-affinity binding. FIG. 11 shows the results of simultaneous titration of the constructs shown in FIG. 10 with thrombin. Formation of aptamer construct-thrombin complexes was followed by EMSA. Each of the constructs bound thrombin with high affinity. However, it is clear that the construct with 7 nt poly dT linker had significantly lower affinity to thrombin compared to constructs with 17 and 27 nt linkers. This is best illustrated by inspecting the lane marked with the asterisk which shows that at this particular concentration of thrombin almost all of the 17 and 27 nt poly dT linker constructs were bound by thrombin whereas a significant (~50%) fraction of the 7 nt poly dT construct remained unbound. In summary, the results described in FIGS. 10 and 11 show that the alternative design of bivalent aptamer constructs illustrated in FIG. 10 is feasible and that at least a 17 nt long poly dT linker connecting the aptamers with the DNA duplex is more optimal for binding of the constructs to thrombin.

Figure 12:
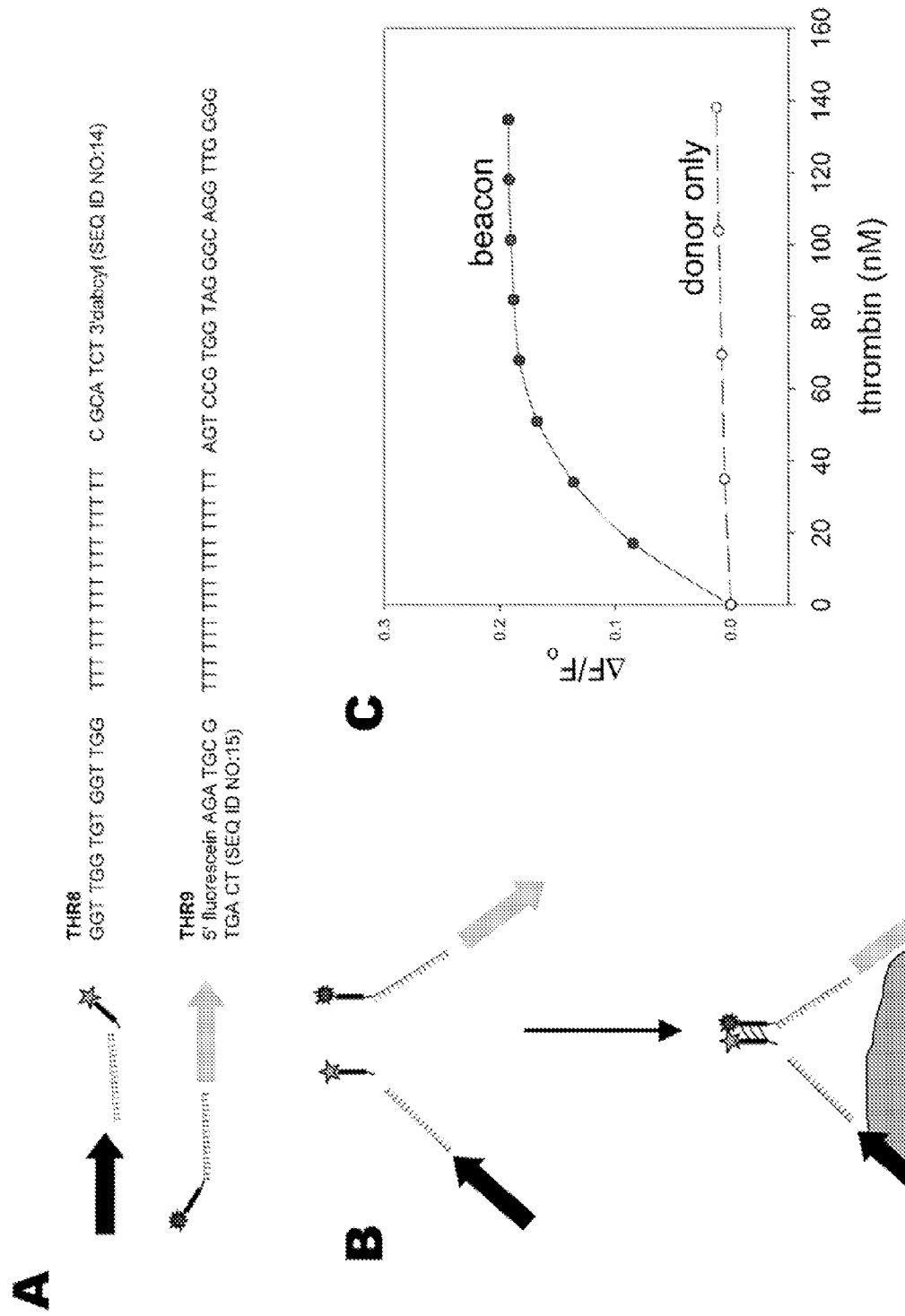
FIG. 12. Thrombin beacon design using G15D (black arrows) and 60-18 [29] (gray arrows) aptamers connected to 9 bp fluorophore (or quencher)-labeled "signaling" duplex through 17 nt poly T linker. (A) Nucleotide sequence of the fluorescein-labeled G15D construct (THR9) and dabcyl-labeled 60-18 [29] construct (THR8). (B) Mechanism of signaling by thrombin beacon. (C) Fluorescence signal change detected upon addition of thrombin to the thrombin beacon. For comparison, titration of the fluorescein-labeled G15D construct (THR9) with thrombin in the absence of dabcyl-labeled 60-18 [29] construct (THR8) is also shown (donor only curve).

The experimental data presented in FIGS. 3-11 provided evidence that all necessary conditions for the signaling beacon shown in FIG. 3B to function were met in the case of thrombin and the two aptamers binding to two distinct region of thrombin. Based on the information provided by the experiments illustrated in FIGS. 3-11, we designed and tested a thrombin-signaling beacon. The beacon shown in FIGS. 12A and B is a derivative of THR16/THR17 bivalent aptamer construct. Aptamers were connected using a 17 nt long poly dT linker to 7 nt complementary oligonucleotides (signaling oligos) labeled at 5' and 3' with fluorescein and dabcyl, respectively. The addition of thrombin to a mixture of THR8 and THR9 resulted in a protein-dependent quenching of fluorescence intensity (FIG. 12C). No fluorescence change was observed upon addition of thrombin to THR9 in the absence of dabcyl-labeled partner (THR8) (FIG. 12C). Clearly, these data show that indeed the expected thrombin-driven association between THR8 and THR9 (as illustrated in FIG. 12B) was observed and a functional thrombin-signaling beacon was thus obtained.

Figure 13:
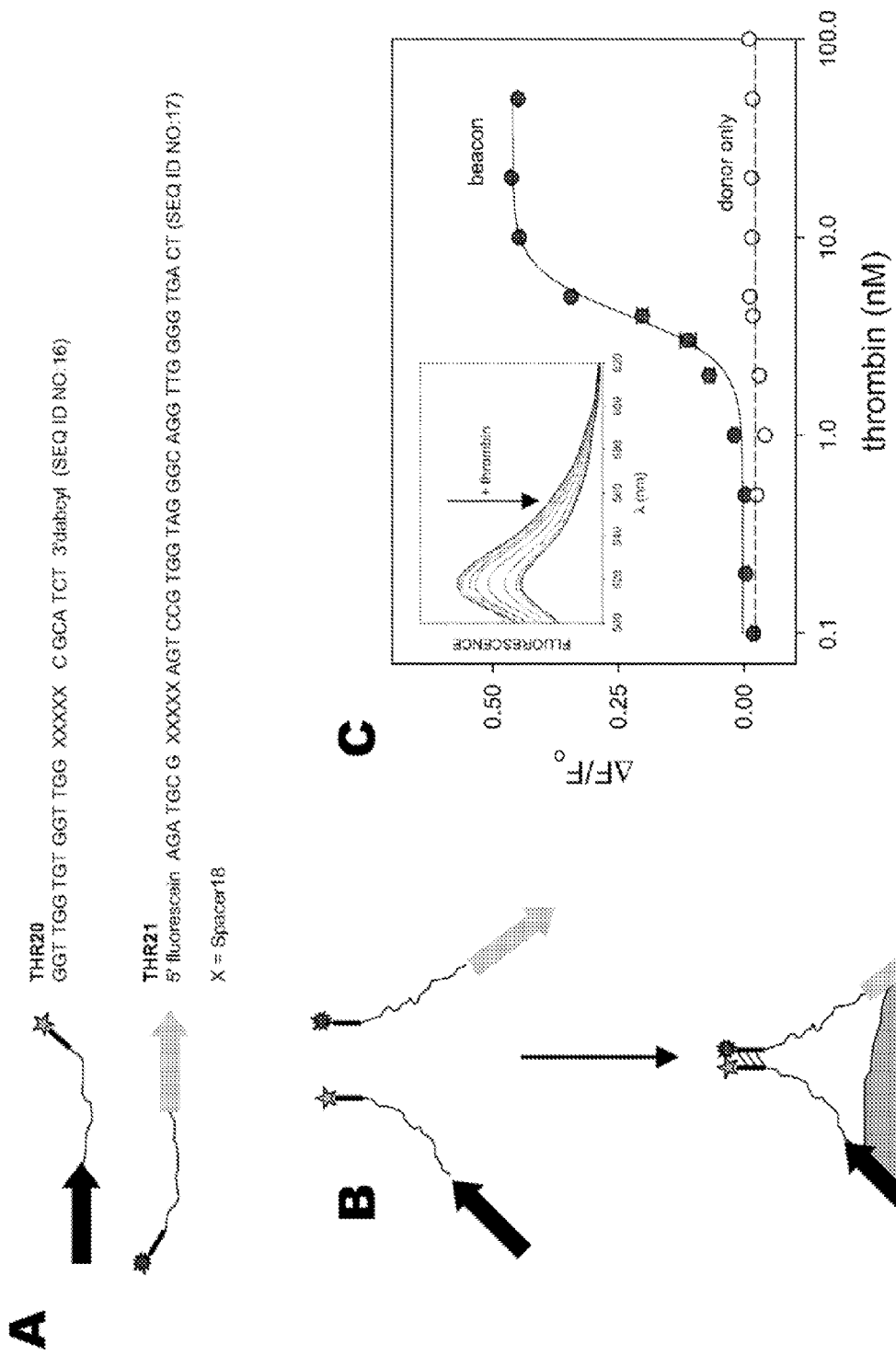
FIG. 13. A thrombin beacon design. G15D (black arrows) and 60-18 [29] (gray arrows) aptamers were connected to 7 bp fluorophore (or quencher)-labeled "signaling" duplex through a linker containing 5 Spacer18 units. (A) Nucleotide sequence of the fluorescein-labeled G15D construct (THR21) and dabcyl-labeled 60-18 [29] construct (THR20). X corresponds to Spacer 18 moiety. (B) Mechanism of signaling by thrombin beacon. (C) Fluorescence signal change detected upon addition of thrombin to the thrombin beacon. For comparison, titration of the fluorescein-labeled G15D construct (THR21) with thrombin in the absence of dabcyl-labeled 60-18 [29] construct (THR20) is also shown (donor only curve). Signal change (%) was calculated as $100*(Io-I)/Io$ where I and Io correspond to dilution-corrected fluorescence emission intensity observed in the presence and absence of a given thrombin concentration, respectively. Inset shows fluorescence emission spectra recorded at various concentrations of thrombin corresponding to data points in the main graph.

The magnitude of the fluorescence change induced by thrombin, while very reproducible and specific, initially was not very large (~20%). We therefore sought to improve this property of the thrombin-signaling beacon by replacing the poly dT linkers with the more flexible Spacer 18 linker (FIGS. 13A & B). We reasoned that poly dT linkers, while flexible, exhibit some residual rigidity (Mills, J. B., Vacano, E., and Hagerman, P. J. Flexibility of single-stranded DNA: use of gapped duplex helices to determine the persistence lengths of poly (dT) and poly (dA), J. Mol. Biol. 285, 245-57, 1999; which is incorporated herein by reference), which could impede the association of the signaling duplex when the two aptamers are bound to thrombin. The beacon shown in FIG. 13 differs only in the nature of the linkers from the beacon shown in FIG. 12. The remaining sequence is otherwise identical. FIG. 13 C shows that upon addition of thrombin to a mixture of THR20 and THR21, protein concentration-dependent quenching of fluorescence was observed whereas no change of fluorescence was detected when thrombin was added to THR21 alone. Response of the beacon to thrombin in the case of this particular beacon was much larger (a ~2-fold decrease in fluorescence). The degree of fluorescence signal change in this case was comparable to what we had previously observed with beacons for detecting DNA binding proteins (supra). We concluded thus that a functional thrombin beacon was obtained and that the design utilizing a more flexible Spacer18 linker resulted in a better signal change upon thrombin binding compared to the design with poly dT linker. We next conducted a series of experiments to further characterize the behavior of this thrombin beacon.

Figure 14:
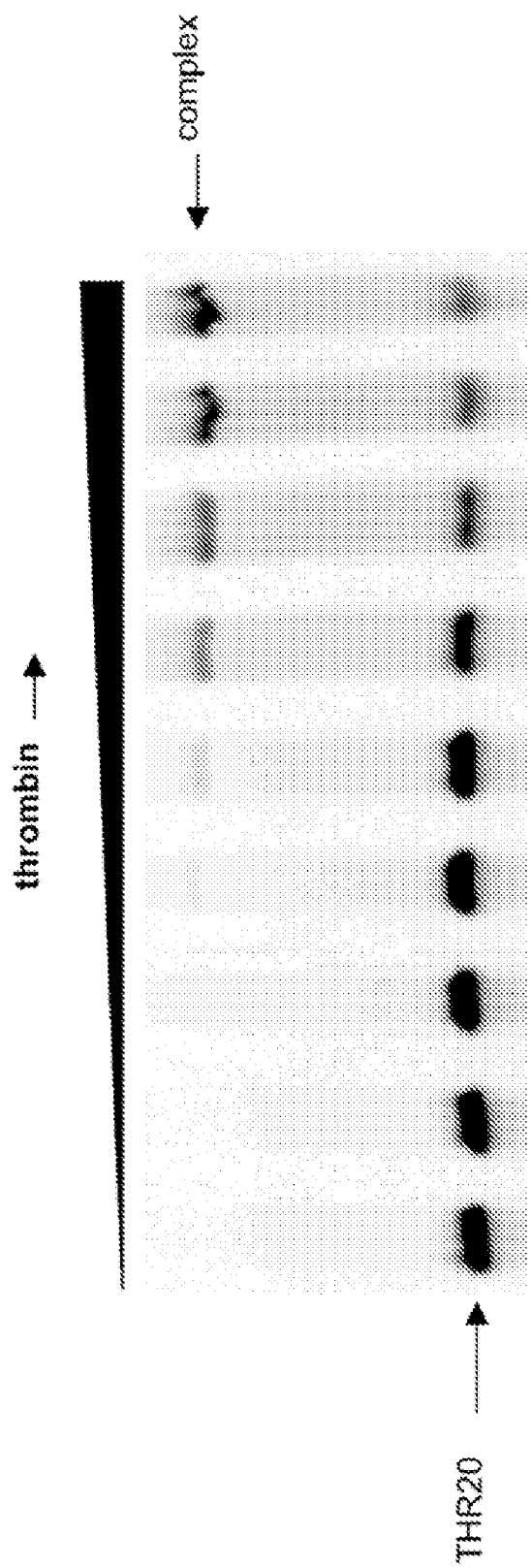
FIG. 14. Binding of thrombin to the beacon illustrated in FIG. 13 (THR20/THR21) detected by gel electrophoresis mobility shift assay. The gel was imaged for fluorescein emission (i.e. only THR21 component of the beacon is visible).
Figure 15:
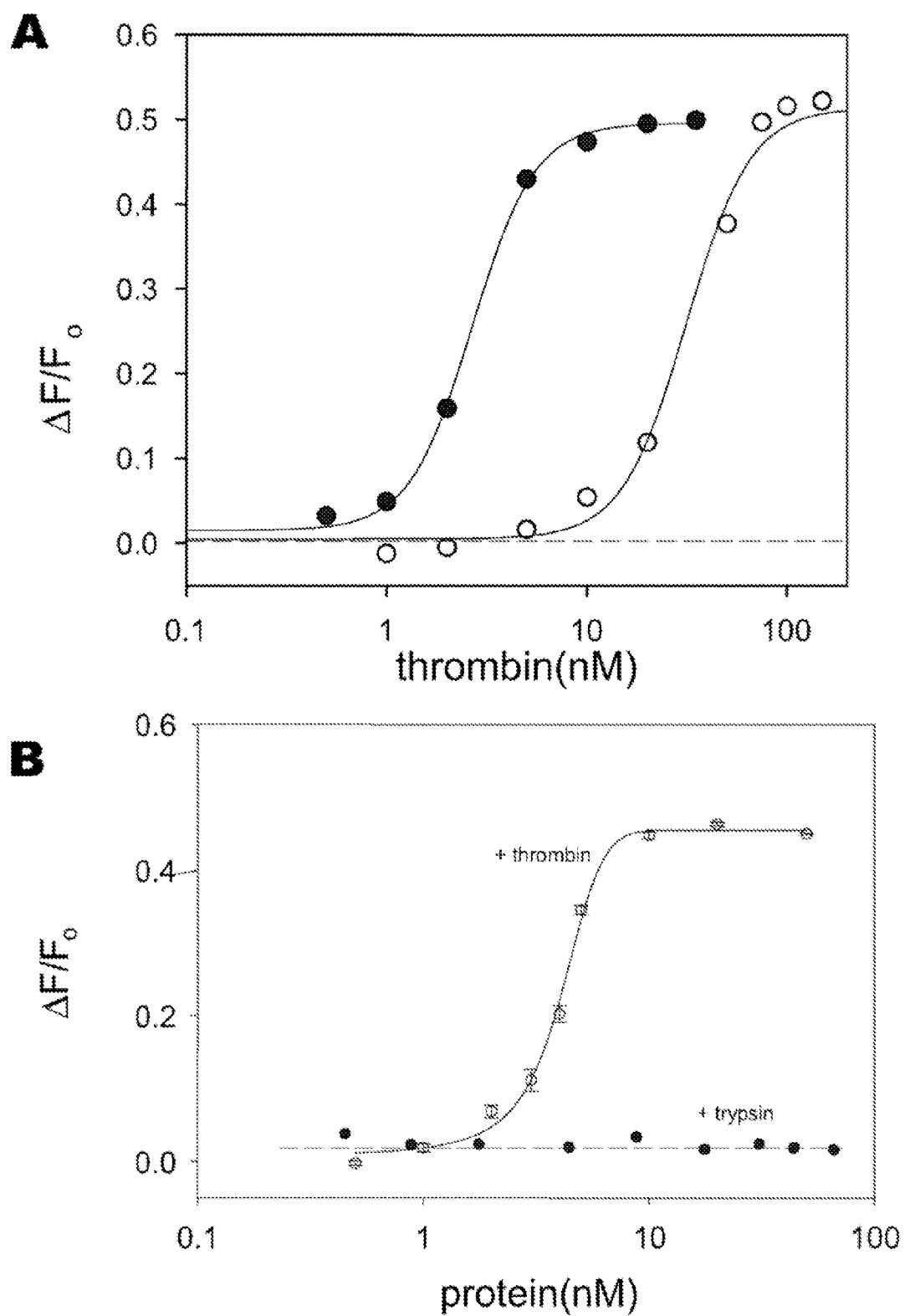
FIG. 15. (A) Sensitivity of thrombin detection at two different concentrations of the beacon. Squares: 50 nM THR21 and 95 nM THR20. Circles: 5 nM THR21 and 9.5 nM THR20. (B) Specificity of the beacon for thrombin. 50 nM THR21 and 95 nM THR20 were titrated with thrombin (open circles) and trypsin (closed circles).

The experiment illustrated in FIG. 14 was conducted to provide confirmation that indeed the fluorescein-labeled aptamer construct (THR21) was incorporated into a stable complex in the presence of THR20 and thrombin. FIG. 15 shows the results, which illustrates the sensitivity of thrombin detection (FIG. 15A) and specificity of thrombin detection (FIG. 15B). Because the binding of thrombin to bivalent aptamer constructs was extremely tight (pM Kd's), and since the assay appears to be limited only by the sensitivity of detection of fluorescein signal, the sensitivity of thrombin detection could be manipulated by changing the concentration of the aptamer constructs. This is illustrated in FIG. 15A where using 50 nM THR21 and 75 nM THR20, ~10 nM of thrombin could be detected whereas, when 10 fold smaller concentrations of aptamer constructs were used (5 nM THR21 and 7.5 nM THR20), a 10 fold lower (~1 nM) concentration of thrombin could be detected. Using even lower aptamer construct concentrations (500 μM THR21 and 750 μM THR22), ~100 μM thrombin could be detected (not shown), but this low concentration of fluorescein-labeled aptamer construct is close to the limits of sensitivity of our instrumentation and the quality of the data was concomitantly decreased. To demonstrate the specificity of thrombin detection, we compared the response of the aptamer constructs to thrombin with the response to trypsin, a protease belonging to the same family as thrombin and sharing structural homologies with thrombin. No signal was detected upon addition of trypsin (FIG. 15B), indicating a high specificity of the aptamer constructs for thrombin.

Figure 16:
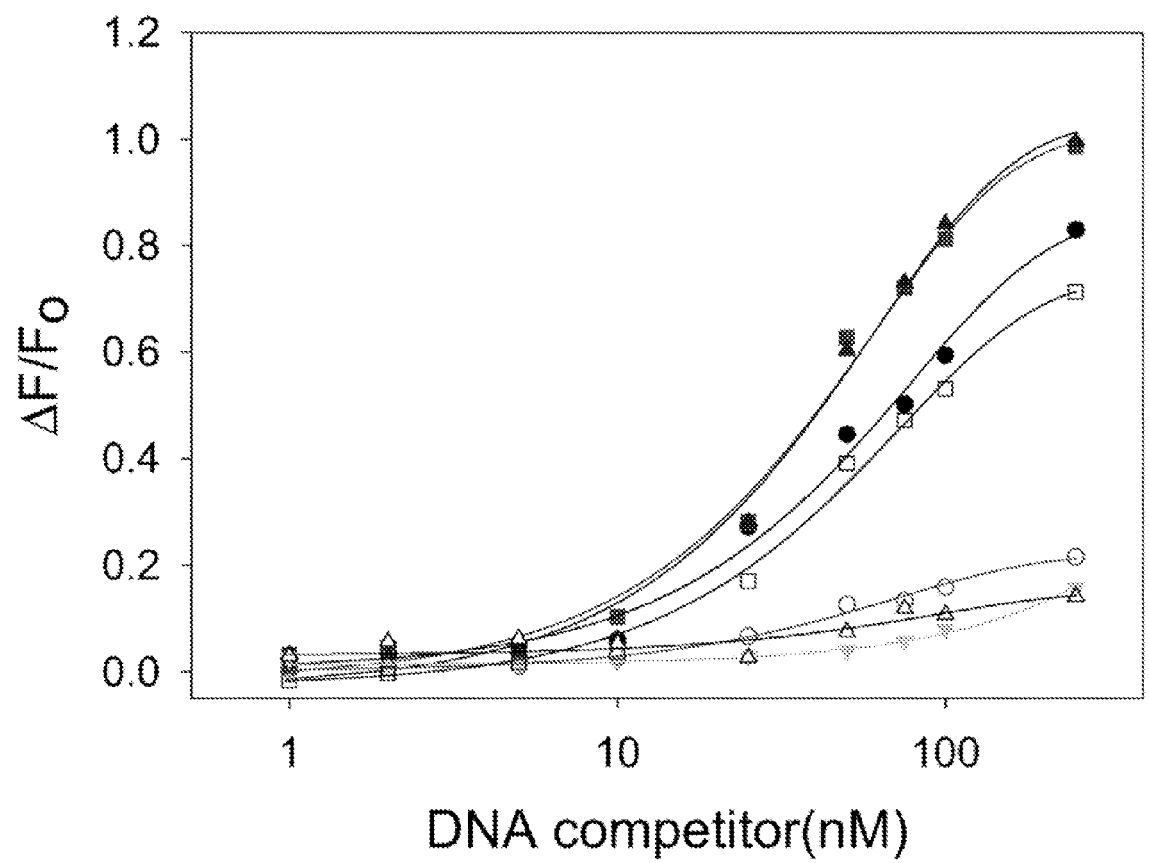
FIG. 16. Reversal of thrombin beacon signal by competitor aptamer constructs. Fluorescence intensity of 50 nM THR21, 95 nM THR20, and 100 nM thrombin was measured at increasing concentrations of competitor DNA's. The data are plotted as a relative fluorescence increase with respect to a signal (Fo) of a starting beacon and thrombin mixture. Open squares: THR7; filled circles: THR14/THR15; filled squares: THR16/THR17; filled triangles: THR18/THR19; open triangles: THR3; gray filled inverted triangles: THR4; open triangles: nonspecific single stranded DNA.

FIG. 16 shows the results of competition experiments, in which the ability of various aptamer constructs to dissociate the preformed thrombin-aptamer construct complex was tested. The data obtained showed that all bivalent aptamer constructs were by far much more efficient competitors than any of the individual epitope-specific aptamers, in agreement with similar experiments performed with fluorescein-labeled individual aptamer (supra, THR2; FIG. 6). Among the bivalent aptamer constructs, THR18/THR19 (a construct with 27 nt long poly dT linker) and THR16/THR17 (a construct with 17 nt long poly dT linker) were the most efficient competitors followed by THR14/THR15 (a construct with 7 nt poly dT linker) and THR7 (which has a Spacer18 linker). It appears thus that although additional flexibility of Spacer18 linkers was beneficial in terms of the magnitude of fluorescence signal change produced by the aptamer construct signal change, it also resulted in somewhat reduced affinity for binding thrombin in comparison with the constructs containing more rigid poly dT linkers.

Conclusions

We obtained data providing basic physicochemical characterization of the bivalent aptamer constructs containing two aptamers recognizing two different epitopes of thrombin. The bivalent constructs exhibited much higher affinity for thrombin than the individual aptamer components of the bivalent construct. This suggested that addition of thrombin to a mixture of aptamers "half-sites" should induce association of the two "half-sites" generating fluorescence signal as a result of bringing the fluorophore and the quencher to close proximity. Experiments with beacon constructs fully validated this prediction. We expect that it will be possible to develop analogous beacons for a large number of target proteins. We also note that the beacon design described here can also be adopted to improve beacons for detecting proteins exhibiting natural DNA binding activity (FIG. 1B). In this case one of the aptamers "half-sites" can be replaced with the DNA duplex (containing the protein binding site sequence) connected to signaling complementary oligonucleotide via flexible linker.

Example 3

Analyte Detection in a Sample

Materials

Purified thrombin was a gift from Dr. Ray Rezaie (St. Louis University). Factor Xa, prothrombin, ovalbumin, bovine serum albumin, single-stranded binding protein, trypsin and plasma were purchased from Sigma (St. Louis, Mo.). HeLa cellular extracts were from ProteinOne (College Park, Md.). Texas Red-NHS and Sybr Green were from Molecular Probes (Eugene, Oreg.), Cy5-NHS and Cy3-NHS were from Amersham Biosciences (Piscataway, N. J.), and AMCA-sulfoNHS was from Pierce (Rockford, Ill.). All other reagents were commercially available analytical grade.

Oligonucleotide constructs used throughout this work are listed in Table 1. Oligonucleotides were obtained from Keck Oligonucleotide Synthesis Facility at Yale University or from IDT (Coralville, Iowa). 5' fluorescein and 3' dabcyl were incorporated using appropriate phosphoramidates during oligonucleotide synthesis. All other fluorophores were incorporated into oligonucleotides by post-synthetic modification of oligonucleotides containing 5' amino or C6 amino-dt at appropriate positions with NHS esters of the dyes. Oligonucleotides labeled with fluorescence probes were purified by reverse-phase HPLC as described previously (Heyduk, E.; Heyduk, T. Anal. Biochem. 1997, 248, 216-227). Modification of oligonucleotides with europium chelate (($Eu3+$) DTPA-AMCA) was performed by a two-step procedure described in Heyduk, E.; Heyduk, T.; Claus, P.; Wisniewski, J. R. J. Biol. Chem. 1997, 272, 19763-19770. Concentrations of all oligonucleotides were calculated from UV absorbance at 260 nm after correction for the contribution of the fluorophore absorbance at 260 nm.

Fluorescence Measurements

All fluorescence measurements were performed in 50 mM Tris (pH 7.5), 100 mM NaCl, 5 mM KCl, 1 mM $MgCl_2$. Fluorescence spectra were recorded on Aminco Bowman Series 2 spectrofluorometer (Spectronic Instruments, Rochester, N. Y.). Spectra were corrected for buffer and instrument response. Fluorescence in microplates was read with a Tecan Spectra Fluor Plus microplate reader (Research Triangle Park, N.C.). Alternatively, microplates were imaged on Molecular Imager FX (BioRad, Hercules, Calif.) and fluorescence intensity was determined by integrating the areas of images corresponding to individual wells using QuantityOne software (BioRad). Experiments in 96-well plates and 384-well plates were conducted in 100 μl and 20 μl volumes, respectively. Depending on particular instrumentation, slightly different beacon signal changes are recorded due to different buffer background readings with different instruments (depending on the sensitivity of the instrumentation) and different wavelengths of excitation and emission available with each instrument.

Time-resolved fluorescence in the case of europium chelate—Cy5 labeled beacons was recorded on a laboratory-built instrumentation (Heyduk, T.; Heyduk, E. Analytical Biochemistry 2001, 289, 60-67), which employed a pulsed nitrogen laser as the excitation source. Emission was integrated for 100 ms with 30 msec delay after laser pulse.

Competition Assay to Determine Thrombin Aptamer Dissociation Constants.

Fluorescence intensity of THR2 in the presence and absence of the competitor was determined. Concentration of thrombin, THR2, and the competitor (when present) were 150 nM, 200 nM, and 200 nM, respectively. Under these conditions, binding of aptamers to thrombin was essentially stoichiometric. The previously described method (Matlock, D. L.; Heyduk, T. Biochemistry 2000, 39, 12274-12283) was used to calculate the ratio of the dissociation constant for THR2 to that of the competitor under these experimental conditions.

Thrombin Aptamer Binding by Electrophoretic Mobility Shift Analysis (EMSA).

Five microliter samples of 417 nM THR7 were incubated with various amounts of thrombin (0 to 833 nM). After 15 min incubation, 1 ml of 30% Ficoll were added and the samples were run on a 10% polyacrylamide gel in TBE buffer. After the run, the gel was stained for 30 min with Sybr Green and the image of the gel was obtained using Molecular Imager FX (BioRad). Intensity of the bands in the gel was determined by integrating the areas of image corresponding to individual bands using Quantityone software (BioRad).

Design of Aptamer-Based Molecular Beacons

FIG. 3B illustrates the overall concept of molecular beacons for proteins lacking natural sequence-specific DNA binding activity. This design shares some general similarities with molecular beacons for DNA binding proteins described previously by inventor (Heyduk, T.; Heyduk, E. Nature Biotechnology 2002, 20, 171-176; Heyduk, E.; Knoll, E.; Heyduk, T. Analyt. Biochem. 2003, 316, 1-10; Knoll, E.; Heyduk, T. Analyt. Chem. 2004, 76, 1156-1164; Heyduk, E.; Fei, Y.; Heyduk, T. Combinatorial Chemistry and High-throughput Screening 2003, 6, 183-194), (FIG. 3A). Instead of splitting the DNA duplex containing the natural binding site for a protein into the two "half-sites," two aptamers recognizing two non overlapping epitopes of the protein are used as functional equivalents of the "half-sites." Short complementary "signaling" oligonucleotides containing the fluorophore and the quencher are attached to the two aptamers via flexible linkers (FIG. 3B). In the absence of the target protein the two-aptamer "half-sites" cannot associate since the complementary oligonucleotides are too short to promote efficient annealing. Binding of the aptamer "half-sites" to the target protein brings the two "signaling" oligonucleotides into relative proximity increasing their local concentrations. This results in the annealing of the "signaling" oligonucleotides, which brings the fluorophore and the quencher into close proximity resulting in a change of fluorescence signal.

Properties of Bivalent Thrombin Aptamers

We used thrombin as a model system to provide "proof-of-principle" verification of the concept illustrated in FIG. 3B. Thrombin is a proteolytic enzyme involved in the blood-clotting cascade and naturally does not bind to DNA or RNA. Two laboratories have previously developed DNA aptamers, which selectively recognized two distinct epitopes of the protein (Bock, L. C.; Griffin, L. C.; Latham, J. A.; Vermass, E. H.; Toole, J. J. Nature 1992, 355, 564-566, Tasset, D. M.; Kubik, M. F.; Steiner, W. J. Mol. Biol. 1997, 272, 688 698). One aptamer (G15D; THR4, Table 1) was shown to bind to the heparin-binding exosite (Bock, 1992) whereas the other (60-18 [29]; THR3, Table 1) was shown to bind to fibrinogen-binding exosite (Tasset 1997). As a first step towards developing a beacon recognizing thrombin, we have prepared various aptamer constructs in which the above aptamers were covalently linked by flexible linkers. The primary purpose of these experiments was to determine if linking the two aptamers recognizing two distinct epitopes on a protein surface with a flexible linker would produce a bivalent aptamer capable of binding the protein with higher affinity compared to the individual aptamers. This is an essential condition for the assay illustrated in FIG. 3B to work. It was essential to experimentally address this question since it is impossible to predict the effect of long flexible linkers on the affinity of these bivalent constructs. A second purpose of these experiments was to establish a suitable length of the linker and the appropriate orientation of the 5' and 3' ends of the two aptamers with respect to the linker.

Figure 17:
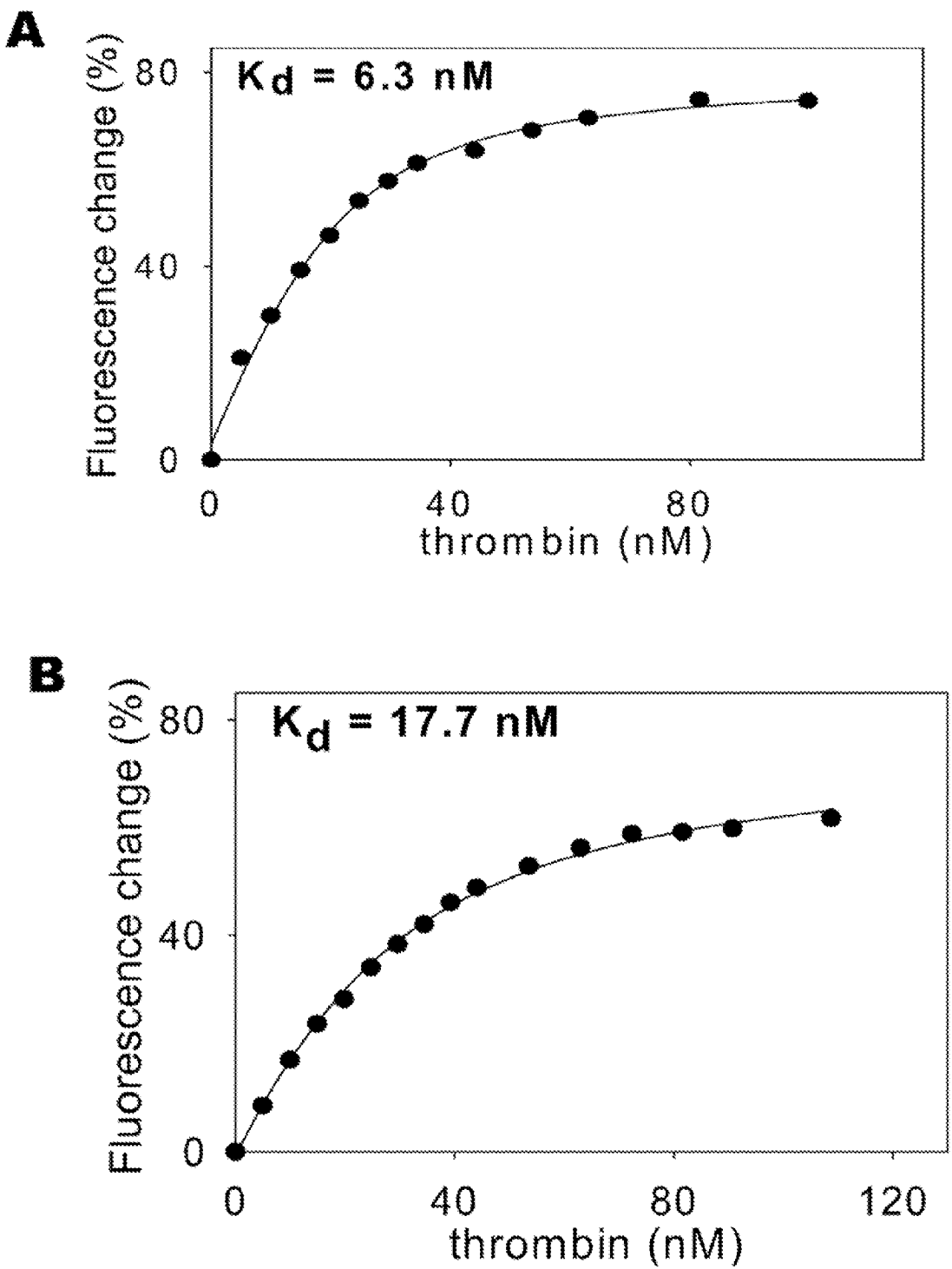
FIG. 17. The binding of aptamer constructs to thrombin. (A) Binding of G15D aptamer (THR2) (50 nM) detected by change in fluorescence intensity of 5' fluorescein moiety. Solid line represents the best fit of the experimental data to a simple 1:1 binding isotherm. (B) Binding of G15D aptamer (THR2) in the presence of 10× excess of unlabeled 60-18 [29] aptamer. Solid line represents the best fit of the experimental data to a simple 1:1 binding isotherm. (C) Summary of experiments probing competition between thrombin aptamer constructs and fluorescein-labeled G15D aptamer (THR2). Fluorescence intensity of THR2 (200 nM) was used to determine % THR2 bound in the presence of competitor (200 nM). Thrombin was 150 nM. The labels above each bar indicate relative affinity (expressed as fold increase of affinity constant) of the competitor compared to the affinity of THR2 aptamer. (D) Binding of THR7 aptamer construct to thrombin detected by gel electrophoresis mobility shift assay. Intensity of the band corresponding to THR7-thrombin complex is plotted as a function of thrombin concentration. Inset: Image of the gel stained with Sybr Green. Fluorescence change (%) was calculated as $100*(I-Io)/Io$ where I and Io correspond to dilution-corrected fluorescence emission intensity observed in the presence and absence of a given thrombin concentration, respectively.
Figure 17:
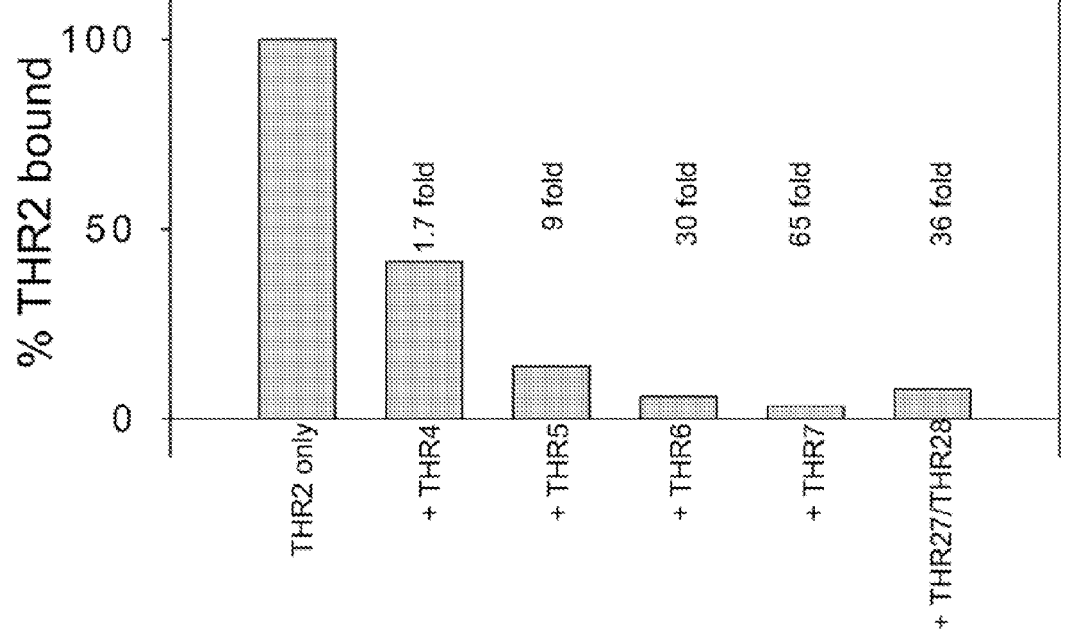
Figure 17:
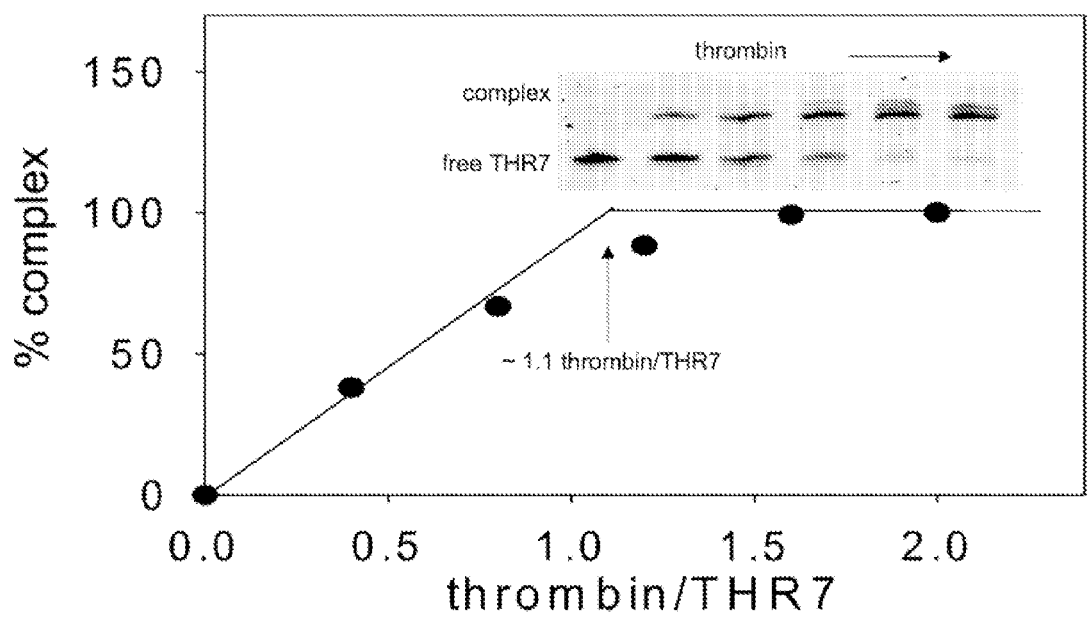

Individual aptamers were labeled with fluorescein (i.e., THR1 (Table 1) specific for the fibrinogen-binding exosite and THR2 (Table 1) specific for the heparin-binding exosite) to facilitate determination of the affinity of various constructs for thrombin. Formation of a complex between thrombin and the fluorescein-labeled 60-18 [29] aptamer (THR1) could be conveniently followed by fluorescence polarization (not shown) whereas binding of the fluorescein-labeled G15D aptamer (THR2) could be followed by changes in fluorescence intensity (FIG. 17A). Both aptamers bound thrombin in the nanomolar concentration range (data not shown for THR1 and FIG. 17A). Quantitative analysis of the binding in the case of THR2 (FIG. 17A) returned the value of Kd of 6.3 nM. This is somewhat higher affinity then previously suggested (Bock 1992, Tasset 1997) which is probably because we used a true equilibrium-binding assay whereas non-equilibrium methodology was used previously. When the binding of THR2 was performed in 10× excess of unlabeled 60-18 [29] aptamer (THR3) (FIG. 17B) only a small, insignificant decrease in affinity was observed (Kd was 17.7 nM). This confirmed that, as reported previously, G15D and 60-18 [29] aptamers bound independently to two distinct epitopes of thrombin.

In the next step, the ability of various aptamer constructs to compete with THR2 for binding to thrombin was evaluated. Fluorescence intensity change of THR2 upon addition of thrombin in the presence and absence of the competitor was measured and the amount of THR2 bound to thrombin in the presence of the competitor was calculated as described in Materials and Methods. No aptamer-aptamer interactions could be detected by fluorescence polarization assay (not shown) at aptamer concentrations used in these experiments indicating that the competition data correctly reported on the relative affinity of THR2 and the competitor for binding to thrombin. THR3 was not a competitor (FIG. 17C) in agreement with the data shown in FIGS. 17A and B. THR4 (unlabeled variant of THR2), as expected, was able to compete (FIG. 17C). Quantitative analysis of the competition in this case showed that THR4 bound thrombin 1.7 times better then THR2 indicating that labeling this aptamer with fluorescein had small (insignificant) negative effect on aptamer binding to thrombin. It is obvious that all of the bivalent aptamer constructs were by far better competitors than THR4 (FIG. 17C). THR7 appeared to be the best competitor, essentially completely blocking THR2 binding at 1:1 ratio. Quantitative analysis of the competition in this case revealed that THR7 bound thrombin at least 65 fold tighter then THR2 (estimated Kd for THR7 was <97 μM). The data shown in FIG. 17C confirmed the expectation that linking two aptamers recognizing two different epitopes of the protein with flexible linkers would produce high-affinity thrombin ligands. Additionally, these data showed that linking the two aptamers by a longer linker (containing 10 Spacer18 units vs. 5 Spacer18) produced slightly better affinity for thrombin (compare binding of THR5 vs. THR6). Also, these data showed that orientation of the aptamers with respect to the linker as in THR7 produced better affinity (compare affinity of THR6 vs. THR7). Thus, in all subsequent constructs, aptamer orientation as in THR7 was used.

The complex between the bivalent aptamer construct (THR7) and thrombin was stable enough to survive electrophoresis in native polyacrylamide gel (FIG. 17D). We took advantage of this observation and determined stoichiometry of the complex using electrophoretic mobility shift assay (EMSA) (Fried, M. G.; Crothers, D. M. Nucleic Acid Res. 1981, 9, 6505-6525) to follow THR7-thrombin complex formation. We performed a titration of THR7 with thrombin at high concentrations of both molecules. Under these conditions the binding should be stoichiometric. The plot of the complex formed vs. the ratio of thrombin to THR7 indicated 1:1 stoichiometry of the complex (FIG. 17D) consistent with the notion that both aptamer components of THR7 bind to their respective epitopes in THR7-thrombin complex.

Aptamer-Based Molecular Beacon Detecting Thrombin

Experimental data described above provided evidence that all necessary conditions for successful implementation of the design of the signaling beacon shown in FIG. 3B were met. Based on these data we have designed the thrombin beacon illustrated in FIG. 13A. Thrombin aptamers were connected using 5 Spacer18 linkers to a 7 nucleotide ("nt") complementary oligonucleotides labeled at 5' and 3' with fluorescein and dabcyl, respectively. Mixture of these two constructs bound thrombin much more tightly (~36 times) compared to individual aptamers (FIG. 17C) in agreement with high affinity thrombin binding observed for bivalent aptamer constructs in which the two aptamers were permanently linked with a flexible linker. Addition of thrombin to a mixture of fluorochrome and quencher-labeled THR20 and THR21 resulted in protein concentration-dependent quenching of fluorescence intensity (FIG. 13C). Maximum quenching observed was ~40%. No fluorescence change was observed (FIG. 13C) upon addition of thrombin to THR21 in the absence of dabcyl-labeled partner (THR20) indicating that fluorescence quenching occurred due to protein-induced increased proximity of signaling oligonucleotides resulting in their annealing as illustrated in FIG. 13B. At nanomolar concentrations of the beacon components and thrombin ~15 min of incubation was sufficient to produce maximal response of the beacon. We have also tested thrombin beacons analogous to one shown in FIG. 13 but in which 17 nt poly dT linkers were used in place of Spacer18 linkers. While thrombin-dependent quenching of fluorescence was observed, the quenching was ~2 times smaller than with the construct containing Spacer18 linkers. It is likely that poly dT linkers, while flexible, exhibited some residual rigidity (Mills, J. B.; Vacano, E.; Hagerman, P. J. J. Mol. Biol. 1999, 285, 245-257), which perhaps might impede association of the signaling duplex when the two aptamers are bound to thrombin. When the beacon shown in FIG. 13 was titrated with trypsin, a proteolytic enzyme structurally similar to thrombin, no change of fluorescence intensity was observed. We concluded that a functional thrombin beacon according to the design illustrated in FIG. 3B was obtained.

Improvements in Beacon Performance

Figure 18:
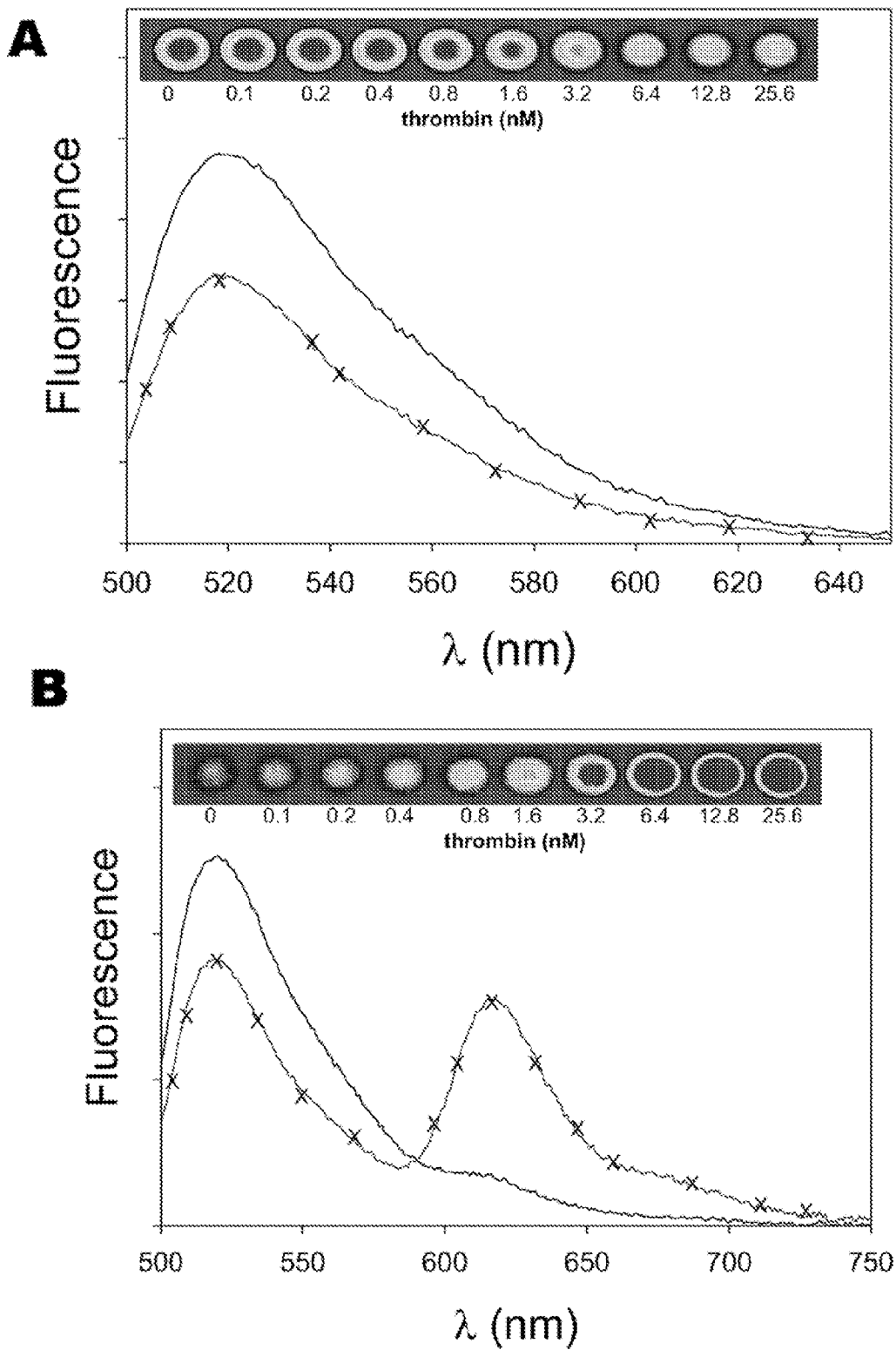
FIG. 18. Variants of thrombin beacon with various combinations of donor-acceptor fluorophores. (A) fluorescein-dabcyl; (B) fluorescein-Texas Red; (C) fluorescein-Cy5, (D) Cy3-Cy5. Emission spectra of the beacon in the absence (solid line) and presence (line with Xs) of thrombin are shown. Insets show images of microplate wells containing corresponding beacon and indicated concentrations of thrombin. The images were obtained on Bio-Rad Molecular Imager FX using the following excitation-emission settings: (A) 488 nm laser—530 nm bandpass filter; (B) 488 nm laser—640 nm bandpass filter; (C) 488 nm laser—695 nm bandpass filter.
Figure 18:
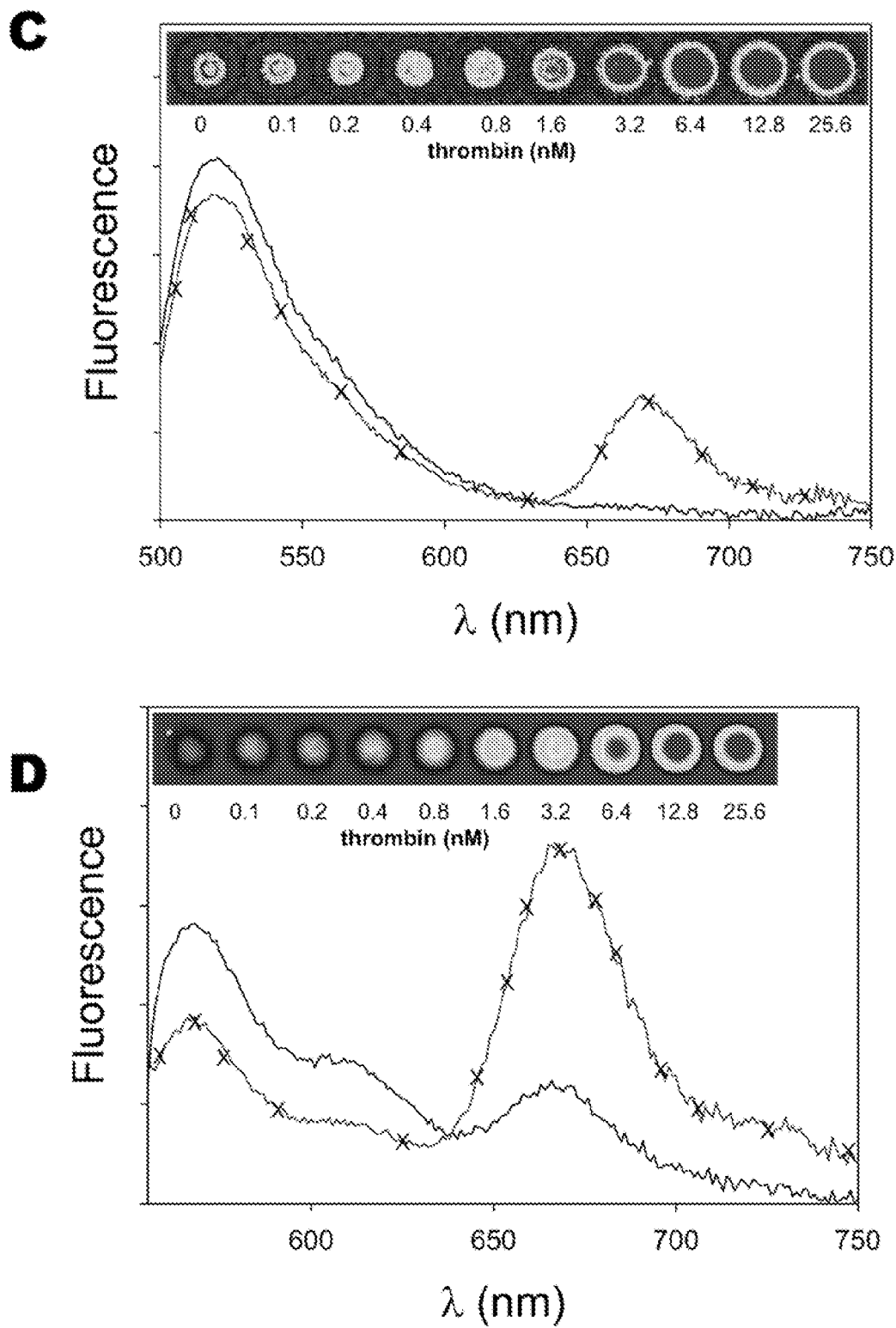

In the next set of experiments, we sought to improve the performance of the beacon by using alternative donor-acceptor label pairs. It has been shown previously that in assays employing FRET as the readout, enhancement of acceptor emission provides potentially better signal to background ratio, higher dynamic range, and better sensitivity (Heyduk, E.; Knoll, E.; Heyduk, T. Analyt. Biochem. 2003, 316, 1-10). We have prepared a series of thrombin beacon constructs analogous to the one depicted in FIG. 3B, but in which various combinations of fluorescent donor and fluorescent acceptor were incorporated into the signaling oligonucleotides in place of fluorescein-dabcyl pair. THR21 (or THR28 labeled with appropriate NHS ester of the dye) and THR27 labeled with appropriate NHS ester of the dye were used to prepare these beacons. FIG. 18 shows fluorescence spectra of beacons (without and with thrombin addition) labeled with: fluorescein-Texas Red (FIG. 18B), fluorescein-Cy5 (FIG. 18C) and Cy3-Cy5 (FIG. 18D). In all cases functional beacons were obtained and with each beacon containing a fluorescent donor and fluorescent acceptor, a large thrombin concentration-dependent increase of sensitized acceptor emission was observed (FIG. 18, insets and FIG. 19A-D). For comparison, FIG. 18A illustrates fluorescence quenching observed in the presence of thrombin in the case of a fluorophore-quencher pair (fluorescein-dabcyl). FIG. 19E illustrates results obtained with europium chelate-Cy5 donor-acceptor pair which allowed the use of time-resolved FRET (TR-FRET) as a detection method (Selvin, P. R.; Rana, T. M.; Hearst, J. E. J. Am. Chem. Soc. 1994, 116, 6029-6030; Selvin, P. R.; Hearst, J. E. Proc. Natl. Acad. Sci. USA 1994, 91, 10024-10028; Mat this, G. Clinic. Chem. 1995, 41, 1391-1397). With TR-FRET it is possible to eliminate background due to light scattering and prompt fluorescence of directly excited acceptor to further improve signal-to-background ratio of the beacon. FIG. 19F summarizes the performance of beacon variants with various combinations of donor and acceptor probes. The figure shows the fold of signal change in the presence of saturating concentrations of thrombin compared to background signal of the beacon observed in the absence of the protein. This ratio varied from ~2 in the case of fluorescein-dabcyl pair to ~22 in the case of europium chelate-Cy5 pair. Thus, a substantial improvement of beacon performance can be obtained by selecting optimal donor-acceptor pairs and using sensitized acceptor emission as the mode of signal detection. An additional advantage of beacon variants with a fluorescent donor and a fluorescent acceptor is that their response can be measured by a two-color determination of the ratio of acceptor to donor signals. Such ratiometric measurement provides a more stable signal, which is more resistant to nonspecific effects due to light absorption, light scattering or fluorescence quenching caused by additives present in the sample. Increased signal-to-background ratio obtained with optimized donor-acceptor pairs resulted in an increased sensitivity of the beacon. This is illustrated in FIG. 20, which shows responses of three selected beacon variants to low concentrations of thrombin. In the case of the fluorescein-dabcyl labeled beacon (the lowest (~2 fold) signal change in the presence of saturating concentration of thrombin), statistically significant signal change could only be detected at the highest thrombin concentration tested (1 nM). In the case of the fluorescein-Texas Red labeled beacon (~5 fold signal change at saturating thrombin concentration), statistically significant signal change could be detected at lower thrombin concentration (200 μM). In the case of the fluorescein-Cy5 labeled beacon (~15 fold signal change at saturating thrombin concentration), statistically significant signal change could be detected at the lowest thrombin concentration tested (50 μM).

Signaling oligos play two important roles in assays that use FRET detection. The first role, as in other assays, is to provide the means for generating a FRET signal, thereby reporting the presence of the target protein. It is important to emphasize that the use of the signaling oligos (as opposed to direct labeling of the epitope binding agents with fluorescence probes) allows the reliable generation of a FRET signal regardless of the specific configuration of the complex and the size of the complex (within the range of the reach of flexible linkers). This is because the FRET signal is generated due to target protein dependent annealing of the signaling oligos, which brings the fluorescent probes into close proximity. This proximity does not depend on the architecture of the complex but is determined by a simple and predictable geometry of duplex DNA. Typically, the relatively short distance between probes (~50 Å or less) necessary for efficient FRET can be difficult to incorporate into an assay design. The signaling oligos eliminate one of the difficulties in designing assays based on FRET.

The second role of the signaling oligos is less obvious but equally important. Favorable free energy of association between the signaling oligos, together with their high local concentration (resulting from their attachment through flexible linkers) increases the stability of the complex. A simple model was used to study the rules of free energy additivity in multivalent ligands connected by flexible linkers. This analysis indicated that the stability of the complex could be 10-10,000 times better (depending on the affinity of individual epitope binding agents, length of signaling oligos, and the length of flexible linkers) compared to the same complex without a signaling oligo component. Increased stability of the complex will result in increased sensitivity and increased specificity of the assay.

FIG. 21 illustrates the excellent reproducibility and stability of the thrombin beacon signal. The beacon signal was measured at four thrombin concentrations in five independent measurements. Coefficients of variation were small at each protein concentration tested (FIG. 21A). The beacon signal was stable for at least 24 hours (FIG. 21B).

Coincidence of three molecular contacts is required to generate a signal with the beacon illustrated in FIG. 3B: two contacts between each of the aptamers and the protein and the contact between the two complementary "signaling" oligonucleotides. Each of these contacts provides its own free energy contribution to the overall stability of beacon-protein complex. Due to an exponential relationship between the free energy and equilibrium dissociation constant of the complex, the overall stability of the complex would greatly decreased in the absence of any of the above three molecular contacts. Thus, it is expected that molecular beacons described here should exhibit greater specificity of protein detection compared to an assay based on a single molecular contact (for example, a single aptamer-based assay). To illustrate this concept we have compared the response of a single thrombin aptamer and thrombin beacon to SSB (Single Stranded DNA binding protein from *E. coli*), a protein exhibiting high non-specific affinity for binding ss DNA (data not shown). SSB at nanomolar concentrations produced a large signal (as measured by fluorescence polarization assay) with the single, fluorescein-labeled aptamer (THR1, Table 1). SSB produced the response in a concentration range very similar to the concentration of thrombin required to bind this aptamer. Thus, single thrombin aptamer exhibited very poor discrimination between SSB and thrombin. In contrast, exposure of thrombin beacon to nanomolar SSB concentration did not produce any significant beacon response, while thrombin at the same concentration range produces large beacon response. Thus, the thrombin beacon exhibited excellent discrimination between SSB and thrombin illustrating enhanced specificity of the beacon.

The primary application of the assay design described here will be in homogeneous high-throughput protein detection. Zhang et al. (Biomol. Screening 1999, 4, 67-73) developed a simple statistical parameter, which could be used to evaluate assay for the use in a high-throughput manner. Z'-factor is calculated from large number of repeats of the measurement in the absence and the presence of the protein. Z' value of 1 indicates an ideal assay, Z' value of 0.5 to 1 indicates an excellent assay. Z' values below 0.5 indicate an assay not well suited for high-throughput applications. Z' value for the thrombin beacon was 0.94 (FIG. 22) which shows that it will be an outstanding high-throughput assay.

Detection of Thrombin in Complex Mixtures

The next series of experiments addressed the specificity of the thrombin beacon and its ability to detect thrombin in cell extracts and in plasma. Response of the beacon to 1 nM thrombin was not affected by 100 and 1000 fold excess of unrelated protein (ovalbumin, FIG. 23A). Also, 100-fold excess of factor Xa, another clotting protease structurally similar to thrombin, did not affect the beacon response to 1 nM thrombin (FIG. 23A). A 1000-fold excess of factor Xa slightly attenuated the beacon response but 1 nM thrombin was still readily detectable under these conditions (FIG. 23A). Ovalbumin and factor Xa up to 1 mM concentration had no effect on the beacon signal in the absence of thrombin (FIG. 23A). We concluded that the beacon was highly selective for thrombin.

To test if the beacon could detect thrombin in a complex mixture, we spiked HeLa cellular extract with varying amounts of thrombin and determined beacon response to this mixture (FIG. 23B). Low nanomolar concentrations of thrombin were readily detected. A total of 8 µg of protein were added to a 20 µl assay, which is within a typical range used in experiments with cellular extracts. The signal observed upon addition of cell extract could be completely abrogated by addition of a specific competitor (unlabeled thrombin aptamer) confirming that the observed signal in the cell extract was due to thrombin. One difficulty we've encountered working with cellular extracts was the degradation of oligonucleotides—components of the assay—by nucleases present in cellular extracts. We have tested various buffer additives to find conditions in which the thrombin beacon would remain stable in the presence of cell extracts for a sufficiently long period of time. We found that addition of high concentrations of random sequence 30 bp ds DNA (10 mM), high concentrations of 20 nt random sequence ss DNA (0.1 mM), and 2.5 mM EGTA protected the thrombin beacon from degradation in the presence of cellular extracts without significantly affecting the response of the beacon to thrombin. Data shown in FIG. 23B were obtained in the presence of the above additives.

Since thrombin is a plasma protein, we determined if the beacon could be used to detect the protein in plasma. All of the thrombin in plasma is present in a precursor form, prothrombin, which is converted to thrombin via proteolytic processing by factor Xa. Prothrombin was recognized by the thrombin beacon albeit with much reduced (>20 fold) sensitivity compared to thrombin (not shown). This is well illustrated by the experiment shown in FIG. 23C in which the sensitized acceptor emission of the beacon in the presence of prothrombin was monitored as a function of time. At the point marked by the arrow, factor Xa was added to the mixture to initiate conversion of prothrombin to thrombin. This conversion resulted in a time-dependent increase of beacon signal consistent with a much higher sensitivity of the beacon to thrombin. Thus, in order to detect thrombin in plasma, factor Xa was included in the assay mixture (FIG. 23D). Adding increasing amounts of plasma resulted in a proportional increase of beacon signal (FIG. 23D). Addition of plasma produced a response from the beacon only if factor Xa was present in the assay. The signal observed upon addition of plasma could be completely abrogated by addition of a specific competitor (unlabeled thrombin aptamer) confirming that the observed signal in the cell extract was due to thrombin. A 5 nL sample of plasma produced a measurable response of the beacon in a 20 µl reaction volume. In summary, the experiments illustrated in FIG. 23 demonstrated functionality of the thrombin beacon for detecting the protein in complex biological mixtures.

Blood-Clotting Experiments

Experiments were designed to compare the effects on the rate of blood clotting of a thrombin beacon and its aptamer components. Thrombin was mixed with either a beacon or an individual aptamer in 1 mL of assay buffer (20 mM Tris-HCl, pH 7.4, 0.15 mM NaCl). The final concentration of thrombin was 242 nM. After incubation at room temperature for 30 min, 45 µL of this mixture was added to 280 µL of whole blood that had been diluted 50% with assay buffer. The blood clotting time was measured with a hand-held instrument. The final concentration of either the beacon or each component aptamer is shown FIG. 44. Under these assay conditions, the beacon is about 50 times more effective than THR4 and 240 times more effective than THR3 in blocking the blood clotting process induced by thrombin.

Discussion

The design of aptamer-based molecular beacons described here is a generalization of the design of molecular beacons for detecting sequence-specific DNA binding proteins previously developed by us (FIG. 3). Experiments with thrombin as a model protein presented here provide proof-of-principle evidence for the feasibility of this design. We believe this design will have several important advantages. Since the design of molecular beacons described here is not limited to any specific protein, it will be generally applicable to a large number of proteins. Signaling in the presence of the target protein by our beacon requires a cooperative recognition of two separate epitopes of the protein by two distinct aptamers. This will result in an enhanced specificity of the beacon and increased affinity (i.e. sensitivity of detection). This cooperative action of two aptamers will also allow the use of aptamers with modest affinity to produce molecular beacons binding to target proteins with high affinity and specificity. Aptamers—components of the beacon, do not require any engineering of their structure to tailor their distribution of conformations to allow "switching" between different states in the presence of the protein. Such engineering could be dependent on a particular sequence (structure) of the aptamer and, such balancing of the energetics of alternative conformations of nucleic acids is not necessarily a trivial matter. Since the signaling elements ("signaling" oligonucleotides) in the instant beacon design are separate from its aptamer components, any aptamer sequence (and structure) should be compatible with our beacon design. It is also unlikely that the addition of the "signaling" oligonucleotides will have any deleterious effect on the affinity and specificity of the aptamer components of the beacon. Thus, any protein for which it will be possible to obtain two aptamers recognizing two distinct epitopes of the protein should be a good target for developing molecular beacons according to scheme in FIG. 3.

Antibodies recognizing distinct epitopes of the protein can be obtained relatively easily. Similarly, there are no reasons why aptamers recognizing distinct epitopes could not be developed for many target proteins and several examples are already available (Jayasena, S. D. Clinical Chem. 1999, 45, 1628-1650). Several approaches towards achieving this goal would be possible. The first approach would be to perform in vitro selections (SELEX) using different methods for separation of protein-bound and unbound oligonucleotides. The rationale here is that in these different partitioning methods different regions of the protein could be preferentially displayed resulting in aptamers directed to different regions of the protein surface. Aptamers selected to thrombin are an example of such approach (Bock, 1992; Tasset, 1997). The second approach could be to raise the aptamers to peptides corresponding to different regions of the target protein molecule. Experimental evidence exists to show that such strategy can be used to develop aptamers capable of recognizing the intact protein from which the peptide used as a target for aptamer development was derived (Wei, X.; Ellington, A. D. Proc. Natl. Acad. Sci. USA 1996, 93, 7475-7480). Such an approach is widely used to generate antibodies recognizing proteins. Two aptamers recognizing different epitopes of the protein can also be produced by a two-step sequential SELEX in which the second step involves selecting an aptamer in the presence of saturating concentration of the aptamer selected in the first step. We have validated this procedure using thrombin as a model system (Heyduk, E. and Heyduk, T., unpublished). Finally, we have developed a novel in vitro selection strategy to produce pairs of aptamers specifically designed to function in our molecular beacon design (Heyduk, E., Kalucka, J., Kinnear, B., Knoll, E., and Heyduk, T., unpublished). Thus, multiple routes to obtain pairs of aptamers recognizing non-overlapping epitopes of the protein will be available.

Example 4

Sensor Design Variations

Figure 25B:
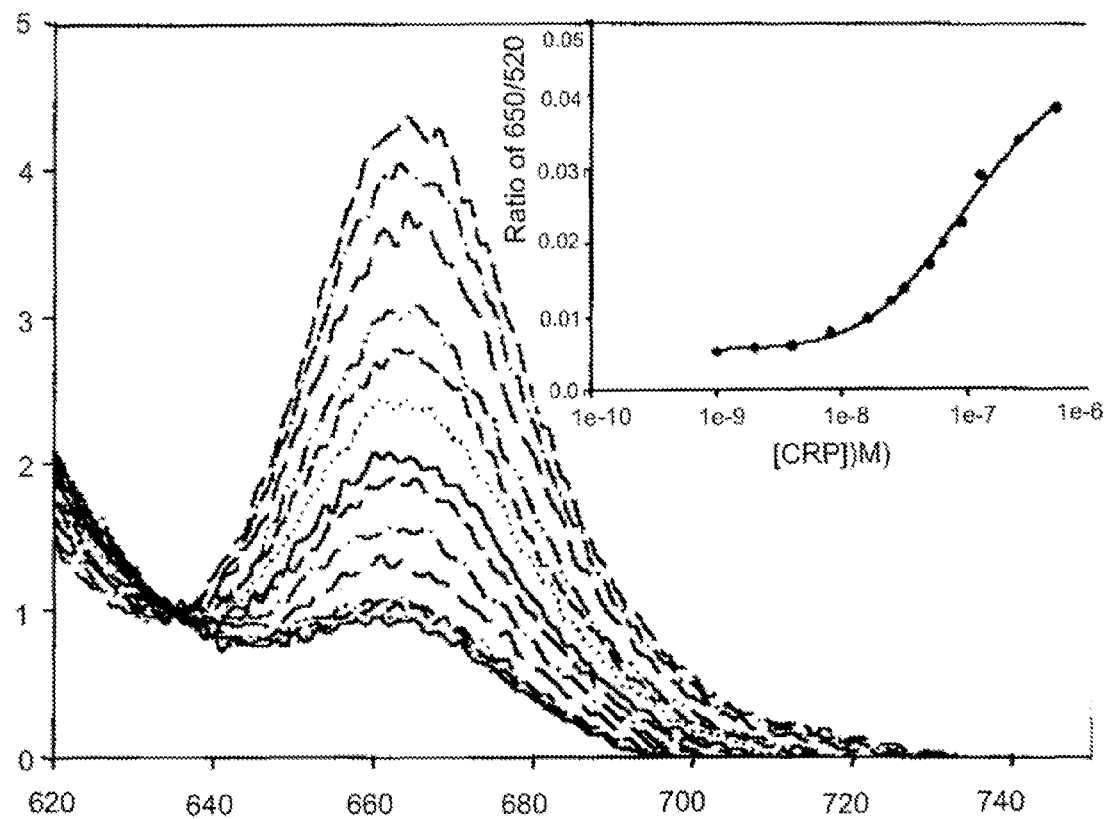

Several variations of the instant molecular beacon are applicable in the practice of this invention. Those variants of the sensor design are depicted in FIG. 24 and summarized herein (supra). The sensor design depicted in FIG. 24F is demonstrated to effectively detect DNA binding proteins. Upon the titration of cAMP response element binding protein ("CRP"), which is an example of a DNA binding protein, to a mixture of donor and acceptor labeled sensor components, there is a concomitant increase in sensitized acceptor fluorescence intensity (FIG. 25B).

The sensor design depicted in FIG. 24G is demonstrated in FIG. 26. Panel A depicts the principle of the sensor function. Upon the addition of single stranded DNA, which contains two distinct sequence elements that are complementary to elements in the sensor, to the mixture of two donor and acceptor labeled sensor components, there is a concomitant increase in sensitized acceptor fluorescence intensity (FIG. 26, B, line with + sign). The sensor in this particular case contained Texas Red-labeled THR29 and THR32.

The increased specificity of the instant molecular beacon sensor design compared to assays based on a single, target macromolecule-recognizing element was experimentally demonstrated (FIG. 27). Recognition of the target molecule by the sensor involves coincidence of three molecular contacts each providing a free energy (DG) contribution to the overall stability of the complex resulting in high specificity of target molecule recognition. Due to an exponential relationship between the free energy and equilibrium dissociation constant of the complex, the overall stability of the complex would greatly decrease in the absence of any of the above three molecular contacts. A nonspecific single stranded DNA binding protein ("SSB") at nanomolar concentrations produced a large signal (as measured by fluorescence polarization assay) with the single, fluorescein-labeled aptamer (THR1, Table 1). SSB produced the response in a concentration range very similar to the concentration of thrombin required to bind this aptamer. Thus, a single thrombin aptamer exhibited very poor discrimination between SSB and thrombin. (Panel B) Exposure of the thrombin sensor (a mixture of THR21 (fluorescein-labeled) and Texas Red labeled THR27) to nanomolar SSB concentration did not produce any significant beacon response (dashed lines), while thrombin at the same concentration range produces large beacon response (Panel C). Thus, the thrombin beacon exhibited excellent discrimination between SSB and thrombin, illustrating the enhanced specificity of the beacon.

Methods for Preparing Aptamers for the Variant Sensors

The selection of an aptamer binding to thrombin at an epitope distinct from the binding site of G15D aptamer was performed using the SELEX procedure starting from a construct containing a 33 nt random sequence (THR11) in the presence of excess G15D aptamer-containing construct (THR22) (FIG. 28, panel A). Panel B depicts the thrombin binding activity of single stranded DNAs obtained after each indicated round of selection. Measurable thrombin binding activity appeared after the 4th selection and reached a maximum after the 12th selection. Binding was measured in the presence of the excess of THR22. DNA obtained after the 12th selection was cloned and DNA obtained from individual clones was sequenced. Panel C depicts the sequence alignment (using ClustalX) of the individual clones. Clones obtained from 4 independent selection experiments are shown. These selections were performed using the following pairs of aptamer constructs and random sequence-containing nucleic acid constructs: THR22 and THR 11; THR25 and THR 11; THR42 and THR11; THR43 and THR 11. Several families of highly conserved sequences are easily visible in panel C.

A functional thrombin sensor comprising Texas Red-labeled THR27 and fluorescein-labeled THR35 or THR36, which contain sequences corresponding to that of clones 20, 21, 24, and 26 from FIG. 28C, is depicted in FIG. 29. THR35 and THR36 differ by the length of DNA sequence flanking the sequence of clones 20, 21, 24, and 26. The fluorescence image (sensitized acceptor emission) of wells of a microplate containing 20 nM (panel A) or 100 nM (panel B) of the indicated thrombin sensor and the indicated concentrations of thrombin are shown. For comparison, a sensor comprising THR21 and THR27 is shown.

FIG. 30 depicts the results of simultaneously selecting two aptamers that bind to a target at distinct epitopes. The selection procedure began with two types of nucleic acid constructs, each containing a 30 nt random sequence (THR49 and THR50) (Table 1), and the target thrombin (panel A). Five mM of THR49 was added to 5 mM THR50 in a total of 1 mL of buffer (50 mM Tris-HCl (pH 7.5), 100 mM NaCl, 5 mM KCl and 1 mM $MgCl_2$). The mixture was boiled for approximately 1 min, and allowed to cool to room temperature (RT). Thrombin (200 nM) was added, and the mixture was incubated for 15-30 min at RT. Next, the mixture was spun through a nitrocellulose filter (NCF), followed by 2 washes of 1 mL and a single wash of 0.5 mL. Pre-warmed urea (200 µL of 7M solution containing 1M NaCl) was loaded on the NCF, and incubated for 15 min at 37° C. The DNA/urea mixture was eluted, and the DNA was precipitated with ethanol (added cold ethanol (2.5× the volume of eluted DNA) and incubated for at least two hours at −20° C.). The precipitated DNA was centrifuged, the supernatant removed, and the subsequent pellet was dried in a speed-vac. The pellet was re-dissolved in 20 µL of water, and used as a template for the PCR reaction.

Each PCR reaction contained 80 µL of dd $H_2O$, 10 µL 10×PCR buffer, 6 µL of $MgCl_2$, 0.8 µL 25 mM dNTPs, 1 µL 50 µM primer 1 (modified with fluorescein), 1 µL 50 µM primer 2 (biotinylated), 0.5 µL Taq polymerase, and 1 µL of template. Two different sets of PCR reactions were performed corresponding to the two different types of nucleic acid constructs used (THR 49 and THR 50). The reaction cycle consisted of 5 min at 95° C., sixteen cycles of 30 s at 95° C., 30 s at 50° C., and 1 min at 72° C., and 5 min at 72° C. The samples were allowed to cool, and subsequently separated on a polyacrylamide gel. The band(s) of interest were visualized by utilizing the fluorescein tag, and were excised from the gel. The gel pieces were transferred to a microtube and crushed using a pipette tip. The gel pieces were covered with diffusion buffer (100 mM Tris (pH 8.0), 0.5 M NaCl, 5 mM EDTA) and the mixture was incubated for at least two hours at 50° C. After centrifugation the supernatant was filtered through an empty Bio-Rad microspin column. The gel pieces were washed with fresh diffusion buffer, and the process repeated for a second time. The supernatants from the first and second procedures were combined.

Pre-equilibrated (1 M NaCl, 50 mM Tris (pH 8.0), and 1 mM EDTA) DYNAL magnetic streptavidin beads were mixed with the gel-purified DNA, and incubated at RT for 30 min with constant shaking. The supernatant was removed, and the beads were washed once with 500 µL, once with 250 µL, and once with 100 µL of buffer. Next, the beads were incubated for 30 min at 37° C. with 50 µL of 0.15N NaOH. The supernatant containing the fluorescein labeled DNA was removed and filtered through a G-25 Sephadex microspin column pre-equilibrated with buffer. The estimated concentration of the recovered DNA was calculated by comparison to a known amount of fluorescein-labeled primer.

The second round of selection began by combining 50 nM of the recovered DNA and 50-1000 nM of THR22 in a total of 50 µL of selection buffer. The DNA mixture was boiled for 1 min, and allowed to cool to RT. Subsequently, the DNA mixture was filtered through a pre-equilibrated NCF to remove DNA sequences with affinity for the NCF. Thrombin (20 nM) was added to the filtered DNA and the mixture was incubated for 15-10 min at RT. Next, the mixture was spun through another pre-equilibrated NCF, followed by two washes of 100 µL. After incubation with 100 µL of urea (7M in a buffer of 1M NaCl) for 15 min at 37° C., the DNA-thrombin complexes were eluted from the NCF. The DNA in the eluted solution was precipitated with alcohol (see above) and re-suspended in 20 µL of water. This was used as a template for the PCR reaction. PCR products were purified by electrophoresis on a polyacrylamide gel and the single-stranded DNA was obtained from purified PCR products as described above for the first selection. Subsequent selections were repeated until the detected thrombin-binding activity reached a maximum (FIG. 30B).

The thrombin-binding activity of the mixture of single-stranded DNAs obtained after each indicated round of selection is shown in panel B. Measurable thrombin-binding activity appeared after the 8th selection and reached a maximum after the 13th selection. DNA obtained after the 13th selection was cloned and the DNA from individual clones was sequenced. Panel C depicts the sequence alignment (using ClustalX) of the clones. Several families of highly conserved sequences are easily visible.

Aptamer-based molecular beacons were developed for cAMP response element binding protein ("CRP"). Aptamers were selected to bind at sites distinct from the DNA binding site of the protein. Selection was performed using the SELEX procedure starting from a construct containing a 33 nucleotide random sequence (MIS12) in the presence of excess of CRP binding site-containing construct (MIS10X3 hybridized with MIS11) (FIG. 31, panel A). CRP binding activity of single stranded DNA that was obtained after indicated round of selection is depicted in FIG. 31, panel B. Measurable CRP binding activity appeared after 6th selection and reached maximum after 12th selection. Binding was measured in the presence of excess MIS10X3 hybridized with MIS11. DNA obtained after 12th selection was cloned and DNA obtained from the individual clones were sequenced. The sequence alignment (using ClustalX) of the clones is depicted in panel C. Conserved core sequence of ~16 nucleotides could be identified.

Example 5

Sensors Employing Antibodies

There are several sensor configurations that employ antibodies as epitope binding agents. FIG. 24, panels D and E, illustrate two possibilities. Preliminary experiments using a simple model system were performed with the molecular biosensor design shown in FIG. 24D. This model system (FIG. 34A) consists of an anti-biotin antibody, biotin-labeled CRP protein (biotin attached at a single-cysteine residue at the N-terminal of the protein), and a DNA molecule containing a CRP binding site. A short signaling oligo labeled with Cy5 was attached via a long flexible linker to the DNA molecule containing the CRP binding site. Then, the anti-biotin antibody was conjugated to a short signaling oligo labeled with fluorescein. (See below for more details on the method of conjugation.) When CRP-biotin was added to a mixture of the anti-biotin antibody and the CRP DNA, a FRET (Fluorescence Resonance Energy Transfer signal is generated, validating the ability of the labeled antibody to function within the molecular biosensor design.

The signal (FRET from fluorescein to Cy5) increased with increasing CRP-biotin concentration (up to ~40 nM), consistent with the ~50 nM concentration of beacon components used (FIG. 34B). The signal was specific as essentially no FRET increase was observed when CRP-biotin was added in the absence of cAMP (which is required for CRP-DNA interaction) (FIG. 34C) or when excess of streptavidin (which will block antibody binding) was present (FIG. 34C).

The FRET measurements were performed in 384-well low-volume microplates (Corning) in 20 mM Tris (pH 8.0), 100 mM NaCl, 10 µM EDTA buffer. Fluorescence intensities were measured using a Tecan Spectrofluor Plus fluorescence plate reader. A 20 µl mixture of 50 nM anti-biotin antibody (Sigma) conjugated to the fluorescein-labeled ANTB8 (see Table 1) signaling oligo and 50 nM Cy5-labeled BICAP/ANTB7 DNA duplex (Table 1) were titrated with increasing concentration of biotinylated cAMP receptor protein (CRP) in the presence of 200 µM cAMP (FIG. 34B). Specificity control experiments (FIG. 34C) were performed with 20 µl mixture of 50 nM anti-biotin antibody conjugated to fluorescein-labeled ANTB8 (Table 1) signaling oligonucleotide, 50 nM Cy5-labeled BICAP/ANTB7 DNA duplex (Table 1), and 100 nM biotinylated CRP. Streptavidin and cAMP, when used, were present at 1 µM and 200 µM respectively.

CRP that was biotinylated at a single site was obtained by reacting mutant CRP containing a single reactive cysteine at its N-terminus with maleimide PEO2-EZ-link-biotin (Pierce). A 100 µl sample of ~15 µM CRP was incubated with 0.1 mM DTT for 30 min at room temperature. Excess DTT was removed on a ZEBA spin column equilibrated with 20 mM NaH$_2$PO$_4$ (pH 7.4) buffer containing 0.15 M NaCl and 2.5 mM EDTA. Reduced CRP was then reacted with a 20 fold molar excess of maleimide PEO2-EZ-link-biotin in 20 mM NaH$_2$PO$_4$ (pH 7.4) buffer containing 0.15 M NaCl and 2.5 mM EDTA for 2 hrs at room temperature. Excess unreacted biotin reagent was removed on a ZEBA spin column equilibrated with 20 mM Tris (pH 8.0), 100 mM NaCl, 10 µM EDTA buffer.

Another possible antibody based biosensor design employs two antibodies recognizing two distinct epitopes of the target protein (FIG. 24E). Each of the antibodies is conjugated, via a long flexible linker, to a fluorophore-labeled signaling oligo. In the presence of the target molecule both antibodies will bind to the target molecule resulting in a great increase of the local concentration of signaling oligos. This in turn leads to annealing of the oligos, which brings the fluorophores into close proximity, allowing generation of a FRET signal.

This sensor design was used in the experiments represented by FIG. 35. An example of the model system is shown in FIG. 35A. Anti-biotin and anti-digoxin antibodies were labeled with complementary 7 nt signaling oligos via long flexible linkers. The complementary signaling oligos contained fluorescein and Cy5, respectively. As a mimic of a target macromolecule with two epitopes, a short (30 bp) duplex DNA labeled on opposite ends with biotin and digoxin was used When biotin and digoxin-labeled DNA duplex was added to a mixture of labeled anti-biotin and anti-digoxin antibodies, a dose-dependent FRET signal was observed until the saturation point where more or less equal molar amounts of biot-DNA-dig and antibodies were present in the mix (FIG. 35B). FRET signal in the presence of dig-DNA-biot was specific since no FRET signal was observed when DNA labeled with biotin-only or with digoxin-only were added to the mixture of labeled antibodies (FIG. 35C).

The FRET measurements were performed in 384-well low-volume microplates (Corning) in 20 mM Tris (pH 8.0), 100 mM NaCl, 10 µM EDTA buffer. Fluorescence intensities were measured using a Tecan Spectrofluor Plus fluorescence plate reader. A 20 µl sample containing 25 nM anti-biotin antibody conjugated with fluorescein-labeled ANTB8 (Table 1) signaling oligonucleotide and 30 nM anti-digoxin antibody (Jackson ImmunoResearch) conjugated with Cy5-labeled ANTB6 (Table 1) signaling oligonucleotide was titrated with increasing concentrations of biotin and digoxin-labeled DNA duplex (obtained by annealing ANTB9 and ANTB7 oligos, see Table 1) (FIG. 35B). Specificity control experiments (FIG. 35C) were performed with a 20 µl mixture of 25 nM anti-biotin antibody conjugated to fluorescein-labeled ANTB8 (Table 1) signaling oligonucleotide and 37.5 nM anti-digoxin antibody conjugated with Cy5-labeled ANTB6 (Table 1) signaling oligonucleotide. To this mixture 50 nM biotin and digoxin-labeled DNA duplex, 1 µM biotin-only DNA (ANTB9, see Table 1), or 1 µM digoxin-only DNA (ANTB7DIG, see Table 1) were added (FIG. 35C).

Conjugation of Signaling Oligos to Antibodies

Signaling oligos were conjugated to antibodies by crosslinking the amino group at the end of the oligo with a free —SH group introduced into the antibody. Signaling oligos were synthesized with an amino group at the 5' end, and with a fluorescent probe or a —S—S— group at the 3' end. When a fluorescent label was introduced at the 3' end of the oligo during synthesis, maleimide addition to the 5' end could be performed immediately. When the —S—S— group was present at the 3' end, it was first reduced to free —SH and then modified with a sulfhydryl-reactive fluorescent probe. The —S—S— group of the oligo was reduced to a free —SH group by incubating 50 µl of ~2 mM oligonucleotide in 50 mM DTT for 5 hrs at room temperature followed by overnight incubation at 40. Excess DTT was removed by two successive Sephadex G-25 spin column purifications. The columns were equilibrated with 0.1 M NaHCO$_3$ buffer (pH 8.3). Five molar excess of fluorescein maleimide (Molecular Probes) dissolved in DMF were added and the sample was incubated 2-3 hrs at room temperature. Excess fluorescein maleimide was removed on Sephadex G-25 spin column equilibrated with 0.1 M NaHCO$_3$ buffer (pH 8.3). A malemide group was added to the 5' end of the construct by adding 10 molar excess of SMCC (Pierce) dissolved in DMF. The reaction was allowed to continue for 2 hrs at room temperature and was loaded on a 150×4.1 mm 5 µm PRP-1 reverse phase column (Hamilton)

equilibrated in buffer "A" (25 mM TAA Buffer, 2% acetonitrile). Labeled oligos were eluted at 1 ml/min with a gradient of 0 to 90% 25 mM TAA, 95% acetonitrile buffer. The fractions containing purified SMCC and fluorescein-labeled oligonucleotide were pooled and dried by Speed-Vac. They were stored dry at −200 until needed.

Free —SH groups were introduced to the antibody by treating 100 µl of the antibody at ~5 mg/ml in 20 mM $NaH_2PO_4$ (pH 7.4) buffer containing 0.15 M NaCl and 2.5 mM EDTA with 50 molar excess of Traut's reagent (Pierce) for 1.5 hrs at room temperature. Excess unreacted Traut's reagent was removed on a ZEBA spin column (Pierce) equilibrated with the phosphate buffer described above. A 7-8 molar excess of SMCC-labeled signaling oligos were added and the mixture was incubated for 6 hrs at room temperature followed by overnight incubation at 40. Excess unreacted oligonucleotide was removed by chromatography on a 1 ml Protein A-HP Sepharose column (Pharmacia). The column was equilibrated with 0.1 M Tris (pH 8.0). A 100 µl reaction mixture was diluted to 500 µL with 0.1 M Tris (pH 8.0) and loaded on the column. The column was washed with 5 ml of 0.1 M Tris (pH 8.0). Antibodies conjugated to the oligonucleotide were eluted with 100 mM glycine (pH 3.0). Fractions (0.5 ml) were collected in tubes containing 100 µl of 1M Tris (pH 8.0). Fractions containing antibodies conjugated to the oligonucleotide were pooled and dialyzed overnight with 20 mM Tris (pH 8.0), 100 mM NaCl and 10 µM EDTA. Analysis on a native polyacrylamide gel revealed that the final product was a mixture of unlabeled antibodies, antibodies labeled with one oligonucleotide, and antibodies labeled with more then one oligonucleotide. While these three species could be resolved on a 1 ml Resource Q column (Pharmacia), in this experiment the pooled fractions from Protein A Sepharose were used.

Molecular Biosensor for Troponin I

In addition to the above model system, a sensor of the design illustrated in FIG. 24E will be created to detect human troponin I. Troponin is a protein whose serum concentration has been linked to evidence of an acute myocardial infarction. A pair of cardiac troponin I antibodies (anti-cardiac troponin monoclonal antibodies clones M18 and MF4 from RDI) will be conjugated to fluorescein and Cy-5 labeled complementary signaling oligos. This particular pair of antibodies have successfully been used in ELISA analyses. Seven nt long ANTB6 (Table 1) and ANTB8 (Table 1) signaling oligo constructs, which we used to obtain the data described above, will be used. The antibodies will be labeled and purified as described above. A 20 µl mixture of 50 nM of each labeled antibody will be titrated with 0-100 nM of purified troponin I (recombinant human cardiac troponin I, cat #: J344122352, BiosPacific). Fluorescence intensity at 670 nM (Cy5 emission) with the excitation at 490 nm (fluorescein excitation) will be measured using a Spectrofluor Plus fluorescence plate reader (Tecan). Incubation time necessary for the maximum FRET signal will be established by measuring the FRET signal over time after addition of a fixed troponin I concentration. Negative controls will involve an analogous titration using an antibody conjugated with a fluorescein-labeled signaling oligonucleotide paired with unlabeled second antibody (donor-only control) and an analogous titration using an antibody conjugated with a Cy5-labeled signaling oligonucleotide paired with unlabeled second antibody (acceptor-only control). To show that the FRET signal is specific for troponin, the FRET signal of the molecular biosensor for troponin will be determined in the presence of 50, 250 and 1250 nM concentrations of bovine serum albumin, rabbit skeletal muscle troponin C, and human skeletal muscle troponin I. A cardiac troponin concentration-dependent increase in FRET signal will be observed when both labeled antibodies are present and no signal will be observed with donor-only, acceptor only, BSA, and skeletal troponin controls.

Optimal Concentrations of Antibodies

The concentration of labeled antibodies will have a significant effect on the signal-to-background ratio and the sensitivity of the assay. The 50 nM concentrations of antibodies used in the initial experiments are starting points, but are not necessarily optimal concentrations. Lowering the concentrations of antibodies could allow detection of lower concentrations of the target protein because a larger fraction of the total concentration of the antibodies could be present in a FRET-producing ternary complex with the target protein. On the other hand, lowering the concentration of antibodies could result in a decrease of the amount of ternary complex (due to mass action law) and consequently result in low fluorescence intensity causing poor signal-to-background ratio. The optimal concentration of labeled antibodies will be driven by a compromise between these sometimes opposing effects of labeled-antibody concentration. Thus, the FRET signals generated by 0.2 nM, 1 nM, 5 nM and 25 nM cardiac troponin will be compared using molecular biosensor reaction mixtures containing variable concentrations of fluorescein and Cy5-labeled antibodies (in 1-100 nM range). Signal-to-background ratios will be determined for each reaction condition and will be used to establish optimal concentrations of labeled antibodies. Depending on what is found to be the optimal antibody concentration, it may also be necessary to adjust the length of the complementary signaling oligos. For example, if very low concentrations of antibodies are optimal, the length of the complementary signaling oligos could be increased to 8 bp since at these low concentrations even 8 bp oligos will not anneal significantly in the absence of the target protein while the increased length of oligos will result in the increased stability of the ternary complex.

Optimal Number of Signaling Oligos Per Antibody

The experimental procedure used to attach signaling oligos to antibodies described above produces a heterogeneous preparation containing unlabeled antibody, antibody labeled with a single signaling oligonucleotide, and antibody labeled with multiple signaling oligos (FIG. 36). While this heterogeneously labeled antibody preparation has performed well in other molecular biosensors, the performance of a molecular biosensor may be improved through the use of a more homogenous labeled antibody preparation. Labeled antibody preps can be further purified on Resource Q columns resulting in separate fractions containing antibody labeled with a single signaling oligonucleotide and multiple signaling oligos. Samples of labeled troponin antibodies will be passed over Resource Q columns to obtain homogenous preparations of these antibodies labeled with one or more signaling oligos. Then FRET signals generated by 0.2 nM, 1 nM, 5 nM and 25 nM cardiac troponin will be compared using molecular biosensors prepared from the above homogeneous preps of labeled antibodies. Antibodies will be used at their optimal concentrations.

Optimal Length of Flexible Linker

Antibodies are significantly larger than aptamers. Therefore, it is likely that the optimal linker length in the case of antibodies will be longer. Thus, the pair of troponin antibodies will be labeled with variants of ANTB6 (Table 1) and ANTB8 (Table 1) signaling oligos containing 10, 15 and 20 Spacer18 units (corresponding to total linker lengths of ~200

Å, ~300 Å, and ~400 Å). The FRET signals generated by 0.2 nM, 1 nM, 5 nM and 25 nM cardiac troponin will be compared using molecular biosensors prepared from labeled antibody pairs containing the above variants of linker length. The linker length that produces the best FRET signal is the optimal length.

Comparison Between Entire Antibody Vs Antibody Fragments

Molecular biosensors can also be comprised of antibody fragments. The smaller size of the antibody fragments can reduce the possibility of steric hinderance due to the bulky antibody molecules (i.e., the smaller fragments might make it easier for the signaling oligos to anneal). Additionally, the use of monovalent antibody fragments could provide a solution to any difficulties encountered from the multivalent nature of the intact antibodies. To investigate these issues F(ab)$_2$ and Fab fragments of signaling oligo-labeled cardiac troponin antibodies will be prepared using a ImmunoPure IgG1 Fab and F(ab') Preparation Kit from Pierce. This kit has already been tested for preparing fragments of anti-biotin antibody with excellent results (data not shown). The fragments will be labeled with ANTB6 (Table 1) and ANTB8 (Table 1) signaling oligos. The FRET signals generated by 0.2 nM, 1 nM, 5 nM and 25 nM cardiac troponin will be compared using a molecular biosensor prepared from labeled antibody fragment pairs with the signals obtained with intact antibodies.

Comparison Between FRET and LRET Signal Detection

Preliminary experiments were performed with a complementary pair of signaling oligos labeled with fluorescein and Cy5. These two probes were selected because of the very low background signal in the absence of FRET (direct excitation of Cy5 at the 480 nm used for excitation of fluorescein is minimal and residual fluorescein emission at 670 nm is also very low). The performance of various donor-acceptor probes for FRET signaling in a molecular beacon for thrombin have previously been compared (FIG. 37). These data indicated that the fluororescein/Cy5 pair produced the best signal among commonly used fluorescence probes. However, an even better signal could be obtained when the Eu3+/Cy5 pair was used with time-resolved gated signal acquisition (FIG. 37). Lanthanide chelates have been shown to offer significant advantages as donor labels in homogenous assays based on energy transfer. Long luminescence life-times of these probes allow elimination of the background derived from light scattering and direct excitation of the acceptor, which can significantly improve signal-to-background ratio. An additional benefit of using lanthanide chelate labels is that it is possible to use molar excess of the acceptor-labeled molecules (which widens the range of labeled antibody concentrations which can be used in the assay) since gated signal acquisition eliminates the background due to directly excited acceptor. Versions of ANTB6 (Table 1) and ANTB8 (Table 1) signaling oligos labeled with europium chelate and Cy5, respectively, will be prepared. LRET (lanthanide-based resonance energy transfer) signals generated by 0.2 nM, 1 nM, 5 nM and 25 nM will be measured using molecular biosensors prepared from Eu3+/Cy5-labeled antibody and compare these signals to FRET signals obtained with fluorescein/Cy5 labeled antibody pair under identical experimental conditions. It is expected that the use of Eu3+/Cy5 donor-acceptor pair will produce better signals and will result in improved sensitivity compared to fluorescein/Cy5 pair.

Competition-Based Sensor

FIG. 38 illustrates another variant of the molecular biosensor, which requires only a single antibody. This design is based on competition between a signaling oligo-labeled peptide corresponding to the target protein epitope and the target protein. In the absence of the target protein the antibody and the peptide will form a complex, and the signaling oligos will anneal, producing a FRET signal. When the target protein is present, it will compete for antibody binding with the signaling oligonucleotide-labeled peptide resulting in a decreased FRET signal. The attractive feature of this sensor variant is that only a single antibody recognizing a defined solvent-exposed peptide epitope will be required. Thus, this design could be applied in situations where a pair of antibodies recognizing two distinct epitopes of the target molecular would be unavailable.

A Cy5-labeled construct containing a short signaling oligonucleotide attached to a long flexible linker modified with biotin at its end (ANTB6BIOT, see Table 1) was made and used with labeled anti-biotin antibody. Upon mixing of this construct with the anti-biotin antibody construct a large FRET signal (~5 fold increase) was observed (FIG. 39B). When the same experiment was performed in the presence of increasing amounts of the competitor (unrelated biotin-labeled oligonucleotide), a dose-dependent decrease in the FRET signal was observed (FIG. 39B) allowing for the detection of the unlabeled competitor.

The measurements were performed in 384-well low-volume microplates (Corning) in 20 mM Tris (pH 8.0), 100 mM NaCl, 10 µM EDTA buffer. A 20 R$^1$ sample containing 50 nM anti-biotin antibody conjugated with fluorescein-labeled ANTB8 (Table 1) signaling oligonucleotide and 50 nM Cy5-labeled and biotin-labeled ANTB6 (Table 1) signaling oligonucleotide was titrated with increasing concentration of biotin-labeled competitor oligonucleotide (TIRF2, see Table 1).

The relative affinity of the target protein and the isolated epitope peptide for the antibody will be an important factor in determining the behavior of a competitive molecular biosensor. In most cases, the affinity of the isolated peptide is expected to be much lower in comparison to the affinity of the intact target protein. This is beneficial for the assay design because the signaling oligonucleotide attached to the peptide via a flexible linker will increase the affinity of the peptide for the antibody (10-10,000 times; Tian and Heyduk, unpublished). The increased affinity is due to the additional favorable free energy (from the hybridization of signaling oligos) contributing to the stability of the ternary complex. Thus, even if the affinity of the isolated peptide is low, it will most likely be usable due to the increase in affinity provided by the oligonucleotide hybridization energy. Additionally, the affinity of the peptide-signaling oligonucleotide conjugate can be tuned to match the need for optimal assay performance by manipulating peptide sequence and/or the length of signaling oligonucleotide.

Competitive Molecular Biosensor for Cardiac Troponin I

The peptide MADGSSDAAREPRPAC (SEQ ID NO: 135) (corresponding to residues 1-15 of human cardiac troponin plus an additional C-terminal cysteine added to facilitate attachment to a signaling oligonucleotide) will be coupled with a Cy5-labeled ANTB8 (Table 1) signaling oligo using a SMCC crosslinking reaction in a manner analogous to the procedure described above for attaching signaling oligos to antibodies. The peptide-oligo conjugate will be purified by reverse phase HPLC and the identity of the product will be confirmed by MALDI mass spectroscopy. Goat anti-troponin I polyclonal antibody (cat #G-131-C, BiosPacific) will be conjugated with fluorescein-labeled ANTB6 (Table 1) signaling oligo. This affinity purified antibody has been raised using the above synthetic peptide as an antigen. The FRET signal generated upon mixing 50 nM ANTB8-peptide conjugate with 50 nM ANTB6-labeled antibody will be determined. A large FRET signal resulting from binding the peptide to the antibody is expected. In addition, different peptide-antibody pairs may be explored (three more such pairs are available from BiosPacific). Once a suitable peptide-antibody pair is identified, the troponin concentration dependent decrease of FRET signal due to competition between the peptide and troponin will be observed. A 20 μl mixture of antibody-signaling oligonucleotide conjugate and peptide-signaling oligonucleotide conjugate will be titrated with 0-100 nM of purified troponin I. Fluorescence intensity at 670 nM (Cy5 emission) with the excitation at 490 nm (fluorescein excitation) will be measured using a Spectrofluor Plus fluorescence plate reader (Tecan). The necessary incubation time will be established by measuring the FRET signal over time after addition of a fixed concentration of troponin I. To show that the decrease of FRET signal is specific for troponin, we will determine the FRET signal of the competitive molecular biosensor for troponin in the presence of 50, 250 and 1250 nM concentrations of bovine serum albumin, rabbit skeletal muscle troponin C and human skeletal muscle troponin I. We expect to observe a cardiac troponin concentration-dependent decrease in FRET and no change in FRET signal with BSA and skeletal troponins.

Another Competition-Based Assay

FIG. 40 illustrates another variant of a competition-based assay. This assay again utilizes a biosensor comprising two epitope binding agent constructs. Each construct has an epitope binding agent attached via a flexible linker to a signaling oligo. When the epitope binding agent constructs are in solution with an antibody that recognizes the epitope binding agents, the signaling oligos anneal, producing a FRET signal (FIG. 40). When free antigen is introduced to the solution, the free antigen competes for the antibody binding with the sensor. Without the antibody to hold the epitope binding agents in close proximity, the signaling oligos fall apart, resulting in a detectable decrease in FRET. Subsequently, the addition of the competitor can be tracked by the corresponding decrease in FRET signal.

FIG. 41 shows a specific embodiment of the competition-based sensor illustrated in FIG. 40. In FIG. 41, the epitope binding agents are solvent-exposed peptide fragments of a protein. When the anti-protein antibody is present, the signaling oligos anneal, producing a FRET signal. When competing protein is added, however, the protein competes with the sensor for antibody binding. Without the antibody to hold the epitope binding agents in close proximity, the signaling oligos fall apart, resulting in a detectable decrease in FRET.

Figure 42A:
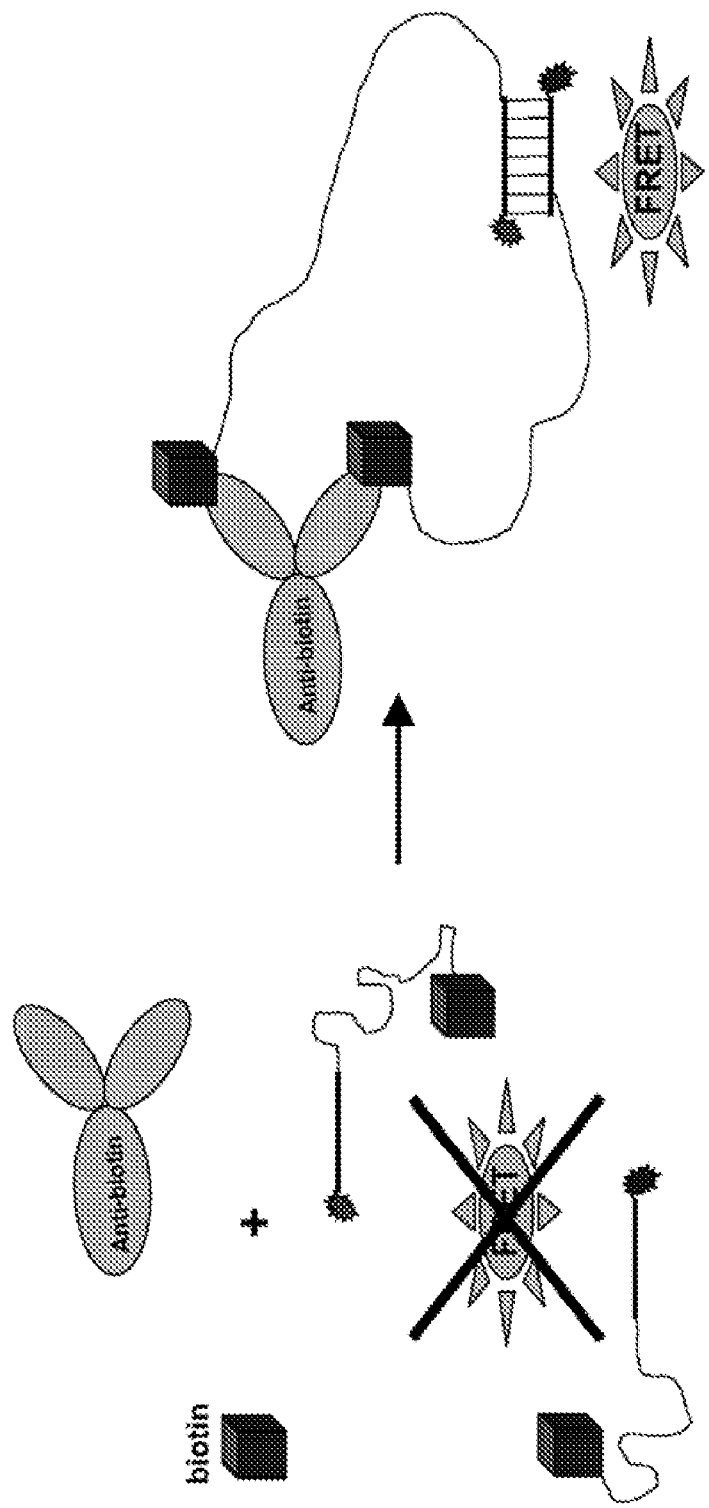
Figure 42B:
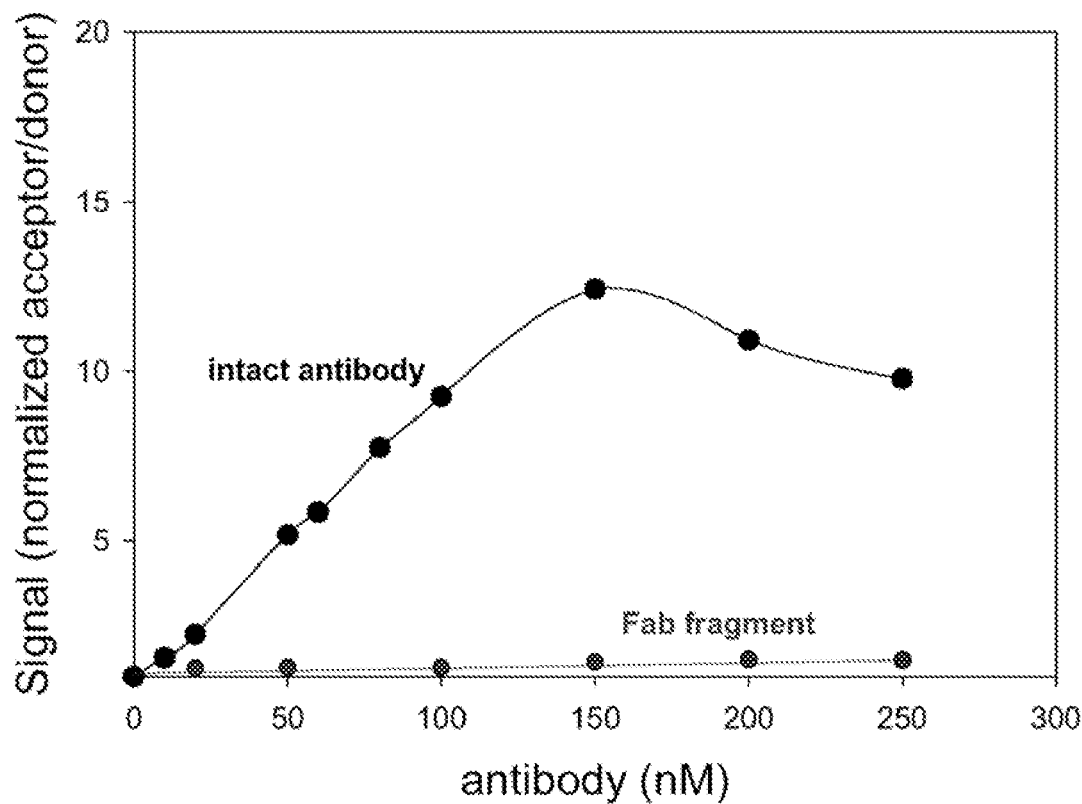

A specific example of this type of competition-based sensor is illustrated in FIG. 42A. Here, biotin is used as the epitope binding agent, and the antibody is an anti-biotin Ab. When increasing amounts of the Ab are added to a solution comprising the epitope binding agent constructs, an increase in FRET signal is observed (FIG. 42B). This is due to the annealing of the signaling oligos resulting from the antibody bringing the epitope binding agents into close proximity. FIGS. 43A and B confirm that in the presence of a competitor, here biotin, the FRET signal is diminished.

Relative Affinity of the Epitope-Containing Peptide-Signaling Oligonucleotide Conjugate The ratio of the affinity of the peptide-oligonucleotide conjugate and the intact protein for the antibody will be one of the most important parameters for the performance of the competitive molecular biosensor. Ideally, the affinity of the peptide-oligo conjugate should be lower than the affinity of the target protein to allow effective competition. However, it is difficult to predict the optimal ratio of these affinities. Thus this ratio will be determined experimentally. The relative affinity of the peptide and the protein for the antibody will be measured using surface plasmon resonance. The affinity of a series of peptide variants with mutations at various positions will also be measured. The affinity of these mutant peptides should be differentially altered depending on the importance of a particular mutated residue for the overall affinity of the peptide. Thus, a series of peptides of varying relative affinity for the antibody will be obtained. The performance of these peptides in a competitive molecular biosensor will be compared to learn about the sensitivity of the assay performance to the affinity ratio and to learn about the minimal value of this ratio necessary for preparing a functioning competitive molecular biosensor.

Molecular Biosensor for p53 Protein

A biosensor comprising an antibody and a DNA molecule containing a protein binding site (as shown FIG. 24D) was made to detect p53 protein. The sensor comprised a double-stranded DNA molecule containing a p53 binding site and an anti-p53 antibody (the design is shown in FIG. 45A). The anti-p53 antibody was linked to a fluorescein-labeled signaling oligonucleotide and the ds DNA containing the p53 binding site was linked to a Cy5-labeled signaling oligonucleotide. 20 μl samples of the sensor components (at 10 nM) were incubated with varying concentrations (0-80 nM) of full-length recombinant p53, and the FRET signal (emission at 656 nm with excitation at 485 nm) was read in 384 well plates, as described above. The FRET signal increased with increasing concentrations of p53 protein (FIG. 45A). The FRET signal in the presence of 20 nM p53 was reduced by 100 nM of a specific competitor (ds DNA containing p53 binding site), but not affected by 100 nM of a nonspecific competitor (ds DNA of an unrelated sequence) (FIG. 45B). These data support the utility of this type of two-component biosensor.

Molecular Biosensor for Cardiac Troponin I

A biosensor comprising two antibodies that recognize distinct and nonoverlapping epitopes of a protein (see FIG. 24E) was constructed for cardiac troponin I (see schematic in FIG. 46). Monoclonal antibodies MF4 and M18 (RDI, Concord, Mass.) where modified with signaling oligonucleotides labeled with fluorescein and Cy5, respectively. Sensor components were mixed at a concentration of 50 nM in 20 mM Tris pH 8.0, 100 mM NaCl, 10 μM EDTA. Cardiac Troponin complex containing troponin I at varying concentrations (0-20 nM) was then added. The mixes were incubated 1 hour at room temperature and the FRET signal (emission at 665 nm with excitation at 485 nm) was read in 384 well plates. The FRET signal was linear to 10 nM troponin I and then began to plateau (FIG. 46).

The response of the troponin sensor was examined at various concentrations of sensor components. Sensor components at 3 nM, 10 nM, 20 nM, 50 nM, and 100 nM were mixed in 20 mM Tris pH 8.0, 100 mM NaCl, 10 μM EDTA, and 0.2 mg/mL BSA. Cardiac troponin complex containing troponin I (CtnI) at various concentrations (0-25 nM) was then added, and the mix was incubated for 1 hour at room temperature. Assays were performed in a 384 well black plate. FRET signal at 665 nm with the excitation at 485 nm was measured (FIG. 47). Low concentrations of the sensor components resulted in good sensitivity at low troponin concentrations but sub-optimal sensitivity at high troponin concentrations. Similarly, high concentrations of the sensor components produce good responses at high troponin concentrations but had low sensitivity at low troponin concentrations. These data illustrate the possibility of tailoring the sensitivity of the sensor to a desired range of target concentrations.

Competitive Sensor for Cardiac Troponin I

A competitive sensor for cardiac troponin I (CTnI) was constructed and tested. The sensor comprised two components: the N-terminal (residues 1 to 15) CTnI peptide conjugated to a fluorescein labeled signaling oligonucleotide and the N-terminal CTnI peptide conjugated to a Cy5 labeled signaling oligonucleotide (as diagrammed in FIG. 48). Mixtures of the sensor components (at 50 nM) were titrated with an anti-troponin antibody (G-131-C affinity purified goat polyclonal antibody against the N-terminus of cardiac troponin I, BiosPacific, Emeryville, Calif.). The FRET signal (at 665 nm with the excitation at 485 nm) increased with increasing concentrations (0-80 nM) of the antibody (FIG. 48A), indicating that the oligos of the sensor had annealed. Unlabeled N-terminal CTnI peptide competed for antibody binding (FIG. 48A inset). The intact CTnI protein successfully competed for the biosensor. Increasing concentration of the intact CTnI protein (0-100 nM) reduced the FRET signal generated with the antibody and 20 nM of the sensor components (FIG. 48B).

Example 6

Three-Component Sensors

FIG. 49 diagrams the two-component and the three-component sensor designs. In the two-component design (A) the two signaling oligonucleotides are complementary to each other. When the S1 and S2 sensor components bind to the target, the resulting proximity (high local concentration) of the signaling oligonucleotides induces their hybridization and a proximity-dependent signal (for example, FRET) is generated. In the three-component design (B), the two signaling oligonucleotides are not complementary to each other but are complementary to the two segments on the third sensor component (S3). When S1 and S2 sensor components bind to the target, the resulting complex has a much higher affinity to bind (hybridize) to S3 compared to the individual S1 or S2 components in the absence of the target. This is because in such complexes both S1 and S2 are near each other (increased local concentration) and, thus, cooperate in binding to S3. Simultaneous binding of S1 and S2 to the same molecule of S3 generates a proximity-dependent signal (for example, FRET).

Response of a Three-Component Sensor

The sensor components (S1 and S2) that recognized the target (T) each comprised a 12 nt oligonucleotide. The target was a single-stranded oligonucleotide with complementarity to both the binding oligonucleotides of S1 and S2. S1 and S2 were conjugated to europium chelate-labeled and Cy5-labeled signaling oligonucleotides, respectively. S3 comprised a single-stranded oligonucleotide with complementarity to signaling oligonucleotides of S1 and S2. The response of the sensor was measured at S1, S2 and S3 concentrations of 10 nM, 10 nM, and 10 µM, respectively. FRET (time-resolved LRET) was measured at 670 nm using pulsed excitation at 330 nm. Emission of Cy5 was measured with 50 µsec delay. The FRET signal of the sensor was measured at target concentrations of 0, 1 µM, 10 µM, 100 µM, 1 nM, and 10 nM. The FRET signal was highest at a target concentration of 10 nM.

When the concentration of S3 is high, S1 and S2 will be driven to bind to the S3 even in the absence of the target. However, in the absence of the target, S1 and S2 will bind independently, and in the presence of large excess of S3, it will be unlikely that they will be bound by the same S3 molecules. Thus, no (or very little) FRET signal will be observed in the absence of the target even though the great majority of S1 and S2 could, in fact, be bound to S3 (see FIG. 51A, top). In the presence of the target, S1 and S2 will preferentially bind S3 in a manner where both S1 and S2 are bound by the same S3 molecule (see FIG. 51A, bottom) generating FRET signal. One advantage of the three-component sensor design may be that the affinity of S1 and S2 to S3 will not have to be finely tuned. A large range of affinities will be compatible with sensor design, as long as a large excess of S3 is used over S1 and S2. This is in contrast with the two-component sensor, in which the affinity of S1 and S2 will need to be designed carefully and only a narrow range of these affinities will work.

Figure 51B:
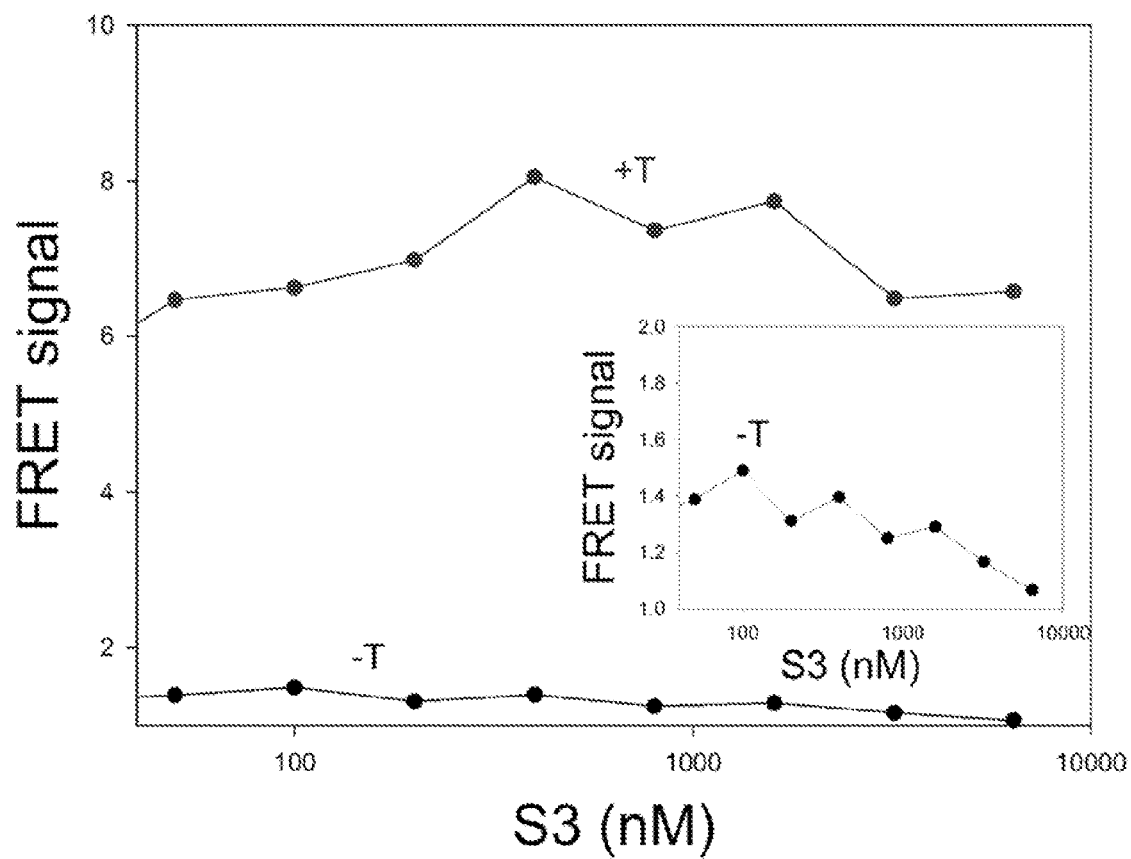

FIG. 51B confirms these principles. The FRET signal of the sensor in the presence of the target (T) was essentially independent of the concentration of S3 (over several orders of magnitude), whereas the background signal in the absence of T (inset) decreased at high concentrations of S3. This decrease was expected since when S3 concentration is increased, the probability of S1 and S2 binding to the same S3 by chance is reduced.

Homogenous Signal Amplification Using a Three-Component Sensor

A three-component system was designed in which the S3 component contained a sequence recognized by a restriction enzyme when it is hybridized to S1 and S2 (see FIG. 52). Although the Hinc II sequence was used, essentially any restriction enzyme that cleaves ds DNA but is inactive on ss DNA could be used. In this embodiment, the S1 and S2 components were not labeled with fluorescent probes. Instead, S3 contained the fluorescent probes attached to two complementary oligonucleotides, which in turn were attached to S3 via flexible linkers. When the S3 component is intact, the complementary oligonucleotides will be annealed (generating proximity-dependent signal such as, for example, FRET) due to the high local concentration resulting from their attachment to S3. In the presence of the target, S1 and S2 bind the target, and as part of a complex with the target, they bind S3. The signaling oligonucleotides of S1 and S2 are designed to anneal to S3 such that such that when they are hybridized there is a gap between the two signaling oligonucleotides exactly at the position where Hinc II would normally cleave the intact strand of the DNA duplex. Thus, when Hinc II is present in the sample, it will cleave S3 only when it is annealed to both S1 and S2 (i.e. when the target is present). Upon cleavage of S3, the complex will dissociate (cleavage of S3 will greatly decrease both the stability of the complex as well as it will result in dissociation of the two signaling oligonucleotides which in turn will eliminate the proximity-dependent signal). The complex of T with S1 and S2 can now associate with another molecule of S3 and the cleavage and dissociation cycle could be repeated many times. This will lead to amplification of the signal since one binding event involving S1, S2 and T will result in multiple cleavage reactions.

Figure 53C:
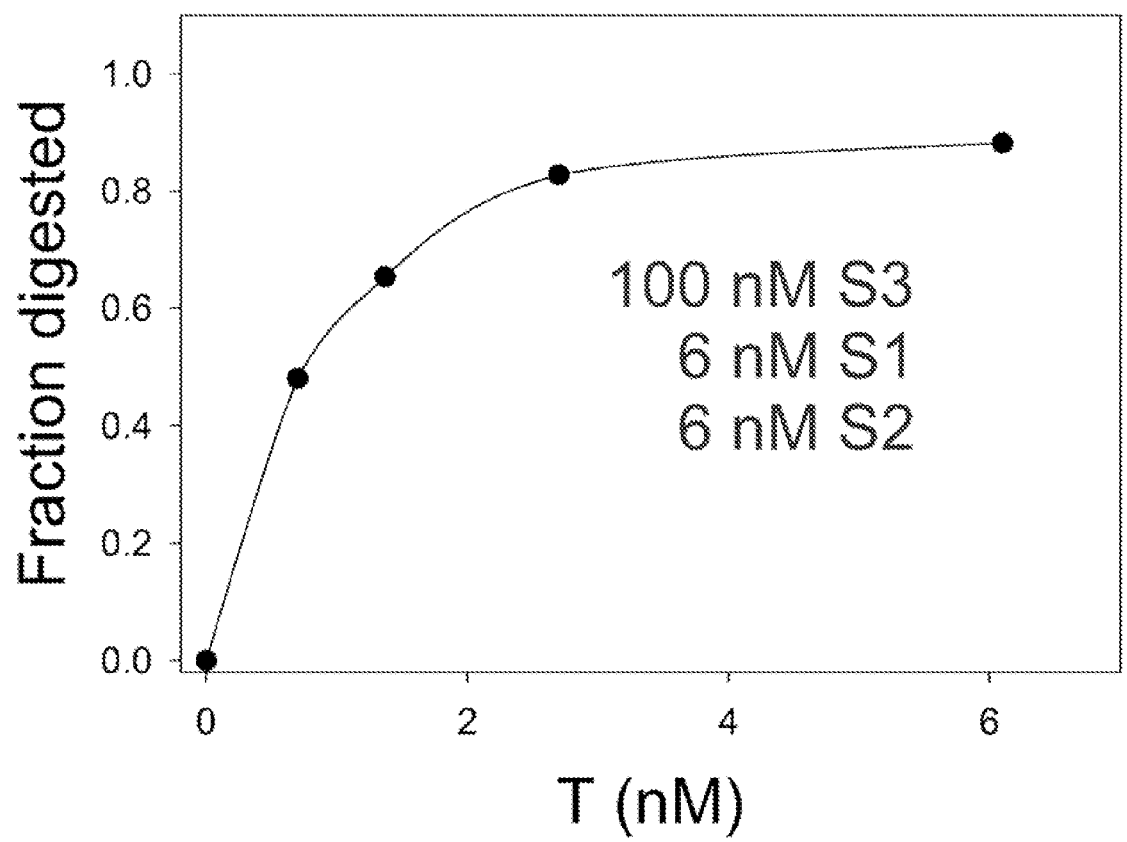

Proof-of-principle for the signal amplification scheme described above is presented in FIG. 53. Cleavage of S3 by Hinc II was monitored by native gel electrophoresis at various concentrations of target (T). S1 and S2 contained 12 nt oligonucleotides and the target (T) used was a single-stranded oligonucleotide complementary to the both S1 and S2. The concentrations of S1 and S2 were 6 nM, and the concentration of S3 was 100 nM. The reaction was carried out at room temperature for 4 hrs (FIG. 53A) or 24 hours (FIG. 53B). The fraction of S3 cleaved after 4 hours increased as a function of the concentration of T (FIG. 53C). The cleavage of S3 by Hinc II was strictly dependent on the presence of T, since there was no significant cleavage of S3 even after 24 hrs of incubation in the absence of T. Signal amplification was evident, for example, by the almost complete digestion of S3 in the presence of 2.7 nM T in 4 hrs, indicating ~30-fold amplification. After a longer incubation period, complete digestion of S3 was achieved even at 700 pM T, indicating at least ~150-fold signal amplification.

Solid-Surface Implementation of the Three-Component Biosensor

The S3 component may be immobilized on a solid surface (slides, microplate wells, beads, etc.) and the three-component system may be used for microarray analyses. FIG. 54 diagrams an immobilized sensor system. In the presence of the target, the S1-S2-T complex will bind to the immobilized S3. Any surface-specific technique may then be used to detect the S1-S2-T complex associated with the solid surface. These would include detecting the probes attached to S1 and/or S2 after washing out the unbound components and/or using surface specific real-time detection methods, such as, for example, surface plasmon resonance (SPR) or total internal reflection fluorescence (TIRF).

Proof-of-principle for the solid-surface implementation of the three-component biosensor design using TIRF detection is presented in FIG. 55. Biotinylated S3 was immobilized on streptavidin-coated quartz slide. S1 and S2 contained 12 nt oligonucleotides and the target (T) was a single-stranded oligonucleotide complementary to the both S1 and S2. S1 and S2 were Cy3 and Cy5 labeled, respectively, and were used at concentrations of 20 nM. TIRF excitation was at 550 nm using a commercial prism-based TIRF accessory (TIRF Technologies, Inc., Morrisville, N.C.) for Fluorolog 3 fluorometer (Jobin Yvon) and FRET emission signal was monitored at 670 nm. TIRF limits the excitation to few hundred nanometers above the surface of the slide so only the FRET signal from S1 and S2 associated with the surface of the slide would be detected. FIG. 55B presents FRET signals in the presence and absence of target (T). Injection of 10 nM of S1 and S2 in the absence of T produced a small background FRET signal. In contrast, injection of 20 nM of S1 and S2 together with 20 nM of T produced a large FRET signal (~10-fold over the background) indicating target-induced association of S1 and S2 with the S3 immobilized of the slide surface. Differences in kinetic stability of complexes in the presence and absence of the target could be utilized to further improve the sensor signal. In the presence of the target, the complex associated with the surface was relatively stable. Thus, when the slide was washed with buffer (upper arrow) only a slow gradual decrease of the signal was observed. In contrast, the nonspecific complex in the absence of the target was kinetically unstable. When the slide was washed with buffer in this case (lower arrow), nonspecific complexes rapidly dissociated and the background signal quickly dropped to a value near that observed before addition of sensor components. Thus, when signals in the presence and absence of the target were measured shortly after switching to the buffer, a ~30-fold signal change in the presence of T is measured (i.e., a ~3-fold improvement). The slide was quickly regenerated by washing it with water, since low ionic strength greatly destabilizes nucleic acid associations leading to rapid dissociation of the S3 bound components.

FIG. 56 diagrams the use of the three-component biosensor design for a microarray format of target detection. S3 oligonucleotides containing sequences complementary to the pairs of S1 and S2 components specific for a specific target may be spotted on a glass slide. In the presence of the targets, S1-S2-T complexes will bind to their corresponding spots. After washing out the unbound components, microarray scanning will be used to detect the presence of the targets in the sample.

TABLE 1

| CONSTRUCT | SEQUENCE | SEQUENCE IDENTIFIER | DESCRIPTION |
| --- | --- | --- | --- |
| THR1 | 5' Fluorescein AGT CCG TGG TAG GGC AGG TTG GGG TGA CT | SEQ ID NO: 1 | 60-18 [29][a] aptamer labeled with fluorescein |
| THR2 | 5' Fluorescein GGT TGG TGT GGT TGG | SEQ ID NO: 2 | G15D[b] aptamer labeled with fluorescein |
| THR3 | AGT CCG TGG TAG GGC AGG TTG GGG TGA CT | SEQ ID NO: 3 | 60-18 [29] aptamer |
| THR4 | GGT TGG TGT GGT TGG | SEQ ID NO: 4 | G15D aptamer |
| THR5 | AGT CCG TGG TAG GGC AGG TTG GGG TGA CTX XXX XGG TTG GTG TGG TTG G | SEQ ID NO: 5 | 60-18 [29] aptamer connected to G15D aptamer via 5 Spacer18 linkers (X) |
| THR6 | AGT CCG TGG TAG GGC AGG TTG GGG TGA CTX XXX XXX XXX GGT TGG TGT GGT TGG | SEQ ID NO: 6 | 60-18 [29] aptamer connected to G15D aptamer via 10 Spacer18 linkers (X) |
| THR7 | GGT TGG TGT GGT TGG XXX XXX XXX XAG TCC GTG GTA GGG CAG GTT GGG GTG ACT | SEQ ID NO: 7 | G15D aptamer connected to 60-18 [29] aptamer via 10 Spacer18 linkers (X) |

TABLE 1-continued

| CONSTRUCT | SEQUENCE | SEQUENCE IDENTIFIER | DESCRIPTION |
|---|---|---|---|
| THR14 | GGT TGG TGT GGT TGG TTT TTTT CTG TCG TTA GTG AAG GTT | SEQ ID NO: 8 | Aptamer with a poly dT linker |
| THR15 | AAC CTT CAC TAA CGA CAG TTT TTT T AGT CCG TGG TAG GGC AGG TTG GGG TGA CT | SEQ ID NO: 9 | Aptamer with a poly dT linker |
| THR16 | GGT TGG TGT GGT TGG TTT TTT TTT TTT TTT TT CTG TCG TTA GTG AAG GTT | SEQ ID NO: 10 | Aptamer with a poly dT linker |
| THR17 | AAC CTT CAC TAA CGA CAG TTT TTT TTT TTT TT AGT CCG TGG TAG GGC AGG TTG GGG TGA CT | SEQ ID NO: 11 | Aptamer with a poly dT linker |
| THR18 | GGT TGG TGT GGT TGG TTT TTT TTT TTT TTT TTT TTT TTT TTT CTG TCG TTA GTG AAG GTT | SEQ ID NO: 12 | Aptamer with a poly dT linker |
| THR19 | AAC CTT CAC TAA CGA CAG TTT TTT TTT TTT TTT TTT TTT TTT AGT CCG TGG TAG GGC AGG TTG GGG TGA CT | SEQ ID NO: 13 | Aptamer with a poly dT linker |
| THR8 | GGT TGG TGT GGT TGG TTT TTT TTT TTT TTT TTC GCA TCT 3' dabcyl | SEQ ID NO: 14 | Aptamer with a poly dT linker |
| THR9 | 5' fluorescein AGA TGC G TTT TTT TTT TTT TTT TT AGT CCG TGG TAG GGC AGG TTG GGG TGA CT | SEQ ID NO: 15 | Aptamer with a poly dT linker |
| THR20 | GGT TGG TGT GGT TGG XXX XXC GCA TCT 3'dabcyl | SEQ ID NO: 16 | G15D aptamer connected via 5 Spacer18 linkers (X) to 7 nt "signaling" oligonucleotide labeled with dabcyl at 3' end |
| THR21 | 5' fluorescein AGA TGC GXX XXX AGT CCG TGG TAG GGC AGG TTG GGG TGA CT | SEQ ID NO: 17 | 7 nt "signaling" oligonucleotide labeled at 5' with fluorescein connected to 60-18 [29] aptamer via 5 Spacer18 linkers (X) |
| THR27 | GGT TGG TGT GGT TGG XXX XX CZC GCA TCT | SEQ ID NO: 18 | G15D aptamer connected via 5 Spacer18 linkers to 7 nt "signaling" oligonucleotide containing amino-dT (Z) (near its 5' end) |
| THR28 | 5' amino AGA TGC GXX XXX AGT CCG TGG TAG GGC AGG TTG GGG TGA CT | SEQ ID NO: 19 | 7 nt "signaling" oligonucleotide containing 5' amino connected to 60-18 [29] aptamer via 5 Spacer18 linkers (X) |
| THR11 | CTG TCG TTA GTG AAG GTT NNN NNN NNN | SEQ ID NO: 20 | Construct containing 33 nt random DNA |

TABLE 1-continued

| CONSTRUCT | SEQUENCE | SEQUENCE IDENTIFIER | DESCRIPTION |
|---|---|---|---|
| | NNN NNN NNN NNN NNN NNN NNN NNN AAC GCC ATA TCA CAG ACG | | sequence for thrombin aptamer selection |
| THR12 | 5' fluorescein CTG TCG TTA GTG AAG GTT | SEQ ID NO: 21 | Primer1 for THR11 |
| THR13 | 5' biotin CGT CTG TGA TAT GGC GTT | SEQ ID NO: 22 | Primer2 for THR11 |
| THR22 | GGT TGG TGT GGT TGG XXGA CAG | SEQ ID NO: 23 | Co-aptamer for thrombin aptamer selection, with 2 Spacer18 linkers (X) |
| THR25 | GGT TGG TGT GGT TGG XXX XXA CGA CAG | SEQ ID NO: 24 | Co-aptamer for thrombin aptamer selection, with 5 Spacer18 linkers (X) |
| THR29 | GAACGAGAGTGC XXXXX amino CGCA TCT | SEQ ID NO: 25 | ss DNA sensor component, with 5 Spacer18 linkers (X) |
| THR32 | 5' fluorescein AGA TGC G XXXXX TTG AAC TGGACC | SEQ ID NO: 26 | ss DNA sensor component, with 5 Spacer18 linkers (X) |
| THR33 | GGTCCAGTTCAA TT GCACTCTCGTTC | SEQ ID NO: 27 | target ss DNA for ss DNA sensor |
| THR42 | GGT TGG TGT GGT TGG XX XXX AAC GAC AG | SEQ ID NO: 28 | co-aptamer for thrombin aptamer selection |
| THR43 | CTG TCG TT XXXXX TTGAGTCAGCGTCGAG CA NNN NNN NNN NNN NNN NNN NNN NNN NNN NNN NNN TTC ACT GTG CTG CGG CTA | SEQ ID NO: 29 | Construct containing 33 nt random DNA sequence for thrombin aptamer selection, with 5 Spacer18 linkers (X) |
| THR44 | 5' fluorescein CTG TCG TT XXXXX TTG AGT GAG CGT CGA GCA | SEQ ID NO: 30 | Primer1 for THR43, with 5 Spacer18 linkers (X) |
| THR45 | 5'biotin TAGCCGCAGCACAGTG AA | SEQ ID NO: 31 | Primer2 for THR43 |
| THR49 | CACCTGATCGCTCCTCG T NNN NNN NNN NNN NNN NNN NNN NNN NNN NNN GAG GAT GCA GAG GCA CAA | SEQ ID NO: 32 | Construct containing 30 nt random DNA sequence for simultaneous selection of two thrombin aptamers |
| THR50 | AGCCGCCATTCCATAGT G NNN NNN NNN NNN NNN NNN NNN NNN NNN NNN GAG GAT GCC GAT GAG GTG | SEQ ID NO: 33 | Construct containing 30 nt random DNA sequence for simultaneous selection of two thrombin aptamers |
| THR51 | 5' fluorescein GAG CTG ATC GCT CCT CGT | SEQ ID NO: 34 | Primer1 for THR49 |
| THR52 | 5'biotin TTG TGC CTG TGC ATC CTG | SEQ ID NO: 35 | Primer2 for THR49 |
| THR53 | 5' fluorescein-AGC CGC CAT TCC ATA GTG | SEQ ID NO: 36 | Primer3 for THR50 |

TABLE 1-continued

| CONSTRUCT | SEQUENCE | SEQUENCE IDENTIFIER | DESCRIPTION |
|---|---|---|---|
| THR54 | 5'biotin GAG CTG ATC GGCATCCTG | SEQ ID NO: 37 | Primer4 for THR50 |
| THR35 | 5' fluorescein AGA TGC G XXXXX AG GTT GGG GGT ACT AGG TAT CAA TGG GTA GGG TGG TGT AAC GC | SEQ ID NO: 38 | Thrombin sensor component, with 5 Spacer18 linkers (X) |
| THR36 | 5' fluorescein AGA TGC G XXXXX A GTG AAG GTT GGG GGT ACT AGG TAT CAA TGG GTA GGG TGG TGT AAC GCC_ATA T | SEQ ID NO: 39 | Thrombin sensor component, with 5 Spacer18 linkers (X) |
| MIS10X3 | AAC GCA ATA AAT GTG AAG TAG ATC ACA TTT TAG GCA CC XXXXX GA TGGCT | SEQ ID NO: 40 | co-aptamer for CRP aptamer selection, with 5 Spacer18 linkers (X) |
| MIS12 | AGCCA T CTA ACT ATT CCC NNN NNN NNN NNN NNN NNN NNN NNN NNN NNN NNN GAG CGA GAA ATT CTA GGT | SEQ ID NO: 41 | Construct containing 33 nt random DNA sequence for CRP aptamer selection |
| MIS11 | GGT GCC TAA AAT GT G ATC TAC TTC ACA TTT ATT GCG TT | SEQ ID NO: 42 | Complement to MIS10X3 |
| MIS13 | 5'-fluorescein - AGC CAT CTA ACT ATT CCC | SEQ ID NO: 43 | Primer1 for MIS10X3 |
| MIS14 | 5' biotin- ACC TAG AAT TTC TCG CTC | SEQ ID NO: 44 | Primer2 for MIS10X3 |
| Clone 1 | ggcggtatgg gcatagcgta atgggaggtt ggt | SEQ ID NO: 45 | Clone from FIG. 28 |
| Clone 2 | ggatgcgtaa tggttagggt gggtagggta tcc | SEQ ID NO: 46 | Clone from FIG. 28 |
| Clone 3 | ggatgcgtaa tggttagggt gggtagggta tcc | SEQ ID NO: 47 | Clone from FIG. 28 |
| Clone 4 | ggatgcgtaa tggttagggt gggtagggta tcc | SEQ ID NO: 48 | Clone from FIG. 28 |
| Clone 5 | gcagtaggta ctatattggc tagggtggtc tgc | SEQ ID NO: 49 | Clone from FIG. 28 |
| Clone 6 | gcagtaggta ctatattggc tagggtggtc tgc | SEQ ID NO: 50 | Clones from FIG. 28 |
| Clone 7 | ggcggtatgg gcatagcgta atgggaggtc tgc | SEQ ID NO: 51 | Clone from FIG. 28 |
| Clone 8 | ggatgcgtaa tggttagggt gggtagggta tcc | SEQ ID NO: 52 | Clone from FIG. 28 |
| Clone 9 | ggcggtatgg gtatagcgta atgggaggtt ggt | SEQ ID NO: 53 | Clone from FIG. 28 |
| Clone 10 | ggggggtacta ggtattaatg ggtagggtgg tgt | SEQ ID NO: 54 | Clone from FIG. 28 |
| Clone 11 | cagcagggaa cggaacggtt agggtgggta ggg | SEQ ID NO: 55 | Clone from FIG. 28 |
| Clone 12 | gcggngatag gtcgcgtaag ttgggtaggg tgg | SEQ ID NO: 56 | Clone from FIG. 28 |
| Clone 13 | caggatgggt agggtggtca gcgaagcagt agg | SEQ ID NO: 57 | Clone from FIG. 28 |

TABLE 1-continued

| CONSTRUCT | SEQUENCE | SEQUENCE IDENTIFIER | DESCRIPTION |
|---|---|---|---|
| Clone 14 | caacggttgg gtgaactgta gtggcttggg gtg | SEQ ID NO: 58 | Clone from FIG. 28 |
| Clone 15 | caggatgggt agggtggtca gcgaagcagt agg | SEQ ID NO: 59 | Clone from FIG. 28 |
| Clone 16 | caggatgggt agggtggtca gcgaagcagt ag | SEQ ID NO: 60 | Clone from FIG. 28 |
| Clone 17 | ggcgagagca gcgtgatagg gtgggtaggg tgg | SEQ ID NO: 61 | Clone from FIG. 28 |
| Clone 18 | cagggtcagg gctagatgat gcgattaacc atg | SEQ ID NO: 62 | Clone from FIG. 28 |
| Clone 19 | caggatgggt agggtggtca gcgaagcagt agg | SEQ ID NO: 63 | Clone from FIG. 28 |
| Clone 20 | gggggtacta ggtatcaatg ggtagggtgg tgt | SEQ ID NO: 64 | Clone from FIG. 28 |
| Clone 21 | gggggtacta ggtatcaatg ggtagggtgg tgt | SEQ ID NO: 65 | Clone from FIG. 28 |
| Clone 22 | ggagacgtaa tgggttggtt gggaagngga tcc | SEQ ID NO: 66 | Clone from FIG. 28 |
| Clone 23 | gcatacgtaa tggtccggtt ggggcgggta tgt | SEQ ID NO: 67 | Clone from FIG. 28 |
| Clone 24 | gggggtacta ggtatcaatg ggtagggtgg tgt | SEQ ID NO: 68 | Clone from FIG. 28 |
| Clone 25 | gaggggactt aggatgggta gggtggtagg ccc | SEQ ID NO: 69 | Clone from FIG. 28 |
| Clone 26 | gggggtacta ggtatcaatg ggtagggtgg tgt | SEQ ID NO: 70 | Clone from FIG. 28 |
| Clone 27 | ggtcggggca tagtaatgct ggattgggca gct | SEQ ID NO: 71 | Clone from FIG. 28 |
| Clone 28 | gggtaggagc agtacacgct ggaatgggtc act | SEQ ID NO: 72 | Clone from FIG. 28 |
| Clone 29 | gcagtaggta ctatattggc tagggtggtc tgc | SEQ ID NO: 73 | Clone from FIG. 28 |
| Clone 30 | gggtagggtg acagggagga cggaatgggc act | SEQ ID NO: 74 | Clone from FIG. 28 |
| Clone 31 | gcagtaggta ctatattggc tagggtggtc tgc | SEQ ID NO: 75 | Clone from FIG. 28 |
| Clone 32 | gcagtaggta ctatattggc tagggtggtc tgc | SEQ ID NO: 76 | Clone from FIG. 28 |
| Clone 33 | gcagtaggta ctatattggc tagggtggtc tgc | SEQ ID NO: 77 | Clone from FIG. 28 |
| Clone 34 | gggggtgcta ggtattaaag ggtagggtgg tgt | SEQ ID NO: 78 | Clone from FIG. 28 |
| Clone 35 | gcagtaggta ctatgtcggg tcgggtggtc tgc | SEQ ID NO: 79 | Clone from FIG. 28 |
| Clone 1-1 | gggtagggtg gttgtaatag ggattgcgat | SEQ ID NO: 80 | Clone from FIG. 30 |
| Clone 1-2 | gggtagggtg gttgtaatag ggattgcgat | SEQ ID NO: 81 | Clone from FIG. 30 |
| Clone 1-3 | ggcacaaccc gatatggcta tgaatctgcc | SEQ ID NO: 82 | Clone from FIG. 30 |

TABLE 1-continued

| CONSTRUCT | SEQUENCE | SEQUENCE IDENTIFIER | DESCRIPTION |
|---|---|---|---|
| Clone 1-4 | gggtagggtg gttgtaatag ggattgcgat | SEQ ID NO: 83 | Clone from FIG. 30 |
| Clone 1-5 | gggtagggtg gttgtaatag ggattgcgat | SEQ ID NO: 84 | Clone from FIG. 30 |
| Clone 1-6 | ggtgtgggtg gttattggtg tagagcgggt | SEQ ID NO: 85 | Clone from FIG. 30 |
| Clone 1-7 | aatgggagg ttggggtgcg ggagagtggt | SEQ ID NO: 86 | Clone from FIG. 30 |
| Clone 1-8 | acgcgtagga tgggtagggt ggtcgcgtta | SEQ ID NO: 87 | Clone from FIG. 30 |
| Clone 1-9 | gggtagggtg gttgtaatag ggattgcgat | SEQ ID NO: 88 | Clone from FIG. 30 |
| Clone 1-10 | gggcgaaggt acgaagacgg atgcacgtgc | SEQ ID NO: 89 | Clone from FIG. 30 |
| Clone 2-1 | aaggccgcca tctgggtccg acgagtacca | SEQ ID NO: 90 | Clone from FIG. 30 |
| Clone 2-2 | tagggtgggt agggtggtca actatggggg | SEQ ID NO: 91 | Clone from FIG. 30 |
| Clone 2-3 | gggtggctgg tcaaggagat agtacgatgc | SEQ ID NO: 92 | Clone from FIG. 30 |
| Clone 2-4 | ggtagggtgg ttaaaatagg ggaatggcag | SEQ ID NO: 93 | Clone from FIG. 30 |
| Clone 2-5 | cacaagaagg gcgagcgctg agcatagtgc | SEQ ID NO: 94 | Clone from FIG. 30 |
| Clone 2-6 | ccaacgacac atagggtaca cgccgcctcc | SEQ ID NO: 95 | Clone from FIG. 30 |
| Clone 2-7 | ggtagggtgg ttaaaatagg ggaatggcag | SEQ ID NO: 96 | Clone from FIG. 30 |
| Clone 2-8 | taggatgggt agggtggtcc caggaatggc | SEQ ID NO: 97 | Clone from FIG. 30 |
| Clone 2-9 | taggatgggt agggtggccc caggaatggc | SEQ ID NO: 98 | Clone from FIG. 30 |
| Clone 2-10 | ggtagggtgg ttaaaatagg ggaatggcag | SEQ ID NO: 99 | Clone from FIG. 30 |
| Clone 2-11 | gatgtggccc agaagcataa cacgacgtac | SEQ ID NO: 100 | Clone from FIG. 30 |
| Clone 2-12 | taggatgggt agggtggtcc caggaatggc | SEQ ID NO: 101 | Clone from FIG. 30 |
| Clone 2-13 | ggagatgcag gtactgagta gggagtgtgc | SEQ ID NO: 102 | Clone from FIG. 30 |
| Clone 2-14 | taggatgggt agggtggtcc caggaatggc | SEQ ID NO: 103 | Clone from FIG. 30 |
| Clone 1 | aatcaagggc tggtgttaaa ggtgatcgac tag | SEQ ID NO: 104 | Clone from FIG. 31 |
| Clone 2 | aaggggagcc atcacacagg aggtcgcttc gct | SEQ ID NO: 105 | Clone from FIG. 31 |
| Clone 3 | aaaggcatca cctagagttg ccgccgatac ttg | SEQ ID NO: 106 | Clone from FIG. 31 |
| Clone 4 | ggggatgtgc gaaactggtg actatgcggg tgc | SEQ ID NO: 107 | Clone from FIG. 31 |

TABLE 1-continued

| CONSTRUCT | SEQUENCE | SEQUENCE IDENTIFIER | DESCRIPTION |
|---|---|---|---|
| Clone 5 | cgaaaggagc catcaacctt gaaacgcccg tcc | SEQ ID NO: 108 | Clone from FIG. 31 |
| Clone 6 | cagacgggag ccatcgacat agaggtgatt gcc | SEQ ID NO: 109 | Clone from FIG. 31 |
| Clone 7 | agggaaagcc atcacctaga cacatacagc atg | SEQ ID NO: 110 | Clone from FIG. 31 |
| Clone 8 | ataagaagcc atcataggga cctagctagc ccc | SEQ ID NO: 111 | Clone from FIG. 31 |
| Clone 9 | ccaacagacg gtagcacaac actagtactc tgg | SEQ ID NO: 112 | Clone from FIG. 31 |
| Clone 10 | acagacgccc ctagtaaaca ataaccgatg gcc | SEQ ID NO: 113 | Clone from FIG. 31 |
| Clone 11 | atagctactc gccaagggtg acttctgcta ttg | SEQ ID NO: 114 | Clone from FIG. 31 |
| Clone 12 | atggggcaac gcggagacct gtcggtactg cct | SEQ ID NO: 115 | Clone from FIG. 31 |
| Clone 13 | gcaatatagc actaagcctt aactccatgg tgg | SEQ ID NO: 116 | Clone from FIG. 31 |
| Clone 14 | gcaaggaaaa acaagcaagc catcacgacc tag | SEQ ID NO: 117 | Clone from FIG. 31 |
| Clone 15 | caggcatccc aagaagtgtc agccgtttcg tgg | SEQ ID NO: 118 | Clone from FIG. 31 |
| Clone 16 | caacaggaga gcccgacaca cagatctggc ccc | SEQ ID NO: 119 | Clone from FIG. 31 |
| Clone 17 | acaagccatc acgtgaatgc cgaccggtac tgt | SEQ ID NO: 120 | Clone from FIG. 31 |
| Clone 18 | accgacaaac aagtcaatac gggacacgat cct | SEQ ID NO: 121 | Clone from FIG. 31 |
| Clone 19 | cagtgggtcg ggtcacagcc atgagtgttg ctg | SEQ ID NO: 122 | Clone from FIG. 31 |
| Clone 20 | aacgggaaag ccatcaccat atttatcgtc ctg | SEQ ID NO: 123 | Clone from FIG. 31 |
| Clone 21 | acgggcgcaa acaagatgta caaaagcatg gtg | SEQ ID NO: 124 | Clone from FIG. 31 |
| Clone 22 | agcgggatag ggaactatcg gacaatcgtc gtg | SEQ ID NO: 125 | Clone from FIG. 31 |
| Clone 23 | gaggataaaa gccatcaact agaatgcgca tgg | SEQ ID NO: 126 | Clone from FIG. 31 |
| ANTB6 | 5'-amino-XXX XXX AGA TGC G 3'fluorescein | SEQ ID NO: 127 | X = Spacer 18 |
| ANTB6BIOT | 5'-biotin-XXX XXX AGA TGC G 3'Cy5 | SEQ ID NO: 128 | X = Spacer 18 |
| ANTB7 | CAA TAA ATG TGA TCT AGA TCA CAT TTT AGG XXX XXX AGA TGC G 3'C3 S-S CPG | SEQ ID NO: 129 | X = Spacer 18 |
| ANTB7DIG | CAA TAA ATG TGA TCT AGA TCA CAT TTT AGG-digoxin | SEQ ID NO: 130 | X = Spacer 18 |
| BICAP 30 | CCT AAA ATG TGA TCT AGA TCA CAT TTA TTG | SEQ ID NO: 131 | |

TABLE 1-continued

| CONSTRUCT | SEQUENCE | SEQUENCE IDENTIFIER | DESCRIPTION |
|---|---|---|---|
| ANTB8 | 5'-amino-XXX XXX CGC ATC T 3'C3 S-S CPG | SEQ ID NO: 132 | X = Spacer 18 |
| ANTB9 | AAA ATG TGA TCT AGA TCA CAT TTA TTG-3' TEG Biotin | SEQ ID NO: 133 | |
| TIRF2 | biotin XX GGT TGG TGT GGT TGG XX XXX CGC ATC | SEQ ID NO: 134 | X = Spacer 18 |
| N-terminal cardiac troponin I peptide | MADGSSDAAREPRPAC | SEQ ID NO: 135 | |

What is claimed is:

1. A molecular biosensor, the molecular biosensor comprising two epitope binding agent constructs, which together have formula (VI):

$$R^{47}\text{—}R^{48}\text{—}R^{49}\text{—}R^{50}; \text{ and}$$

$$R^{51}\text{—}R^{52}\text{—}R^{53}\text{—}R^{54};$$

wherein:
- $R^{47}$ is an epitope-binding agent that binds to a first epitope on a target molecule and is selected from the group consisting of a peptide, a small molecule, and a protein;
- $R^{48}$ is a flexible linker attaching $R^{47}$ to $R^{49}$;
- $R^{49}$ and $R^{53}$ are a pair of complementary nucleotide sequences having a free energy for association from about 5.5 kcal/mole to about 8.0 kcal/mole at a temperature from about 21° C. to about 40° C. and at a salt concentration from about 1 mM to about 100 mM;
- $R^{50}$ and $R^{54}$ together comprise a detection means such that when $R^{49}$ and $R^{53}$ associate a detectable signal is produced;
- $R^{51}$ is an epitope binding agent selected from the group consisting of an antibody, an antibody fragment, peptide, protein, and an aptamer that binds to $R^{47}$ such that in the absence of a target molecule:
  (i) $R^{51}$ binds to $R^{47}$,
  (ii) $R^{49}$ and $R^{53}$ associate, and
  (iii) $R^{50}$ and $R^{54}$ produce a detectable signal; and
- $R^{52}$ is a flexible linker attaching $R^{51}$ to $R^{53}$.

2. The molecular biosensor of claim 1, wherein $R^{51}$ is an antibody or antibody fragment selected from the group consisting of polyclonal antibodies, ascites, Fab fragments, Fab' fragments, monoclonal antibodies and humanized antibodies.

3. The molecular biosensor of claim 1, wherein $R^{48}$ and $R^{52}$ are from about 50 to about 250 angstroms in length and are selected independently selected from the group consisting of a heterobifunctional chemical linker, a homobifunctional chemical linker, polyethylene glycol, and nucleic acid.

4. The molecular biosensor of claim 1, wherein $R^{49}$ and $R^{53}$ are from about 2 to about 20 nucleotides in length.

5. The molecular biosensor of claim 1, wherein $R^{50}$ and $R^{54}$ are independently selected from the group consisting of fluorescence resonance electron transfer (FRET), lanthamide resonance electron transfer (LRET), fluorescence cross-correlation spectroscopy, fluorescence quenching, fluorescence polarization, flow cytometry, scintillation proximity, luminescence resonance energy transfer, direct quenching, ground-state complex formation, chemiluminescence energy transfer, bioluminescence resonance energy transfer, excimer formation, colorimetric substrates detection, phosphorescence, electro-chemical changes, and redox potential changes.

6. A molecular biosensor, the molecular biosensor comprising two epitope binding agent constructs, which together have formula (VI):

$$R^{47}\text{—}R^{48}\text{—}R^{49}\text{—}R^{50}; \text{ and}$$

$$R51\text{—}R52\text{—}R53\text{—}R54;$$

wherein:
- $R^{47}$ is an antibody or antibody fragment epitope-binding agent that binds to a first epitope on a target molecule;
- $R^{48}$ is a flexible linker attaching $R^{47}$ to $R^{49}$;
- $R^{49}$ and $R^{53}$ are a pair of complementary nucleotide sequences having a free energy for association from about 5.5 kcal/mole to about 8.0 kcal/mole at a temperature from about 21° C. to about 40° C. and at a salt concentration from about 1 mM to about 100 mM;
- $R^{50}$ and $R^{54}$ together comprise a detection means such that when $R^{49}$ and $R^{53}$ associate a detectable signal is produced;
- $R^{51}$ is a peptide or protein epitope binding agent that binds to $R^{47}$ such that in the absence of a target molecule:
  (i) $R^{51}$ binds to $R^{47}$,
  (ii) $R^{49}$ and $R^{53}$ associate, and
  (iii) $R^{50}$ and $R^{54}$ produce a detectable signal, and;
- $R^{52}$ is a flexible linker attaching $R^{51}$ to $R^{53}$.

7. The molecular biosensor of claim 6, wherein $R^{51}$ is an antibody or antibody fragment selected from the group consisting of polyclonal antibodies, ascites, Fab fragments, Fab' fragments, monoclonal antibodies and humanized antibodies.

8. The molecular biosensor of claim 7, wherein $R^{48}$ and $R^{52}$ are from about 50 to about 250 angstroms in length and are selected independently selected from the group consisting of a heterobifunctional chemical linker, a homobifunctional chemical linker, polyethylene glycol, and nucleic acid.

9. The molecular biosensor of claim 8, wherein $R^{49}$ and $R^{53}$ are from about 2 to about 20 nucleotides in length.

10. The molecular biosensor of claim 9, wherein $R^{50}$ and $R^{54}$ are independently selected from the group consisting of fluorescence resonance electron transfer (FRET), lanthamide resonance electron transfer (LRET), fluorescence cross-correlation spectroscopy, fluorescence quenching, fluorescence polarization, flow cytometry, scintillation proximity, luminescence resonance energy transfer, direct quenching, ground-state complex formation, chemiluminescence energy transfer, bioluminescence resonance energy transfer, excimer formation, colorimetric substrates detection, phosphorescence, electro-chemical changes, and redox potential changes.

11. A method for determining the presence of a target molecule in a sample, the method comprising:
   a) measuring the signal of a molecular biosensor without the target molecule being present, the molecular biosensor comprising two epitope binding agent constructs, which together have formula (VI)

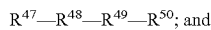
   $R^{47}$—$R^{48}$—$R^{49}$—$R^{50}$; and

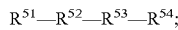
   $R^{51}$—$R^{52}$—$R^{53}$—$R^{54}$;

wherein:
   $R^{47}$ is an epitope-binding agent that binds to a first epitope on a target molecule and is selected from the group consisting of a peptide, a small molecule, and a protein;
   $R^{48}$ is a flexible linker attaching $R^{47}$ to $R^{49}$;
   $R^{49}$ and $R^{53}$ are a pair of complementary nucleotide sequences having a free energy for association from about 5.5 kcal/mole to about 8.0 kcal/mole at a temperature from about 21° C. to about 40° C. and at a salt concentration from about 1 mM to about 100 mM;
   $R^{50}$ and $R^{54}$ together comprise a detection means such that when $R^{49}$ and $R^{53}$ associate a detectable signal is produced;
   $R^{51}$ is an epitope binding agent selected from the croup consisting of an antibody, an antibody fragment, and an aptamer that binds to $R^{47}$ such that in the absence of a target molecule:
      (i) $R^{51}$ binds to $R^{47}$,
      (ii) $R^{49}$ and $R^{53}$ associate, and
      (iii) $R^{50}$ and $R^{54}$ produce a detectable signal; and
   $R^{52}$ is a flexible linker attaching $R^{51}$ to $R^{53}$.
   b) combining the molecular biosensor with the sample; and
   c) measuring the signal of the biosensor, wherein a decrease in signal indicates the presence of a target molecule.

12. The method of claim 10, wherein $R^{51}$ is an antibody or antibody fragment selected from the group consisting of polyclonal antibodies, ascites, Fab fragments, Fab' fragments, monoclonal antibodies and humanized antibodies.

13. The method of claim 12, wherein $R^{48}$ and $R^{52}$ are from about 50 to about 250 angstroms in length and are selected independently selected from the group consisting of a heterobifunctional chemical linker, a homobifunctional chemical linker, polyethylene glycol, and nucleic acid.

14. The method of claim 13, wherein $R^{49}$ and $R^{53}$ are from about 2 to about 20 nucleotides in length.

15. The method of claim 14, wherein $R^{50}$ and $R^{54}$ are independently selected from the group consisting of fluorescence resonance electron transfer (FRET), lanthamide resonance electron transfer (LRET), fluorescence cross-correlation spectroscopy, fluorescence quenching, fluorescence polarization, flow cytometry, scintillation proximity, luminescence resonance energy transfer, direct quenching, ground-state complex formation, chemiluminescence energy transfer, bioluminescence resonance energy transfer, excimer formation, colorimetric substrates detection, phosphorescence, electro-chemical changes, and redox potential changes.

16. The method of claim 11, wherein the concentration of the target molecule is determined.

17. The method of claim 11, wherein the target molecule is a macromolecule selected from the group consisting of a protein, a polypeptide, a prion, a nucleic acid, a lipid, and a carbohydrate.

18. The method of claim 11, wherein the target molecule is selected from a kinase, a binding protein, and an antigen.

* * * * *

UNITED STATES PATENT AND TRADEMARK OFFICE
CERTIFICATE OF CORRECTION

PATENT NO. : 7,811,809 B2  
APPLICATION NO. : 11/836339  
DATED : October 12, 2010  
INVENTOR(S) : Tomasz Heyduk et al.

It is certified that error appears in the above-identified patent and that said Letters Patent is hereby corrected as shown below:

Col. 123, line 57, "selected independently selected" should read -- independently selected --

Col. 124, line 35, "R51-R52-R53-R54;" should read -- $R^{51}$-$R^{52}$-$R^{53}$-$R^{54}$ --

Signed and Sealed this
Twenty-second Day of November, 2011

David J. Kappos
*Director of the United States Patent and Trademark Office*

SEQUENCE LISTING

<160> NUMBER OF SEQ ID NOS: 135

<210> SEQ ID NO 1
<211> LENGTH: 29
<212> TYPE: DNA
<213> ORGANISM: Homo sapiens

<400> SEQUENCE: 1
agtccgtggt agggcaggtt ggggtgact                                      29

<210> SEQ ID NO 2
<211> LENGTH: 15
<212> TYPE: DNA
<213> ORGANISM: Homo sapiens

<400> SEQUENCE: 2
ggttggtgtg gttgg                                                     15

<210> SEQ ID NO 3
<211> LENGTH: 29
<212> TYPE: DNA
<213> ORGANISM: Homo sapiens

<400> SEQUENCE: 3
agtccgtggt agggcaggtt ggggtgact                                      29

<210> SEQ ID NO 4
<211> LENGTH: 15
<212> TYPE: DNA
<213> ORGANISM: Homo sapiens

<400> SEQUENCE: 4
ggttggtgtg gttgg                                                     15

<210> SEQ ID NO 5
<211> LENGTH: 49
<212> TYPE: DNA
<213> ORGANISM: Homo sapiens
<220> FEATURE:
<221> NAME/KEY: misc_feature
<222> LOCATION: (30)..(34)
<223> OTHER INFORMATION: N = Spacer18 linker

<400> SEQUENCE: 5

```
agtccgtggt agggcaggtt ggggtgactn nnnnggttgg tgtggttgg          49

<210> SEQ ID NO 6
<211> LENGTH: 54
<212> TYPE: DNA
<213> ORGANISM: Homo sapiens
<220> FEATURE:
<221> NAME/KEY: misc_feature
<222> LOCATION: (30)..(39)
<223> OTHER INFORMATION: N = SPACER18 LINKER

<400> SEQUENCE: 6
agtccgtggt agggcaggtt ggggtgactn nnnnnnnnng gttggtgtgg ttgg     54

<210> SEQ ID NO 7
<211> LENGTH: 54
<212> TYPE: DNA
<213> ORGANISM: Homo sapiens
<220> FEATURE:
<221> NAME/KEY: misc_feature
<222> LOCATION: (16)..(25)
<223> OTHER INFORMATION: N = SPACER18 LINKER

<400> SEQUENCE: 7
ggttggtgtg gttggnnnnn nnnnnagtcc gtggtagggc aggttggggt gact     54

<210> SEQ ID NO 8
<211> LENGTH: 41
<212> TYPE: DNA
<213> ORGANISM: Homo sapiens
<220> FEATURE:
<221> NAME/KEY: misc_feature
<222> LOCATION: (15)..(15)
<223> OTHER INFORMATION: n is a, c, g, or t

<400> SEQUENCE: 8
ggttggtgtg gttgngtttt tttctgtcgt tagtgaaggt t                  41

<210> SEQ ID NO 9
<211> LENGTH: 54
<212> TYPE: DNA
<213> ORGANISM: Homo sapiens

<400> SEQUENCE: 9
aaccttcact aacgacagtt tttttagtcc gtggtagggc aggttggggt gact     54

<210> SEQ ID NO 10
<211> LENGTH: 50
<212> TYPE: DNA
<213> ORGANISM: Homo sapiens

<400> SEQUENCE: 10
ggttggtgtg gttggttttt tttttttttt ttctgtcgtt agtgaaggtt          50

<210> SEQ ID NO 11
<211> LENGTH: 64
<212> TYPE: DNA
<213> ORGANISM: Homo sapiens

<400> SEQUENCE: 11
aaccttcact aacgacagtt tttttttttt tttttagtcc gtggtagggc aggttggggt   60
gact                                                              64

<210> SEQ ID NO 12
<211> LENGTH: 60
```

```
<212> TYPE: DNA
<213> ORGANISM: Homo sapiens

<400> SEQUENCE: 12
ggttggtgtg gttggttttt tttttttttt ttctgtcgtt agtgaaggtt          60

<210> SEQ ID NO 13
<211> LENGTH: 74
<212> TYPE: DNA
<213> ORGANISM: Homo sapiens

<400> SEQUENCE: 13
aaccttcact aacgacagtt tttttttttt tttttttttt ttttagtccc gtggtagggc          60
aggttggggt gact                                                 74

<210> SEQ ID NO 14
<211> LENGTH: 39
<212> TYPE: DNA
<213> ORGANISM: Homo sapiens

<400> SEQUENCE: 14
ggttggtgtg gttggttttt tttttttttt ttcgcatct                      39

<210> SEQ ID NO 15
<211> LENGTH: 53
<212> TYPE: DNA
<213> ORGANISM: Homo sapiens

<400> SEQUENCE: 15
agatgcgttt tttttttttt ttttagtccg tggtagggca ggttggggtg act       53

<210> SEQ ID NO 16
<211> LENGTH: 27
<212> TYPE: DNA
<213> ORGANISM: Homo sapiens
<220> FEATURE:
<221> NAME/KEY: misc_feature
<222> LOCATION: (16)..(20)
<223> OTHER INFORMATION: N = SPACER18 LINKER

<400> SEQUENCE: 16
ggttggtgtg gttggnnnnn cgcatct                                   27

<210> SEQ ID NO 17
<211> LENGTH: 41
<212> TYPE: DNA
<213> ORGANISM: Homo sapiens
<220> FEATURE:
<221> NAME/KEY: misc_feature
<222> LOCATION: (8)..(12)
<223> OTHER INFORMATION: N = SPACER18 LINKER

<400> SEQUENCE: 17
agatgcgnnn nnagtccgtg gtagggcagg ttggggtgac t                   41

<210> SEQ ID NO 18
<211> LENGTH: 29
<212> TYPE: DNA
<213> ORGANISM: Homo sapiens
<220> FEATURE:
<221> NAME/KEY: misc_feature
<222> LOCATION: (16)..(20)
<223> OTHER INFORMATION: N= SPACER18 LINKER
<220> FEATURE:
<221> NAME/KEY: misc_feature
<222> LOCATION: (22)..(22)
```

<223> OTHER INFORMATION: 5' AMINO GROUP

<400> SEQUENCE: 18
ggttggtgtg gttggnnnnn ctcgcatct                                              29

<210> SEQ ID NO 19
<211> LENGTH: 41
<212> TYPE: DNA
<213> ORGANISM: Homo sapiens
<220> FEATURE:
<221> NAME/KEY: misc_feature
<222> LOCATION: (8)..(12)
<223> OTHER INFORMATION: N = SPACER18 LINKER

<400> SEQUENCE: 19
agatgcgnnn nnagtccgtg gtagggcagg ttggggtgac t                                41

<210> SEQ ID NO 20
<211> LENGTH: 69
<212> TYPE: DNA
<213> ORGANISM: Homo sapiens
<220> FEATURE:
<221> NAME/KEY: misc_feature
<222> LOCATION: (19)..(51)
<223> OTHER INFORMATION: n is a, c, g, or t

<400> SEQUENCE: 20
ctgtcgttag tgaaggttnn nnnnnnnnnn nnnnnnnnnn nnnnnnnnnn naacgccata            60
tcacagacg                                                                   69

<210> SEQ ID NO 21
<211> LENGTH: 18
<212> TYPE: DNA
<213> ORGANISM: Homo sapiens

<400> SEQUENCE: 21
ctgtcgttag tgaaggtt                                                         18

<210> SEQ ID NO 22
<211> LENGTH: 18
<212> TYPE: DNA
<213> ORGANISM: Homo sapiens

<400> SEQUENCE: 22
cgtctgtgat atggcgtt                                                         18

<210> SEQ ID NO 23
<211> LENGTH: 22
<212> TYPE: DNA
<213> ORGANISM: Homo sapiens
<220> FEATURE:
<221> NAME/KEY: misc_feature
<222> LOCATION: (16)..(17)
<223> OTHER INFORMATION: N = SPACER18 LINKER

<400> SEQUENCE: 23
ggttggtgtg gttggnngac ag                                                    22

<210> SEQ ID NO 24
<211> LENGTH: 27
<212> TYPE: DNA
<213> ORGANISM: Homo sapiens
<220> FEATURE:
<221> NAME/KEY: misc_feature
<222> LOCATION: (16)..(20)
<223> OTHER INFORMATION: N = SPACER18 LINKER

<400> SEQUENCE: 24
ggttggtgtg gttggnnnnn acgacag                                    27

<210> SEQ ID NO 25
<211> LENGTH: 24
<212> TYPE: DNA
<213> ORGANISM: Homo sapiens
<220> FEATURE:
<221> NAME/KEY: misc_feature
<222> LOCATION: (13)..(17)
<223> OTHER INFORMATION: N = SPACER18 LINKER

<400> SEQUENCE: 25
gaacgagagt gcnnnnncgc atct                                       24

<210> SEQ ID NO 26
<211> LENGTH: 24
<212> TYPE: DNA
<213> ORGANISM: Homo sapiens
<220> FEATURE:
<221> NAME/KEY: misc_feature
<222> LOCATION: (8)..(12)
<223> OTHER INFORMATION: N = SPACER18 LINKER

<400> SEQUENCE: 26
agatgcgnnn nnttgaactg gacc                                       24

<210> SEQ ID NO 27
<211> LENGTH: 26
<212> TYPE: DNA
<213> ORGANISM: Homo sapiens

<400> SEQUENCE: 27
ggtccagttc aattgcactc tcgttc                                     26

<210> SEQ ID NO 28
<211> LENGTH: 28
<212> TYPE: DNA
<213> ORGANISM: Homo sapiens
<220> FEATURE:
<221> NAME/KEY: misc_feature
<222> LOCATION: (16)..(20)
<223> OTHER INFORMATION: N = SPACER18 LINKER

<400> SEQUENCE: 28
ggttggtgtg gttggnnnnn aacgacag                                   28

<210> SEQ ID NO 29
<211> LENGTH: 82
<212> TYPE: DNA
<213> ORGANISM: Homo sapiens
<220> FEATURE:
<221> NAME/KEY: misc_feature
<222> LOCATION: (9)..(13)
<223> OTHER INFORMATION: N = SPACER18 LINKER
<220> FEATURE:
<221> NAME/KEY: misc_feature
<222> LOCATION: (32)..(64)
<223> OTHER INFORMATION: n is a, c, g, or t

<400> SEQUENCE: 29
ctgtcgttnn nnnttgagtc agcgtcgagc annnnnnnnn nnnnnnnnnn nnnnnnnnn    60 nnnnttcact gtgctgcggc ta                                          82

<210> SEQ ID NO 30

```
<211> LENGTH: 31
<212> TYPE: DNA
<213> ORGANISM: Homo sapiens
<220> FEATURE:
<221> NAME/KEY: misc_feature
<222> LOCATION: (9)..(13)
<223> OTHER INFORMATION: N = SPACER18 LINKER

<400> SEQUENCE: 30
ctgtcgttnn nnnttgagtc agcgtcgagc a                               31

<210> SEQ ID NO 31
<211> LENGTH: 18
<212> TYPE: DNA
<213> ORGANISM: Homo sapiens

<400> SEQUENCE: 31
tagccgcagc acagtgaa                                              18

<210> SEQ ID NO 32
<211> LENGTH: 66
<212> TYPE: DNA
<213> ORGANISM: Homo sapiens
<220> FEATURE:
<221> NAME/KEY: misc_feature
<222> LOCATION: (19)..(48)
<223> OTHER INFORMATION: n is a, c, g, or t

<400> SEQUENCE: 32
cacctgatcg ctcctcgtnn nnnnnnnnnn nnnnnnnnnn nnnnnnnnca ggatgcacag  60
gcacaa                                                            66

<210> SEQ ID NO 33
<211> LENGTH: 66
<212> TYPE: DNA
<213> ORGANISM: Homo sapiens
<220> FEATURE:
<221> NAME/KEY: misc_feature
<222> LOCATION: (19)..(48)
<223> OTHER INFORMATION: n is a, c, g, or t

<400> SEQUENCE: 33
agccgccatt ccatagtgnn nnnnnnnnnn nnnnnnnnnn nnnnnnnnca ggatgccgat  60
caggtg                                                            66

<210> SEQ ID NO 34
<211> LENGTH: 18
<212> TYPE: DNA
<213> ORGANISM: Homo sapiens

<400> SEQUENCE: 34
cacctgatcg ctcctcgt                                              18

<210> SEQ ID NO 35
<211> LENGTH: 18
<212> TYPE: DNA
<213> ORGANISM: Homo sapiens

<400> SEQUENCE: 35
ttgtgcctgt gcatcctg                                              18

<210> SEQ ID NO 36
<211> LENGTH: 18
<212> TYPE: DNA
<213> ORGANISM: Homo sapiens
```

```
<400> SEQUENCE: 36
agccgccatt ccatagtg                                                18

<210> SEQ ID NO 37
<211> LENGTH: 18
<212> TYPE: DNA
<213> ORGANISM: Homo sapiens

<400> SEQUENCE: 37
cacctgatcg gcatcctg                                                18

<210> SEQ ID NO 38
<211> LENGTH: 55
<212> TYPE: DNA
<213> ORGANISM: Homo sapiens
<220> FEATURE:
<221> NAME/KEY: misc_feature
<222> LOCATION: (8)..(12)
<223> OTHER INFORMATION: N = SPACER18 LINKER

<400> SEQUENCE: 38
agatgcgnnn nnaggttggg ggtactaggt atcaatgggt agggtggtgt aacgc        55

<210> SEQ ID NO 39
<211> LENGTH: 65
<212> TYPE: DNA
<213> ORGANISM: Homo sapiens
<220> FEATURE:
<221> NAME/KEY: misc_feature
<222> LOCATION: (8)..(12)
<223> OTHER INFORMATION: N = SPACER18 LINKER

<400> SEQUENCE: 39
agatgcgnnn nnagtgaagg ttgggggtac taggtatcaa tgggtagggt ggtgtaacgc   60
catat                                                              65

<210> SEQ ID NO 40
<211> LENGTH: 50
<212> TYPE: DNA
<213> ORGANISM: Homo sapiens
<220> FEATURE:
<221> NAME/KEY: misc_feature
<222> LOCATION: (39)..(43)
<223> OTHER INFORMATION: N = SPACER18 LINKER

<400> SEQUENCE: 40
aacgcaataa atgtgaagta gatcacattt taggcaccnn nnngatggct              50

<210> SEQ ID NO 41
<211> LENGTH: 69
<212> TYPE: DNA
<213> ORGANISM: Homo sapiens
<220> FEATURE:
<221> NAME/KEY: misc_feature
<222> LOCATION: (19)..(51)
<223> OTHER INFORMATION: n is a, c, g, or t

<400> SEQUENCE: 41
agccatctaa ctattcccnn nnnnnnnnn nnnnnnnnnn nnnnnnnnnn ngagcgagaa    60
attctaggt                                                          69

<210> SEQ ID NO 42
<211> LENGTH: 38
<212> TYPE: DNA
```

<210> SEQ ID NO 42
<211> LENGTH: 38
<212> TYPE: DNA
<213> ORGANISM: Homo sapiens

<400> SEQUENCE: 42
ggtgcctaaa atgtgatcta cttcacattt attgcgtt                                  38

<210> SEQ ID NO 43
<211> LENGTH: 18
<212> TYPE: DNA
<213> ORGANISM: Homo sapiens

<400> SEQUENCE: 43
agccatctaa ctattccc                                                        18

<210> SEQ ID NO 44
<211> LENGTH: 18
<212> TYPE: DNA
<213> ORGANISM: Homo sapiens

<400> SEQUENCE: 44
acctagaatt tctcgctc                                                        18

<210> SEQ ID NO 45
<211> LENGTH: 33
<212> TYPE: DNA
<213> ORGANISM: Homo sapiens

<400> SEQUENCE: 45
ggcggtatgg gcatagcgta atgggaggtt ggt                                       33

<210> SEQ ID NO 46
<211> LENGTH: 33
<212> TYPE: DNA
<213> ORGANISM: Homo sapiens

<400> SEQUENCE: 46
ggatgcgtaa tggttagggt gggtagggta tcc                                       33

<210> SEQ ID NO 47
<211> LENGTH: 33
<212> TYPE: DNA
<213> ORGANISM: Homo sapiens

<400> SEQUENCE: 47
ggatgcgtaa tggttagggt gggtagggta tcc                                       33

<210> SEQ ID NO 48
<211> LENGTH: 33
<212> TYPE: DNA
<213> ORGANISM: Homo sapiens

<400> SEQUENCE: 48
ggatgcgtaa tggttagggt gggtagggta tcc                                       33

<210> SEQ ID NO 49
<211> LENGTH: 33
<212> TYPE: DNA
<213> ORGANISM: Homo sapiens

<400> SEQUENCE: 49
gcagtaggta ctatattggc tagggtggtc tgc                                       33

<210> SEQ ID NO 50
<211> LENGTH: 33

```
<212> TYPE: DNA
<213> ORGANISM: Homo sapiens

<400> SEQUENCE: 50
gcagtaggta ctatattggc tagggtggtc tgc                                33

<210> SEQ ID NO 51
<211> LENGTH: 33
<212> TYPE: DNA
<213> ORGANISM: Homo sapiens

<400> SEQUENCE: 51
ggcggtatgg gcatagcgta atgggaggtc tgc                                33

<210> SEQ ID NO 52
<211> LENGTH: 33
<212> TYPE: DNA
<213> ORGANISM: Homo sapiens

<400> SEQUENCE: 52
ggatgcgtaa tggttagggt gggtagggta tcc                                33

<210> SEQ ID NO 53
<211> LENGTH: 33
<212> TYPE: DNA
<213> ORGANISM: Homo sapiens

<400> SEQUENCE: 53
ggcggtatgg gtatagcgta atgggaggtt ggt                                33

<210> SEQ ID NO 54
<211> LENGTH: 33
<212> TYPE: DNA
<213> ORGANISM: Homo sapiens

<400> SEQUENCE: 54
gggggtacta ggtattaatg ggtagggtgg tgt                                33

<210> SEQ ID NO 55
<211> LENGTH: 33
<212> TYPE: DNA
<213> ORGANISM: Homo sapiens

<400> SEQUENCE: 55
cagcagggaa cggaacggtt agggtgggta ggg                                33

<210> SEQ ID NO 56
<211> LENGTH: 33
<212> TYPE: DNA
<213> ORGANISM: Homo sapiens
<220> FEATURE:
<221> NAME/KEY: misc_feature
<222> LOCATION: (5)..(5)
<223> OTHER INFORMATION: n is a, c, g, or t

<400> SEQUENCE: 56
gcggngatag gtcgcgtaag ttgggtaggg tgg                                33

<210> SEQ ID NO 57
<211> LENGTH: 33
<212> TYPE: DNA
<213> ORGANISM: Homo sapiens

<400> SEQUENCE: 57
```
caggatgggt agggtggtca gcgaagcagt agg    33

<210> SEQ ID NO 58
<211> LENGTH: 33
<212> TYPE: DNA
<213> ORGANISM: Homo sapiens

<400> SEQUENCE: 58
caacggttgg gtgaactgta gtggcttggg gtg    33

<210> SEQ ID NO 59
<211> LENGTH: 33
<212> TYPE: DNA
<213> ORGANISM: Homo sapiens

<400> SEQUENCE: 59
caggatgggt agggtggtca gcgaagcagt agg    33

<210> SEQ ID NO 60
<211> LENGTH: 32
<212> TYPE: DNA
<213> ORGANISM: Homo sapiens

<400> SEQUENCE: 60
caggatgggt agggtggtca gcgaagcagt ag    32

<210> SEQ ID NO 61
<211> LENGTH: 33
<212> TYPE: DNA
<213> ORGANISM: Homo sapiens

<400> SEQUENCE: 61
ggcgagagca gcgtgatagg gtgggtaggg tgg    33

<210> SEQ ID NO 62
<211> LENGTH: 33
<212> TYPE: DNA
<213> ORGANISM: Homo sapiens

<400> SEQUENCE: 62
cagggtcagg gctagatgat gcgattaacc atg    33

<210> SEQ ID NO 63
<211> LENGTH: 33
<212> TYPE: DNA
<213> ORGANISM: Homo sapiens

<400> SEQUENCE: 63
caggatgggt agggtggtca gcgaagcagt agg    33

<210> SEQ ID NO 64
<211> LENGTH: 33
<212> TYPE: DNA
<213> ORGANISM: Homo sapiens

<400> SEQUENCE: 64
gggggtacta ggtatcaatg ggtagggtgg tgt    33

<210> SEQ ID NO 65
<211> LENGTH: 33
<212> TYPE: DNA
<213> ORGANISM: Homo sapiens

<400> SEQUENCE: 65

```
gggggtacta ggtatcaatg ggtagggtgg tgt                                33

<210> SEQ ID NO 66
<211> LENGTH: 33
<212> TYPE: DNA
<213> ORGANISM: Homo sapiens
<220> FEATURE:
<221> NAME/KEY: misc_feature
<222> LOCATION: (27)..(27)
<223> OTHER INFORMATION: n is a, c, g, or t

<400> SEQUENCE: 66
ggagacgtaa tgggttggtt gggaagngga tcc                                33

<210> SEQ ID NO 67
<211> LENGTH: 33
<212> TYPE: DNA
<213> ORGANISM: Homo sapiens

<400> SEQUENCE: 67
gcatacgtaa tggtccggtt ggggcgggta tgt                                33

<210> SEQ ID NO 68
<211> LENGTH: 33
<212> TYPE: DNA
<213> ORGANISM: Homo sapiens

<400> SEQUENCE: 68
gggggtacta ggtatcaatg ggtagggtgg tgt                                33

<210> SEQ ID NO 69
<211> LENGTH: 33
<212> TYPE: DNA
<213> ORGANISM: Homo sapiens

<400> SEQUENCE: 69 gagggggactt aggatgggta gggtggtagg ccc                               33

<210> SEQ ID NO 70
<211> LENGTH: 33
<212> TYPE: DNA
<213> ORGANISM: Homo sapiens

<400> SEQUENCE: 70
gggggtacta ggtatcaatg ggtagggtgg tgt                                33

<210> SEQ ID NO 71
<211> LENGTH: 33
<212> TYPE: DNA
<213> ORGANISM: Homo sapiens

<400> SEQUENCE: 71
ggtcggggca tagtaatgct ggattgggca gct                                33

<210> SEQ ID NO 72
<211> LENGTH: 33
<212> TYPE: DNA
<213> ORGANISM: Homo sapiens

<400> SEQUENCE: 72
gggtaggagc agtacacgct ggaatgggtc act                                33

<210> SEQ ID NO 73
```

```
<211> LENGTH: 33
<212> TYPE: DNA
<213> ORGANISM: Homo sapiens

<400> SEQUENCE: 73
gcagtaggta ctatattggc tagggtggtc tgc                              33

<210> SEQ ID NO 74
<211> LENGTH: 33
<212> TYPE: DNA
<213> ORGANISM: Homo sapiens

<400> SEQUENCE: 74
gggtagggtg acagggagga cggaatgggc act                              33

<210> SEQ ID NO 75
<211> LENGTH: 33
<212> TYPE: DNA
<213> ORGANISM: Homo sapiens

<400> SEQUENCE: 75
gcagtaggta ctatattggc tagggtggtc tgc                              33

<210> SEQ ID NO 76
<211> LENGTH: 33
<212> TYPE: DNA
<213> ORGANISM: Homo sapiens

<400> SEQUENCE: 76
gcagtaggta ctatattggc tagggtggtc tgc                              33

<210> SEQ ID NO 77
<211> LENGTH: 33
<212> TYPE: DNA
<213> ORGANISM: Homo sapiens

<400> SEQUENCE: 77
gcagtaggta ctatattggc tagggtggtc tgc                              33

<210> SEQ ID NO 78
<211> LENGTH: 33
<212> TYPE: DNA
<213> ORGANISM: Homo sapiens

<400> SEQUENCE: 78
gggggtgcta ggtattaaag ggtagggtgg tgt                              33

<210> SEQ ID NO 79
<211> LENGTH: 33
<212> TYPE: DNA
<213> ORGANISM: Homo sapiens

<400> SEQUENCE: 79
gcagtaggta ctatgtcggg tcgggtggtc tgc                              33

<210> SEQ ID NO 80
<211> LENGTH: 30
<212> TYPE: DNA
<213> ORGANISM: Homo sapiens

<400> SEQUENCE: 80
gggtagggtg gttgtaatag ggattgcgat                                  30
```

```
<210> SEQ ID NO 81
<211> LENGTH: 30
<212> TYPE: DNA
<213> ORGANISM: Homo sapiens

<400> SEQUENCE: 81
gggtagggtg gttgtaatag ggattgcgat                                     30

<210> SEQ ID NO 82
<211> LENGTH: 30
<212> TYPE: DNA
<213> ORGANISM: Homo sapiens

<400> SEQUENCE: 82
ggcacaaccc gatatggcta tgaatctgcc                                     30

<210> SEQ ID NO 83
<211> LENGTH: 30
<212> TYPE: DNA
<213> ORGANISM: Homo sapiens

<400> SEQUENCE: 83
gggtagggtg gttgtaatag ggattgcgat                                     30

<210> SEQ ID NO 84
<211> LENGTH: 30
<212> TYPE: DNA
<213> ORGANISM: Homo sapiens

<400> SEQUENCE: 84
gggtagggtg gttgtaatag ggattgcgat                                     30

<210> SEQ ID NO 85
<211> LENGTH: 30
<212> TYPE: DNA
<213> ORGANISM: Homo sapiens

<400> SEQUENCE: 85
ggtgtgggtg gttattggtg tagagcgggt                                     30

<210> SEQ ID NO 86
<211> LENGTH: 30
<212> TYPE: DNA
<213> ORGANISM: Homo sapiens

<400> SEQUENCE: 86
aatggggagg ttggggtgcg ggagagtggt                                     30

<210> SEQ ID NO 87
<211> LENGTH: 30
<212> TYPE: DNA
<213> ORGANISM: Homo sapiens

<400> SEQUENCE: 87
acgcgtagga tgggtagggt ggtcgcgtta                                     30

<210> SEQ ID NO 88
<211> LENGTH: 30
<212> TYPE: DNA
<213> ORGANISM: Homo sapiens

<400> SEQUENCE: 88
gggtagggtg gttgtaatag ggattgcgat                                     30
```

```
<210> SEQ ID NO 89
<211> LENGTH: 30
<212> TYPE: DNA
<213> ORGANISM: Homo sapiens

<400> SEQUENCE: 89
gggcgaaggt acgaagacgg atgcacgtgc                                    30

<210> SEQ ID NO 90
<211> LENGTH: 30
<212> TYPE: DNA
<213> ORGANISM: Homo sapiens

<400> SEQUENCE: 90
aaggccgcca tctgggtccg acgagtacca                                    30

<210> SEQ ID NO 91
<211> LENGTH: 30
<212> TYPE: DNA
<213> ORGANISM: Homo sapiens

<400> SEQUENCE: 91
tagggtgggt agggtggtca actatggggg                                    30

<210> SEQ ID NO 92
<211> LENGTH: 30
<212> TYPE: DNA
<213> ORGANISM: Homo sapiens

<400> SEQUENCE: 92
gggtggctgg tcaaggagat agtacgatgc                                    30

<210> SEQ ID NO 93
<211> LENGTH: 30
<212> TYPE: DNA
<213> ORGANISM: Homo sapiens

<400> SEQUENCE: 93
ggtagggtgg ttaaaatagg ggaatggcag                                    30

<210> SEQ ID NO 94
<211> LENGTH: 30
<212> TYPE: DNA
<213> ORGANISM: Homo sapiens

<400> SEQUENCE: 94
cacaagaagg gcgagcgctg agcatagtgc                                    30

<210> SEQ ID NO 95
<211> LENGTH: 30
<212> TYPE: DNA
<213> ORGANISM: Homo sapiens

<400> SEQUENCE: 95
ccaacgacac atagggtaca cgccgcctcc                                    30

<210> SEQ ID NO 96
<211> LENGTH: 30
<212> TYPE: DNA
<213> ORGANISM: Homo sapiens

<400> SEQUENCE: 96
ggtagggtgg ttaaaatagg ggaatggcag                                    30
```

<210> SEQ ID NO 97
<211> LENGTH: 30
<212> TYPE: DNA
<213> ORGANISM: Homo sapiens

<400> SEQUENCE: 97
taggatgggt agggtggtcc caggaatggc                                    30

<210> SEQ ID NO 98
<211> LENGTH: 30
<212> TYPE: DNA
<213> ORGANISM: Homo sapiens

<400> SEQUENCE: 98
taggatgggt agggtggccc caggaatggc                                    30

<210> SEQ ID NO 99
<211> LENGTH: 30
<212> TYPE: DNA
<213> ORGANISM: Homo sapiens

<400> SEQUENCE: 99
ggtagggtgg ttaaaatagg ggaatggcag                                    30

<210> SEQ ID NO 100
<211> LENGTH: 30
<212> TYPE: DNA
<213> ORGANISM: Homo sapiens

<400> SEQUENCE: 100
gatgtggccc agaagcataa cacgacgtac                                    30

<210> SEQ ID NO 101
<211> LENGTH: 30
<212> TYPE: DNA
<213> ORGANISM: Homo sapiens

<400> SEQUENCE: 101
taggatgggt agggtggtcc caggaatggc                                    30

<210> SEQ ID NO 102
<211> LENGTH: 30
<212> TYPE: DNA
<213> ORGANISM: Homo sapiens

<400> SEQUENCE: 102
ggagatgcag gtactgagta gggagtgtgc                                    30

<210> SEQ ID NO 103
<211> LENGTH: 30
<212> TYPE: DNA
<213> ORGANISM: Homo sapiens

<400> SEQUENCE: 103
taggatgggt agggtggtcc caggaatggc                                    30

<210> SEQ ID NO 104
<211> LENGTH: 33
<212> TYPE: DNA
<213> ORGANISM: Homo sapiens

<400> SEQUENCE: 104

| | |
|---|---|
| aatcaagggc tggtgttaaa ggtgatcgac tag | 33 |

<210> SEQ ID NO 105
<211> LENGTH: 33
<212> TYPE: DNA
<213> ORGANISM: Homo sapiens

<400> SEQUENCE: 105

| | |
|---|---|
| aaggggagcc atcacacagg aggtcgcttc gct | 33 |

<210> SEQ ID NO 106
<211> LENGTH: 33
<212> TYPE: DNA
<213> ORGANISM: Homo sapiens

<400> SEQUENCE: 106

| | |
|---|---|
| aaaggcatca cctagagttg ccgccgatac ttg | 33 |

<210> SEQ ID NO 107
<211> LENGTH: 33
<212> TYPE: DNA
<213> ORGANISM: Homo sapiens

<400> SEQUENCE: 107

| | |
|---|---|
| ggggatgtgc gaaactggtg actatgcggg tgc | 33 |

<210> SEQ ID NO 108
<211> LENGTH: 33
<212> TYPE: DNA
<213> ORGANISM: Homo sapiens

<400> SEQUENCE: 108

| | |
|---|---|
| cgaaaggagc catcaacctt gaaacgcccg tcc | 33 |

<210> SEQ ID NO 109
<211> LENGTH: 33
<212> TYPE: DNA
<213> ORGANISM: Homo sapiens

<400> SEQUENCE: 109

| | |
|---|---|
| cagacgggag ccatcgacat agaggtgatt gcc | 33 |

<210> SEQ ID NO 110
<211> LENGTH: 33
<212> TYPE: DNA
<213> ORGANISM: Homo sapiens

<400> SEQUENCE: 110

| | |
|---|---|
| agggaaagcc atcacctaga cacatacagc atg | 33 |

<210> SEQ ID NO 111
<211> LENGTH: 33
<212> TYPE: DNA
<213> ORGANISM: Homo sapiens

<400> SEQUENCE: 111

| | |
|---|---|
| ataagaagcc atcataggga cctagctagc ccc | 33 |

<210> SEQ ID NO 112
<211> LENGTH: 33
<212> TYPE: DNA
<213> ORGANISM: Homo sapiens

<400> SEQUENCE: 112

-continued ccaacagacg gtagcacaac actagtactc tgg         33

<210> SEQ ID NO 113
<211> LENGTH: 33
<212> TYPE: DNA
<213> ORGANISM: Homo sapiens

<400> SEQUENCE: 113
acagacgccc ctagtaaaca ataaccgatg gcc         33

<210> SEQ ID NO 114
<211> LENGTH: 33
<212> TYPE: DNA
<213> ORGANISM: Homo sapiens

<400> SEQUENCE: 114
atagctactc gccaagggtg acttctgcta ttg         33

<210> SEQ ID NO 115
<211> LENGTH: 33
<212> TYPE: DNA
<213> ORGANISM: Homo sapiens

<400> SEQUENCE: 115
atggggcaac gcggagacct gtcggtactg cct         33

<210> SEQ ID NO 116
<211> LENGTH: 33
<212> TYPE: DNA
<213> ORGANISM: Homo sapiens

<400> SEQUENCE: 116
gcaatatagc actaagcctt aactccatgg tgg         33

<210> SEQ ID NO 117
<211> LENGTH: 33
<212> TYPE: DNA
<213> ORGANISM: Homo sapiens

<400> SEQUENCE: 117
gcaaggaaaa acaagcaagc catcacgacc tag         33

<210> SEQ ID NO 118
<211> LENGTH: 33
<212> TYPE: DNA
<213> ORGANISM: Homo sapiens

<400> SEQUENCE: 118
caggcatccc aagaagtgtc agccgtttcg tgg         33

<210> SEQ ID NO 119
<211> LENGTH: 33
<212> TYPE: DNA
<213> ORGANISM: Homo sapiens

<400> SEQUENCE: 119
caacaggaga gcccgacaca cagatctggc ccc         33

<210> SEQ ID NO 120
<211> LENGTH: 33
<212> TYPE: DNA
<213> ORGANISM: Homo sapiens

```
<400> SEQUENCE: 120
acaagccatc acgtgaatgc cgaccggtac tgt                                33

<210> SEQ ID NO 121
<211> LENGTH: 33
<212> TYPE: DNA
<213> ORGANISM: Homo sapiens

<400> SEQUENCE: 121
accgacaaac aagtcaatac gggacacgat cct                                33

<210> SEQ ID NO 122
<211> LENGTH: 33
<212> TYPE: DNA
<213> ORGANISM: Homo sapiens

<400> SEQUENCE: 122
cagtgggtcg ggtcacagcc atgagtgttg ctg                                33

<210> SEQ ID NO 123
<211> LENGTH: 33
<212> TYPE: DNA
<213> ORGANISM: Homo sapiens

<400> SEQUENCE: 123
aacgggaaag ccatcaccat atttatcgtc ctg                                33

<210> SEQ ID NO 124
<211> LENGTH: 33
<212> TYPE: DNA
<213> ORGANISM: Homo sapiens

<400> SEQUENCE: 124
acgggcgcaa acaagatgta caaaagcatg gtg                                33

<210> SEQ ID NO 125
<211> LENGTH: 33
<212> TYPE: DNA
<213> ORGANISM: Homo sapiens

<400> SEQUENCE: 125
agcgggatag ggaactatcg gacaatcgtc gtg                                33

<210> SEQ ID NO 126
<211> LENGTH: 33
<212> TYPE: DNA
<213> ORGANISM: Homo sapiens

<400> SEQUENCE: 126
gaggataaaa gccatcaact agaatgcgca tgg                                33

<210> SEQ ID NO 127
<211> LENGTH: 13
<212> TYPE: DNA
<213> ORGANISM: Homo sapiens
<220> FEATURE:
<221> NAME/KEY: misc_feature
<222> LOCATION: (1)..(6)
<223> OTHER INFORMATION: N = SPACER18 LINKER

<400> SEQUENCE: 127
nnnnnnagat gcg                                                      13
```

```
<210> SEQ ID NO 128
<211> LENGTH: 13
<212> TYPE: DNA
<213> ORGANISM: Homo sapiens
<220> FEATURE:
<221> NAME/KEY: misc_feature
<222> LOCATION: (1)..(6)
<223> OTHER INFORMATION: N = SPACER18 LINKER

<400> SEQUENCE: 128
nnnnnnagat gcg                                                          13

<210> SEQ ID NO 129
<211> LENGTH: 43
<212> TYPE: DNA
<213> ORGANISM: Homo sapiens
<220> FEATURE:
<221> NAME/KEY: misc_feature
<222> LOCATION: (31)..(36)
<223> OTHER INFORMATION: N = SPACER18 LINKER

<400> SEQUENCE: 129
caataaatgt gatctagatc acatttagg nnnnnnagat gcg                          43

<210> SEQ ID NO 130
<211> LENGTH: 30
<212> TYPE: DNA
<213> ORGANISM: Homo sapiens

<400> SEQUENCE: 130
caataaatgt gatctagatc acatttagg                                         30

<210> SEQ ID NO 131
<211> LENGTH: 30
<212> TYPE: DNA
<213> ORGANISM: Homo sapiens

<400> SEQUENCE: 131
cctaaaatgt gatctagatc acatttattg                                        30

<210> SEQ ID NO 132
<211> LENGTH: 13
<212> TYPE: DNA
<213> ORGANISM: Homo sapiens
<220> FEATURE:
<221> NAME/KEY: misc_feature
<222> LOCATION: (1)..(6)
<223> OTHER INFORMATION: N = SPACER18 LINKER

<400> SEQUENCE: 132
nnnnnncgca tct                                                          13

<210> SEQ ID NO 133
<211> LENGTH: 27
<212> TYPE: DNA
<213> ORGANISM: Homo sapiens

<400> SEQUENCE: 133
aaaatgtgat ctagatcaca tttattg                                           27

<210> SEQ ID NO 134
<211> LENGTH: 28
<212> TYPE: DNA
<213> ORGANISM: Homo sapiens
<220> FEATURE:
<221> NAME/KEY: misc_feature
<222> LOCATION: (1)..(2)
```

```
-continued
<223> OTHER INFORMATION: N = SPACER18 LINKER
<220> FEATURE:
<221> NAME/KEY: misc_feature
<222> LOCATION: (18)..(22)
<223> OTHER INFORMATION: N = SPACER18 LINKER

<400> SEQUENCE: 134
nnggttggtg tggttggnnn nncgcatc                                              28

<210> SEQ ID NO 135
<211> LENGTH: 16
<212> TYPE: PRT
<213> ORGANISM: Homo sapiens

<400> SEQUENCE: 135

Met Ala Asp Gly Ser Ser Asp Ala Ala Arg Glu Pro Arg Pro Ala Cys
1               5                   10                  15
```